United States Patent
Wong et al.

(10) Patent No.: US 11,566,076 B2
(45) Date of Patent: *Jan. 31, 2023

(54) ANTI-CSF1R ANTIBODY AND ANTI-PD-1 ANTIBODY COMBINATION THERAPY FOR SELECTED CANCERS

(71) Applicants: Five Prime Therapeutics, Inc., South San Francisco, CA (US); Bristol-Myers Squibb Company, Princeton, NJ (US)

(72) Inventors: Brian Wong, Los Altos, CA (US); Julie Hambleton, San Francisco, CA (US); Robert Sikorski, Woodside, CA (US); Emma Masteller, Redwood City, CA (US); Kevin Hestir, Kensington, CA (US); David Bellovin, San Jose, CA (US); Katherine E. Lewis, Lake Forest Park, WA (US)

(73) Assignees: Five Prime Therapeutics, Inc., Thousand Oaks, CA (US); Bristol-Myers Squibb Company, Princeton, NJ (US)

( * ) Notice: Subject to any disclaimer, the term of this patent is extended or adjusted under 35 U.S.C. 154(b) by 357 days.

This patent is subject to a terminal disclaimer.

(21) Appl. No.: 16/808,910

(22) Filed: Mar. 4, 2020

(65) Prior Publication Data
US 2020/0299392 A1     Sep. 24, 2020

Related U.S. Application Data

(60) Division of application No. 16/243,510, filed on Jan. 9, 2019, now Pat. No. 10,618,967, which is a division of application No. 15/680,664, filed on Aug. 18, 2017, now Pat. No. 10,221,244, which is a continuation of application No. 14/925,534, filed on Oct. 28, 2015, now Pat. No. 9,765,147.

(60) Provisional application No. 62/192,025, filed on Jul. 13, 2015, provisional application No. 62/157,368, filed on May 5, 2015, provisional application No. 62/072,035, filed on Oct. 29, 2014.

(51) Int. Cl.
*C07K 16/28*     (2006.01)
*C07K 16/30*     (2006.01)
*A61K 39/00*     (2006.01)

(52) U.S. Cl.
CPC ...... *C07K 16/2866* (2013.01); *C07K 16/2803* (2013.01); *C07K 16/2818* (2013.01); *C07K 16/3046* (2013.01); *C07K 16/3069* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/33* (2013.01); *C07K 2317/565* (2013.01); *C07K 2317/76* (2013.01); *C07K 2317/90* (2013.01); *C07K 2317/92* (2013.01)

(58) Field of Classification Search
CPC ........ A61K 2039/505; A61K 2039/545; C07K 16/2818; C07K 16/2866
See application file for complete search history.

(56) References Cited

U.S. PATENT DOCUMENTS

| | | |
|---|---|---|
| 5,866,114 A | 2/1999 | Pandit et al. |
| 6,184,354 B1 | 2/2001 | Koths et al. |
| 7,108,852 B2 | 9/2006 | Devalaraja et al. |
| 7,247,618 B2 | 7/2007 | Rajavashisth |
| 7,455,836 B2 | 11/2008 | Hamilton et al. |
| 7,807,389 B2 | 10/2010 | Ritchlin et al. |
| 7,919,594 B2 | 4/2011 | Smith et al. |
| 8,008,449 B2 | 8/2011 | Korman et al. |
| 8,206,715 B2 | 6/2012 | Wong et al. |
| 8,513,199 B2 | 8/2013 | Brasel et al. |
| 8,747,845 B2 | 6/2014 | Wong et al. |
| 9,765,147 B2 | 9/2017 | Wong et al. |
| 10,072,082 B2 | 9/2018 | Cogswell et al. |
| 10,221,244 B2 | 3/2019 | Wong et al. |
| 10,556,957 B2 | 2/2020 | Beebe et al. |
| 10,618,967 B2 | 4/2020 | Wong et al. |
| 2002/0119494 A1 | 8/2002 | Jung et al. |
| 2002/0193575 A1 | 12/2002 | Holmes et al. |
| 2003/0103976 A1 | 6/2003 | Serizawa et al. |
| 2006/0286102 A1 | 12/2006 | Jin et al. |
| 2007/0072797 A1 | 3/2007 | Robinson et al. |
| 2007/0148172 A1 | 6/2007 | Lawson et al. |
| 2007/0166788 A1 | 7/2007 | Jin et al. |
| 2008/0219971 A1 | 9/2008 | Smith et al. |
| 2009/0148883 A1 | 6/2009 | Manthey |
| 2009/0155164 A1 | 6/2009 | Brasel et al. |
| 2010/0136006 A1 | 6/2010 | Lin et al. |
| 2010/0136007 A1 | 6/2010 | Lin et al. |
| 2011/0123550 A1 | 5/2011 | Shibayama et al. |
| 2011/0129456 A1 | 6/2011 | Wang et al. |
| 2011/0243947 A1 | 10/2011 | Doody et al. |

(Continued)

FOREIGN PATENT DOCUMENTS

| | | |
|---|---|---|
| CA | 2388298 | 5/2001 |
| EP | 2241333 A1 | 10/2010 |

(Continued)

OTHER PUBLICATIONS

Extended European Search Report in European Patent Application No. 20207287.2 dated May 18, 2021, 18 pages.

(Continued)

*Primary Examiner* — Elly-Gerald Stoica
(74) *Attorney, Agent, or Firm* — McNeill Baur PLLC

(57) ABSTRACT

Methods of treating cancer with antibodies that bind colony stimulating factor 1 receptor (CSF1R) in combination with PD-1/PD-L1 inhibitors are provided.

25 Claims, 12 Drawing Sheets
Specification includes a Sequence Listing.

(56) References Cited

U.S. PATENT DOCUMENTS

| | | |
|---|---|---|
| 2011/0274683 A1 | 11/2011 | Wong et al. |
| 2012/0121634 A1 | 5/2012 | Chen et al. |
| 2013/0302322 A1 | 11/2013 | Wong et al. |
| 2013/0309250 A1 | 11/2013 | Cogswell et al. |
| 2014/0079699 A1 | 3/2014 | Wong et al. |
| 2015/0073129 A1 | 3/2015 | Herting et al. |
| 2016/0152715 A1 | 6/2016 | Wong et al. |
| 2019/0025308 A1 | 1/2019 | Cummings et al. |
| 2019/0219586 A1 | 7/2019 | Fabrizio et al. |
| 2020/0223931 A1 | 7/2020 | Wong et al. |

FOREIGN PATENT DOCUMENTS

| | | |
|---|---|---|
| JP | 2013535952 A | 9/2013 |
| WO | WO 89/03687 | 5/1989 |
| WO | WO 99/29345 | 6/1999 |
| WO | WO 01/34177 | 5/2001 |
| WO | WO 2002/102972 | 12/2002 |
| WO | WO 2004/045532 | 6/2004 |
| WO | WO 2005/070447 | 8/2005 |
| WO | WO 2006/012451 | 2/2006 |
| WO | WO 2007/075933 | 7/2007 |
| WO | WO 2007/081879 | 7/2007 |
| WO | WO 2007/120252 | 10/2007 |
| WO | WO 2008/060610 | 5/2008 |
| WO | WO 2008/124858 | 10/2008 |
| WO | WO 2008/150383 | 12/2008 |
| WO | WO 2009/026303 | 2/2009 |
| WO | WO 2009/058968 | 5/2009 |
| WO | WO 2009/075344 | 6/2009 |
| WO | WO 2009/112245 | 9/2009 |
| WO | WO 2010/062399 | 6/2010 |
| WO | WO 2010/062401 | 6/2010 |
| WO | WO 2011/070024 | 6/2011 |
| WO | WO 2011/107553 | 9/2011 |
| WO | WO 2011/131407 | 10/2011 |
| WO | WO 2011/140249 | 11/2011 |
| WO | WO 2012/082573 | 6/2012 |
| WO | WO 2012/110360 | 8/2012 |
| WO | WO 2013/057281 | 4/2013 |
| WO | WO 2013/057290 | 4/2013 |
| WO | WO 2013/132044 | 9/2013 |
| WO | WO 2013/169264 | 11/2013 |
| WO | WO 2013/173223 | 11/2013 |
| WO | WO 2014/036357 | 6/2014 |
| WO | WO 2015/036511 | 3/2015 |
| WO | 2016069727 A1 | 5/2016 |
| WO | 2016081947 A2 | 5/2016 |

OTHER PUBLICATIONS

Fend et al., "Therapeutic Effects of Anti-CD115 Monoclonal Antibody in Mouse Cancer Models through Dual Inhibition of Tumor-Associated Macrophages and Osteoclasts," PLOS ONE, 2013, 8(9):e73310, 11 pages.
Fujii et al., "Simulation-based analyses reveal stable microsatellite sequences in human pancreatic cancer," Cancer Genet. Cytogenet., 2009, 189(1):5-14.
Gale, "Cellular and Molecular Basis of Cancer," The Merck Manuals Online Medical Library, Merck Research Laboratories, 2007-2007, retrieved on Oct. 19, 2020, https://www.merckmanuals.com/professional/hematology-and-oncology/overview-of-cancer/cellular-and-molecular-basis-of-cancer, 8 pages.
Lloyd et al., "Modelling the human immune response: performance of a 1011 human antibody repertoire against a broad panel of therapeutically relevant antigens," Protein Engineering, Design and Selection, 2009, 22(3):159-168.
Torres et al., "Serum Cytokine Profile in Patients with Pancreatic Cancer," Pancreas., 2014, 43(7):1042-9.
Anonymous, Nivolumab and Ipilimumab and Radiation Therapy in MSS and MSI High Colorectal and Pancreatic, ClinicalTrials.gov, NCT03104439, Apr. 7, 2017, 13 pages.
Chiorean et al., "Pancreatic Cancer: Optimizing Treatment Options, New, and Emerging Targeted Therapies," Drug Des Devel Ther, 2015, 9:3529-3545.
Aharinejad et al., Colony-stimulating Factor-1 Blockade by Antisense Oligonucleotides and Small Interfering RNAs Suppresses Growth of Human Mammary Tumor Xenografts in Mice, Cancer Research, vol. 64, Aug. 2004, pp. 5378-5384.
Aharinejad et al., Colony-stimulating Factor-1 Antisense Treatment Suppresses Growth of Human Tumor Xenografts in Mice, Cancer Research, vol. 62, Sep. 2002, pp. 5317-5324.
Ando et al., Imatinib Mesylate Inhibits Osteoclastogenesis and Joint Destruction in Rats with Collagen-induced Arthritis, J. Bone Miner. Metab., vol. 24, Jan. 2006, pp. 274-282.
Anonymous, "Bristol-Myers Squibb and Five Prime Therapeutics Announce Exclusive Clinical Collaboration to Evaluate the Combination of Investigational Immunotherapies Opvido (nivolumab) and FPA008 in Six Tumor Types," XP055243984, Nov. 24, 2014, pp. 1-4.
Anonymous, "Study of FPA008 in Combination with Nivolumab in Patients with Selected Advance Cancers," XP055243978, Aug. 17, 2015, pp. 1-4.
Anonymous, "APX005M With Nivolumab and Cabiralizumab in Advanced Melanoma, Non-Small Cell Lung Cancer or Renal Cell Carcinoma," ClinicalTrials.gov, NCT03502330, Apr. 18, 2018, 14 pages.
Anonymous, "Study of Cabiralizumab in Patients with pigmented Villonodular Synovitis / Diffuse Type Tenosynovial Giant Cell Tumor (FPA008-002)", ClinicalTrials.gov, NCT02471716, Jun. 15, 2015, 6 pages.
Anonymous, "Study of Cabiralizumab in Combination with Nivolumab in Patients with Selected Advanced Cancers (FPA008-003)," ClinicalTrials.gov, NCT02526017, Aug. 18, 2015, 7 pages.
Anonymous, "A Study of Cabiralzumab Given by Itself or with Nivolumab in Advanced Cancer or Cancerthat has Spread," ClinicalTrials.gov, NCT03158272, May 18, 2017, 7 pages.
Anonymous, "An Adaptive Study to Match Patients with Solid Tumors to Various Immunotherapy Combinations Based Upon a Broad Biomarker Assessment," ClinicalTrials.gov, NCT03335540, Nov. 7, 2017, 7 pages.
Anonymous, "A Study of Cabiralizumab Give with Nivolumab With or Without Chemotherapy in Patients with Advanced Pancreatic Cancer," NCT03336216, Nov. 8, 2017, 8 pages.
Anonymous, "Stereotactic Body Radiotherapy (SBRT) Plus Immunotherapy for Cancer (C4-MOSART)," ClinicalTrials.gov, NCT03431948, 9 pages.
Anonymous, "Study of Nivolumab, Cabiralizumab, and Sterotactic Body Radiotherapy (SBRT) for Locally Advanced Unresectable Pancreatic Cancer," ClinicalTrials.gov, NCT03599362, Jul. 25, 2018, 8 pages.
Anonymous, Nivolumab + Cabiralizumab + Gemcitabine Versus Gemcitabine in Patients with Stage IV Pancreatic Cancer Achieving Disease Control in Response to First-line Chemotherapy (GemCaN Trial), ClinicalTrials.gov, NCT03697564, Oct. 5, 2018, 7 pages.
Anonymous, "Safety and Tolerability Study of Nivolumab and Cabiralizumab for Resectable Biliary Tract Cancer," ClinicalTrials.gov, NCT03768531, Dec. 7, 2018, 6 pages.
Anonymous, "Nivolumab and the Antagonistic CSF-1R Monoclonal Antibody Cabiralizumab (BMS-986227) in Patients with Relapsed/Refractory Peripheral T Cell Lymphoma," ClinicalTrials.gov, NCT03927105, Apr. 25, 2019, 9 pages.
Anonymous, "Five Prime Therapeutics Provides Update on Phase 2 Trial of Cabiralizumab Combined with Opdivo® in Pancreatic Cancer," Feb. 18, 2020, available at htps://www.fiveprime.com.
Ansari, et al., "The Programmed Death-1 (PD-1) Pathway Regulates Autoimmune Diabetes in Nonobese Diabetic (NOD) Mice," J Exp Med., 2003, 198(1):63-9.
Apollo Cytokine Research, Human hcx™ M-CSF R, Fc Chimera, Product Information Sheet from http://www.biocompare.com/itemdetails.asp?itemid=837066, Feb. 4, 2008.
Birchenall-Roberts, Inhibition of Murine Monocyte Proliferation by a Colony-stimulating Factor-1 Antisense Oligodeoxynucleotide, J. Immunol., vol. 15, Nov. 1990, pp. 3290-3296.

(56) References Cited

OTHER PUBLICATIONS

Bischof et al., Exacerbation of Acute Inflammatory Arthritis by the Colony-stimulating Factors CSF-1 and Granulocyte Macrophage (GM)-CSF: Evidence of Macrophage Infiltration and Local Proliferation, Clin. Exp. Immunol., vol. 119, 2000, pp. 361-367.
Blazar, et al., "Blockade of Programmed Death-1 Engagement Accelerates Graft-Versus-Host Disease Lethality by an IFN-α-Dependent Mechanism," J Immunol., 2003, 171:1272-7.
Campbell et al., The Colony-stimulating Factors and Collagen-induced Arthritis: Exacerbation of Disease by M-CSF and G-CSF and Requirement for Endogenous M-CSF, Journal of Leukocyte Biology, vol. 68, Jul. 2000.
Carter et al., "PD-1:PD-L Inhibitory Pathway Affects both $CD4^+$ and $CD8^+$ T Cells and is Overcome by IL-2," Eur J Immunol., 2002, 32(3):634-43.
Cassier et al., "Phase 1 Study of RG7155, a Novel Anti-CSF1R Antibody, in Patients with Locally Advanced Pigmented Villonodular Synovitis (PVNS)," J Clin Oncol suppl., 2014, 32:5 abstract 10504.
Chaika et al., CSF-1 Receptor/Insulin Chimera Permits CSF-1-dependent Differentiation of 3T3-L1 Preadipocytes, J. Biol. Chem., vol. 272, No. 18, May 1997, pp. 11968-11974.
Chemnitz, et al., "SHP-1 and SHP-2 Associate with Immunoreceptor Tyrosine-Based Switch Motif of Programmed Death 1 upon Primary Human T Cell Stimulation, but only Receptor Ligation Prevents T Cell Activation," J Immunol., 2004, 173:945-54.
Chitu et al., Colony-stimulating Factor-1 in Immunity and Inflammation, Current Opinion in Immunology, vol. 18, No. 1, Feb. 2006, pp. 39-48.
Conway et al., Inhibition of Colony-stimulating-factor-1 Signaling in Vivo with the Orally Bioavailable cFMS Kinase Inhibitor GW2580, PNAS, vol. 102, Nov. 2005, pp. 16078.
Conway et al., Effects of the cFMS Kinase Inhibitor 5-(3-Methoxy-4-((4-methoxybenzyl)oxy)benzyl)pyrimidine-2,4-diamine (GW2580) IN Normal And Arthritic Rats, J. Pharmacology and Experimental Therapeutics, vol. 326, No. 1, Apr. 2008, pp. 41-50.
Dai et al., "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects," Blood, 2002, 99:111-20.
Dandekar et al., Comparison of the Signaling Abilities of the Cytoplasmic Domains of the Insulin Receptor and the Insulin Receptor-related Receptor in 3T3-L1 Adipocytes, Endocrinology, vol. 139, No. 8, Jan. 2008, pp. 3578-3584.
Dewar et al., Imatinib as a Potential Antiresorptive Therapy for Bone Disease, Blood, vol. 107, No. 11, Jun. 2006, pp. 4334-4337.
Dunn et al., "Cancer Immunoediting: from Immunosurveillance to Tumor Escape," Nat Immunol, 2002, 3:991-8.
Freeman, et al., "Engagement of the PD 1 Immunoinhibitory Receptor by a Novel B7 Family Member Leads to Negative Regulation of Lymphocyte Activation," J Exp Med, 2000, 192(7): 1027-34.
Gabbay, et al., "A Randomized Crossover Trial of the Impact of Additional Spermicide on Condom Failure Rates," Sex Transm Dis, 2008, 35:862-8.
Garceau, V. et al., "Pivotal Advance: Avian Colony-Stimulating Factor 1 (CSF-1), Interlukin-34 (IL-34), and CSF-1 Receptor Genes and Gene Products," Journal of Leukocyte Biology, 2010, vol. 87, pp. 753-764.
Goswami et al., Macrophages Promote the Invasion of Breast Carcinoma Cells via a Colony-stimulating Factor-1/Epidermal Growth Factor . . . , Cancer Research., vol. 65, Jun. 2005.
Greenwald, et al., "The B7 Family Revisited," Annu Rev Immunol, 2005, 23:515-48.
Habicht, et al., "A Link Between PDL 1 and T Regulatory Cells in Fetomaternal Tolerance," J Immunol, 2007, 179:5211-9.
Haegel, et al., "A Unique Anti-CD115 Monoclonal Antibody Which Inhibits Osteolysis and Skews Human Monocyte Differentiation from M2-Polarized Macrophages Toward Dendritic Cells," mAbs, 2013, 5:5, pp. 736-747.
Haegel, et al., "A Unique Anti-CD115 Monoclonal Antibody Which Inhibits Osteolysis and Skews Human Monocyte Differentiation from M2-Polarized Macrophages Toward Dendritic Cells," mAbs, 5:5, 2013, Suppl., 12 pages.
Hamilton, et al., "Colony Stimulating Factors and Myeloid Cell Biology in Health and Disease," Trends in Immunology, 2013, 34:81-89.
Hamilton, CSF-1 Signal Transduction, Journal of Leukocyte Biology, vol. 62, Aug. 1997, pp. 145-155.
Hamilton, Colony-stimulating Factors in Inflammation and Autoimmunity, Nature Reviews, vol. 8, Jul. 2008, pp. 533-544.
Hegen et al., Utility of Animal Models for Identification of Potential Therapeutics for Rheumatoid Arthritis, Ann. Rheum. Dis., vol. 67, published online Nov. 2007, pp. 1505-1515.
Ide et al., Expression of Colony-stimulating Factor 1 Receptor During Prostate Development and Prostate Cancer Progression, PNAS, vol. 99, No. 22, Oct. 2002, pp. 14404-14409.
Ide et al., Serum Level of Macrophage Colony-stimulating Factor is Increased in Prostate Cancer Patients with Bone Metastasis, Human Cell, vol. 21, No. 1, Feb. 2008, pp. 1-6.
Irvine et al., A CSF-1 Receptor Kinase Inhibitor Targets Effector Functions and Inhibits Pro-inflammatory Cytokine Production . . . , FASEB, vol. 20, Sep. 2006, pp. E1315-E1326.
Kaufmann, et al., "Programmed Death-1 as a Factor in Immune Exhaustion and Activation in HIV Infection," Curr Opin HIV Aids, 2008, 3(3):362-7.
Kestelman, et al., "Efficacy of the Simultaneous Use of Condoms and Spermicides," Family Planning Perspectives, 1991, 23(5):226-7.
Kingsley et al., Molecular Biology of Bone Metastasis, Mol. Cancer Ther., vol. 6, No. 10, Oct. 2007, pp. 2609-2617.
Kitaura et al., M-CSF Mediates TNF-induced Inflammatory Osteolysis, The Journal of Clinical Investigation, vol. 115, No. 12, Dec. 2005, pp. 3418-3427.
Kitaura et al., An M-CSF Receptor c-Fms Antibody Inhibits Mechanical Stress-Induced Root Resorption during Orthodontic Tooth Movement in Mice, Angle Orthodontist, vol. 79, No. 5, 2009, pp. 835-841.
Kluger et al., Macrophage Colony-stimulating Factor-1 Receptor Expression is Associated with Poor Outcome in Breast Cancer by Large Cohort Tissue Microarray Analysis, Clinical Cancer Res, vol. 10, Jan. 2004, pp. 173.
Komohara, et al, "Clinical Significance of Macrophage Heterogeneity in Human Malignant Tumors," Cancer Sci, 2014, 105:1-8.
Kuang, et al., "Activated Monocytes in Peritumoral Stroma of Hepatocellular Carcinoma Foster Immune Privilege and Disease Progression through PD-L1," J Exp Med, 2009, 206(6):1327-37.
Kubota et al., M-CSF Inhibition Selectively Targets Pathological Angiogenesis and Lymphangiogenesis, J. Exp. Med., vol. 206, No. 5, Apr. 2009, pp. 1089-1102.
Kutza et al., Macrophage Colony-stimulating Factor Antagonists Inhibit Replication of HIV-1 in Human Macrophages, The Journal of Immunology, 2000, vol. 164, pp. 4955-4960.
Latchman, et al., "PD-L2 is a Second Ligand for PD-1 and Inhibits T Cell Activation," Nat Immunol, 2001, 2(3):261-268.
Lavin, et al., "Macrophages: Gate Keepers of Tissue Integrity," Cancer Immunol Res., 2013, 1 (4):201-9.
Lavin, et al., "Tissue-Dependent Macrophage Enhancer Landscapes are Shaped by the Local Microenvironment," Cell, 2014, 159:1312-26.
Lee et al., Functional Dissection of Structural Domains in the Receptor for Colony-stimulating Factor-1, J. Biol. Chem., vol. 267, Aug. 1992, pp. 16472-16483.
Li et al., Conditional Deletion of the Colony Stimulating Factor-1 Receptor (c-fms Proto-Oncogene) in Mice, Genesis, vol. 44, May 2006, pp. 328-335.
Li et al., Role of Dimerization and Modification of the CSF-1 Receptor in its Activation and Internalization During the CSF-1 Response, The EMBO Journal, 1991, pp. 277-288.
Lim et al., Antibody blockade of c-fms suppresses the progression of inflammation and injury in early diabetic nephropathy in obese db/db mice, Diabetologia, vol. 52, 2009, pp. 1669-1679.

(56) References Cited

OTHER PUBLICATIONS

Lin et al., Colony-stimulating Factor 1 Promotes Progression of Mammary Tumors to Malignancy, J. Exp. Med., vol. 193, No. 6, Mar. 2001, pp. 727-739.
Lin et al., The Macrophage Growth Factor CSF-1 in Mammary Gland Development and Tumor Progression, J. Mammary Gland Biology and Neoplasia, vol. 7, Apr. 2002, pp. 147-162.
Lin et al., Discovery of a Cytokine and Its Receptor by Functional Screening of the Extracellular Proteome, Science, vol. 320, May 2008, pp. 807-811.
Lin et al. Regulation of Myeloid Growth and Differentiation by a Novel Cytokine, Interleukin-34 (IL-34), via the CSF-1 Receptor, poster presented at Cytokines in Health & Disease, Fifteenth Annual Conference of the International Cytokine Society (San Francisco, CA, Oct. 26-30, 2007, 1 page.
Lipton, Future Treatment of Bone Metastases, Clin. Cancer Res., vol. 12, 20 Suppl., Oct. 2006, pp. 6305s-6308s.
Llosa, et al., "The Vigorous Immune Microenvironment of Microsatellite Instable Colon Cancer is Balanced by Multiple Counter-Inhibitory Checkpoints," Cancer Discov, 2015, 5(1):43-51.
Lopez-Diego et al., Novel Therapeutic Strategies for Multiple Sclerosis—A Multifaceted Adversary, Nature Reviews Drug Discovery, vol. 7, Nov. 2008, pp. 909-925.
MacDonald et al., An Antibody Against the Colony-stimulating Factor 1 Receptor Depletes the Resident Subset of Monocytes and Tissue- and Tumor-associated Macrophages But Does Not Inhibit Inflammation, Blood, vol. 116, Aug. 2010, pp. 3955-3963.
Mancino et al., Breast Cancer Increases Osteoclastogenesis by Secreting M-CSF and Upregulating RANKL in Stromal Cells, J. Surgical Research, vol. 100, Jul. 2001, pp. 18-24.
Masteller, et al, "Targeting IL-34 in Chronic Inflammation," Drug Discov Today, 2014, 19:1212-16.
Mroczko et al., Serum Macrophage-colony Stimulating Factor Levels in Colorectal Cancer Patients Correlate with Lymph Node Metastasis and Poor Prognosis, Clinica Chimica Acta., vol. 380, Feb. 2007, pp. 208-212.
Montell, Metastasis Movies, Macrophages, Molecules and More, EMBO Reports, vol. 4, No. 5, Apr. 2003, pp. 458-462.
Murray et al., SU11248 Inhibits Tumor Growth and CSF-1 R-dependent Osteolysis in an Experimental Breast Cancer Bone Metastasis Model, Clinical & Experimental Metastasis, vol. 2, Aug. 2003, pp. 757-766.
Nishimura, et al., "Development of Lupus-Like Autoimmune Diseases by Distruption of the PD-1 Gene Encoding an ITM Motif-Carrying Immunoreceptor," Immunity, 1999, 11:141-51.
Nishimura, et al., "PD-1: An Inhibitory Immunoreceptor Involved in Peripheral Tolerance," Trends Immunol., 2001, 22:265-8.
Nishimura, et al., "Autoimmune Dilated Cardiomyopathy in PD-1 Receptor-Deficient Mice," Science, 2001, 291:319-22.
Noy, et al., "Tumor-Associated Macrophages: from Mechanisms to Therapy," Immunity, 2014, 41:49-61.
Ohno et al., A c-Fms Tyrosine Kinase Inhibitor, Ki20227, Suppresses Osteoclast Differentiation and Osteolytic Bone Destruction in a Bone Metastasis, Mol. Cancer Ther., vol. 5, Nov. 2006, pp. 2634.
Ohno et al., The Orally-active and Selective c-FMS tyrosine Kinase Inhibitor Ki20227 Inhibits Disease Progression in a Collagen-induced Arthritis Mouse Model, Eur. J. Immunol., 2008, vol. 38:283-291.
Okazaki, et al., "Autoantibodies against Cardiac Troponin I are Responsible for Dilated Cardiomyopathy in PD-1-Deficient Mice," Nat Med, 2003, 9:1477-83.
Opdivo [package insert]. Princeton, NJ: Bristol-Myers Squibb Company; Mar. 2015.
Paniagua et al., c-Fms-mediated Differentiation and Priming of Monocyte Lineage Cells Plays a Central Role in Autoimmune Arthritis, Arthritis Research & Therapy, vol. 12, No. R32, Feb. 2010, pp. 1-45.
Pardoll, "Does the Immune System see Tumors as Foreign or Self?" Annu Rev Immunol, 2003, 21:807-39.
Paulus et al., Colony-stimulating Factor-1 Antibody Reverses Chemoresistance in Human MCF-7 Breast Cancer Xenografts, Cancer Res., vol. 66, No. 8, Apr. 2006, pp. 4349-4356.
Pederson et al., Identification of Breast Cancer Cell Line-derived Paracrine Factors That Stimulate Osteoclast Activity, Cancer Research, vol. 59, Nov. 1999, pp. 5849-5855.
Pixley et al., CSF-1 Regulation of the Wandering Macrophage: Complexity in Action, Trends in Cell Biology, vol. 14, No. 11, Nov. 2004, pp. 628-638.
Prince et al., 8: Disorders of Bone and Mineral Other Than Osteoporosis, MJA, vol. 180, Apr. 2004, pp. 354-359.
Pyonteck, et al., "CSF-1R Inhibition Alters Macrophage Polarization and Blocks Glioma Progression," Nat Med, 2013, 19:1264-72.
Qiu et al., Primary Structure of c-kit: Relationship with the CSF-1/PDGF Receptor Kinase Family—Oncogenic Activation of v-kit Involves Deletion of Extracellular Domain and C Terminus, The EMBO Journal, vol. 7, No. 4, Jan. 1988, pp. 1003-1011.
R&D Systems, Inc., Recombinant Human M-CSF R/Fc Chimera, Specifications and Use, Catalog No. 329-MR, Nov. 2007, 2 pages.
Radi, et al., "Increased Connective Tissue Extracellular Matrix in the Op/Op Model of Osteopetrosis," Pathobiology, 2009, 76:199-203.
Radi, et al., "Increased Serum Enzyme Levels Associated with Kupffer Cell Reduction with No Signs of Hepatic or Skeletal Muscle Injury," Am J Pathol, 2011, 179:240-247.
Rahimi et al., Receptor Chimeras Indicate that the Vascular Endothelial Growth Factor Receptor-1 (VEGFR-1) Modulates Mitogenic Activity of VEGFR-2 in Endothelial Cells, J. Biol. Chem., vol. 275, No. 22, Jun. 2000, pp. 16986-16992.
Ries, et al., "Targeting Tumor-Associated Macrophages with Anti-CSF-1R Antibody Reveals a Strategy for Cancer Therapy," Cancer Cell, 2014, 25(6): 846-859.
Ries, et al., "CSF-1/CSF-1R Targeting Agents in Clinical Development for Cancer Therapy," Current Opinion in Pharmacology, 2015, 23: 45-51.
Rizvi, et al., "Activity and Safety of Nivolumab, an Anti-PD-1 Immune Checkpoint Inhibitor, for Patients with Advanced, Refractory Squamous Non-Small-Cell Lung Cancer (CheckMate 063): A Phase 2, Single-Arm Trial," Lancet Oncol., 2015, 16(3):257-65.
Ross, M-CSF, c-Fms, and Signaling in Osteoclasts and Their Precursors, Annals NY Acad. Sci., vol. 1068, 2006, pp. 110-116.
Roussel et al., Colony-stimulating Factor 1-mediated Regulation of a Chimeric c-fms/v-fms Receptor Containing the v-fms-encoded Tyrosine Kinase Domain, PNAS, vol. 85, Aug. 1988, pp. 5903-5907.
Ruffell, et al., "Macrophages and Therapeutic Resistance in Cancer," Cancer Cell, 2015, 27:462-72.
Rutebemberwa, et al., "High-Programmed Death-1 Levels of Hepatitis C Virus-Specific T Cells During Acute Infection are Associated with Viral Persistence and Require Preservation of Cognate Antigen during Chronic Infection," J Immunol, 2008, 181:8215-25.
Sadis, et al., "Safety, Pharmacokinetics, and Pharmacodynamics of PD-0360324, a Human Monoclonal Antibody to Monocyte/Macrophage Colony Stimulating Factor, in Healthy Volunteers," ACR/ARHP Scientific Meeting 2009, Oct. 17-21, Philadelphia, PA, Poster 408.
Salama, et al., "Critical Role of the Programmed Death-1 (PD-1) Pathway in Regulation of Experimental Autoimmune Encephalomyelitis," J Exp Med, 2003, 198:71-8.
Sapi, The Role of CSF-1 in Normal Physiology of Mammary Gland and Breast Cancer: An Update, Exp. Biol. Med., vol. 229, 2004, pp. 1-11.
Sarma et al., Macrophage Colony-stimulating Factor Induces Substantial Osteoclast Generation and Bone Resorption in Human Bone Marrow Cultures, Blood, vol. 88, No. 7, Oct. 1996, pp. 2531-2540.
Shaposhink et al., Arterial Colony Stimulating Factor-1 Influences Atherosclerotic Lesions by Regulating Monocyte Migration and Apoptosis, J. Lipid Research, vol. 51, 2010, pp. 1962-1970.
Sharpe, et al., "The Function of Programmed Cell Death 1 and its Ligands in Regulating Autoimmunity and Infection," Nature Immunol, 2007, 8:239-45.

(56) References Cited

OTHER PUBLICATIONS

Sheppard, et al., "PD-1 Inhibits T-Cell Receptor Induced Phosphorylation of the ZAP70/CD3zeta Signalosome and Downstream Signaling to PKC-theta," FEBS Letters, 2004, 574:37-41.
Sherr et al., Inhibition of Colony-Stimulating Factor-1 Activity by Monoclonal Antibodies to the Human CSF-1 Receptor, Blood, vol. 73, No. 7, May 1989, pp. 1786-1793.
Sherr, Colony-Stimulating Factor-1 Receptor, Blood, vol. 75, No. 1, Jan. 1990, pp. 1-12.
Sigma Product Information, "Macrophage Cologny Stimulating Factor Receptor/Fc Chimera (M-CSF R, CD115) Human, Recombinant, Expressed in mouse NS0 cells," Product No. M 7559, no date available.
Steinman et al., Virtues and Pitfalls of EAE for the Development of Therapies for Multiple Sclerosis, Trends in Immunology, 2005, 26(11):565-571.
Suzuki et al., Differences in Bone Responses to Recombinant Human Granulocyte Colony-stimulating Factor Between Mice and Rats, J. Toxicol. Sci., vol. 33, No. 2, 2008, pp. 245-249.
Sweet et al., CSF-1 as a Regulator of Macrophage Activation and Immune Response, AI&TE, vol. 51, 2003, pp. 169-177.
Tamura et al., Tyrosine Kinase as Targets for Anti-inflammatory Therapy, Anti-Inflammatory & Anti-Allergy Agents in Medicinal Chemistry, vol. 6, No. 1,2007, pp. 47-60.
Tanaka et al., Macrophage Colony-stimulating Factor is Indispensable for Both Proliferation and Differentiation of Osteoclast Progenitors, J. Clin. Invest., vol. 91, Jan. 1993, pp. 257-263.
Teitelbaum, Osteoclasts: What Do They Do and How Do They Do It? Am. J. Pathol., vol. 170, No. 2, Feb. 2007, pp. 427-435.
Tumeh, et al., "PD-1 Blockade Induces Responses by Inhibiting Adaptive Immune Resistance," Nature, 2014, 515:568-71.
Uemura et al., The Selective M-CSF Receptor Tyrosine Kinase Inhibitor Ki20227 Suppresses Experimental Autoimmune Encephalomyelitis, J. Neuroimmunology, vol. 195, Jan. 2008, pp. 73-80.
Usbiological, CD115, Recombinant, Human, Fc Chimera (BSA Free) (c-fms, Fms, CSF-1R, M-CSFR), from Google's cache of http://usbio.net/Product.spx?ProdSku+C2447-52E1, as retrieved on Jan. 16, 2008 (1 page).
Van Daalen Wetters et al., Random Mutagenesis of CSF-1 Receptor (FMS) Reveals Multiple Sites for Activating Mutations within the Extracellular Domain, The EMBO Journal, 1992, 11:551-557.
Velu, et al., "Enhancing SIV-Specific Immunity in vivo by PD-1 Blockade," Nature, 2009, 458:206-10.
Virk et al., Tumor Metastasis to Bone, Arthritis Research & Therapy, vol. 9, Suppl. 1, 2007, S5, pp. 1-10.
Walsh et al., Post-translational Modifications in the Context of Therapeutic Proteins, Nature Biotechnology, vol. 24, No. 10, Oct. 2006, pp. 1241-1252.
Wang, et al., "In Vitro Characterization of the Anti-PD-1 Antibody Nivolumab, BMS-936558, and in vivo Toxicology in Non-Human Primates," Cancer Immunol Res., 2014, 2:846-56.
Wang et al., Identification of the Ligand-binding Regions in the Macrophage Colony-stimulating Factor Receptor Extracellular Domain, Mol. Cell Biol., Sep. 1993, pp. 5348-5359.
Weber, et al., "Nivolumab Versus Chemotherapy in Patients with Advanced Melanoma who Progressed after Anti-CTLA-4 Treatment (CheckMate 037): A Randomised, Controlled, Open-Label, Phase 3 Trial," Lancet Oncol, 2015, 16(4):375-84.
Weihofen et al., Release of Signal Peptide Fragments Into the Cytosol Requires Cleavage in the Transmembrane Region by a Protease Activity That is Specifically Blocked by a Novel Cysteine Protease Inhibitor, J. Biol. Chem., vol. 275, No. 40, Oct. 2000, pp. 30951-30956.
Wolchok, et al., "Guidelines for the Evaluation of Immune Therapy Activity in Solid Tumors: Immune-Related Response Criteria," Clin Cancer Res., 2009, 15:7412-20.
Wu et al., Enhancement of J6-1 Human Leukemic Cell Proliferation by Membrane-bound M-CSF Through a Cell-Cell Contact Mechanism II. Role of an M-CSF Receptor-like Membrane Protein, Leukemia Research, vol. 22, 1998, pp. 55-60.

Wyckoff et al., A Paracrine Loop Between Tumor Cells and Macrophages is Required for Tumor Cell Migration in Mammary Tumors, Cancer Research, vol. 64, Oct. 2004, pp. 7022-7029.
Yano et al., Macrophage Colony-stimulating Factor Gene Transduction into Human Lung Cancer Cells Differentially Regulates Metastasis . . . , Cancer Research, Feb. 1997, pp. 784.
Yao et al., Tumor Necrosis Factor-α Increases Circulating Osteoclast Precursor Numbers by Promoting Their Proliferation and Differentiation in the Bone Marrow Through Up-regulation of c-Fms Expression, J. Biol Chem., vol. 281, Apr. 2006, pp. 11846.
Yoshimoto et al., Elevated levels of Fractalkine Expression and Accumulation of CD16+ Monocytes in Glomeruli of Active Lupus Nephritis, Am. J. Kidney Disease, vol. 50, No. 1, Jul. 2007, pp. 47-58.
Zheng et al., Expression of Bioactive Human M-CSF Soluble Receptor in Transgenic Tobacco Products, Protein Expression and Purification, 2006, 46:367-373; available online Aug. 15, 2005.
Zhu, et al., "CSF1/CSF1R Blockade Reprograms Tumor-Infiltrating Macrophages and Improves Response to T-cell Checkpoint Immunotherapy in Pancreatic Cancer Models," Cancer Research, 2014, 74(18): 5057-5069.
Zitvogel, et al., "Cancer Despite Immunosurveillance: Immunoselection and Immunosubversion," Nat Rev Immunol, 2006, 6:715-27.
International Search Report for PCT/US2015/057781, dated Feb. 1, 2016, pp. 1-17.
International Search Report and the Written Opinion dated Jan. 31, 2012 for International Patent Application PCT/US2011/035231, filed May 4, 2011.
International Search Report and Written Opinion dated May 24, 2010 for Application No. PCT/US2009/006301, filed Nov. 25, 2009.
International Search Report and Written Opinion dated Jun. 9, 2010 for Application No. PCT/US2009/006299, filed Nov. 25, 2009.
Response to Restriction Election Requirement filed May 3, 2011, for U.S. Appl. No. 12/626,583 (3 pages).
Office Action dated Jun. 21, 2011, for U.S. Appl. No. 12/626,583 (14 pages).
Reply to Office Action filed Aug. 1, 2011, for U.S. Appl. No. 12/626,583 (15 pages).
Notice of Allowance and Fees Due and Examiner initiated interview summary dated Dec. 8, 2011, for U.S. Appl. No. 12/626,583 (9 pages).
Office Action dated Nov. 16, 2010, for U.S. Appl. No. 12/626,598 (7 pages).
Amendment and Response to Restriction Requirement filed Feb. 16, 2011, for U.S. Appl. No. 12/626,598 (7 pages).
Office Action dated Mar. 16, 2001, for U.S. Appl. No. 12/626,598 (12 pages).
Reply to Office Action filed Jun. 16, 2011 for U.S. Appl. No. 12/626,598 (7 pages).
Final Office Action dated Aug. 3, 2011, for U.S. Appl. No. 12/626,598 (6 pages).
Amendment After Final filed Aug. 16, 2011, for U.S. Appl. No. 12/626,598 (8 pages).
Notice of Allowance and Fees Due dated Oct. 13, 2011, for U.S. Appl. No. 12/626,598 (6 pages).
Burns & Wilks, c-FMS inhibitors: a patent review, Expert Opin Ther Pat., 2011, 21(2):147-165.
File History of U.S. Appl. No. 13/891,455, filed May 10, 2013.
File History of U.S. Appl. No. 14/014,446, filed Aug. 30, 2013.
Priceman et al., Targeting distinct tumor-infiltrating myeloid cells by inhibiting CSF-1 receptor: combating tumor evasion of antiangiogenic therapy, Blood, 2010 115(7):1461-1471.
Sasmono et al., Mouse neutrophilic granulocytes express mRNA encoding the macrophage colony-stimulating factor receptor (CSF-1R) as well as many other macrophage-specific transcripts and can transdifferentiate into macrophages in vitro in response to CSF-1, J Leukoc Biol, 2007, 82(1):111-123.
Sigma Product Information, "Macrophage Cologny Stimulating Factor Receptor/Fc Chimera (M-CSF R, CD115) Human, Recombinant, Expressed in mouse NS0 cells," Product No. M 7559, 2011, 2 pages.

(56) References Cited

OTHER PUBLICATIONS

Aikawa et al., PU.1-mediated upregulation of CSF1R is crucial for leukemia stem cell potential induced by MOZ-TIF2, Nature Medicine, vol. 16, May 2010, pp. 580-585.
Pasternak et al., ACC/AHA/NHLBI Clinical Advisory on the Use and Safety of Statins, J Am College Cardiology, 2002, 40(3):567-572.
Seeff, Should There Be a Standard of Care (SOC) for Drug-Induced Liver Injury (DILI)?, Presentation, Drug-Induced Liver Injury: Are We Ready to Look, Mar. 23-24, 2011, AASLD, FDA/CDER, PhRMA, 20 pages.
International Search Report and Written Opinion dated Jan. 7, 2014, for Application No. PCT/US2013/057442, filed Aug. 30, 2013, 15 pages.
Paul, WE, Fundamental Immunology, $3^{rd}$ Ed., Raven Press, NY, Chapter 9, pp. 292-295 (1993).
Rudikoff et al., "Single amino acid substitution altering antigen-binding specificity," Proc. Natl. Acad. Sci. USA, 79: 1979-1983 (1982).
Colman, "Effects of amino acid sequence changes on antibody-antigen interactions," Research in Immunology, Elsevier, NY, 145(1): 33-36 (1994).
Bloom et al., Colony stimulating factor-1 in the induction of lupus nephritis, Kidney International, 1993, 43:1000-1009.
Carayannopoulos & Capra, Immunoglobulins: Structure and Function, Fundamental Immunology, 3rd Edition, Paul ed., Raven Press, NY, 1993, 292-295.
Chara et al., Monocyte populations as markers of response to adalimumab plus MTX in rheumatoid arthritis, Arthritis Research & Therapy, 2012, 14:R175 including supplemental data, 13 pages.
Chemel et al., Interleukin 34 expression is associated with synovitis severity in rheumatoid arthritis patients, Ann Rheum Dis, 2012, 71(1):150-154.
Cooper et al., FcεRIIIa Expression on Monocytes in Rheumatoid Arthritis: Role in Immune-Complex Stimulated TNF Production and Non-Response to Methotrexate Therapy, PLoS One, 2012, 7(1):e28918, 10 pages.
Cros et al., Human CD14dim Monocytes Patrol and Sense Nucleic Acids and Viruses via TLR7 and TLR8 Receptors, Immunity, 2010, 33:375-386.
Garcia et al., Colony-Stimulating Factor (CSF)-1 Receptor Blockade Overcomes Overlapping Effects of M-CSF and IL-34 on Myeloid Differentiation and Gene Expression to Reduce Inflammation in Human and Murine Models of Rheumatoid Arthritis, ACR Poster, Nov. 2012, 1 page.
Garnero et al., Biochemical markers of joint tissue turnover in early rheumatoid arthritis, Clin Exp Rheumatol, 2003, 21(Suppl. 31):S54-S58.
Kawanaka et al., CD14+, CD16+ Blood Monocytes and Joint Inflammation in Rheumatoid Arthritis, Arthritis & Rheumatism, 2002, 46(10):2578-2586.
Kelley, Leukocyte-Renal Epithelial Cell Interactions Regulate Lupus Nephritis, Semin Nephrol, 27:59-68 Jan. 2007.
Koch et al., Investigating the role of proinflammatory CD16+ monocytes in the pathogenesis of inflammatory bowel disease, Clin Exper Immunol, 2010, 161:332-341.
Kutzelnigg et al., Cortical demyelination and diffuse white matter injury in multiple sclerosis, Brain, 2005, 128:2705-2712.
Le Meur et al., Macrophage accumulation at a site of renal inflammation is dependent on the M-CSF/c-fms pathway, J Leukoc Biol, 2002, 72(3):530-537.
Lenda et al., Negative role of colony-stimulating factor-1 in macrophage, T cell, and B cell mediated autoimmune disease in MRL-Fas(lpr) mice, J Immunol, 2004, 173(7):4744-4754.
Liu et al., The mechanism of shared but distinct CSF-1R signaling by the non-homologous cytokines IL-34 and CSF-1, Biochimica et Biophysica Acta, 2012, 1824:938-945.
Menke et al., Circulating CSF-1 Promotes Monocyte and Macrophage Phenotypes that Enhance Lupus Nephritis, j Am Soc Nephrol, 2009, 20:2581-2592.
Menke et al., CSF-1 signals directly to renal tubular epithelial cells to mediate repair in mice, J Clin Invest, 2009, 119(8):2330-2342.
Patel & Player, Colony-Stimulating Factor-1 Receptor Inhibitors forthe Treatment of Cancer and Inflammatory Disease, Curr Topics Med Chem, 2009, 9:599-610.
Rauen & Mertens, Unravelling the pathogenesis of lupus nephritis: novel genetic study confirms decisive contribution of circulating colony-stimulating factor-1 (CSF-1), Int Urol Nephrol, 2010, 42:419-521.
Rossol et al., The CD14-bright CD16+ Monocyte Subset Is Expanded in Rheumatoid Arthritis and Promotes Expansion of the Th17 Cell Population, Arthritis & Rheumatism, 2012, 64(3):671-677.
Seshan & Jennette, Renal Disease in Systemic Lupus Erythematosus With Emphasis on Classification of Lupus Glomerulonephritis, Arch Pathol Lab Med, 2009, 133:233-248.
Subimerb et al., Circulating CD14+CD16+ monocyte levels predict tissue invasive character of cholangiocarcinoma, Clinical and Experimental Immunology, 2010, 161:471-479.
TECOmedical Group, TRAP5b Tartrate-Resistant Acid Phosphatase active isoform 5b, A biomarker for osteoclastic bone-resporption activity, Bone-resporption in renal insufficiency, Catalog, Jul. 2011, 20 pages.
Toh et al., Colony Stimulating Factor 1 Receptor Inhibition Has Anti-Inflammatory and Potent Early Onset Bone and Cartilage Protective Effects, Abstract, ACR/ARHP Scientific Meeting, Nov. 7, 2011, 1 page.
Wada et al., Systemic autoimmune nephritogenic components induce CSF-1 and TNF-alpha in MRL kidneys, Kidney International, 1997, 52:934-941.
Wei et al., Functional overlap but differential expression of CSF-1 and IL-34 in their CSF-1 receptor-mediated regulation of myeloid cells, J Leukoc Biol, 2010, 88(3):495-505.
Wentworth & Davis, Systemic lupus erythematosus, Nature Rev, 2009, 8:103-104.
Wijngaarden et al., Fc-gamma receptor expression levels on monocytes are elevated in rheumatoid arthritis patients with high erythrocyte sedimentation rate who do not use anti-rheumatic drugs, Rheumatology, 2003, 42:681-688.
Yang et al., Increase in the level of macrophage colony-stimulating factor in patients with systemic lupus erythematosus, Ann Rheum Dis, 2008, 67:429-430.
Zhang et al., Hyper-Activated Pro-Inflammatory CD16+ Monocytes Correlate with the Severity of Liver Injury and Fibrosis in Patients with Chronic Hepatitis B, PLoS One, 2011, 6:(3):e17484, 10 pages.
Ziegler-Heitbrock, The CD14 CD16 blood monocytes: their role in infection and inflammation, J Leuko Biol, 2007, 81:584-592.
International Search Report and Written Opinion dated Sep. 7, 2012 for Application No. PCT/US2012/037520, filed May 11, 2012, 13 pages.
File History of U.S. Appl. No. 13/100,990, filed May 4, 2011.
Extended European Search Report, European Patent Appl. No. 11778283.9, dated Apr. 22, 2015.
T Tsuboi et al., Leukemia 14: 1460-66 (2000).
File History of U.S. Appl. No. 14/266,209, filed Apr. 30, 2014.
File History of U.S. Appl. No. 13/464,503, filed May 4, 2012.
File History of U.S. Appl. No. 14/924,568, filed Oct. 27, 2015.
File History of U.S. Appl. No. 15/279,853, filed Sep. 29, 2016.
File History of U.S. Appl. No. 14/925,534, filed Oct. 28, 2015.
File History of U.S. Appl. No. 15/680,664, filed Aug. 18, 2017.
File History of U.S. Appl. No. 16/243,510, filed Jan. 9, 2019.
Opposition Brief in European Patent No. 2287192, dated May 25, 2016, 22 pages.
Anonymous, "Archive History for NCT02713529—Safety and Efficacy Study of AMG 820 and Pembrolizumab Combination in Select Advanced Solid Tumor Cancer," ClinicalTrials.gov, NCT02713529, Sep. 6, 2017, 4 pages.
File History of U.S. Appl. No. 16/646,690, filed Mar. 12, 2020.
International Search Report for PCT/US2018/050711, dated Feb. 20, 2019, 18 pages.
Papadopoulos et al., "First-in-human Study of AMG 820, a Monoclonal Anti-Colony Stimulating Factor 1 Receptor Antibody, in Patients with Advanced Solid Tumors," Clin Cancer Research, 2017, 23(19): 5703-5710.

Summary of Study Design

Screening Assessments (All Cohorts): Within 28 days of first study drug dose

---

Phase 1a
1) HuAB1 Monotherapy (two cohorts)
2) HuAB1 + Nivolumab Dose Escalation (three cohorts)

Phase 1b Dose Expansion at the Recommended Combination Dose of HuAB1 + Nivolumab

---

HuAB1 Monotherapy (q2w)
Cohort 1aM1:
2 mg/kg HuAB1(FPA008)
  Cohort 1aM2:
  4 mg/kg HuAB1
(6 - 12 pts with advanced cancers)

3+3 Dose Escalation Combinational Therapy (q2w):
Cohort 1aC1:
1 mg/kg HuAB1 + 3 mg/kg nivolumab
  Cohort 1aC2:
  2 mg/kg HuAB1 + 3 mg/kg nivolumab
    Cohort 1aC3:
    4 mg/kg HuAB1 + 3 mg/kg nivolumab
(9 - 18 pts with advanced cancers)

RD (Recommended Dose) →

Cohort 1b1: Squamous/Non-squamaous NSCLC (Second/third line, anti-PD-1 therapy naïve)
Cohort 1b2: NSCLC (Refractory on anti-PD-1 targeting drug)
Cohort 1b3: Melanoma (anti-PD-1 therapy naïve)
Cohort 1b4: Melanoma (Refractory/Relapse on anti-PD-1 targeting drug)
Cohort 1b5: SCCHN (Second line)
Cohort 1b6: Pancreatic Cancer (Second line)
Cohort 1b7: Colorectal Cancer (Third line)
Cohort 1b8: GBM (1st Recurrence)

(About 30 pts per cohort, a total of 240 pts)

---

Treatment Completion/Early Termination Visit:
28 Days after last dose of study drug(s)

ANTI-CSF1R ANTIBODY AND ANTI-PD-1 ANTIBODY COMBINATION THERAPY FOR SELECTED CANCERS

CROSS-REFERENCE TO RELATED APPLICATIONS

The present application is a divisional of U.S. application Ser. No. 16/243,510, filed Jan. 9, 2019, which is a divisional of U.S. application Ser. No. 15/680,664, filed Aug. 18, 2017, now U.S. Pat. No. 10,221,244, which is a continuation of U.S. application Ser. No. 14/925,534, filed Oct. 28, 2015, now U.S. Pat. No. 9,765,147, which claims the benefit of priority of US Provisional Application Nos. 62/072,035, filed Oct. 29, 2014, 62/157,368, filed May 5, 2015, and 62/192,025, filed Jul. 13, 2015, all of which are incorporated by reference herein in their entirety for any purpose.

SEQUENCE LISTING

The present application is filed with a Sequence Listing in electronic format. The Sequence Listing is provided as a file entitled "01134-0036-00US_SeqList_ST25.txt" created on Oct. 28, 2015, which is 167,217 bytes in size. The information in the electronic format of the sequence listing is incorporated herein by reference in its entirety.

TECHNICAL FIELD

Methods of treating cancer with antibodies that bind colony stimulating factor 1 receptor (CSF1R) in combination with PD-1/PD-L1 inhibitors.

BACKGROUND

Colony stimulating factor 1 receptor (referred to herein as CSF1R; also referred to in the art as FMS, FIM2, C-FMS, M-CSF receptor, and CD115) is a single-pass transmembrane receptor with an N-terminal extracellular domain (ECD) and a C-terminal intracellular domain with tyrosine kinase activity. Ligand binding of CSF1 or the interleukin 34 ligand (referred to herein as IL-34; Lin et al., Science 320: 807-11 (2008)) to CSF1R leads to receptor dimerization, upregulation of CSF1R protein tyrosine kinase activity, phosphorylation of CSF1R tyrosine residues, and downstream signaling events. CSF1R activation by CSF1 or IL-34 leads to the trafficking, survival, proliferation, and differentiation of monocytes and macrophages, as well as other monocytic cell lineages such as osteoclasts, dendritic cells, and microglia.

Many tumor cells or tumor stromal cells have been found to produce CSF1, which activates monocyte/macrophage cells through CSF1R. The level of CSF1 in tumors has been shown to correlate with the level of tumor-associated macrophages (TAMs) in the tumor. Higher levels of TAMs have been found to correlate with poorer patient prognoses in the majority of cancers. In addition, CSF1 has been found to promote tumor growth and progression to metastasis in, for example, human breast cancer xenografts in mice. See, e.g., Paulus et al., Cancer Res. 66: 4349-56 (2006). Further, CSF1R plays a role in osteolytic bone destruction in bone metastasis. See, e.g., Ohno et al., Mol. Cancer Ther. 5: 2634-43 (2006). TAMs promote tumor growth, in part, by suppressing anti-tumor T cell effector function through the release of immunosuppressive cytokines and the expression of T cell inhibitory surface proteins.

Genetic alterations in cancer provide a diverse set of antigens that can mediate anti-tumor immunity. Antigen recognition through T-cell receptors (TCRs) initiate T-cell-responses, which are regulated by a balance between activating and inhibitory signals. The inhibitory signals, or "immune checkpoints," play an important role in normal tissues by preventing autoimmunity. Up-regulation of immune checkpoint proteins allows cancers to evade anti-tumor immunity. Two immune checkpoint proteins have been the focus of clinical cancer immunotherapeutics, cytotoxic T-lymphocyte-associated antigen 4 (CTLA-4) and programmed cell death protein 1 (PD-1). The combination of an anti-CTLA-4 antibody and an anti-PD-1 antibody has been approved for the treatment of metastatic melanoma and several additional clinical trials are also ongoing to study the use of this combination for the treatment of other cancers. Anti-PD-1 antibodies and anti-CTLA-4 antibodies for use as monotherapies are also currently being studied in clinical trials as a treatment for many different types of cancer. Anti-PD-L1 antibodies which bind PD-L1, one of the ligands for PD-1, are also currently in clinical development.

Many tumors often express multiple checkpoint molecules simultaneously. Therefore, combinations of checkpoint modulators are undergoing clinical testing with aim of improved efficacy. Initial clinical results of the combination of an anti-CTLA-4 antibody (anti-CTLA-4 Ab) and an anti-PD-1 antibody (anti-PD-1 Ab) have demonstrated improved overall response rates, increased complete response rates, as well as overall survival rates in metastatic melanoma, compared to anti-CTLA-4 Ab alone or historical controls.

As described herein, significant antitumor activity of an anti-PD-1 antibody in combination with an anti-CSF1R antibody has been demonstrated in clinical trials.

SUMMARY

In some embodiments, methods of treating cancer in a subject are provided, comprising administering to the subject an anti-CSF1R antibody and a PD-1/PD-L1 inhibitor. In some embodiments, the PD-1/PD-L1 inhibitor is an antibody. In some embodiments, the PD-1/PD-L1 inhibitor is an anti-PD-1 antibody. In some embodiments, the anti-PD-1 antibody comprises the heavy chain and light chain CDRs of an antibody selected from nivolumab and pembrolizumab. In some embodiments, the anti-PD-1 antibody comprises the heavy chain and light chain variable regions of an antibody selected from nivolumab and pembrolizumab. In some embodiments, the anti-PD-1 antibody is selected from nivolumab and pembrolizumab. In some embodiments, the PD-1/PD-L1 inhibitor is an anti-PD-L1 antibody. In some embodiments, the anti-PD-L1 antibody comprises the heavy chain and light chain CDRs of an antibody selected from BMS-936559, MPDL3280A, MEDI4736, and MSB0010718C. In some embodiments, the anti-PD-L1 antibody comprises the heavy chain and light chain variable regions of an antibody selected from BMS-936559, MPDL3280A, MEDI4736, and MSB0010718C. In some embodiments, the anti-PD-L1 antibody is selected from BMS-936559, MPDL3280A, MEDI4736, and MSB0010718C. In some embodiments, the PD-1/PD-L1 inhibitor is a fusion protein. In some embodiments, the fusion protein is AMP-224.

In some embodiments, the anti-CSF1R antibody and the PD-1/PD-L1 inhibitor are administered concurrently or sequentially. In some embodiments, the anti-CSF1R antibody and the PD-1/PD-L1 inhibitor are administered concurrently. In some embodiments, one or more doses of the PD-1/PD-L1 inhibitor are administered prior to administering an anti-CSF1R antibody. In some embodiments, the subject received a complete course of PD-1/PD-L1 inhibitor therapy prior to administration of the anti-CSF1R antibody. In some embodiments, the anti-CSF1R antibody is administered during a second course of PD-1/PD-L1 inhibitor therapy. In some embodiments, the subject received at least one, at least two, at least three, or at least four doses of the PD-1/PD-L1 inhibitor prior to administration of the anti-CSF1R antibody. In some embodiments, at least one dose of the PD-1/PD-L1 inhibitor is administered concurrently with the anti-CSF1R inhibitor. In some embodiments, one or more doses of the anti-CSF1R antibody are administered prior to administering a PD-1/PD-L1 inhibitor. In some embodiments, the subject received at least two, at least three, at least three, or at least four doses of the anti-CSF1R antibody prior to administration of the PD-1/PD-L1 inhibitor. In some embodiments, at least one dose of the anti-CSF1R antibody is administered concurrently with the PD-1/PD-L1 inhibitor. In some embodiments, the two drugs are administered on the same day. In some embodiments, the drugs are mixed together prior to administration and thus administered as a mixtre. For example, in some embodiments, the drugs may be packaged and stored in the same vial (i.e., fixed dose formulation), or alternatively, vials containing each separate drug may be mixed together just prior to administration. In various embodiments, the drugs may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation.

In some embodiments, the anti-CSF1R antibody is administered at a dose of about 0.1, about 0.3, about 0.5, about 1, about 2, about 3, about 4, about 5 or about 10 mg/kg. In some embodiments, the PD-1/PD-L1 inhibitor is administered at a dose of 0.1-10 mg/kg, such as, for example about 0.1, about 0.3, about 0.5, about 1, about 2, about 3, about 4, about 5 or about 10 mg/kg mg/kg. In some embodiments, the anti-CSF1R antibody and the PD-1/PD-L1 inhibitor are administered, for example at one of the above doses, about once per 1, 2, 3, 4, or 5 weeks, such as about once every 2 weeks.

In certain embodiments, the first dose is a therapeutic dose and the second dose is a therapeutic dose. In other embodiments, the first dose is a subtherapeutic dose and the second dose is a therapeutic dose. In some embodiments, the first dose is administered at a dose ranging from at least about 80 mg to at least about 800 mg or at least about 0.1 mg/kg to at least about 10.0 mg/kg body weight. In some embodiments, the second dose is administered at a dose ranging from at least about 80 mg to at least about 800 mg or at least about 0.1 mg/kg to at least about 10.0 mg/kg body weight. In one particular embodiment, the first dose is administered at a dose of at least about 3 mg/kg body weight or 240 mg once about every 2 weeks.

In some embodiments, the subject is administered at least two doses, at least three doses, at least four doses, at least five doses, at least six doses, at least seven doses, at least eight doses, at least nine doses, at least ten doses, at least 12 doses, at least 20 doses.

In some embodiments, the first dose is a flat dose or a weight based dose. In other embodiments, the second dose is a flat dose or a weight based dose.

In some embodiments, the cancer is selected from non-small cell lung cancer, melanoma, squamous cell carcinoma of the head and neck, ovarian cancer, pancreatic cancer, renal cell carcinoma, hepatocellular carcinoma, bladder cancer, and endometrial cancer. In some embodiments, the cancer is a central nervous system neoplasm. In some embodiments, the central nervous system neoplasm is a malignant glioma or glioblastoma. In some embodiments, the cancer is recurrent or progressive after a therapy selected from surgery, chemotherapy, radiation therapy, or a combination thereof. In some embodiments, the patient has stage III or stage IV cancer, as defined in the definitions section below with respect to particular cancers. In some embodiments, the patient's cancer is metastatic. In some embodiments, the subject is a PD-1/PD-L1 inhibitor inadequate responder or is refractory to prior treatment with a PD-1/PD-L1 inhibitor. In some embodiments, the subject has previously received PD-1/PD-L1 inhibitor therapy, and in other embodiments the subject has not previously received PD-1/PD-L1 inhibitor therapy. In some embodiments, the patient has previously received one or more of chemotherapy, radiation therapy, or surgery; in some such embodiments the patient has documented tumor progression in spite of such prior treatment. In some embodiments, administration of the anti-CSF1R antibody and the PD-1/PD-L1 inhibitor results in a synergistic effect on tumor growth, weight, and/or volume compared in a mouse xenograft model for the cancer compared to administration of the anti-CSF1R antibody or PD-1/PD-L1 inhibitor alone.

In some embodiments of the methods a patient with non-small cell lung cancer (NSCLC) is treated with the anti-CSF1R antibody (for instance, an anti-CSF1R antibody as described herein, such as an antibody comprising the heavy and light chain CDRs of HuAB1) and the PD-1/PD-L1 inhibitor (for instance, an anti-PD-1 antibody comprising the heavy chain and light chain CDRs of nivolumab or pembrolizumab or a PD-1/PD-L1 inhibitor fusion protein or peptide such as AMP-224 or AUR-012). In some such embodiments, the patient has Stage IIIB or IV disease and/or has demonstrated disease progression or recurrence during and/or after a platinum doublet-based or other chemotherapy regimen for advanced or metastatic disease. In some embodiments, the patient has not had prior exposure to a PD-1/PD-L1 inhibitor, and in other embodiments, the patient is refractory to PD-1/PD-L1 inhibitor treatment. In some embodiments, the anti-CSF1R antibody is administered at a dose of about 0.1, about 0.3, about 0.5, about 1, about 2, about 3, about 4, about 5 or about 10 mg/kg. In some embodiments, the PD-1/PD-L1 inhibitor is administered at a dose of 0.1-10 mg/kg, such as, for example about 0.1, about 0.3, about 0.5, about 1, about 2, about 3, about 4, about 5 or about 10 mg/kg mg/kg. In some embodiments, the anti-CSF1R antibody and the PD-1/PD-L1 inhibitor are administered, for example at one of the above doses, once per 1, 2, 3, 4, or 5 weeks, such as about once every 2 weeks. In some embodiments, administration of the anti-CSF1R antibody and the PD-1/PD-L1 inhibitor results in a synergistic effect on tumor growth, weight, and/or volume compared in a mouse xenograft model for NSCLC compared to administration of the anti-CSF1R antibody or PD-1/PD-L1 inhibitor alone.

In some embodiments of the methods, melanoma is treated with the anti-CSF1R antibody (for instance, an anti-CSF1R antibody as described herein, such as an antibody comprising the heavy and light chain CDRs of HuAB1) and the PD-1/PD-L1 inhibitor (for instance, an anti-PD-1 antibody comprising the heavy chain and light chain CDRs of nivolumab or pembrolizumab or a PD-1/PD-L1 inhibitor fusion protein or peptide such as AMP-224 or AUR-012). In some such embodiments, the patient has Stage III or IV melanoma. In some embodiments, the patient has demonstrated disease progression during or after treatment with at least one BRAF inhibitor, or is BRAF wildtype. In some embodiments, the patient has not had prior exposure to a PD-1/PD-L1 inhibitor, and in other embodiments, the patient is refractory to PD-1/PD-L1 inhibitor treatment. In some embodiments, the anti-CSF1R antibody is administered at a dose of about 0.1, about 0.3, about 0.5, about 1, about 2, about 3, about 4, about 5 or about 10 mg/kg. In some embodiments, the PD-1/PD-L1 inhibitor is administered at a dose of 0.1-10 mg/kg, such as, for example about 0.1, about 0.3, about 0.5, about 1, about 2, about 3, about 4, about 5 or about 10 mg/kg mg/kg. In some embodiments, the anti-CSF1R antibody and the PD-1/PD-L1 inhibitor are administered, for example at one of the above doses, once per 1, 2, 3, 4, or 5 weeks, such as about once every 2 weeks. In some embodiments, administration of the anti-CSF1R antibody and the PD-1/PD-L1 inhibitor results in a synergistic effect on tumor growth, weight, and/or volume compared in a mouse xenograft model for melanoma compared to administration of the anti-CSF1R antibody or PD-1/PD-L1 inhibitor alone.

In some embodiments of the methods, squamous cell carcinoma of the head and neck (SSCHN) is treated with the anti-CSF1R antibody (for instance, an anti-CSF1R antibody as described herein, such as an antibody comprising the heavy and light chain CDRs of HuAB1) and the PD-1/PD-L1 inhibitor (for instance, an anti-PD-1 antibody comprising the heavy chain and light chain CDRs of nivolumab or pembrolizumab or a PD-1/PD-L1 inhibitor fusion protein or peptide such as AMP-224 or AUR-012). In some embodiments, the patient has Stage III or IV SSCHN or has recurrent or metastatic SSCHN. In some embodiments, the patient has previously received chemotherapy, such as platinum therapy, but has demonstrated tumor progression or recurrence. In some embodiments, the patient has previously received radiation therapy, optionally along with platinum therapy, but has demonstrated tumor progression or recurrence. In some embodiments, the patient has not had prior exposure to a PD-1/PD-L1 inhibitor, and in other embodiments, the patient is refractory to PD-1/PD-L1 inhibitor treatment. In some embodiments, the anti-CSF1R antibody is administered at a dose of about 0.1, about 0.3, about 0.5, about 1, about 2, about 3, about 4, about 5 or about 10 mg/kg. In some embodiments, the PD-1/PD-L1 inhibitor is administered at a dose of 0.1-10 mg/kg, such as, for example about 0.1, about 0.3, about 0.5, about 1, about 2, about 3, about 4, about 5 or about 10 mg/kg mg/kg. In some embodiments, the anti-CSF1R antibody and the PD-1/PD-L1 inhibitor are administered, for example at one of the above doses, once per 1, 2, 3, 4, or 5 weeks, such as about once every 2 weeks. In some embodiments, administration of the anti-CSF1R antibody and the PD-1/PD-L1 inhibitor results in a synergistic effect on tumor growth, weight, and/or volume compared in a mouse xenograft model for squamous cell carcinoma compared to administration of the anti-CSF1R antibody or PD-1/PD-L1 inhibitor alone.

In some embodiments of the methods, pancreatic cancer is treated with the anti-CSF1R antibody (for instance, an anti-CSF1R antibody as described herein, such as an antibody comprising the heavy and light chain CDRs of HuAB1) and the PD-1/PD-L1 inhibitor (for instance, an anti-PD-1 antibody comprising the heavy chain and light chain CDRs of nivolumab or pembrolizumab or a PD-1/PD-L1 inhibitor fusion protein or peptide such as AMP-224 or AUR-012). In some embodiments, the patient has documented localized or metastatic adenocarcinoma of the pancreas. In some embodiments, the patient may previously have received surgery and/or radiation therapy. In some embodiments, the patient has not had prior exposure to a PD-1/PD-L1 inhibitor, and in other embodiments, the patient is refractory to PD-1/PD-L1 inhibitor treatment. In some embodiments, the anti-CSF1R antibody is administered at a dose of 0.1, 0.3, 1, 2, 3, or 4 mg/kg. In some embodiments, the PD-1/PD-L1 inhibitor is administered at a dose of 0.5-10 mg/kg, such as, for example 1, 2, 3, 4, or 5 mg/kg. In some embodiments, the anti-CSF1R antibody and the PD-1/PD-L1 inhibitor are administered, for example at one of the above doses, once per 1, 2, 3, 4, or 5 weeks, such as once every 2 weeks. In some embodiments of the methods, colorectal cancer is treated with the anti-CSF1R antibody (for instance, an anti-CSF1R antibody as described herein, such as an antibody comprising the heavy and light chain CDRs of HuAB1) and the PD-1/PD-L1 inhibitor (for instance, an anti-PD-1 antibody comprising the heavy chain and light chain CDRs of nivolumab or pembrolizumab or a PD-1/PD-L1 inhibitor fusion protein or peptide such as AMP-224 or AUR-012). In some embodiments, the patient has adenocarcinoma of the colon or rectum. In some embodiments, the patient has metastatic colorectal cancer. In some embodiments, the patient has metastatic colorectal cancer despite prior treatment with one or more of fluoropyrimidine, oxaliplatin, irinotecan, bevacizumab, cetuximab, or panitumumab. In some embodiments, the patient has not had prior exposure to a PD-1/PD-L1 inhibitor, and in other embodiments, the patient is refractory to PD-1/PD-L1 inhibitor treatment. In some embodiments, the anti-CSF1R antibody is administered at a dose of about 0.1, about 0.3, about 0.5, about 1, about 2, about 3, about 4, about 5 or about 10 mg/kg. In some embodiments, the PD-1/PD-L1 inhibitor is administered at a dose of 0.1-10 mg/kg, such as, for example about 0.1, about 0.3, about 0.5, about 1, about 2, about 3, about 4, about 5 or about 10 mg/kg mg/kg. In some embodiments, the anti-CSF1R antibody and the PD-1/PD-L1 inhibitor are administered, for example at one of the above doses, once per 1, 2, 3, 4, or 5 weeks, such as about once every 2 weeks. In some embodiments, administration of the anti-CSF1R antibody and the PD-1/PD-L1 inhibitor results in a synergistic effect on tumor growth, weight, and/or volume compared in a mouse xenograft model for pancreatic cancer (such as a model comprising $KRas^{G12D}/Ink4a^{-/-}$ murine pancreatic ductal adenocarcinoma (PDAC) cells) compared to administration of the anti-CSF1R antibody or PD-1/PD-L1 inhibitor alone.

In some embodiments of the methods, malignant glioma (e.g. glioblastoma or gliosarcoma) is treated with the anti-CSF1R antibody (for instance, an anti-CSF1R antibody as described herein, such as an antibody comprising the heavy and light chain CDRs of HuAB1) and the PD-1/PD-L1 inhibitor (for instance, an anti-PD-1 antibody comprising the heavy chain and light chain CDRs of nivolumab or pembrolizumab or a PD-1/PD-L1 inhibitor fusion protein or peptide such as AMP-224 or AUR-012). In some embodiments, the patient has previously been treated with surgery, radiotherapy, and/or temozolomide. In some embodiments, the patient has Grade IV malignant glioma. In some embodiments, the patient has not had prior exposure to a PD-1/PD-L1 inhibitor, and in other embodiments, the patient is refractory to PD-1/PD-L1 inhibitor treatment. In some embodiments, the anti-CSF1R antibody is administered at a dose of about 0.1, about 0.3, about 0.5, about 1, about 2, about 3, about 4, about 5 or about 10 mg/kg. In some embodiments, the PD-1/PD-L1 inhibitor is administered at a dose of 0.1-10 mg/kg, such as, for example about 0.1, about 0.3, about 0.5, about 1, about 2, about 3, about 4, about 5 or about 10 mg/kg mg/kg. In some embodiments, the anti-CSF1R antibody and the PD-1/PD-L1 inhibitor are administered, for example at one of the above doses, once per 1, 2, 3, 4, or 5 weeks, such as about once every 2 weeks. In some embodiments, administration of the anti-CSF1R antibody and the PD-1/PD-L1 inhibitor results in a synergistic effect on tumor growth, weight, and/or volume compared in a mouse xenograft model for glioma compared to administration of the anti-CSF1R antibody or PD-1/PD-L1 inhibitor alone.

In some embodiments, the method further comprises administering one or more additional anti-cancer agents. In certain embodiments, the anti-cancer agent is selected from the group consisting of an antibody or antigen-binding portion thereof that binds specifically to CTLA-4 ("anti-CTLA-4 antibody or antigen-binding portion thereof") and inhibits CTLA-4 activity, a chemotherapy, a platinum-based doublet chemotherapy, a tyrosine kinase inhibitor, an anti-VEGF inhibitor, an Indoleamine-pyrrole 2,3-dioxygenase (IDO) inhibitor, or any combination thereof. In one embodiment, the anti-cancer agent is ipilimumab.

In some embodiments, compositions are provided, comprising an anti-CSF1R antibody and a PD-1/PD-L1 inhibitor. In some embodiments, the PD-1/PD-L1 inhibitor is an antibody. In some embodiments, the PD-1/PD-L1 inhibitor is an anti-PD-1 antibody. In some embodiments, the anti-PD-1 antibody comprises the heavy chain and light chain CDRs of an antibody selected from nivolumab and pembrolizumab. In some embodiments, the anti-PD-1 antibody comprises the heavy chain and light chain variable regions of an antibody selected from nivolumab and pembrolizumab. In some embodiments, the anti-PD-1 antibody is selected from nivolumab and pembrolizumab. In some embodiments, the PD-1/PD-L1 inhibitor is an anti-PD-L1 antibody. In some embodiments, the anti-PD-L1 antibody comprises the heavy chain and light chain CDRs of an antibody selected from BMS-936559, MPDL3280A, MEDI4736, and MSB0010718C. In some embodiments, the anti-PD-1 antibody comprises the heavy chain and light chain variable regions of an antibody selected from BMS-936559, MPDL3280A, MEDI4736, and MSB0010718C. In some embodiments, the anti-PD-1 antibody is selected from BMS-936559, MPDL3280A, MEDI4736, and MSB0010718C. In some embodiments, the PD-1/PD-L1 inhibitor is a fusion protein. In some embodiments, the fusion protein is AMP-224.

In any of the compositions or methods described herein, the antibody heavy chain and/or the antibody light chain of the anti-CSF1R antibody may have the structure described below.

In any of the compositions or methods described herein, the anti-CSF1R antibody heavy chain may comprise a sequence that is at least 90%, at least 95%, at least 97%, at least 99%, or 100% identical to a sequence selected from SEQ ID NOs: 9, 11, 13, and 39 to 45. In any of the methods described herein, the anti-CSF1R antibody light chain may comprise a sequence that is at least 90%, at least 95%, at least 97%, at least 99%, or 100% identical to a sequence selected from SEQ ID NOs: 10, 12, 14, and 46 to 52. In any of the compositions or methods described herein, the anti-CSF1R antibody heavy chain may comprise a sequence that is at least 90%, at least 95%, at least 97%, at least 99%, or 100% identical to a sequence selected from SEQ ID NOs: 9, 11, 13, and 39 to 45, and the anti-CSF1R antibody light chain may comprise a sequence that is at least 90%, at least 95%, at least 97%, at least 99%, or 100% identical to a sequence selected from SEQ ID NOs: 10, 12, 14, and 46 to 52.

In any of the compositions or methods described herein, the anti-CSF1R antibody HC CDR1, HC CDR2, and HC CDR3 may comprise a set of sequences selected from: (a) SEQ ID NOs: 15, 16, and 17; (b) SEQ ID NOs: 21, 22, and 23; and (c) SEQ ID NOs: 27, 28, and 29. In any of the compositions or methods described herein, the anti-CSF1R antibody LC CDR1, LC CDR2, and LC CDR3 may comprise a set of sequences selected from: (a) SEQ ID NOs: 18, 19, and 20; (b) SEQ ID NOs: 24, 25, and 26; and (c) SEQ ID NOs: 30, 31, and 32.

In any of the compositions or methods described herein, the anti-CSF1R antibody heavy chain may comprise an HC CDR1, HC CDR2, and HC CDR3, wherein the HC CDR1, HC CDR2, and HC CDR3 comprise a set of sequences selected from: (a) SEQ ID NOs: 15, 16, and 17; (b) SEQ ID NOs: 21, 22, and 23; and (c) SEQ ID NOs: 27, 28, and 29; and the light chain may comprise an LC CDR1, LC CDR2, and LC CDR3, wherein the LC CDR1, LC CDR2, and LC CDR3 comprise a set of sequences selected from: (a) SEQ ID NOs: 18, 19, and 20; (b) SEQ ID NOs: 24, 25, and 26; and (c) SEQ ID NOs: 30, 31, and 32.

In any of the compositions or methods described herein, the anti-CSF1R antibody may comprise: (a) a heavy chain comprising a sequence that is at least 95%, at least 97%, at least 99%, or 100% identical to SEQ ID NO: 9 and a light chain comprising a sequence that is at least 95%, at least 97%, at least 99%, or 100% identical to SEQ ID NO: 10; (b) a heavy chain comprising a sequence that is at least 95%, at least 97%, at least 99%, or 100% identical to SEQ ID NO: 11 and a light chain comprising a sequence that is at least 95%, at least 97%, at least 99%, or 100% identical to SEQ ID NO: 12; (c) a heavy chain comprising a sequence that is at least 95%, at least 97%, at least 99%, or 100% identical to SEQ ID NO: 13 and a light chain comprising a sequence that is at least 95%, at least 97%, at least 99%, or 100% identical to SEQ ID NO: 14; (d) a heavy chain comprising a sequence that is at least 95%, at least 97%, at least 99%, or 100% identical to SEQ ID NO: 39 and a light chain comprising a sequence that is at least 95%, at least 97%, at least 99%, or 100% identical to SEQ ID NO: 46; (e) a heavy chain comprising a sequence that is at least 95%, at least 97%, at least 99%, or 100% identical to SEQ ID NO: 40 and a light chain comprising a sequence that is at least 95%, at least 97%, at least 99%, or 100% identical to SEQ ID NO: 46; (f) a heavy chain comprising a sequence that is at least 95%, at least 97%, at least 99%, or 100% identical to SEQ ID NO: 41 and a light chain comprising a sequence that is at least 95%, at least 97%, at least 99%, or 100% identical to SEQ ID NO: 46; (g) a heavy chain comprising a sequence that is at least 95%, at least 97%, at least 99%, or 100% identical to SEQ ID NO: 39 and a light chain comprising a sequence that is at least 95%, at least 97%, at least 99%, or 100% identical to SEQ ID NO: 47; (h) a heavy chain comprising a sequence that is at least 95%, at least 97%, at least 99%, or 100% identical to SEQ ID NO: 40 and a light chain comprising a sequence that is at least 95%, at least 97%, at least 99%, or 100% identical to SEQ ID NO: 47; (i) a heavy chain comprising a sequence that is at least 95%, at least 97%, at least 99%, or 100% identical to SEQ ID NO: 41 and a light chain comprising a sequence that is at least 95%, at least 97%, at least 99%, or 100% identical to SEQ ID NO: 47; and (j) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 48; (k) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 49; (1) a heavy chain comprising a sequence that is at least 95%, at least 97%, at least 99%, or 100% identical to SEQ ID NO: 42 and a light chain comprising a sequence that is at least 95%, at least 97%, at least 99%, or 100% identical to SEQ ID NO: 50; (m) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 48; (n) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 49; (o) a heavy chain comprising a sequence that is at least 95%, at least 97%, at least 99%, or 100% identical to SEQ ID NO: 43 and a light chain comprising a sequence that is at least 95%, at least 97%, at least 99%, or 100% identical to SEQ ID NO: 50; (p) a heavy chain comprising a sequence that is at least 95%, at least 97%, at least 99%, or 100% identical to SEQ ID NO: 44 and a light chain comprising a sequence that is at least 95%, at least 97%, at least 99%, or 100% identical to SEQ ID NO: 51; (q) a heavy chain comprising a sequence that is at least 95%, at least 97%, at least 99%, or 100% identical to SEQ ID NO: 44 and a light chain comprising a sequence that is at least 95%, at least 97%, at least 99%, or 100% identical to SEQ ID NO: 52; (r) a heavy chain comprising a sequence that is at least 95%, at least 97%, at least 99%, or 100% identical to SEQ ID NO: 45 and a light chain comprising a sequence that is at least 95%, at least 97%, at least 99%, or 100% identical to SEQ ID NO: 51; or (s) a heavy chain comprising a sequence that is at least 95%, at least 97%, at least 99%, or 100% identical to SEQ ID NO: 45 and a light chain comprising a sequence that is at least 95%, at least 97%, at least 99%, or 100% identical to SEQ ID NO: 52.

In any of the compositions or methods described herein, the anti-CSF1R antibody may comprise: (a) a heavy chain comprising a heavy chain (HC) CDR1 having the sequence of SEQ ID NO: 15, an HC CDR2 having the sequence of SEQ ID NO: 16, and an HC CDR3 having the sequence of SEQ ID NO: 17, and a light chain comprising a light chain (LC) CDR1 having the sequence of SEQ ID NO: 18, a LC CDR2 having the sequence of SEQ ID NO: 19, and a LC CDR3 having the sequence of SEQ ID NO: 20; (b) a heavy chain comprising a heavy chain (HC) CDR1 having the sequence of SEQ ID NO: 21, an HC CDR2 having the sequence of SEQ ID NO: 22, and an HC CDR3 having the sequence of SEQ ID NO: 23, and a light chain comprising a light chain (LC) CDR1 having the sequence of SEQ ID NO: 24, a LC CDR2 having the sequence of SEQ ID NO: 25, and a LC CDR3 having the sequence of SEQ ID NO: 26; or (c) a heavy chain comprising a heavy chain (HC) CDR1 having the sequence of SEQ ID NO: 27, an HC CDR2 having the sequence of SEQ ID NO: 28, and an HC CDR3 having the sequence of SEQ ID NO: 29, and a light chain comprising a light chain (LC) CDR1 having the sequence of SEQ ID NO: 30, a LC CDR2 having the sequence of SEQ ID NO: 31, and a LC CDR3 having the sequence of SEQ ID NO: 32.

In any of the compositions or methods described herein, the anti-CSF1R antibody may comprise: (a) a heavy chain comprising a sequence of SEQ ID NO: 53 and a light chain comprising a sequence of SEQ ID NO: 60; (b) a heavy chain comprising a sequence of SEQ ID NO: 53 and a light chain comprising a sequence of SEQ ID NO: 61; or (c) a heavy chain comprising a sequence of SEQ ID NO: 58 and a light chain comprising a sequence of SEQ ID NO: 65. In some embodiments, an antibody comprises a heavy chain and a light chain, wherein the antibody comprises: (a) a heavy chain consisting of the sequence of SEQ ID NO: 53 and a light chain consisting of the sequence of SEQ ID NO: 60; (b) a heavy chain consisting of the sequence of SEQ ID NO: 53 and a light chain consisting of the sequence of SEQ ID NO: 61; or (c) a heavy chain consisting of the sequence of SEQ ID NO: 58 and a light chain consisting of the sequence of SEQ ID NO: 65.

In any of the compositions or methods described herein, the anti-CSF1R antibody may bind to human CSF1R and/or binds to cynomolgus CSF1R. In any of the compositions or methods described herein, the anti-CSF1R antibody may block ligand binding to CSF1R. In any of the compositions or methods described herein, the anti-CSF1R antibody may block binding of CSF1 and/or IL-34 to CSF1R. In any of the compositions or methods described herein, the anti-CSF1R antibody may block binding of both CSF1 and IL-34 to CSF1R. In any of the compositions or methods described herein, the anti-CSF1R antibody may inhibit ligand-induced CSF1R phosphorylation. In any of the compositions or methods described herein, the anti-CSF1R antibody may inhibit CSF1- and/or IL-34-induced CSF1R phosphorylation. In any of the compositions or methods described herein, the anti-CSF1R antibody may bind to human CSF1R with an affinity ($K_D$) of less than 1 nM. In any of the compositions or methods described herein, the anti-CSF1R antibody may inhibit monocyte proliferation and/or survival responses in the presence of CSF1 or IL-34.

In any of the compositions or methods described herein, the PD-1/PD-L1 inhibitor may be an antibody, such as an anti-PD-1 antibody, with a structure described below.

In any of the compositions or methods described herein, the PD-1/PD-L1 inhibitor may be an antibody with an antibody heavy chain may comprising a sequence that is at least 90%, at least 95%, at least 97%, at least 99%, or 100% identical to a sequence selected from SEQ ID NOs: 100 and 101. In any of the methods described herein, the PD-1/PD-L1 inhibitor may be an antibody with an antibody light chain comprising a sequence that is at least 90%, at least 95%, at least 97%, at least 99%, or 100% identical to a sequence selected from SEQ ID NOs: 102 and 103.

In any of the compositions or methods described herein, the PD-1/PD-L1 inhibitor may be an antibody with heavy chain (HC) CDR1, HC CDR2, and HC CDR3 comprising a set of sequences selected from SEQ ID NOs: 105, 107, and 109. In any of the compositions or methods described herein, the PD-1/PD-L1 inhibitor may be an antibody with light chain (LC) CDR1, LC CDR2, and LC CDR3 may comprise a set of sequences selected from SEQ ID NOs: 112, 114, and 116.

In any of the compositions or methods described herein, the PD-1/PD-L1 inhibitor may be an antibody comprising: (a) a heavy chain comprising a variable region sequence that is at least 95%, at least 97%, at least 99%, or 100% identical to SEQ ID NO: 100 and a light chain comprising a variable region sequence that is at least 95%, at least 97%, at least 99%, or 100% identical to SEQ ID NO: 102; (b) a heavy chain comprising a constant region sequence that is at least 95%, at least 97%, at least 99%, or 100% identical to SEQ ID NO: 101 and a light chain comprising a constant region sequence that is at least 95%, at least 97%, at least 99%, or 100% identical to SEQ ID NO: 103; (c) a heavy chain comprising a variable region sequence that is at least 95%, at least 97%, at least 99%, or 100% identical to SEQ ID NO: 100 and a light chain comprising a variable region sequence that is at least 95%, at least 97%, at least 99%, or 100% identical to SEQ ID NO: 102; and/or (d) a heavy chain comprising a constant region sequence that is at least 95%, at least 97%, at least 99%, or 100% identical to SEQ ID NO: 101 and a light chain comprising a constant region sequence that is at least 95%, at least 97%, at least 99%, or 100% identical to SEQ ID NO: 103.

In any of the compositions or methods described herein, the PD-1/PD-L1 inhibitor may be an antibody comprising: a heavy chain comprising a heavy chain (HC) CDR1 having the sequence of SEQ ID NO: 105, an HC CDR2 having the sequence of SEQ ID NO: 107, and an HC CDR3 having the sequence of SEQ ID NO: 109, and a light chain comprising a light chain (LC) CDR1 having the sequence of SEQ ID NO: 112, a LC CDR2 having the sequence of SEQ ID NO: 114, and a LC CDR3 having the sequence of SEQ ID NO: 116. In any of the compositions or methods described herein, the PD-1/PD-L1 inhibitor may be an antibody comprising: a heavy chain comprising a heavy chain (HC) FR1 having the sequence of SEQ ID NO: 104, an HC FR2 having the sequence of SEQ ID NO: 106, an HC FR3 having the sequence of SEQ ID NO: 108, and an HC FR4 having the sequence of SEQ ID NO: 110; and/or, a light chain comprising a light chain (LC) FR1 having the sequence of SEQ ID NO: 111, a LC FR2 having the sequence of SEQ ID NO: 113, a LC FR3 having the sequence of SEQ ID NO: 115, and a LC FR4 having the sequence of SEQ ID NO: 117.

In any of the compositions or methods described herein, the anti-CSF1R antibody or PD-1/PD-L1 inhibitor may be a humanized or chimeric antibody. In any of the compositions or methods described herein, the anti-CSF1R or PD-1/PD-L1 inhibitor may be selected from a Fab, an Fv, an scFv, a Fab', and a (Fab')$_2$. In any of the compositions or methods described herein, the anti-CSF1R or PD-1/PD-L1 inhibitor may be selected from an IgA, an IgG, and an IgD. In any of the compositions or methods described herein, the anti-CSF1R antibody or PD-1/PD-L1 inhibitor may be an IgG. In any of the methods described herein, the antibody may be an IgG1, IgG2 or IgG4.

In any of the methods described herein, the tumor may or may not express PD-L1. In some embodiments, the tumor is PD-L1 positive. In other embodiments, the tumor is PD-L1 negative. In any of the methods described herein, the tumor may or may not express PD-L2. In some embodiments, the tumor is PD-L2 positive. In other embodiments, the tumor is PD-L2 negative.

BRIEF DESCRIPTION OF THE FIGURES

FIG. 1A-C show an alignment of the humanized heavy chain variable regions for each of humanized antibodies huAb1 to huAb16, as discussed in Example 1. Boxed residues are amino acids in the human acceptor sequence that were changed back to the corresponding mouse residue.

Figure 2A:
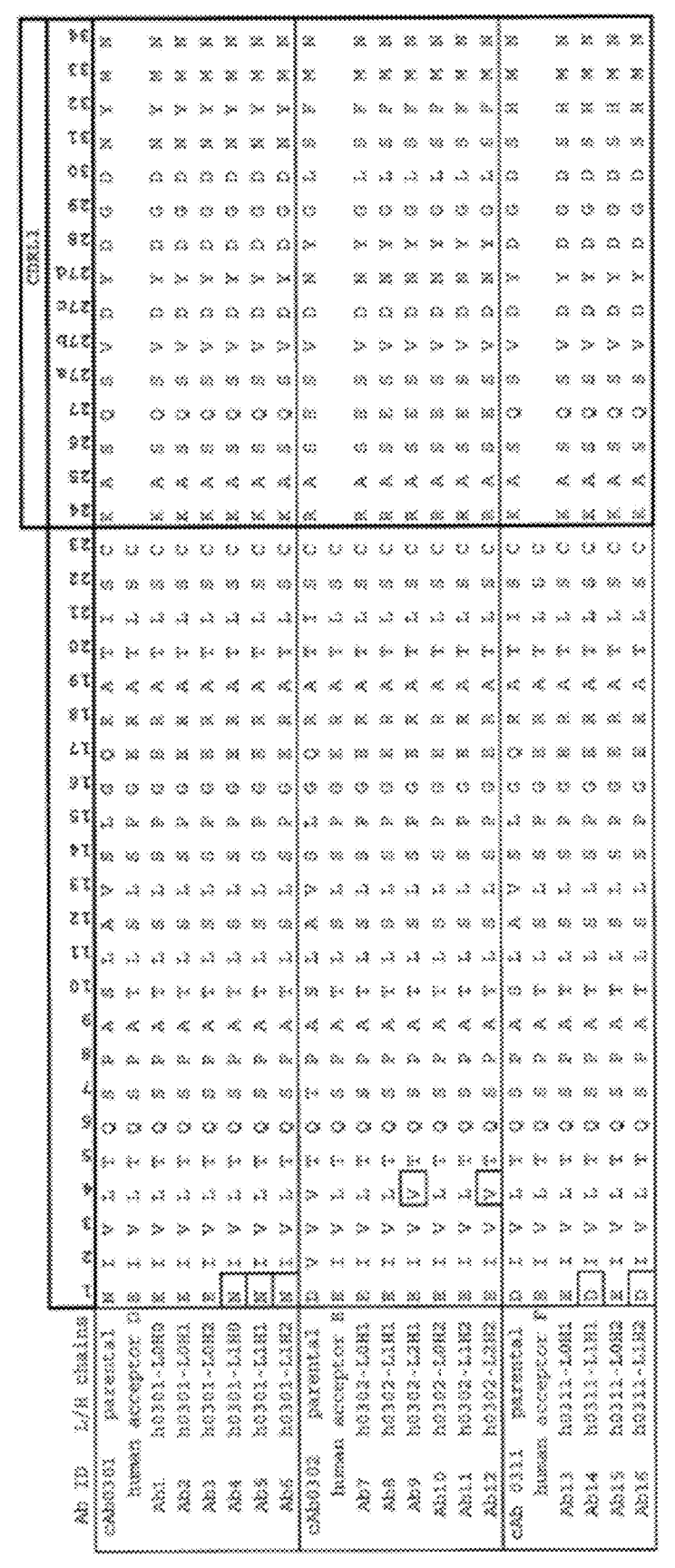
Figure 2B:
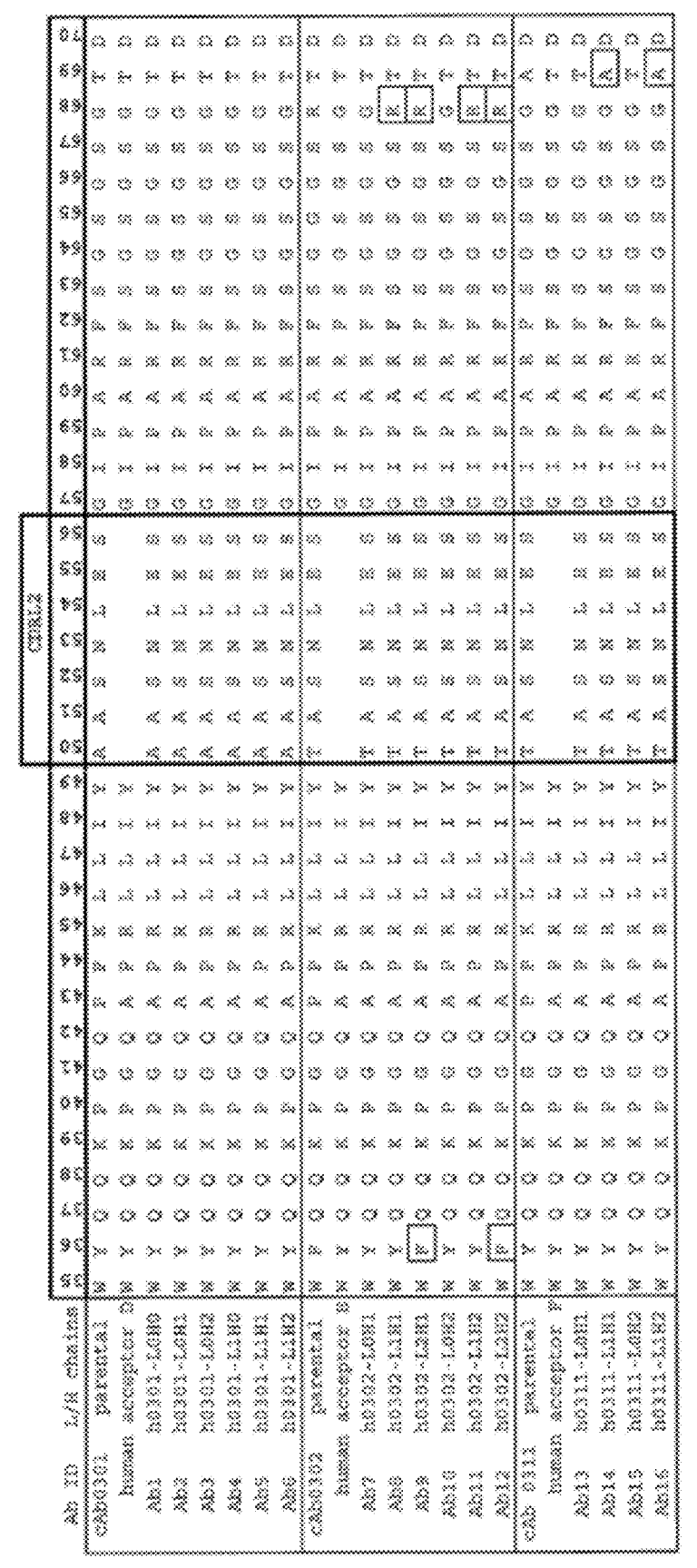
Figure 2C:
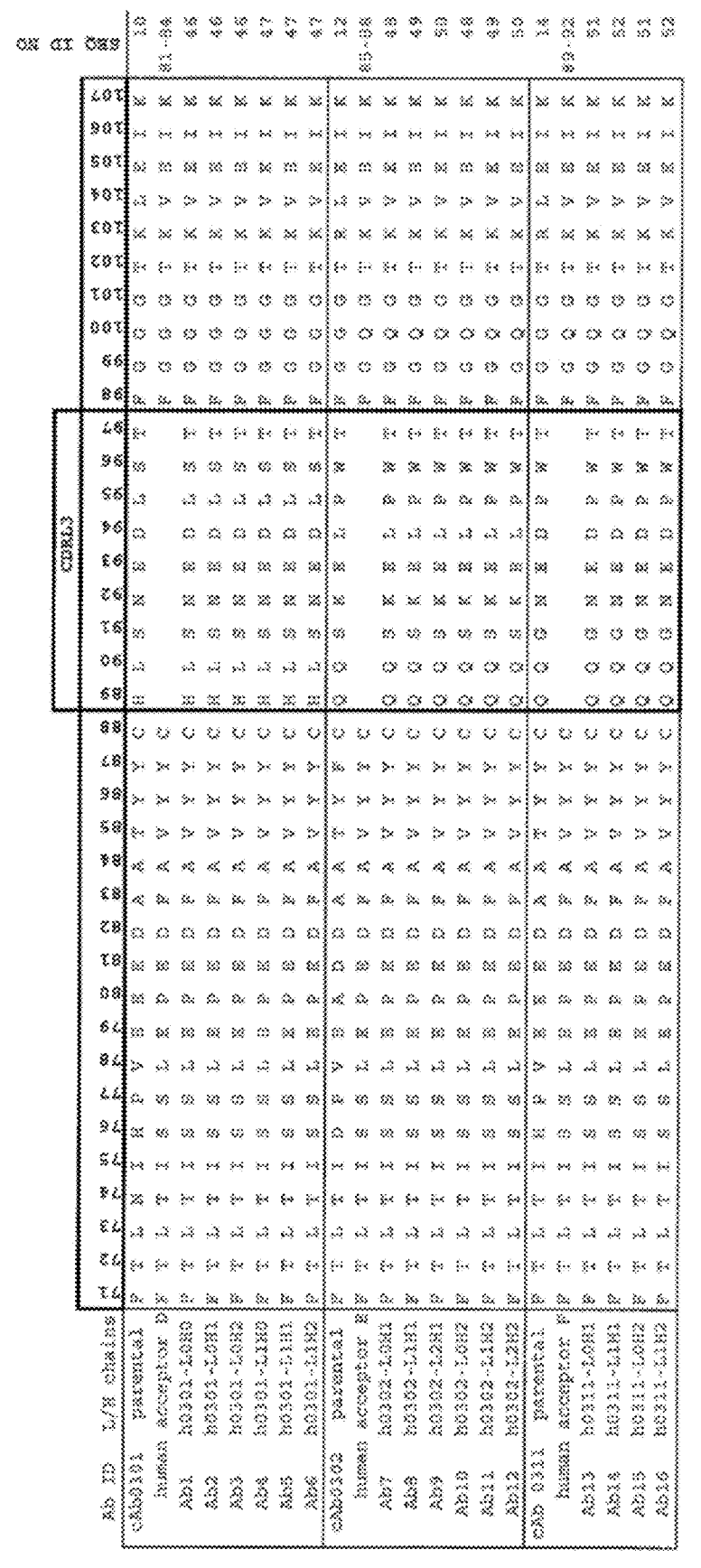

FIG. 2A-C show an alignment of the humanized light chain variable regions for each of humanized antibodies huAb1 to huAb16, as discussed in Example 1. Boxed amino acids are residues in the human acceptor sequence that were changed back to the corresponding mouse residue.

FIG. 6 is a description of the treatment cohorts for the clinical experiments described in Examples 7 and 8 involving huAB1 (also called FPA008) and nivolumab.

DETAILED DESCRIPTION

Figure 1A:
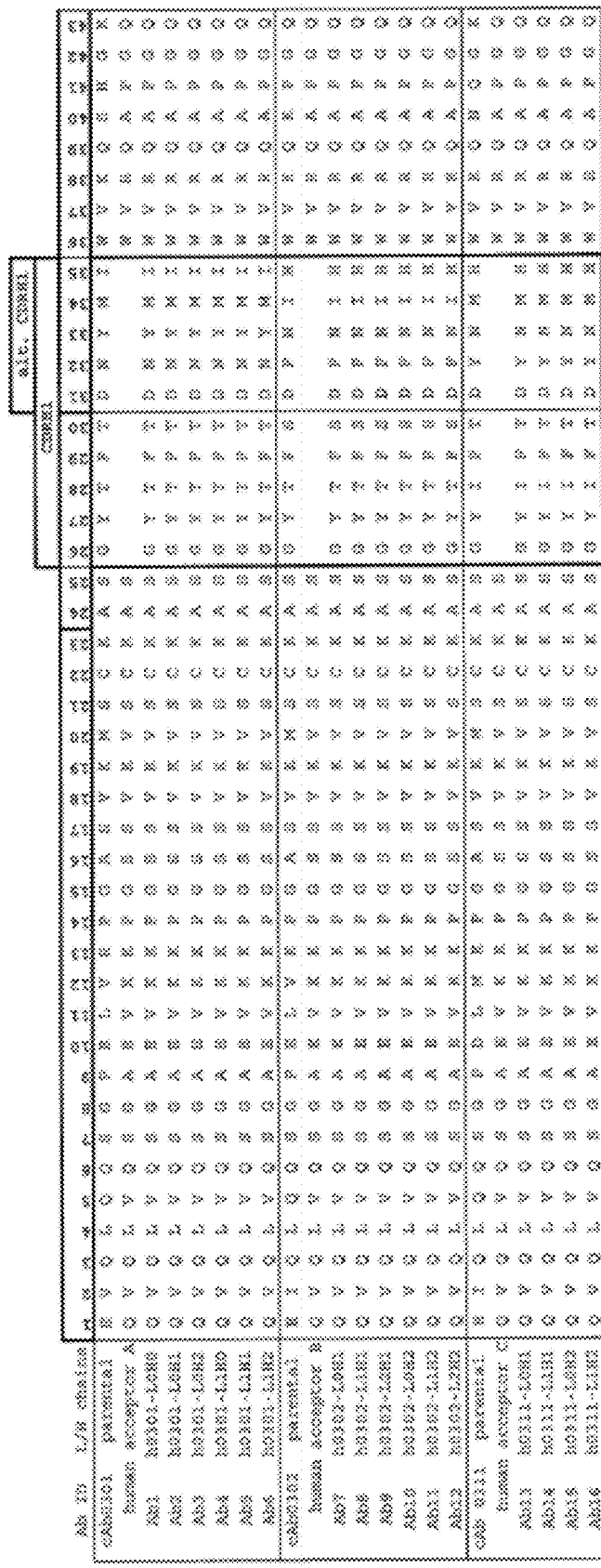

Tumor-associated macrophages (TAMs) are implicated in the pathogenesis of many cancers, and correlate with poor prognosis. Inhibition of CSF1R can reduce immunosuppressive TAMs in mouse models and human tumors. See, e.g., Ries et al., 2014, Cancer Cell, 25: 846-859; Pyontech et al., 2013, Nature Med., 19: 1264-1272; and Zhu et al., 2014, Cancer Res., 74: 5057-5069. Small molecule inhibition of CSF1R synergizes with immune checkpoint blockade in a pancreatic tumor model. See Zhu et al., 2014, Cancer Res., 74: 5057-5069. While not intending to be bound by any particular theory, the present invention is directed to methods of treating tumors that may have both CSF1R-expressing TAMs and PD-1-expressing CD8+ T cells and will be sensitive to combination therapy with an anti-CSF1R antibody and a PD-1/PD-L1 inhibitor. In some instances, tumors that have both CSF1R-expressing TAMs and PD-1-expressing CD8+ T cells may be resistant to PD-1/PD-L1 monotherapy, but should be sensitive to the combination therapy. Through expression analysis, the present inventors have identified certain tumor types that have both CSF1R-expressing TAMs and PD-1-expressing CD8+ T cells, including, but not limited to, bladder cancer, cervical cancer (such as squamous cell cervical cancer), head and neck squamous cell carcinoma (SCCHN), rectal adenocarcinoma, non-small cell lung cancer (NSCLC), endometrial cancer, prostate adenocarcinoma, colon cancer, ovarian cancer (such as serous epithelial ovarian cancer), and melanoma. Similarly, without intending to be bound by any particular theory, tumors that have high levels of CSF1R-expressing TAMs, which are suppressing PD-1-expressing CD8+ T cells may be sensitive to combination therapy, for example, because inhibition of TAMs with an anti-CSF1R antibody may boost PD-1 expressing CD8+ T cells, rendering the tumor sensitive to a PD-1/PD-L1 inhibitor.

Accordingly, the present invention provides methods of treating cancer comprising administering an anti-CSF1R antibody and a PD-1/PD-L1 inhibitor. In some embodiments, a PD-1/PD-L1 inhibitor is an antibody. In some embodiments, a PD-1/PD-L1 inhibitor is an antibody that inhibits PD-1. In some such embodiments, the anti-PD-1 antibody disrupts PD-L1 binding to PD-1. In some embodiments, a PD-1/PD-L1 inhibitor is an antibody that binds to PD-L1. In some such embodiments, the anti-PD-L1 antibody disrupts PD-L1 binding to PD-1. In some embodiments, a PD-1/PD-L1 inhibitor is a fusion protein that disrupts PD-L1 binding to PD-1, such as AMP-224. In some embodiemnts, a PD-1/PD-L1 inhibitor is a peptide that disrupts PD-L1 binding to PD-1, such as AUR-012.

As noted above, in certain embodiments, the PD-1/PD-L1 inhibitor is an anti-PD-L1 antibody. In some embodiments, an anti-PD-L1 Ab can be substituted for the anti-PD-1 Ab in any of the therapeutic methods or compositions disclosed herein. In certain embodiments, the anti-PD-L1 Ab is BMS-936559 (formerly 12A4 or MDX-1105) (see, e.g., U.S. Pat. No. 7,943,743; WO 2013/173223). In other embodiments, the anti-PD-L1 Ab is MPDL3280A (also known as RG7446) (see, e.g., Herbst; U.S. Pat. No. 8,217,149) or MEDI4736 (Khleif, 2013).

The section headings used herein are for organizational purposes only and are not to be construed as limiting the subject matter described. All references cited herein, including patent applications and publications, are incorporated herein by reference in their entireties for any purpose.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses, chemical analyses, pharmaceutical preparation, formulation, and delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As described herein, any concentration range, percentage range, ratio range or integer range is to be understood to include the value of any integer within the recited range and, when appropriate, fractions thereof (such as one tenth and one hundredth of an integer), unless otherwise indicated.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

As utilized in accordance with the present disclosure, the following terms, unless otherwise indicated, shall be understood to have the following meanings:

"Administering" refers to the physical introduction of a composition comprising a therapeutic agent to a subject, using any of the various methods and delivery systems known to those skilled in the art. Routes of administration for the anti-PD-1 Ab and/or the anti-PD-L1 Ab include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Non-parenteral routes include a topical, epidermal or mucosal route of administration, for example, orally, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event can be associated with activation of the immune system or expansion of immune system cells (e.g., T cells) in response to a treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime. The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "CSF1R" refers herein to the full-length CSF1R, which includes the N-terminal ECD, the transmembrane domain, and the intracellular tyrosine kinase domain, with or without an N-terminal leader sequence. In some embodiments, the CSF1R is a human CSF1R having the amino acid sequence of SEQ ID NO: 1 or SEQ ID NO: 2.

The terms "programmed cell death protein 1" and "PD-1" refer to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863. In some embodiments, the PD-1 is a human PD-1 having the amino acid sequence of SEQ ID NO: 96 (precursor, with signal sequence) or SEQ ID NO: 97 (mature, without signal sequence).

The terms "programmed cell death 1 ligand 1" and "PD-L1" (PD-L1; B7 homolog-1; B7-H1; or CD274) and "Programmed Death Ligand-2" (PD-L2; B7-DC; or CD273) are two cell surface glycoprotein ligands for PD-1 that downregulate T-cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7. In some embodiments, the PD-L1 is a human PD-L1 having the amino acid sequence of SEQ ID NO: 98 (precursor, with signal sequence) or SEQ ID NO: 99 (mature, without signal sequence).

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "PD-1/PD-L1 inhibitor" refers to a moiety that disrupts the PD-1/PD-L1 signaling pathway. In some embodiments, the inhibitor inhibits the PD-1/PD-L1 signaling pathway by binding to PD-1 and/or PD-L1. In some embodiments, the inhibitor also binds to PD-L2. In some embodiments, a PD-1/PD-L1 inhibitor blocks binding of PD-1 to PD-L1 and/or PD-L2. Nonlimiting exemplary PD-1/PD-L1 inhibitors include antibodies that bind to PD-1); antibodies that bind to PD-L1; fusion proteins, such as AMP-224; and peptides, such as AUR-012.

The term "antibody that inhibits PD-1" refers to an antibody that binds to PD-1 or binds to PD-L1 and thereby inhibits PD-1 and/or PD-L1 signaling. In some embodiments, an antibody that inhibits PD-1 binds to PD-1 and blocks binding of PD-L1 and/or PD-L2 to PD-1. In some embodiments, an antibody that inhibits PD-1 binds to PD-L1 and blocks binding of PD-1 to PD-L1. An antibody that inhibits PD-1 that binds to PD-L1 may be referred to as an anti-PD-L1 antibody. An antibody that inhibits PD-1 that binds to PD-1 may be referred to as an anti-PD-1 antibody.

"PD-L1 positive" as used herein can be interchangeably used with "PD-L1 expression of at least about 5%." PD-L1 expression can be measured by any methods known in the art. In some embodiments, the PD-L1 expression is measured by an automated IHC. A PD-L1 positive tumor can thus have at least about 5%, at least about 10%, or at least about 20% of tumor cells expressing PD-L1 as measured by an automated IHC. In certain embodiments, "PD-L1 positive" means that there are at least 100 cells that express PD-L1 on the surface of the cells.

"PD-L2 positive" as used herein can be interchangeably used with "PD-L2 expression of at least about 5%." PD-L2 expression can be measured by any methods known in the art. In some embodiments, the PD-L2 expression is measured by an automated IHC. A PD-L2 positive tumor can thus have at least about 5%, at least about 10%, or at least about 20% of tumor cells expressing PD-L2 as measured by an automated IHC. In certain embodiments, "PD-L2 positive" means that there are at least 100 cells that express PD-L2 on the surface of the cells.

With reference to anti-CSF1R antibodies the term "blocks binding of" a ligand, such as CSF1 and/or IL-34, and grammatical variants thereof, are used to refer to the ability to inhibit the interaction between CSF1R and a CSF1R ligand, such as CSF1 and/or IL-34. Such inhibition may occur through any mechanism, including direct interference with ligand binding, e.g., because of overlapping binding sites on CSF1R, and/or conformational changes in CSF1R induced by the antibody that alter ligand affinity, etc. Antibodies and antibody fragments referred to as "functional" are characterized by having such properties.

With reference to anti-PD-1 antibodies the term "blocks binding of" a ligand, such as PD-L1, and grammatical variants thereof, are used to refer to the ability to inhibit the interaction between PD-1 and a PD-1 ligand, such as PD-L1. Such inhibition may occur through any mechanism, including direct interference with ligand binding, e.g., because of overlapping binding sites on PD-1, and/or conformational changes in PD-1 induced by the antibody that alter ligand affinity, etc. Antibodies and antibody fragments referred to as "functional" are characterized by having such properties.

With reference to anti-PD-L1 antibodies the term "blocks binding of" a ligand, such as PD-1, and grammatical variants thereof, are used to refer to the ability to inhibit the interaction between PD-L1 and a PD-L1 ligand, such as PD-1. Such inhibition may occur through any mechanism, including direct interference with ligand binding, e.g., because of overlapping binding sites on PD-L1, and/or conformational changes in PD-L1 induced by the antibody that alter ligand affinity, etc. Antibodies and antibody fragments referred to as "functional" are characterized by having such properties.

The term "antibody" as used herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

The term "heavy chain variable region" as used herein refers to a region comprising heavy chain CDR1, framework (FR) 2, CDR2, FR3, and CDR3. In some embodiments, a heavy chain variable region also comprises at least a portion of an FR1 and/or at least a portion of an FR4. In some embodiments, a heavy chain CDR1 corresponds to Kabat residues 26 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.); and FIG. 1. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See id.

The term "heavy chain constant region" as used herein refers to a region comprising at least three heavy chain constant domains, CH1, CH2, and CH3. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a t constant region is an IgM antibody, and an antibody comprising an a constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_{73}$ constant region), and IgG4 (comprising a $γ_4$ constant region) antibodies; IgA antibodies include, but are not limited to, IgA1 (comprising an at constant region) and IgA2 (comprising an $α_2$ constant region) antibodies; and IgM antibodies include, but are not limited to, IgM1 and IgM2.

In some embodiments, a heavy chain constant region comprises one or more mutations (or substitutions), additions, or deletions that confer a desired characteristic on the antibody. A nonlimiting exemplary mutation is the S241P mutation in the IgG4 hinge region (between constant domains CH1 and CH2), which alters the IgG4 motif CPSCP to CPPCP, which is similar to the corresponding motif in IgG1. That mutation, in some embodiments, results in a more stable IgG4 antibody. See, e.g., Angal et al., *Mol. Immunol.* 30: 105-108 (1993); Bloom et al., *Prot. Sci.* 6: 407-415 (1997); Schuurman et al., *Mol. Immunol.* 38: 1-8 (2001).

The term "heavy chain" (abbreviated HC) as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising light chain CDR1, framework (FR) 2, CDR2, FR3, and CDR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.); and FIG. 1.

The term "light chain constant region" as used herein refers to a region comprising a light chain constant domain, $C_L$. Nonlimiting exemplary light chain constant regions include λ and κ.

The term "light chain" (abbreviate LC) as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "CDR-grafted antibody" as used herein refers to a humanized antibody in which the complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

An "anti-antigen" Ab refers to an Ab that binds specifically to the antigen. For example, an anti-PD-1 Ab binds specifically to PD-1, an anti-PD-L1 Ab binds specifically to PD-L1, and an anti-CTLA-4 Ab binds specifically to CTLA-4.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Exemplary leader sequences include, but are not limited to, antibody leader sequences, such as, for example, the amino acid sequences of SEQ ID NOs: 3 and 4, which correspond to human light and heavy chain leader sequences, respectively. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "elevated level" means a higher level of a protein in a particular tissue of a subject relative to the same tissue in a control, such as an individual or individuals who are not suffering from cancer or other condition described herein. The elevated level may be the result of any mechanism, such as increased expression, increased stability, decreased degradation, increased secretion, decreased clearance, etc., of the protein.

The term "reduce" or "reduces" means to lower the level of a protein in a particular tissue of a subject by at least 10%. In some embodiments, an agent, such as an antibody that binds CSF1R or a PD-1/PD-L1 inhibitor, reduces the level of a protein in a particular tissue of a subject by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%. In some embodiments, the level of a protein is reduced relative to the level of the protein prior to contacting with an agent, such as an antibody that binds CSF1R or a PD-1/PD-L1 inhibitor.

The term "resistant," when used in the context of resistance to a therapeutic agent, means a decreased response or lack of response to a standard dose of the therapeutic agent, relative to the subject's response to the standard dose of the therapeutic agent in the past, or relative to the expected response of a similar subject with a similar disorder to the standard dose of the therapeutic agent. Thus, in some embodiments, a subject may be resistant to therapeutic agent although the subject has not previously been given the therapeutic agent, or the subject may develop resistance to the therapeutic agent after having responded to the agent on one or more previous occasions.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "tissue sample" refers to a collection of similar cells obtained from a tissue of a subject. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, synovial fluid, or interstitial fluid; cells from any time in gestation or development of the subject. In some embodiments, a tissue sample is a synovial biopsy tissue sample and/or a synovial fluid sample. In some embodiments, a tissue sample is a synovial fluid sample. The tissue sample may also be primary or cultured cells or cell lines. Optionally, the tissue sample is obtained from a disease tissue/organ. The tissue sample may contain compounds that are not naturally intermixed with the tissue in nature such as preservatives, anticoagulants, buffers, fixatives, nutrients, antibiotics, or the like. A "control sample" or "control tissue", as used herein, refers to a sample, cell, or tissue obtained from a source known, or believed, not to be afflicted with the disease for which the subject is being treated.

For the purposes herein a "section" of a tissue sample means a part or piece of a tissue sample, such as a thin slice of tissue or cells cut from a solid tissue sample.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells or leukemic cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

The term "recurrent cancer" refers to a cancer that has returned after a previous treatment regimen, following which there was a period of time during which the cancer could not be detected.

The term "progressive cancer" is a cancer that has increased in size or tumor spread since the beginning of a treatment regimen. In certain embodiments, a progressive cancer is a cancer that has increased in size or tumor spread by at least 10%, at least 20%, at least 30%, at least 40%, or at least 50% since the beginning of a treatment regimen.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount of an anti-cancer agent can inhibit cell growth, inhibit tumor growth, or reduce tumor size by at least about 5%, at least about 10%, by at least about 15%, at least about 20%, by at least about 25%, by at least about 30%, by at least about 40%, by at least about 50%, by at least about 60%, by at least about 70%, or by at least about 80%, by at least about 90%, by at least about 95%, or by at least about 100% relative to untreated subjects, relative to baseline, or, in certain embodiments, relative to patients treated with a standard-of-care therapy. In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

By way of example for the treatment of tumors, a therapeutically effective amount of an anti-cancer agent can inhibit cell growth or tumor growth by at least about 20%, by at least about 30%, by at least about 40%, by at least about 50%, by at least about 60%, by at least about 70%, or by at least about 80% relative to untreated subjects.

In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

A "chemotherapeutic agent" is a chemical compound useful in the treatment of cancer. Examples of chemotherapeutic agents include, but are not limited to, alkylating agents such as thiotepa and Cytoxan® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, *Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and Fareston® toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (Avastin®)) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (*W.B. Saunders*, Philadelphia, 1995), e.g., p. 13. The taxanes (paclitaxel and docetaxel) are anticancer drugs both derived from the yew tree.

Docetaxel (Taxotere®, Rhone-Poulenc Rorer), derived from the European yew, is a semisynthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, cancer immunotherapeutic agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, CTLA-4 inhibitors (e.g., anti-CTLA antibody ipilimumab (YERVOY®)), PD-1 inhibitors (e.g., anti-PD-1 antibodies, BMS-936558), PD-L1 inhibitors (e.g., anti-PD-L1 antibodies, MPDL3280A), PD-L2 inhibitors (e.g., anti-PD-L2 antibodies), TIM3 inhibitors (e.g., anti-TIM3 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PD-L1, PD-L2, CTLA-4, TIM3, or VEGF receptor(s), TRAIL/Apo2, and other bioactive and organic chemical agents, etc. Combinations thereof are also included in the invention.

An agent "antagonizes" factor activity when the agent neutralizes, blocks, inhibits, abrogates, reduces, and/or interferes with the activity of the factor, including its binding to one or more receptors when the factor is a ligand.

"Treatment," as used herein, refers to both therapeutic treatment and prophylactic or preventative measures, wherein the object is to prevent or slow down (lessen) the targeted pathologic condition or disorder. In certain embodiments, the term "treatment" covers any administration or application of a therapeutic for disease in a mammal, including a human, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those prone to have the disorder or those in whom the disorder is to be prevented.

"Pre-treatment" or "baseline," as used herein, refers to the status of a subject prior to administration of a particular therapy, e.g., prior to administration of an anti-cancer agent, e.g., an immunotherapy, e.g., an anti-PD-1 Ab or an antigen binding portion thereof or an anti-CSF1R Ab or an antigen binding portion thereof. "Pre-treatment" can refer to the status of a treatment naïve subject or to a subject who has had one or more prior therapies. Accordingly, it is possible that a subject may be considered to be "pre-treatment" even though the subject received some form of treatment or therapy at some time prior to the present treatment or therapy. Furthermore, "pre-treatment" can refer to any moment up until the moment that a treatment is administered. For example, "pre-treatment" can include weeks, days, hours, minutes, or seconds before administration of the treatment. In one particular embodiment, a "pre-treatment" sample can be collected from a subject immediately before administration of a first dose of the treatment or therapy. "Pre-treatment" and "baseline" are used interchangeably herein.

"On-treatment," as used herein, refers to the status of a subject who has received one or more initial dose of a particular therapy, e.g., an anti-cancer agent, e.g., an immunotherapy, e.g., an anti-PD-1 Ab or an antigen binding portion thereof or an anti-CSF1R Ab or an antigen binding portion thereof. "On-treatment" can refer to a subject who has only received a single dose or a subject who has received multiple doses of the anti-PD-1 Ab or an antigen binding portion thereof or the anti-CSF1R Ab or an antigen binding portion thereof. In some aspects, "on-treatment" refers to a subject who is receiving an ongoing regimen of a particular therapy, e.g., the subject is being treated with an anti-PD-1 Ab or an antigen binding portion thereof or an anti-CSF1R Ab or an antigen binding portion thereof. In certain embodiments, the "on-treatment" sample can be collected from a subject on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, on about day 21, or any combination thereof, wherein the treatment is administered on day 1. In certain embodiments, the treatment is administration of an anti-PD-1 Ab or an antigen binding portion thereof or an anti-PD-L1 Ab or an antigen binding portion thereof. In some embodiments, the anti-PD-1 Ab or an antigen binding portion thereof or the anti-CSF1R Ab or an antigen binding portion thereof is administered on day 1 of every 21-day cycle. In certain embodiments, the on-treatment sample is collected from the subject on about day 1, on about day 2, on about day 3, on about day 4, on about day 5, on about day 6, on about day 7, on about day 8, on about day 9, on about day 10, on about day 11, on about day 12, on about day 13, on about day 14, on about day 15, on about day 16, on about day 17, on about day 18, on about day 19, on about day 20, or on about day 21 of the 21 day cycle, or any combination thereof. In one particular embodiment, the on-treatment sample is collected on day 1 of cycle 1, day 1 of cycle 2, day 8 of cycle 2, on day 1 of cycle 4, or any combination thereof. In one embodiment, the on-treatment sample is collect on day 8 of cycle 2.

Pre-treatment and on-treatment samples may be collected in the form of a tumor biopsy (e.g., a core needle biopsy), partial or complete surgical resection, blood draw, or any other method known in the art. In certain embodiments, tumor sites selected for biopsy have not received previous radiation therapy.

The term "immunotherapy" refers to the treatment of a subject afflicted with, or at risk of contracting or suffering a recurrence of, a disease by a method comprising inducing, enhancing, suppressing or otherwise modifying an immune response.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of an anti-CSF1R antibody and/or a PD-1/PD-L1 inhibitor of the invention may vary according to factors such as the disease state, age, sex, and weight of the individual, and the ability of the antibody or antibodies to elicit a desired response in the individual. A therapeutically effective amount encompasses an amount in which any toxic or detrimental effects of the antibody or antibodies are outweighed by the therapeutically beneficial effects. In some embodiments, the expression "effective amount" refers to an amount of the antibody that is effective for treating the cancer. A "therapeutic amount" refers to a dosage of a drug that has been approved for use by a regulatory agency. A "subtherapeutic amount" as used herein refers to a dosage of a drug or therapeutic agent that is significantly lower than the approved dosage. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

A subject may be characterized as having one or more "prior therapies" or as being "treatment naïve." As used herein, unless otherwise indicated, a "prior therapy" refers to any previous systemic therapy for a cancer. A "treatment naïve" subject is one that has never received any previous systemic therapy in the metastatic or adjuvant setting.

As used herein, the term "first dose" includes a single dose, but can be more than one dose, i.e., multiple doses (at least two doses, at least three doses, or more) that are administered prior to the administration of "a second dose" if the multiple doses are administered to determine the susceptibility of the patient for an anti-PD-1 Ab or anti-CSF1R Ab therapy, i.e., differential expression of certain proteins (e.g., PD-L1). The term "first dose" can also be a therapeutic dose, a dose higher than a therapeutic dose, or a subtherapeutic dose.

The term "second dose" as used herein can also include a single dose or multiple doses that are administered after the first dose (single dose or multiple doses). The second dose can be a therapeutic dose.

The use of the term "fixed dose" with regard to a composition or method of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The use of the term "flat dose" with regard to the composition of the invention means a dose that is administered to a patient without regard for the weight or body surface area (BSA) of the patient. The flat dose is, therefore, not provided as a mg/kg dose, but rather as an absolute amount of the agent (e.g., the anti-CSF1R antibody and/or PD-1/PD-L1 inhibitor). For example, a 60 kg person and a 100 kg person would receive the same dose of the composition (e.g., 240 mg of an anti-PD-1 antibody and 80 mg of an anti-CSF1R antibody in a single fixed dosing formulation vial containing both 240 mg of an anti-PD-1 antibody and 80 mg of an anti-CSF1R antibody (or two fixed dosing formulation vials containing 120 mg of an anti-PD-1 antibody and 40 mg of an anti-CSF1R antibody, etc.)).

The term "weight based dose" as referred to herein means that a dose that is administered to a patient is calculated based on the weight of the patient. For example, when a patient with 60 kg body weight requires 3 mg/kg of an anti-PD-1 antibody in combination with 1 mg/kg of an anti-CSF1R antibody, one can draw the appropriate amounts of the anti-PD-1 antibody (i.e., 180 mg) and the anti-CSF1R antibody (i.e., 60 mg) at once from a 3:1 ratio fixed dosing formulation of an anti-PD1 antibody and an anti-CSF1R antibody.

Administration "in combination with" one or more further therapeutic agents includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

The term "refractory" as applied to a treatment means a lack of partial or complete clinical response to that treatment. For example, patients may be considered refractory to a PD-1 or PD-L1 inhibitor if they do not show at least a partial response after receiving at least 2 doses of the inhibitor.

Patients classified as "stage III" or "stage IIIB" or "stage IV" or "grade IV" and the like are so classified based upon the classification systems for their particular disease. For example, NSCLC patients may be classified, for example, as "stage IIIB" or "stage IV" according to version 7 of the International Association for the Study of Lung Cancer Staging manual in Thoracic oncology. Melanoma patients may be classed as "stage III" or "IV" as per the American Joint Committee on Cancer staging system. Malignant glioma patients may be classified as "grade IV" based upon the World Health Organization standards.

Anti-CSF1R Antibodies

Anti-CSF1R antibodies include, but are not limited to, humanized antibodies, chimeric antibodies, mouse antibodies, human antibodies, and antibodies comprising the heavy chain and/or light chain CDRs discussed herein.

Exemplary Humanized Antibodies

In some embodiments, humanized antibodies that bind CSF1R are provided. Humanized antibodies are useful as therapeutic molecules because humanized antibodies reduce or eliminate the human immune response to non-human antibodies (such as the human anti-mouse antibody (HAMA) response), which can result in an immune response to an antibody therapeutic, and decreased effectiveness of the therapeutic.

Nonlimiting exemplary humanized antibodies include huAb1 through huAb16, described herein. Nonlimiting exemplary humanized antibodies also include antibodies comprising a heavy chain variable region of an antibody selected from huAb1 to huAb16 and/or a light chain variable region of an antibody selected from huAb1 to huAb16. Nonlimiting exemplary humanized antibodies include antibodies comprising a heavy chain variable region selected from SEQ ID NOs: 39 to 45 and/or a light chain variable region selected from SEQ ID NOs: 46 to 52. Exemplary humanized antibodies also include, but are not limited to, humanized antibodies comprising heavy chain CDR1, CDR2, and CDR3, and/or light chain CDR1, CDR2, and CDR3 of an antibody selected from 0301, 0302, and 0311.

In some embodiments, a humanized anti-CSF1R antibody comprises heavy chain CDR1, CDR2, and CDR3 and/or a light chain CDR1, CDR2, and CDR3 of an antibody selected from 0301, 0302, and 0311. Nonlimiting exemplary humanized anti-CSF1R antibodies include antibodies comprising sets of heavy chain CDR1, CDR2, and CDR3 selected from: SEQ ID NOs: 15, 16, and 17; SEQ ID NOs: 21, 22, and 23; and SEQ ID NOs: 27, 28, and 29. Nonlimiting exemplary humanized anti-CSF1R antibodies also include antibodies comprising sets of light chain CDR1, CDR2, and CDR3 selected from: SEQ ID NOs: 18, 19, and 20; SEQ ID NOs: 24, 25, and 26; and SEQ ID NOs: 30, 31, and 32.

Nonlimiting exemplary humanized anti-CSF1R antibodies include antibodies comprising the sets of heavy chain CDR1, CDR2, and CDR3, and light chain CDR1, CDR2, and CDR3 in Table 1 (SEQ ID NOs shown; see Table 8 for sequences). Each row of Table 1 shows the heavy chain CDR1, CDR2, and CDR3, and light chain CDR1, CDR2, and CDR3 of an exemplary antibody.

TABLE 1

Heavy chain and light chain CDRs

| | Heavy chain | | | Light chain | | |
|---|---|---|---|---|---|---|
| Ab | CDR1 SEQ ID | CDR2 SEQ ID | CDR3 SEQ ID | CDR1 SEQ ID | CDR2 SEQ ID | CDR3 SEQ ID |
| 0301 | 15 | 16 | 17 | 18 | 19 | 20 |
| 0302 | 21 | 22 | 23 | 24 | 25 | 26 |
| 0311 | 27 | 28 | 29 | 30 | 31 | 32 |

Further Exemplary Humanized Antibodies

In some embodiments, a humanized anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, and wherein the antibody binds CSF1R. In some embodiments, a humanized anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, a humanized anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

As used herein, whether a particular polypeptide is, for example, at least 95% identical to an amino acid sequence can be determined using, e.g., a computer program. When determining whether a particular sequence is, for example, 95% identical to a reference sequence, the percentage of identity is calculated over the full length of the reference amino acid sequence.

In some embodiments, a humanized anti-CSF1R antibody comprises at least one of the CDRs discussed herein. That is, in some embodiments, a humanized anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a humanized anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary humanized anti-CSF1R antibodies also include antibodies that compete for binding to CSF1R with an antibody described herein. Thus, in some embodiments, a humanized anti-CSF1R antibody is provided that competes for binding to CSF1R with an antibody selected from Fabs 0301, 0302, and 0311; and bivalent (i.e., having two heavy chains and two light chains) antibody versions of those Fabs.

Exemplary Humanized Antibody Constant Regions

In some embodiments, a humanized antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a humanized antibody described herein comprises a human IgG constant region. In some embodiments, a humanized antibody described herein comprises a human IgG4 heavy chain constant region. In some such embodiments, a humanized antibody described herein comprises an S241P mutation in the human IgG4 constant region. In some embodiments, a humanized antibody described herein comprises a human IgG4 constant region and a human κ light chain.

The choice of heavy chain constant region can determine whether or not an antibody will have effector function in vivo. Such effector function, in some embodiments, includes antibody-dependent cell-mediated cytotoxicity (ADCC) and/or complement-dependent cytotoxicity (CDC), and can result in killing of the cell to which the antibody is bound. In some methods of treatment, including methods of treating some cancers, cell killing may be desirable, for example, when the antibody binds to a cell that supports the maintenance or growth of the tumor. Exemplary cells that may support the maintenance or growth of a tumor include, but are not limited to, tumor cells themselves, cells that aid in the recruitment of vasculature to the tumor, and cells that provide ligands, growth factors, or counter-receptors that support or promote tumor growth or tumor survival. In some embodiments, when effector function is desirable, an anti-CSF1R antibody comprising a human IgG1 heavy chain or a human IgG3 heavy chain is selected.

An antibody may be humanized by any method. Nonlimiting exemplary methods of humanization include methods described, e.g., in U.S. Pat. Nos. 5,530,101; 5,585,089; 5,693,761; 5,693,762; 6,180,370; Jones et al., *Nature* 321: 522-525 (1986); Riechmann et al., *Nature* 332: 323-27 (1988); Verhoeyen et al., Science 239: 1534-36 (1988); and U.S. Publication No. US 2009/0136500.

As noted above, a humanized antibody is an antibody in which at least one amino acid in a framework region of a non-human variable region has been replaced with the amino acid from the corresponding location in a human framework region. In some embodiments, at least two, at least three, at least four, at least five, at least six, at least seven, at least eight, at least nine, at least 10, at least 11, at least 12, at least 15, or at least 20 amino acids in the framework regions of a non-human variable region are replaced with an amino acid from one or more corresponding locations in one or more human framework regions.

In some embodiments, some of the corresponding human amino acids used for substitution are from the framework regions of different human immunoglobulin genes. That is, in some such embodiments, one or more of the non-human amino acids may be replaced with corresponding amino acids from a human framework region of a first human antibody or encoded by a first human immunoglobulin gene, one or more of the non-human amino acids may be replaced with corresponding amino acids from a human framework region of a second human antibody or encoded by a second human immunoglobulin gene, one or more of the non-human amino acids may be replaced with corresponding amino acids from a human framework region of a third human antibody or encoded by a third human immunoglobulin gene, etc. Further, in some embodiments, all of the corresponding human amino acids being used for substitution in a single framework region, for example, FR2, need not be from the same human framework. In some embodiments, however, all of the corresponding human amino acids being used for substitution are from the same human antibody or encoded by the same human immunoglobulin gene.

In some embodiments, an antibody is humanized by replacing one or more entire framework regions with corresponding human framework regions. In some embodiments, a human framework region is selected that has the highest level of homology to the non-human framework region being replaced. In some embodiments, such a humanized antibody is a CDR-grafted antibody.

In some embodiments, following CDR-grafting, one or more framework amino acids are changed back to the corresponding amino acid in a mouse framework region. Such "back mutations" are made, in some embodiments, to retain one or more mouse framework amino acids that appear to contribute to the structure of one or more of the CDRs and/or that may be involved in antigen contacts and/or appear to be involved in the overall structural integrity of the antibody. In some embodiments, ten or fewer, nine or fewer, eight or fewer, seven or fewer, six or fewer, five or fewer, four or fewer, three or fewer, two or fewer, one, or zero back mutations are made to the framework regions of an antibody following CDR grafting.

In some embodiments, a humanized antibody also comprises a human heavy chain constant region and/or a human light chain constant region.

Exemplary Chimeric Antibodies

In some embodiments, an anti-CSF1R antibody is a chimeric antibody. In some embodiments, an anti-CSF1R antibody comprises at least one non-human variable region and at least one human constant region. In some such embodiments, all of the variable regions of an anti-CSF1R antibody are non-human variable regions, and all of the constant regions of an anti-CSF1R antibody are human constant regions. In some embodiments, one or more variable regions of a chimeric antibody are mouse variable regions. The human constant region of a chimeric antibody need not be of the same isotype as the non-human constant region, if any, it replaces. Chimeric antibodies are discussed, e.g., in U.S. Pat. No. 4,816,567; and Morrison et al. *Proc. Natl. Acad. Sci. USA* 81: 6851-55 (1984).

Nonlimiting exemplary chimeric antibodies include chimeric antibodies comprising the heavy and/or light chain variable regions of an antibody selected from 0301, 0302, and 0311. Additional nonlimiting exemplary chimeric antibodies include chimeric antibodies comprising heavy chain CDR1, CDR2, and CDR3, and/or light chain CDR1, CDR2, and CDR3 of an antibody selected from 0301, 0302, and 0311.

Nonlimiting exemplary chimeric anti-CSF1R antibodies include antibodies comprising the following pairs of heavy and light chain variable regions: SEQ ID NOs: 9 and 10; SEQ ID NOs: 11 and 12; and SEQ ID NOs: 13 and 14.

Nonlimiting exemplary anti-CSF1R antibodies include antibodies comprising a set of heavy chain CDR1, CDR2, and CDR3, and light chain CDR1, CDR2, and CDR3 shown above in Table 1.

Further Exemplary Chimeric Antibodies

In some embodiments, a chimeric anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the antibody binds CSF1R. In some embodiments, a chimeric anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, a chimeric anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

In some embodiments, a chimeric anti-CSF1R antibody comprises at least one of the CDRs discussed herein. That is, in some embodiments, a chimeric anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, a chimeric anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary chimeric anti-CSF1R antibodies also include chimeric antibodies that compete for binding to CSF1R with an antibody described herein. Thus, in some embodiments, a chimeric anti-CSF1R antibody is provided that competes for binding to CSF1R with an antibody selected from Fabs 0301, 0302, and 0311; and bivalent (i.e., having two heavy chains and two light chains) antibody versions of those Fabs.

Exemplary Chimeric Antibody Constant Regions

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some such embodiments, a chimeric antibody described herein comprises an S241P mutation in the human IgG4 constant region. In some embodiments, a chimeric antibody described herein comprises a human IgG4 constant region and a human K light chain.

As noted above, whether or not effector function is desirable may depend on the particular method of treatment intended for an antibody. Thus, in some embodiments, when effector function is desirable, a chimeric anti-CSF1R antibody comprising a human IgG1 heavy chain constant region or a human IgG3 heavy chain constant region is selected. In some embodiments, when effector function is not desirable, a chimeric anti-CSF1R antibody comprising a human IgG4 or IgG2 heavy chain constant region is selected.

Exemplary Human Antibodies

Human antibodies can be made by any suitable method. Nonlimiting exemplary methods include making human antibodies in transgenic mice that comprise human immunoglobulin loci. See, e.g., Jakobovits et al., Proc. Natl. Acad. Sci. USA 90: 2551-55 (1993); Jakobovits et al., Nature 362: 255-8 (1993); Lonberg et al., Nature 368: 856-9 (1994); and U.S. Pat. Nos. 5,545,807; 6,713,610; 6,673,986; 6,162,963; 5,545,807; 6,300,129; 6,255,458; 5,877,397; 5,874,299; and 5,545,806.

Nonlimiting exemplary methods also include making human antibodies using phage display libraries. See, e.g., Hoogenboom et al., J. Mol. Biol. 227: 381-8 (1992); Marks et al., J. Mol. Biol. 222: 581-97 (1991); and PCT Publication No. WO 99/10494.

In some embodiments, a human anti-CSF1R antibody binds to a polypeptide having the sequence of SEQ ID NO: 1. Exemplary human anti-CSF1R antibodies also include antibodies that compete for binding to CSF1R with an antibody described herein. Thus, in some embodiments, a human anti-CSF1R antibody is provided that competes for binding to CSF1R with an antibody selected from Fabs 0301, 0302, and 0311, and bivalent (i.e., having two heavy chains and two light chains) antibody versions of those Fabs.

In some embodiments, a human anti-CSF1R antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some such embodiments, a human antibody described herein comprises an S241P mutation in the human IgG4 constant region. In some embodiments, a human antibody described herein comprises a human IgG4 constant region and a human K light chain.

In some embodiments, when effector function is desirable, a human anti-CSF1R antibody comprising a human IgG1 heavy chain constant region or a human IgG3 heavy chain constant region is selected. In some embodiments, when effector function is not desirable, a human anti-CSF1R antibody comprising a human IgG4 or IgG2 heavy chain constant region is selected.

Additional Exemplary Anti-CSF1R Antibodies

Exemplary anti-CSF1R antibodies also include, but are not limited to, mouse, humanized, human, chimeric, and engineered antibodies that comprise, for example, one or more of the CDR sequences described herein. In some embodiments, an anti-CSF1R antibody comprises a heavy chain variable region described herein. In some embodiments, an anti-CSF1R antibody comprises a light chain variable region described herein. In some embodiments, an anti-CSF1R antibody comprises a heavy chain variable region described herein and a light chain variable region described herein. In some embodiments, an anti-CSF1R antibody comprises heavy chain CDR1, CDR2, and CDR3 described herein. In some embodiments, an anti-CSF1R antibody comprises light chain CDR1, CDR2, and CDR3 described herein. In some embodiments, an anti-CSF1R antibody comprises heavy chain CDR1, CDR2, and CDR3 described herein and light chain CDR1, CDR2, and CDR3 described herein.

In some embodiments, an anti-CSF1R antibody comprises a heavy chain variable region of an antibody selected from Fabs 0301, 0302, and 0311. Nonlimiting exemplary anti-CSF1R antibodies also include antibodies comprising a heavy chain variable region of an antibody selected from humanized antibodies huAb1 to huAb16. Nonlimiting exemplary anti-CSF1R antibodies include antibodies comprising a heavy chain variable region comprising a sequence selected from SEQ ID NOs: 9, 11, 13, and 39 to 45.

In some embodiments, an anti-CSF1R antibody comprises a light chain variable region of an antibody selected from Fabs 0301, 0302, and 0311. Nonlimiting exemplary anti-CSF1R antibodies also include antibodies comprising a light chain variable region of an antibody selected from humanized antibodies huAb1 to huAb16. Nonlimiting exemplary anti-CSF1R antibodies include antibodies comprising a light chain variable region comprising a sequence selected from SEQ ID NOs: 10, 12, 14, and 46 to 52.

In some embodiments, an anti-CSF1R antibody comprises a heavy chain variable region and a light chain variable region of an antibody selected from Fabs 0301, 0302, and 0311. Nonlimiting exemplary anti-CSF1R antibodies also include antibodies comprising a heavy chain variable region and a light chain variable region of an antibody selected from humanized antibodies huAb1 to huAb16. Nonlimiting exemplary anti-CSF1R antibodies include antibodies comprising the following pairs of heavy and light chain variable regions: SEQ ID NOs: 9 and 10; SEQ ID NOs: 11 and 12; and SEQ ID NOs: 13 and 14; SEQ ID NOs: 39 and 40; SEQ ID NOs: 41 and 42; SEQ ID NOs: 43 and 44; SEQ ID NOs: 45 and 46; SEQ ID NOs: 47 and 48; SEQ ID NOs: 49 and 50; and SEQ ID NOs: 51 and 52. Nonlimiting exemplary anti-CSF1R antibodies also include antibodies comprising the following pairs of heavy and light chains: SEQ ID NOs: 33 and 34; SEQ ID NOs: 35 and 36; and SEQ ID NOs: 37 and 38.

In some embodiments, an anti-CSF1R antibody comprises heavy chain CDR1, CDR2, and CDR3 of an antibody selected from Fabs 0301, 0302, and 0311. Nonlimiting exemplary anti-CSF1R antibodies include antibodies comprising sets of heavy chain CDR1, CDR2, and CDR3 selected from: SEQ ID NOs: 15, 16, and 17; SEQ ID NOs: 21, 22, and 23; and SEQ ID NOs: 27, 28, and 29.

In some embodiments, an anti-CSF1R antibody comprises light chain CDR1, CDR2, and CDR3 of an antibody selected from Fabs 0301, 0302, and 0311. Nonlimiting exemplary anti-CSF1R antibodies include antibodies comprising sets of light chain CDR1, CDR2, and CDR3 selected from: SEQ ID NOs: 18, 19, and 20; SEQ ID NOs: 24, 25, and 26; and SEQ ID NOs: 30, 31, and 32.

In some embodiments, an anti-CSF1R antibody comprises heavy chain CDR1, CDR2, and CDR3, and light chain CDR1, CDR2, and CDR3 of an antibody selected from Fabs 0301, 0302, and 0311.

Nonlimiting exemplary anti-CSF1R antibodies include antibodies comprising the sets of heavy chain CDR1, CDR2, and CDR3, and light chain CDR1, CDR2, and CDR3 shown above in Table 1.

Further Exemplary Antibodies

In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the antibody binds CSF1R. In some embodiments, an anti-CSF1R antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the antibody binds CSF1R. In some embodiments, an anti-CSF1R antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52; wherein the antibody binds CSF1R.

In some embodiments, an anti-CSF1R antibody comprises at least one of the CDRs discussed herein. That is, in some embodiments, an anti-CSF1R antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, an anti-CSF1R antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary anti-CSF1R antibodies also include antibodies that compete for binding to CSF1R with an antibody described herein. Thus, in some embodiments, an anti-CSF1R antibody is provided that competes for binding to CSF1R with an antibody selected from Fabs 0301, 0302, and 0311, and bivalent (i.e., having two heavy chains and two light chains) antibody versions of those Fabs.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region. In some embodiments, an antibody described herein comprises a human IgG4 heavy chain constant region. In some such embodiments, an antibody described herein comprises an S241P mutation in the human IgG4 constant region. In some embodiments, an antibody described herein comprises a human IgG4 constant region and a human κ light chain.

As noted above, whether or not effector function is desirable may depend on the particular method of treatment intended for an antibody. Thus, in some embodiments, when effector function is desirable, an anti-CSF1R antibody comprising a human IgG1 heavy chain constant region or a human IgG3 heavy chain constant region is selected. In some embodiments, when effector function is not desirable, an anti-CSF1R antibody comprising a human IgG4 or IgG2 heavy chain constant region is selected.

Exemplary Anti-CSF1R Heavy Chain Variable Regions

In some embodiments, anti-CSF1R antibody heavy chain variable regions are provided. In some embodiments, an anti-CSF1R antibody heavy chain variable region is a mouse variable region, a human variable region, or a humanized variable region.

An anti-CSF1R antibody heavy chain variable region comprises a heavy chain CDR1, FR2, CDR2, FR3, and CDR3. In some embodiments, an anti-CSF1R antibody heavy chain variable region further comprises a heavy chain FR1 and/or FR4. Nonlimiting exemplary heavy chain variable regions include, but are not limited to, heavy chain variable regions having an amino acid sequence selected from SEQ ID NOs: 9, 11, 13, and 39 to 45.

In some embodiments, an anti-CSF1R antibody heavy chain variable region comprises a CDR1 comprising a sequence selected from SEQ ID NOs: 15, 21, and 27.

In some embodiments, an anti-CSF1R antibody heavy chain variable region comprises a CDR2 comprising a sequence selected from SEQ ID NOs: 16, 22, and 28.

In some embodiments, an anti-CSF1R antibody heavy chain variable region comprises a CDR3 comprising a sequence selected from SEQ ID NOs: 17, 23, and 29.

Nonlimiting exemplary heavy chain variable regions include, but are not limited to, heavy chain variable regions comprising sets of CDR1, CDR2, and CDR3 selected from:

SEQ ID NOs: 15, 16, and 17; SEQ ID NOs: 21, 22, and 23; and SEQ ID NOs: 27, 28, and 29.

In some embodiments, an anti-CSF1R antibody heavy chain comprises a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 9, 11, 13, and 39 to 45, wherein the heavy chain, together with a light chain, is capable of forming an antibody that binds CSF1R.

In some embodiments, an anti-CSF1R antibody heavy chain comprises at least one of the CDRs discussed herein. That is, in some embodiments, an anti-CSF1R antibody heavy chain comprises at least one CDR selected from a heavy chain CDR1 discussed herein, a heavy chain CDR2 discussed herein, and a heavy chain CDR3 discussed herein. Further, in some embodiments, an anti-CSF1R antibody heavy chain comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the heavy chain comprising the mutated CDR.

In some embodiments, a heavy chain comprises a heavy chain constant region. In some embodiments, a heavy chain comprises a human heavy chain constant region. In some embodiments, the human heavy chain constant region is of an isotype selected from IgA, IgG, and IgD. In some embodiments, the human heavy chain constant region is an IgG constant region. In some embodiments, a heavy chain comprises a human igG4 heavy chain constant region. In some such embodiments, the human IgG4 heavy chain constant region comprises an S241P mutation.

In some embodiments, when effector function is desirable, a heavy chain comprises a human IgG1 or IgG3 heavy chain constant region. In some embodiments, when effector function is less desirable, a heavy chain comprises a human IgG4 or IgG2 heavy chain constant region.

Exemplary Anti-CSF1R Light Chain Variable Regions

In some embodiments, anti-CSF1R antibody light chain variable regions are provided. In some embodiments, an anti-CSF1R antibody light chain variable region is a mouse variable region, a human variable region, or a humanized variable region.

An anti-CSF1R antibody light chain variable region comprises a light chain CDR1, FR2, CDR2, FR3, and CDR3. In some embodiments, an anti-CSF1R antibody light chain variable region further comprises a light chain FR1 and/or FR4. Nonlimiting exemplary light chain variable regions include light chain variable regions having an amino acid sequence selected from SEQ ID NOs: 10, 12, 14, and 46 to 52.

In some embodiments, an anti-CSF1R antibody light chain variable region comprises a CDR1 comprising a sequence selected from SEQ ID NOs: 18, 24 and 30.

In some embodiments, an anti-CSF1R antibody light chain variable region comprises a CDR2 comprising a sequence selected from SEQ ID NOs: 19, 25, and 31.

In some embodiments, an anti-CSF1R antibody light chain variable region comprises a CDR3 comprising a sequence selected from SEQ ID NOs: 20, 26, and 32.

Nonlimiting exemplary light chain variable regions include, but are not limited to, light chain variable regions comprising sets of CDR1, CDR2, and CDR3 selected from: SEQ ID NOs: 18, 19, and 20; SEQ ID NOs: 24, 25, and 26; and SEQ ID NOs: 30, 31, and 32.

In some embodiments, an anti-CSF1R antibody light chain comprises a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 10, 12, 14, and 46 to 52, wherein the light chain, together with a heavy chain, is capable of forming an antibody that binds CSF1R.

In some embodiments, an anti-CSF1R antibody light chain comprises at least one of the CDRs discussed herein. That is, in some embodiments, an anti-CSF1R antibody light chain comprises at least one CDR selected from a light chain CDR1 discussed herein, a light chain CDR2 discussed herein, and a light chain CDR3 discussed herein. Further, in some embodiments, an anti-CSF1R antibody light chain comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the light chain comprising the mutated CDR.

In some embodiments, a light chain comprises a human light chain constant region. In some embodiments, a human light chain constant region is selected from a human κ and a human λ light chain constant region.

Exemplary Additional CSF1R Binding Molecules

In some embodiments, additional molecules that bind CSF1R are provided. Such molecules include, but are not limited to, non-canonical scaffolds, such as anti-calins, adnectins, ankyrin repeats, etc. See, e.g., Hosse et al., *Prot. Sci.* 15:14 (2006); Fiedler, M. and Skerra, A., "Non-Antibody Scaffolds," pp. 467-499 in Handbook of Therapeutic Antibodies, Dubel, S., ed., Wiley-VCH, Weinheim, Germany, 2007.

Exemplary Properties of Anti-CSF1R Antibodies

In some embodiments, an antibody having a structure described above binds to the CSF1R with a binding affinity ($K_D$) of less than 1 nM, blocks binding of CSF1 and/or IL-34 to CSF1R, and inhibits CSF1R phosphorylation induced by CSF1 and/or IL-34.

In some embodiments, an anti-CSF1R antibody binds to the extracellular domain of CSF1R (CSF1R-ECD). In some embodiments, an anti-CSF1R antibody has a binding affinity ($K_D$) for CSF1R of less than 1 nM, less than 0.5 nM, less than 0.1 nM, or less than 0.05 nM. In some embodiments, an anti-CSF1R antibody has a $K_D$ of between 0.01 and 1 nM, between 0.01 and 0.5 nM, between 0.01 and 0.1 nM, between 0.01 and 0.05 nM, or between 0.02 and 0.05 nM.

In some embodiments, an anti-CSF1R antibody blocks ligand binding to CSF1R. In some embodiments, an anti-CSF1R antibody blocks binding of CSF1 to CSF1R. In some embodiments, an anti-CSF1R antibody blocks binding of IL-34 to CSF1R. In some embodiments, an anti-CSF1R antibody blocks binding of both CSF1 and IL-34 to CSF1R. In some embodiments, an antibody that blocks ligand binding binds to the extracellular domain of CSF1R. In some embodiments, an antibody blocks ligand binding to CSF1R when it reduces the amount of detectable binding of a ligand to CSF1R by at least 50%, using the assay described, e.g., U.S. Pat. No. 8,206,715 B2, Example 7, which is incorporated herein by reference for any purpose. In some embodiments, an antibody reduces the amount of detectable binding of a ligand to CSF1R by at least 60%, at least 70%, at least 80%, or at least 90%. In some such embodiments, the antibody is said to block ligand binding by at least 50%, at least 60%, at least 70%, etc.

In some embodiments, an anti-CSF1R antibody inhibits ligand-induced CSF1R phosphorylation. In some embodiments, an anti-CSF1R antibody inhibits CSF1-induced CSF1R phosphorylation. In some embodiments, an anti-CSF1R antibody inhibits IL-34-induced CSF1R phosphorylation. In some embodiments, an anti-CSF1R antibody inhibits both CSF1-induced and IL-34-induced CSF1R phosphorylation. In some embodiments, an antibody is considered to "inhibit ligand-induced CSF1R phosphorylation" when it reduces the amount of detectable ligand-induced CSF1R phosphorylation by at least 50%, using the assay described, e.g., U.S. Pat. No. 8,206,715 B2, Example 6, which is incorporated herein by reference for any purpose. In some embodiments, an antibody reduces the amount of detectable ligand-induced CSF1R phosphorylation by at least 60%, at least 70%, at least 80%, or at least 90%. In some such embodiments, the antibody is said to inhibit ligand-induced CSF1R phosphorylation by at least at least 50%, at least 60%, at least 70%, etc.

In some embodiments, an antibody inhibits monocyte proliferation and/or survival responses in the presence of CSF1 and/or IL-34. In some embodiments, an antibody is considered to "inhibit monocyte proliferation and/or survival responses" when it reduces the amount of monocyte proliferation and/or survival responses in the presence of CSF1 and/or IL-34 by at least 50%, using the assay described, e.g., U.S. Pat. No. 8,206,715 B2, Example 10, which is incorporated herein by reference for any purpose. In some embodiments, an antibody reduces the amount of monocyte proliferation and/or survival responses in the presence of CSF1 and/or IL-34 by at least 60%, at least 70%, at least 80%, or at least 90%. In some such embodiments, the antibody is said to inhibit monocyte proliferation and/or survival responses by at least at least 50%, at least 60%, at least 70%, etc.

Exemplary PD-1/PD-L1 Inhibitors

Exemplary PD-1/PD-L1 inhibitors include antibodies that inhibit PD-1, such as anti-PD-1 antibodies and anti-PD-L1 antibodies. Such antibodies may be humanized antibodies, chimeric antibodies, mouse antibodies, human antibodies, and antibodies comprising the heavy chain and/or light chain CDRs discussed herein. PD-1/PD-L1 inhibitors also include fusion proteins that block binding of PD-1 to PD-L1, such as AMP-22. Various anti-PD-1 antibodies are known in the art.

Anti-PD-1 Antibodies

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

HuMAbs that bind specifically to PD-1 with high affinity have been disclosed in U.S. Pat. No. 8,008,449. Other anti-PD-1 mAbs have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates Ab responses; and/or (j) inhibits tumor cell growth in vivo. Anti-PD-1 Abs usable in the present invention include mAbs that bind specifically to human PD-1 and exhibit at least one, at least two, at least three, at least four or at least five of the preceding characteristics.

Exemplary anti-PD-1 antibodies also include, but are not limited to, mouse, humanized, human, chimeric, and engineered antibodies that comprise, for example, one or more of the CDR sequences described herein. In some embodiments, an anti-PD-1 antibody comprises a heavy chain variable region described herein. In some embodiments, an anti-PD-1 antibody comprises a light chain variable region described herein. In some embodiments, an anti-PD-1 antibody comprises a heavy chain variable region described herein and a light chain variable region described herein. In some embodiments, an anti-PD-1 antibody comprises heavy chain CDR1, CDR2, and CDR3 described herein, e.g., comprising SEQ ID NOs: 105, 107, and 109. In some embodiments, an anti-PD-1 antibody comprises light chain CDR1, CDR2, and CDR3 described herein, e.g., comprising SEQ ID NOs: 112, 114, and 116. In some embodiments, an anti-PD-1 antibody comprises heavy chain CDR1, CDR2, and CDR3 described herein, e.g., comprising SEQ ID NOs: 105, 107, and 109, and light chain CDR1, CDR2, and CDR3 described herein, e.g., comprising SEQ ID NOs: 112, 114, and 116.

In some embodiments, an anti-PD-1 antibody comprises heavy chain CDR1, CDR2, and CDR3 comprising SEQ ID NOs: 105, 107, and 109 respectively. In some embodiments, an anti-PD-1 antibody comprises light chain CDR1, CDR2, and CDR3 comprising SEQ ID NOs: 112, 114, and 116, respectively. In some embodiments, the anti-PD-1 antibody comprises a heavy chain variable region comprising SEQ ID NO: 100. In some embodiments, the anti-PD-1 antibody comprises a light chain variable region comprising SEQ ID NO: 102. In some embodiments, the anti-PD-1 antibody comprises a heavy chain variable region comprising SEQ ID NO: 100 and a light chain variable region comprising SEQ ID NO: 102. In some embodiments, the anti-PD-1 antibody comprises a heavy chain constant region comprising SEQ ID NO: 101 and/or a light chain constant region comprising SEQ ID NO: 103.

Further Exemplary Antibodies

In some embodiments, an anti-PD-1 antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NOs:100, wherein the antibody binds PD-1. In some embodiments, an anti-PD-1 antibody comprises a light chain comprising a variable region sequence that is at least 90%, at least 91%, at least 92%, at least 93%, at least 94%, at least 95%, at least 96%, at least 97%, at least 98%, or at least 99% identical to SEQ ID NOs: 102, wherein the antibody binds PD-1. In some embodiments, an anti-PD-1 antibody comprises a heavy chain comprising a variable region sequence that is at least 90%, at least 91%, at least 92%, at least 93%, at least 94%, at least 95%, at least 96%, at least 97%, at least 98%, or at least 99% identical to SEQ ID NOs: 100; and a light chain comprising a variable region sequence that is at least 90%, at least 91%, at least 92%, at least 93%, at least 94%, at least 95%, at least 96%, at least 97%, at least 98%, or at least 99% identical to SEQ ID NOs: 102; wherein the antibody binds PD-1.

In some embodiments, an anti-PD-1 antibody comprises at least one of the CDRs discussed herein. That is, in some embodiments, an anti-PD-1 antibody comprises at least one CDR selected from a heavy chain CDR1 discussed herein, a heavy chain CDR2 discussed herein, a heavy chain CDR3 discussed herein, a light chain CDR1 discussed herein, a light chain CDR2 discussed herein, and a light chain CDR3 discussed herein. Further, in some embodiments, an anti-PD-1 antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

In one embodiment, the anti-PD-1 Ab is nivolumab. Nivolumab (also known as "Opdivo®"; formerly designated 5C4, BMS-936558, MDX-1106, or ONO-4538) is a fully human IgG4 (S228P) PD-1 immune checkpoint inhibitor Ab that selectively prevents interaction with PD-1 ligands (PD-L1 and PD-L2), thereby blocking the down-regulation of antitumor T-cell functions (U.S. Pat. No. 8,008,449; Wang et al., 2014 Cancer Immunol Res. 2(9):846-56).

In another embodiment, the anti-PD-1 Ab is pembrolizumab. Pembrolizumab (also known as "Keytruda®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. No. 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 Ab is MEDI0608 (formerly AMP-514), which is a monoclonal antibody against the PD-1 receptor. MEDI0608 is described, for example, in U.S. Pat. No. 8,609,089, B2 or in http://www.cancer.gov/drugdictionary?cdrid=756047 (last accessed Dec. 14, 2014).

Anti-PD-1 Abs usable in the disclosed methods also include isolated Abs that bind specifically to human PD-1 and cross-compete for binding to human PD-1 with nivolumab (see, e.g., U.S. Pat. No. 8,008,449; WO 2013/173223). The ability of Abs to cross-compete for binding to an antigen indicates that these Abs bind to the same epitope region of the antigen and sterically hinder the binding of other cross-competing Abs to that particular epitope region. These cross-competing Abs are expected to have functional properties very similar to those of nivolumab by virtue of their binding to the same epitope region of PD-1. Cross-competing Abs can be readily identified based on their ability to cross-compete with nivolumab in standard PD-1 binding assays such as Biacore analysis, ELISA assays or flow cytometry (see, e.g., WO 2013/173223).

In certain embodiments, the Abs that cross-compete for binding to human PD-1 with, or bind to the same epitope region of human PD-1 as, nivolumab are mAbs. For administration to human subjects, these cross-competing Abs can be chimeric Abs, or can be humanized or human Abs. Such chimeric, humanized or human mAbs can be prepared and isolated by methods well known in the art.

Anti-PD-1 Abs usable in the methods of the disclosed invention also include antigen-binding portions of the above Abs. It has been amply demonstrated that the antigen-binding function of an Ab can be performed by fragments of a full-length Ab. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')2 fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab.

A nonlimiting exemplary fusion protein that is a PD-1/PD-L1 inhibitor is AMP-224 (Amplimmune, GlaxoSmithKline).

A nonlimiting exemplay peptide that is a PD-1/PD-L1 inhibitor is AUR-012.

Exemplary Antibody Conjugates

In some embodiments, an antibody is conjugated to a label and/or a cytotoxic agent. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the intended application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application.

In some embodiments, a label and/or a cytotoxic agent is conjugated to an antibody using chemical methods in vitro. Nonlimiting exemplary chemical methods of conjugation are known in the art, and include services, methods and/or reagents commercially available from, e.g., Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

Exemplary Leader Sequences

In order for some secreted proteins to express and secrete in large quantities, a leader sequence from a heterologous protein may be desirable. In some embodiments, a leader sequence is selected from SEQ ID NOs: 3 and 4, which are light chain and heavy chain leader sequences, respectively. In some embodiments, employing heterologous leader sequences may be advantageous in that a resulting mature polypeptide may remain unaltered as the leader sequence is removed in the ER during the secretion process. The addition of a heterologous leader sequence may be required to express and secrete some proteins.

Certain exemplary leader sequence sequences are described, e.g., in the online Leader sequence Database maintained by the Department of Biochemistry, National University of Singapore. See Choo et al., *BMC Bioinformatics*, 6: 249 (2005); and PCT Publication No. WO 2006/081430.

Nucleic Acid Molecules Encoding Antibodies

Nucleic acid molecules comprising polynucleotides that encode one or more chains of an antibody are provided. In some embodiments, a nucleic acid molecule comprises a polynucleotide that encodes a heavy chain or a light chain of an antibody. In some embodiments, a nucleic acid molecule comprises both a polynucleotide that encodes a heavy chain and a polynucleotide that encodes a light chain, of an antibody. In some embodiments, a first nucleic acid molecule comprises a first polynucleotide that encodes a heavy chain and a second nucleic acid molecule comprises a second polynucleotide that encodes a light chain.

In some such embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Antibody Expression and Production Vectors

Vectors comprising polynucleotides that encode antibody heavy chains and/or light chains are provided. Vectors comprising polynucleotides that encode antibody heavy chains and/or light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NS0 cells. Exemplary such vectors are described, e.g., in Running Deer et al., *Biotechnol. Prog.* 20:880-889 (2004).

In some embodiments, a vector is chosen for in vivo expression of antibody heavy chains and/or antibody light chains in animals, including humans. In some such embodiments, expression of the polypeptide is under the control of a promoter that functions in a tissue-specific manner. For example, liver-specific promoters are described, e.g., in PCT Publication No. WO 2006/076288.

Host Cells

In various embodiments, antibody heavy chains and/or light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S and DG44 cells; PER.C6® cells (Crucell); and NS0 cells. In some embodiments, antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the antibody heavy chains and/or light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., *Molecular Cloning, A Laboratory Manual*, $3^{rd}$ ed. Cold Spring Harbor Laboratory Press (2001). Nucleic acids may be transiently or stably transfected in the desired host cells, according to any suitable method.

In some embodiments, one or more polypeptides may be produced in vivo in an animal that has been engineered or transfected with one or more nucleic acid molecules encoding the polypeptides, according to any suitable method.

Purification of Antibodies

Antibodies may be purified by any suitable method. Such methods include, but are not limited to, the use of affinity matrices or hydrophobic interaction chromatography. Suitable affinity ligands include the antigen and ligands that bind antibody constant regions. For example, a Protein A, Protein G, Protein A/G, or an antibody affinity column may be used to bind the constant region and to purify an antibody. Hydrophobic interactive chromatography, for example, a butyl or phenyl column, may also suitable for purifying some polypeptides. Many methods of purifying polypeptides are known in the art.

Cell-Free Production of Antibodies

In some embodiments, an antibody is produced in a cell-free system.

Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Therapeutic Compositions and Methods

Methods of Treating Cancer

In some embodiments, methods for treating cancer are provided, comprising administering an effective amount of an anti-CSF1R antibody and an effective amount of a PD-1/PD-L1 inhibitor. In some embodiments, the anti-CSF1R antibody and the PD-1/PD-L1 inhibitor are administered concurrently. In some embodiments, the anti-CSF1R antibody and the PD-1/PD-L1 inhibitor are administered sequentially. In some embodiments, at least one, at least two, at least three doses, at least five doses, or at least ten doses of an anti-CSF1R antibody is administered prior to administration of a PD-1/PD-L1 inhibitor. In some embodiments, at least one, at least two, at least three doses, at least five doses, or at least ten doses of a PD-1/PD-L1 inhibitor is administered prior to administration of an anti-CSF1R antibody. In some embodiments, the last dose of PD-1/PD-L1 inhibitor is administered at least one, two, three, five, days or ten, or one, two, three, five, twelve, or twenty four weeks prior to the first dose of CSFR1 inhibitor. In some other embodiment, the last dose of CSFR1 inhibitor is administered at least one, two, three, five, days or ten, or one, two, three, five, twelve, or twenty four weeks prior to the first dose of PD-1/PD-L1 inhibitor. In some embodiments, a subject has received, or is receiving, PD-1/PD-L1 inhibitor therapy, and an anti-CSF1R antibody is added to the therapeutic regimen.

In some embodiments, a method of selecting a patient for combination therapy with an anti-CSF1R antibody and a PD-1/PD-L1 inhibitor is provided, comprising determining the levels of TAMs and/or CD8+ T cells in the patient. In some embodiments, if a patient's TAM levels are high, the patient is selected for combination therapy. In some embodiments, if a patient's TAM and CD8+ T cell levels are high, the patient is selected for combination therapy. The level of TAMs or CD8+ T cells is considered "high" if it is at least 10%, at least 20%, at least 30%, at least 40%, at least 50%, at least 75%, or at least 100% higher than the level in an individual who does not have cancer. In some embodiments, the level of TAMs or CD8+ T cells is considered "high" if it is above the median level found in individuals with cancer. In some embodiments, if a patient's TAM levels are high and CD8+ T cell levels are low, the patient is selected for combination therapy with an anti-CSF1R antibody and a PD-1/PD-L1 inhibitor. The level of CD8+ T cells is considered "low" if it is at or below the median level found in individuals with cancer. In some embodiment, the level of CD8+ T cells is considered "low" if it is at least 10%, at least 20%, at least 30%, at least 40%, at least 50%, at least 75%, or at least 100% lower than the level in an individual who does not have cancer. In some embodiments, expression of CSF1R on the patient's TAMs is determined. In some embodiments, if the patient's TAMs express CSF1R, the patient is selected for combination therapy. In some embodiments, if the patient's TAMs express elevated levels of CSF1R, the patient is selected for combination therapy. In some embodiments, a patient's TAMs are considered to express "elevated" levels of CSF1R if the level of CSF1R is at or above the median level of CSF1R found expressed on TAMS in individuals with cancer. In some embodiments, if the patient's CSF1R expression shows a high correlation with the level of CD8+ T cells, T cells or PD-1/PD-L1 expression, the patient is selected for combination therapy. The correlation of the expressions is considered "high" if it is at or above the median level found in individuals with cancer.

Levels of TAMs, CSF1R expression, CD8+ T cells, regulatory T cells, and/or PD-1 expression may be measured by methods in the art. Nonexemplary methods include immunohistochemistry (IHC), fluorescence-activated cell sorting (FACS), protein arrays, and gene expression assays, such as RNA sequencing, gene arrays, and quantitative PCR. In some embodiments, one or more markers selected from CSF1R, CD68, CD163, CD8, FoxP3, PD-1, and PD-L1 may be detected by IHC, FACS, or gene expression assay on tumor sections, or dissociated cells from tumor sections.

In some embodiments, the cancer is selected from squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. In some embodiments, lung cancer is non-small cell lung cancer or lung squamous cell carcinoma. In some embodiments, leukemia is acute myeloid leukemia or chronic lymphocytic leukemia. In some embodiments, breast cancer is breast invasive carcinoma. In some embodiments, ovarian cancer is ovarian serous cystadenocarcinoma. In some embodiments, kidney cancer is kidney renal clear cell carcinoma. In some embodiments, colon cancer is colon adenocarcinoma. In some embodiments, bladder cancer is bladder urothelial carcinoma. In some embodiments, the cancer is selected from bladder cancer, cervical cancer (such as squamous cell cervical cancer), head and neck squamous cell carcinoma, rectal adenocarcinoma, non-small cell lung cancer, endometrial cancer, prostate adenocarcinoma, colon cancer, ovarian cancer (such as serous epithelial ovarian cancer), and melanoma.

In some embodiments, the anti-CSF1R antibody locks binding of CSF1 and/or IL-34 to CSF1R and/or inhibits CSF1R phosphorylation induced by CSF1 and/or IL-34. In some embodiments, the anti-CSF1R antibody locks binding of CSF1 and IL-34 to CSF1R and/or inhibits CSF1R phosphorylation induced by CSF1 and/or IL-34. In some embodiments, the anti-CSF1R antibody comprises the CDRs of, or the variable regions of, an antibody selected from huAb1 to huAb16, described herein. In some embodiments, the anti-CSF1R antibody comprises the CDRs of, or the variable regions of, huAb1.

In some embodiments, the PD-1/PD-L1 inhibitor is selected from a fusion protein (such as AMP-224) and an antibody. In some embodiments, the PD-1/PD-L1 inhibitor is selected from an anti-PD-1 antibody and an anti-PD-L1 antibody. Nonlimiting exemplary anti-PD-1 antibodies include antibodies comprising the CDRs of, or the variable regions of, an antibody selected from nivolumab and pembrolizumab. In some embodiments, the anti-PD-1 antibody is selected from nivolumab and pembrolizumab. Nonlimiting exemplary anti-PD-L1 antibodies include antibodies comprising the CDRs of, or the variable regions of, an antibody selected from BMS-936559, MPDL3280A, MEDI4736, and MSB0010718C. In some embodiments, the anti-PD-L1 antibody is selected from BMS-936559, MPDL3280A, MEDI4736, and MSB0010718C.

In some embodiments of the methods described herein, the subject is a PD-1/PD-L1 inhibitor inadequate responder. A subject who is a PD-1/PD-L1 inhibitor inadequate responder, may have previously responded to a PD-1/PD-L1 inhibitor, but may have become less responsive to the PD-1/PD-L1 inhibitor, or the subject may have never responded to the PD-1/PD-L1 inhibitor. Inadequate response to a PD-1/PD-L1 inhibitor means that aspects of the condition that would be expected to improve following a standard dose of the PD-1/PD-L1 inhibitor do not improve, and/or improvement only occurs if greater than a standard dose is administered. In some embodiments, a PD-1/PD-L1 inhibitor inadequate responder has experienced, or is experiencing, an inadequate response to the PD-1/PD-L1 inhibitor after receiving a standard dose for at least two weeks, at least three weeks, at least four weeks, at least six weeks, or at least twelve weeks. A "standard" dose is determined by a medical professional, and may depend on the subject's age, weight, healthy history, severity of disease, the frequency of dosing, etc. In some embodiments, a PD-1/PD-L1 inhibitor inadequate responder has experienced, or is experiencing, an inadequate response to an anti-PD-1 antibody and/or an anti-PD-L1 antibody. In some embodiments, a PD-1/PD-L1 inhibitor inadequate responder has experienced, or is experiencing, an inadequate response to AMP-224. In some embodiments, a PD-1/PD-L1 inhibitor inadequate responder has experienced, or is experiencing, an inadequate response to a PD-1/PD-L1 inhibitor selected from nivolumab and pembrolizumab.

Routes of Administration and Carriers

In various embodiments, antibodies may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding an antibody may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, compositions comprising antibodies are provided in formulations with a wide variety of pharmaceutically acceptable carriers (see, e.g., Gennaro, *Remington: The Science and Practice of Pharmacy* with Facts and Comparisons: Drugfacts Plus, 20$^{th}$ ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as Ph adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising antibodies may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of an antibody or combination of antibodies are also provided. In some embodiments, a unit dosage is provided wherein the unit dosage contains a predetermined amount of a composition comprising an antibody or combination of antibodies, with or without one or more additional agents. In some embodiments, such a unit dosage is supplied in single-use prefilled syringe for injection, for example, or as a kit. In various embodiments, the composition contained in the unit dosage may comprise saline, sucrose, or the like; a buffer, such as phosphate, or the like; and/or be formulated within a stable and effective Ph range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, antibodies may be administered in an amount in the range of about 10 µg/kg body weight to about 100 mg/kg body weight per dose. In some embodiments, antibodies may be administered in an amount in the range of about 50 µg/kg body weight to about 5 mg/kg body weight per dose. In some embodiments, antibodies may be administered in an amount in the range of about 100 µg/kg body weight to about 10 mg/kg body weight per dose. In some embodiments, antibodies may be administered in an amount in the range of about 100 µg/kg body weight to about 20 mg/kg body weight per dose. In some embodiments, antibodies may be administered in an amount in the range of about 0.5 mg/kg body weight to about 20 mg/kg body weight per dose. In some embodiments, a PD-1/PD-L1 inhibitor, such as an antibody or fusion protein, is administered at a dose of 1 to 4 mg/kg, and an anti-CSF1R antibody is administered at a dose of 0.5 to 10 mg/kg. In some embodiments, a PD-1/PD-L1 inhibitor is administered at a dose of 1, 2, or 4 mg/kg, and an anti-CSF1R antibody is administered at a dose of about 0.3 to about 10 mg/kg, about 0.5 to about 10 mg/kg, about 0.5 to about 5 mg/kg, or about 1 to about 5 mg/kg body weight, such as at about 0.3, about 0.5, about 1, about 2, about 3, about 4, about 5, or about 10 mg/kg.

In certain embodiments, the dose of a PD-1/PD-L1 inhibitor or anti-CSF1R antibody is a fixed dose in a pharmaceutical composition. In other embodiments, the method of the present invention can be used with a flat dose (a dose given to a patient irrespective of the body weight of the patient). For example, a flat dose of a nivolumab can be about 240 mg. For example, a flat dose of pembrolizumab can be about 200 mg.

In some embodiments, an anti-CSF1R Ab, when combined with the PD-1/PD-L1 inhibitor, can be dosed within the range of about 0.3 to about 10 mg/kg, about 0.5 to about 10 mg/kg, about 0.5 to about 5 mg/kg, or about 1 to about 5 mg/kg body weight, such as at about 0.3, about 0.5, about 1, about 2, about 3, about 4, about 5, or about 10 mg/kg, administered about every two or three weeks. In other embodiments, an anti-CSF1R antibody is administered on a different dosage schedule from the PD-1/PD-L1 inhibitor. In some embodiments, an anti-CSF1R antibody is administered about every week, about every two weeks, about every three weeks, about every 4 weeks, about every five weeks, about every six weeks, about every seven weeks, about every eight weeks, about every nine weeks, about every ten weeks, about every eleven weeks, about every twelve weeks or about every fifteen weeks. A dosage of an anti-CSF1R antibody or PD-1/PD-L1 inhibitor that is significantly lower than the approved therapeutic dose may be regarded as subtherapeutic. For example a dose of, for instance, about 0.3 mg/kg or less about every 3 or 4 weeks, may be regarded as a subtherapeutic dosage in relation to a therapeutic dosage of about 3.0 mg/kg every 3 weeks. In certain embodiments, the PD-1/PD-L1 inhibitor is administered at a dosage of about 0.1, about 0.3, about 0.5, about 1, about 2, about 3, about 4, or about 5 mg/kg in combination with an anti-CSF1R antibody administered at a dosage of about 0.1, about 0.3, about 0.5, about 1, about 2, about 3, about 4, about 5, or about 10 mg/kg, once about every 2 weeks, once about every 3 weeks, or once about every 4 weeks.

In certain embodiments, the combination of an PD-1/PD-L1 inhibitor and an anti-CSF1R Ab is administered intravenously to the subject in an induction phase about every 2 or 3 weeks for 1, 2, 3 or 4 administrations. In certain embodiments, the combination of nivolumab and anti-CSF1R Ab is administered intravenously in the induction phase about every 3 weeks for about 4 administrations. The induction phase is followed by a maintenance phase during which only the PD-1/PD-L1 inhibitor is administered to the subject at a dosage of about 0.1, about 0.3, about 0.5, about 1, about 2, about 3, about 4, about 5 or about 10 mg/kg every two or three weeks for as long as the treatment proves efficacious or until unmanageable toxicity or disease progression occurs. In certain embodiments, nivolumab is administered during the maintenance phase at a dose of about 3 mg/kg body about every 2 weeks.

In certain embodiments, the PD-1/PD-L1 inhibitor and the anti-CSF1R antibody are formulated as a single composition, wherein the dose of the PD-1/PD-L1 inhibitor and the dose of the anti-CSF1R antibody are combined at a ratio of, for example, 1:50, 1:40, 1:30, 1:20, 1:10, 1:5, 1:3, 1:1, 3:1, 5:1, 10:1, 20:1, 30:1, 40:1, or 50:1. In other embodiments, the dose of the anti-CSF1R antibody is a fixed dose.

In certain embodiments, the dose of the anti-CSF1R antibody or PD-1/PD-L1 inhibitor is a flat dose, which is given to a patient irrespective of the body weight. In a specific embodiment, the flat dose of the PD-1/PD-L1 inhibitor is about 80 mg.

For combination with other anti-cancer agents, these agents are administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a subtherapeutic dosage, of the agent is administered in combination with the anti-CSF1R antibody and the PD-1/PD-L1 inhibitor. The anti-CSF1R antibody and the PD-1/PD-L1 inhibitor can be administered at the dosage that has been shown to produce the highest efficacy as monotherapy in clinical trials, e.g., for nivolumab, about 3 mg/kg of nivolumab administered once about every three weeks (Topalian et al., 2012a; Topalian et al., 2012), or at a significantly lower dose, i.e., at a subtherapeutic dose.

Dosage and frequency vary depending on the half-life of the Ab in the subject. In general, human Abs show the longest half-life, followed by humanized Abs, chimeric Abs, and nonhuman Abs. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results. The antibody compositions may be administered as needed to subjects. Determination of the frequency of administration may be made by persons skilled in the art, such as an attending physician based on considerations of the condition being treated, age of the subject being treated, severity of the condition being treated, general state of health of the subject being treated and the like. In some embodiments, an effective dose of an antibody is administered to a subject one or more times. In various embodiments, an effective dose of an antibody is administered to the subject once a month, less than once a month, such as, for example, every two months or every three months. In other embodiments, an effective dose of an antibody is administered more than once a month, such as, for example, every three weeks, every two weeks or every week. In some embodiments, an effective dose of an antibody is administered once per 1, 2, 3, 4, or 5 weeks. In some embodiments, an effective dose of an antibody is administered twice or three times per week. An effective dose of an antibody is administered to the subject at least once. In some embodiments, the effective dose of an antibody may be administered multiple times, including for periods of at least a month, at least six months, or at least a year.

Combination Therapy

Antibodies may be administered alone or with other modes of treatment. They may be provided before, substantially contemporaneous with, or after other modes of treatment, for example, surgery, chemotherapy, radiation therapy, or the administration of a biologic, such as another therapeutic antibody. In some embodiments, the cancer has recurred or progressed following a therapy selected from surgery, chemotherapy, and radiation therapy, or a combination thereof.

For treatment of cancer, as discussed herein, the antibodies may be administered in conjunction with one or more additional anti-cancer agents, such as the chemotherapeutic agent, growth inhibitory agent, anti-angiogenesis agent and/or anti-neoplastic composition. Nonlimiting examples of chemotherapeutic agent, growth inhibitory agent, anti-angiogenesis agent, anti-cancer agent and anti-neoplastic composition that can be used in combination with the antibodies of the present invention are provided herein under "Definitions."

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Humanized Anti-CSF1R Antibodies

Various humanized anti-CSF1R antibodies were developed previously. See, e.g., PCT Publication No. WO 2011/140249.

Figure 1B:
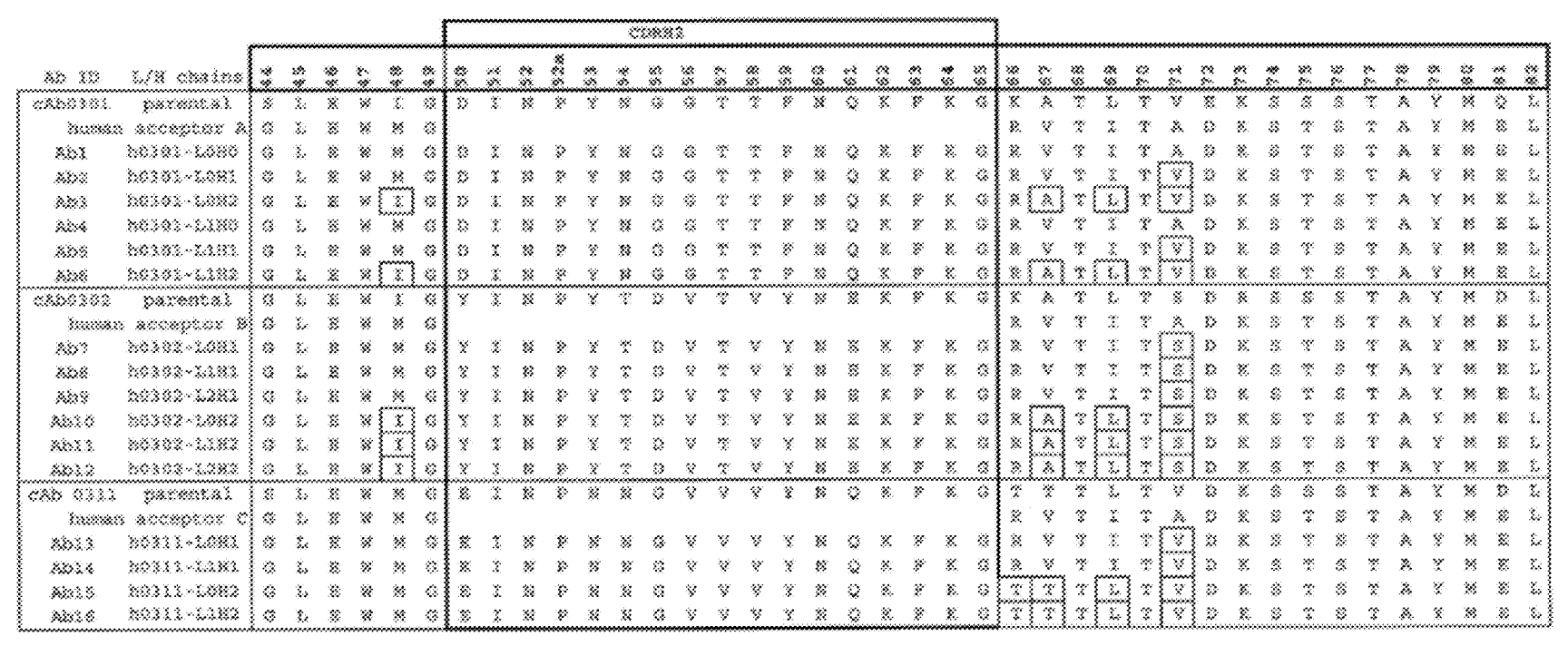
Figure 1C:
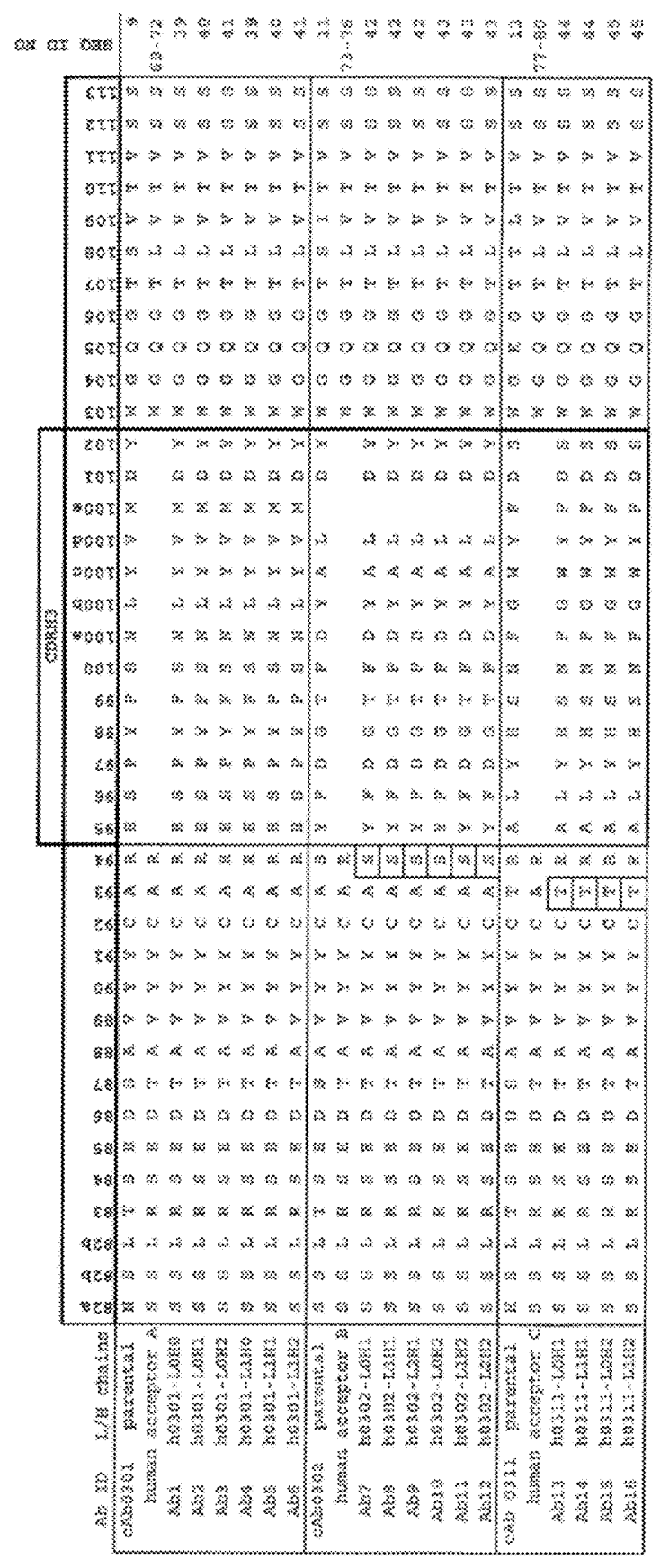

The sequences for each of the humanized heavy chain variable regions and humanized light chain variable regions, aligned with the sequences of the parental chimeric antibody variable regions and the sequences of the human acceptor variable framework regions are shown in FIGS. 1 (heavy chains) and 2 (light chains). The changes in humanized variable region sequences relative to the human acceptor variable framework region sequences are boxed. Each of the CDRs for each of the variable regions is shown in a boxed region, and labeled as "CDR" above the boxed sequences.

Table 8, below, shows the full sequences for the humanized heavy chains and humanized light chains of antibodies huAb1 to huAb16. The name and SEQ ID Nos of the humanized heavy chain and humanized light chain of each of those antibodies is shown in Table 3.

TABLE 3

Humanized heavy chains and light chains of huAb1 to huAb16

| Humanized antibody | Humanized HC | SEQ ID NO | Humanized LC | SEQ ID NO |
|---|---|---|---|---|
| huAb1 | h0301-H0 | 53 | h0301-L0 | 60 |
| huAb2 | h0301-H1 | 54 | h0301-L0 | 60 |
| huAb3 | h0301-H2 | 55 | h0301-L0 | 60 |
| huAb4 | h0301-H0 | 53 | h0301-L1 | 61 |
| huAb5 | h0301-H1 | 54 | h0301-L1 | 61 |
| huAb6 | h0301-H2 | 55 | h0301-L1 | 61 |
| huAb7 | h0302-H1 | 56 | h0302-L0 | 62 |
| huAb8 | h0302-H1 | 56 | h0302-L1 | 63 |
| huAb9 | h0302-H1 | 56 | h0302-L2 | 64 |
| huAb10 | h0302-H2 | 57 | h0302-L0 | 62 |
| huAb11 | h0302-H2 | 57 | h0302-L1 | 63 |
| huAb12 | h0302-H2 | 57 | h0302-L2 | 64 |
| huAb13 | h0311-H1 | 58 | h0311-L0 | 65 |
| huAb14 | h0311-H1 | 58 | h0311-L1 | 66 |
| huAb15 | h0311-H2 | 59 | h0311-L0 | 65 |
| huAb16 | h0311-H2 | 59 | h0311-L1 | 66 |

The 16 humanized antibodies were tested for binding to human, cynomolgus monkey, and mouse CSF1R ECD, as described previously. See, e.g., PCT Publication No. WO 2011/140249. The antibodies were found to bind to both human and cynomolgus monkey CSF1R ECD, but not to mouse CSF1R ECD. The humanized antibodies were also found to block binding of CSF1 and IL-34 to both human and cynomolgus CSF1R and to inhibit CSF1-induced and IL-34-induced phosphorylation of human CSF1R expressed in CHO cells. See, e.g., PCT Publication No. WO 2011/140249.

The $k_a$, $k_d$, and $K_D$ for binding to human CSF1R ECD were previously determined and are shown in Table 4. See, e.g., PCT Publication No. WO 2011/140249.

TABLE 4

Humanized antibody binding affinity for human CSF1R

| huAb | $k_a$ (M$^{-1}$s$^{-1}$) | $K_d$ (s$^{-1}$) | $K_D$ (Nm) |
|---|---|---|---|
| huAb 0301-L0H0 | 3.22 × 10$^6$ | 1.11 × 10$^{-03}$ | 0.35 |
| huAb 0301-L0H1 | 3.56 × 10$^6$ | 1.22 × 10$^{-03}$ | 0.34 |
| huAb 0301-L0H2 | 2.32 × 10$^6$ | 6.60 × 10$^{-04}$ | 0.28 |
| huAb 0301-L1H0 | 3.29 × 10$^6$ | 1.15 × 10$^{-03}$ | 0.35 |
| huAb 0301-L1H1 | 2.87 × 10$^6$ | 9.21 × 10$^{-04}$ | 0.32 |
| huAb 0301-L1H2 | 2.95 × 10$^6$ | 7.42 × 10$^{-04}$ | 0.25 |
| huAb 0302-L0H1 | 3.54 × 10$^6$ | 3.69 × 10$^{-03}$ | 1.04 |
| huAb 0302-L1H1 | 3.47 × 10$^6$ | 4.04 × 10$^{-03}$ | 1.17 |
| huAb 0302-L2H1 | 1.60 × 10$^6$ | 9.14 × 10$^{-04}$ | 0.57 |
| huAb 0302-L0H2 | 3.40 × 10$^6$ | 1.79 × 10$^{-03}$ | 0.53 |
| huAb 0302-L1H2 | 2.71 × 10$^6$ | 1.53 × 10$^{-03}$ | 0.56 |
| huAb 0302-L2H2 | 1.84 × 10$^6$ | 8.40 × 10$^{-04}$ | 0.46 |
| huAb 0311-L0H1 | 1.22 × 10$^6$ | 5.40 × 10$^{-04}$ | 0.44 |
| huAb 0311-L1H1 | 1.32 × 10$^6$ | 6.64 × 10$^{-04}$ | 0.50 |
| huAb 0311-L0H2 | 1.34 × 10$^6$ | 4.73 × 10$^{-04}$ | 0.35 |
| huAb 0311-L1H2 | 1.51 × 10$^6$ | 6.09 × 10$^{-04}$ | 0.40 |

Example 2: Correlation of CSF1R Expression and T Cell Signature in Tumors

Figure 3:
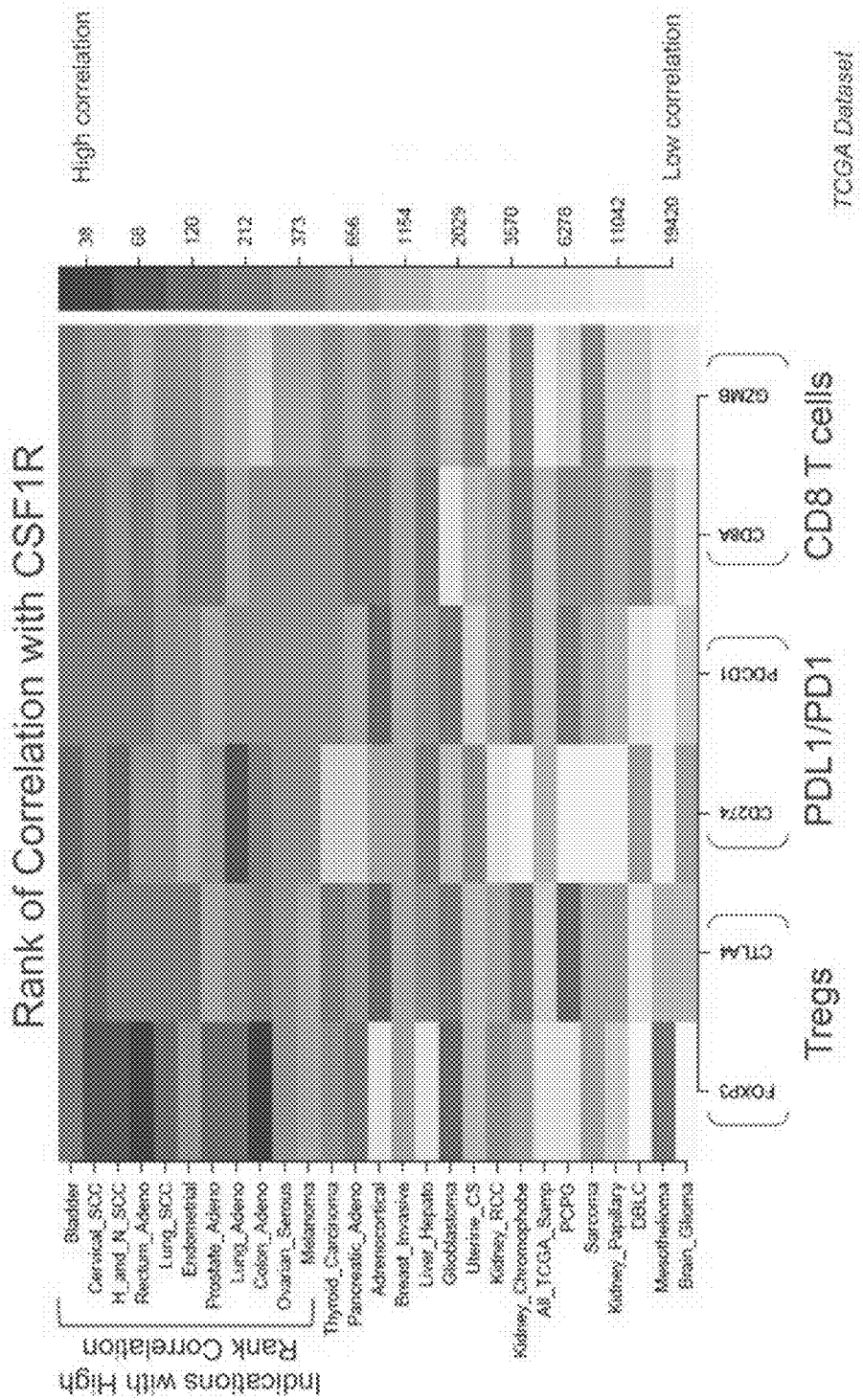
FIG. 3 is a heat map showing the correlation between CSF1R expression and Tregs, PD-L1/PD-1 expression, and CD8+ T cells in various cancers.

To determine the correlation between cancer T cell signatures and CSF1R expression, mRNA expression data from the The Cancer Genome Atlas was used. The Cancer Genome Atlas is a publicly accessible database resulting from a joint effort of the National Cancer Institute (NCI) and the National Human Genome Research Institute (NHGRI). See cancergenome.nih.gov. mRNA levels are determined using the Illumina RNASeq platform. FOXP3, CTLA-4, CD274, PDCD1, CD8A and GZMB correlations are calculated for all genes in the RNASeq data and for each cancer type. The correlations are then ranked. There are approximately 20486 genes in the RNASeq data, so for each gene, a correlation rank is assigned to every other gene. As an example, for FOXP3 in colon cancer, the correlation ranks range from 1 to 20486. CSF1R has a correlation rank of 38, suggesting that it highly correlated to FOXP3 expression. The high correlation of FOXP3 and CSF1R is consistent with the hypothesis that a subset of colon cancers have tumor associated macrophages (TAMs) expressing CSF1R and FOXP3-expressing Treg cells. Extending this analysis to many cancer types and the gene markers can be used to produce a heat map showing the cancer tissues that have CSF1R expression correlated with Treg cells, CD8+ T-cells, and PD-L1 expression. See FIG. 3.

Example 3: Effect of Anti-CSF1R Antibody and an Anti-PD-1 Antibodyon Mouse Colorectal Tumors In Vivo Seven week old female C57BL/6 mice were purchased from Harlan Laboratories (Livermore, Calif.) and were acclimated for six days before the start of the study. The murine colorectal carcinoma cell line MC38 was implanted subcutaneously over the right flank of the mice at $0.5 \times 10^6$ cells/100 l/mouse. Prior to inoculation, the cells were cultured for three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended in cold serum-free RPMI 1640 at $5 \times 10^6$ cells per milliliter.

Mice were monitored twice weekly following cell implantation for tumor growth. For tumor measurements, the length and width of each tumor was measured using calipers and volume was calculated according to the formula: Tumor volume $(mm^3)$=(width (mm)×length $(mm))^2/2$. On Day 7, all tumors were measured, and mice were randomly assigned to treatment groups. The mean tumor volume for all animals enrolled into treatment groups was 58 $mm^3$. Dosing groups were as follows: 1) Mouse IgG1 (Bio X Cell, West Lebanon, N.H., USA; Clone MOPC-21) plus Rat IgG2a (Bio X Cell, Clone 2A3), 2) anti-CSF1R (Bio X Cell, Clone AFS98) plus Rat IgG2a, 3) anti-PD-1 (Bio X Cell, Clone RMP1-14) plus Mouse IgG1, or 4) anti-CSF1R plus anti-PD-1. Tumors continued to be measured at least twice per week until tumor volume exceeded 10% of animal weight, or approximately 2000 $mm^3$.

Figures 4A, 4B:
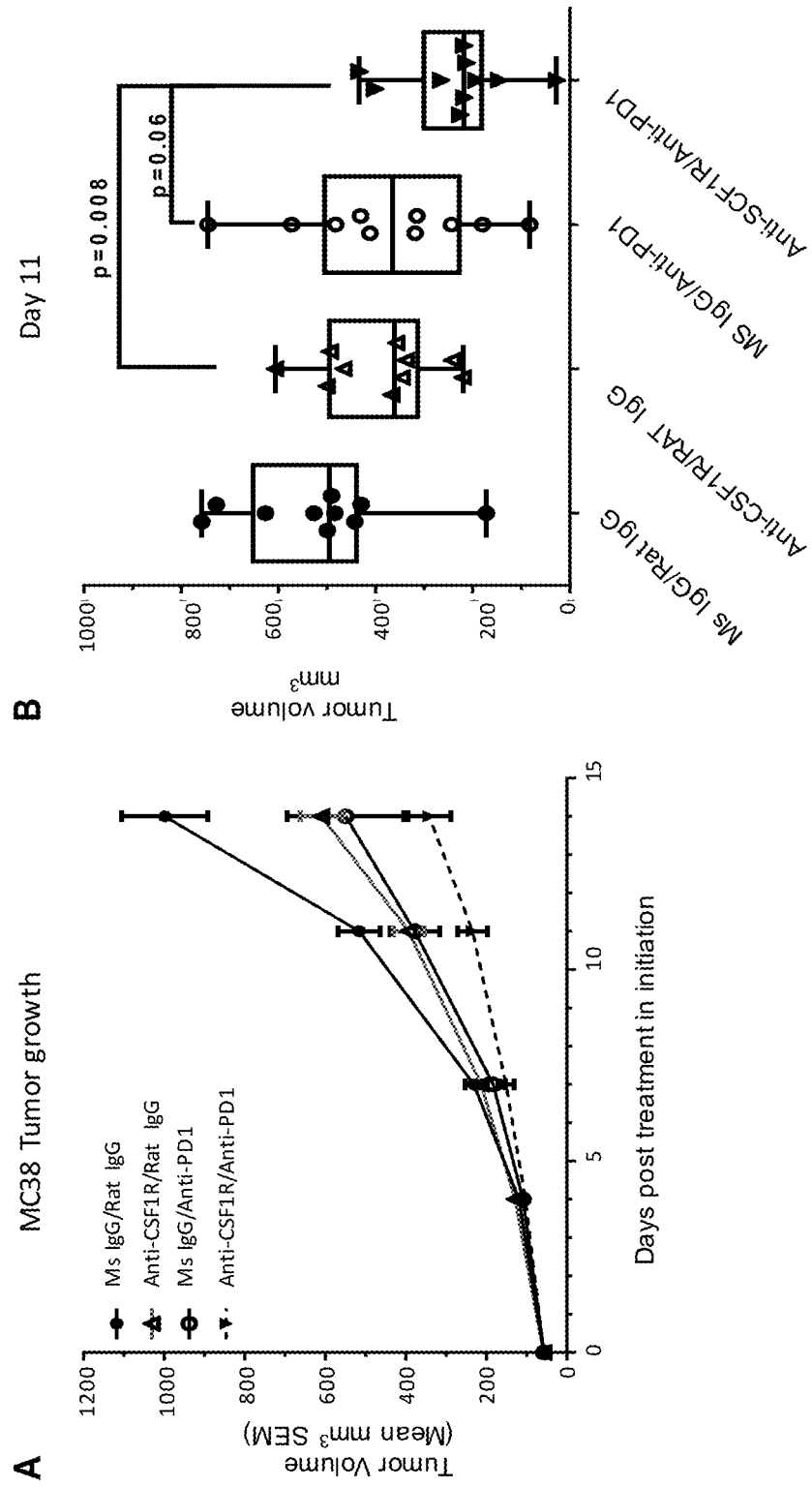
FIG. 4A shows mean change in tumor volume over time in C57BL/6 mice inoculated subcutaneously with MC38 colorectal carcinoma cells and dosed with an anti-CSF1R antibody, an anti-PD-1 antibody, or a combination of both antibodies, or with an IgG control. Both anti-CSF1R or anti-PD-1 treatment reduced the growth rate of MC38 compared to the control. The combination of anti-CSF1R and anti-PD-1 suppressed MC38 growth greater than either treatment alone (P<0.05).
FIG. 4B shows individual MC38 tumor volumes as assessed on day 11 after initiation of treatment (p-values shown on figure). Statistical significance was determined via two-tailed, unpaired t-Test.

The change in tumor size is shown by graphing mean tumor volume relative to the day upon which animals were inoculated with MC38 cells. Treatment with either anti-CSF1R or anti-PD-1 significantly reduced tumor growth compared to IgG control (P<0.05). The combination of anti-CSF1R and anti-PD-1 resulted in significantly reduced tumor growth compared to either anti-CSF1R or anti-PD-1 alone (P<0.05). P-values were calculated using unpaired, two-tailed t-test analyses of the calculated tumor volumes on day 11 after initiation of treatment. (See FIGS. 4A and 4B.)

Example 4: Effect of Anti-CSF1R Antibody and an Anti-PD-1 Antibody on Mouse Pancreatic Tumors In Vivo Eight week old female FVB mice were purchased from Jackson Laboratories and were acclimated for two weeks before the start of the study. A murine pancreatic adenocarcinoma cell line derived from $Kras^{G12D}/Ink4a^{-/-}$ transgenic mice was surgically implanted into the pancreas of the mice at $0.2 \times 10^6$ cells/50 µl/mouse. Prior to inoculation, the cells were cultured for no more than three passages in DMEM medium supplemented with 10% heat-inactivated Fetal Bovine Serum (FBS). Cells were grown at 37° C. in a humidified atmosphere with 5% $CO_2$. Upon reaching 80-85% confluence, cells were harvested and resuspended in cold PBS with Matrigel at $4 \times 10^6$ cells per milliliter.

Mice were monitored twice weekly following cell implantation for tumor growth. Mice were gently palpated at least twice per week to assess the relative size of the pancreatic tumors. On Day 12, all tumors were assessed, and mice were randomly assigned to treatment groups. Dosing groups were as follows: 1) Mouse IgG1 (Bio X Cell; Clone MOPC-21) plus vehicle control, 2) anti-CSF1R antibody (murine antibody with similar affinity for murine CSF1R as that of huAB1 for human CSF1R) plus vehicle, 3) anti-CSF1R plus gemcitabine (GEM), 4) anti-PD-1 antibody (Bio X Cell; Clone RMP1-14) plus GEM, or 5) anti-CSF1R plus anti-PD-1 and GEM. Anti-CSF1R-antibody administration began on Day 12, with anti-PD-1 and GEM treatment beginning on Day 17. Tumors continued to be assessed at least twice per week for 20 days from the start of anti-CSF1R antibody treatment.

Figure 5:
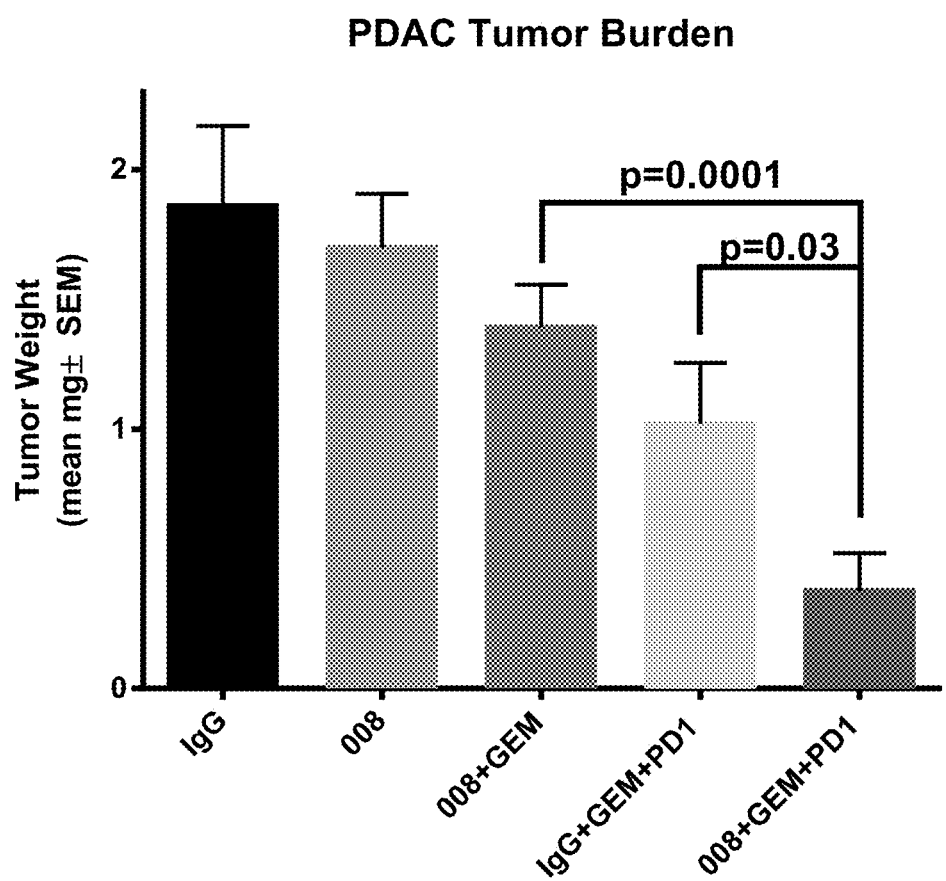
FIG. 5 shows mean tumor weight in C57BL/6 mice inoculated surgically with KRas$^{G12D}$/Ink4a$^{-/-}$ murine pancreatic ductal adenocarincoma (PDAC) cells colorectal carcinoma cells and dosed with an anti-CSF1R antibody (lanes marked "008"), an anti-PD-1 antibody, or a combination of both antibodies, together with gemcitabine (GEM). Treatment with either anti-CSF1R or anti-PD-1 reduced tumor burden compared to control mice. The combination of anti-CSF1R, anti-PD-1, and GEM significantly reduced tumor burden compared to either anti-CSF1R and GEM or anti-PD-1 and GEM (p-values shown on figure). Statistical significance was determined via two-tailed, unpaired t-Test.

The change in tumor size is shown by graphing mean tumor weight for all groups at the end of the study. Treatment with either anti-CSF1R antibody or anti-PD-1 antibody reduced tumor growth compared to the IgG control. The combination of anti-CSF1R and anti-PD-1 resulted in significantly reduced tumor growth compared to either anti-CSF1R or anti-PD-1 alone (P<0.05). P-values were calculated using unpaired, two-tailed t-test analyses of the calculated tumor volumes on day 32. (See FIG. 5.)

Example 5: Anti-CSF1R Antibody Treatment Increases the Frequency of Cytotoxic T Cells and Expression of PD-L1 in Multiple Mouse Tumor Models Seven week old female C57BL/6 and BALB/c mice were purchased from Charles River Laboratories (Hollister, Calif.) and were acclimated for at least three days before the start of the studies. The murine colorectal carcinoma cell lines MC38 and CT26 were implanted subcutaneously over the right flank of immunocompetent mice. MC38 was inoculated at $0.5 \times 10^6$ cells/100 µl/mouse, and CT26 was implanted at $1.0 \times 10^6/200$ µL/mouse. Prior to inoculation, the cells were cultured for three passages in RPMI 1640 medium supplemented with 10% heat-inactivated Fetal Bovine Serum (FBS), 2 mM L-Glutamine. Cells were grown at 37° C. in a humidified atmosphere with 5% $CO_2$. Upon reaching 80-85% confluence, cells were harvested and resuspended at $5 \times 10^6$ cells per milliliter in cold serum-free RPMI 1640 (MC38) or RPMI/Matrigel (CT26).

Mice were monitored twice weekly following cell implantation for tumor growth. For tumor measurements, the length and width of each tumor was measured using calipers and volume was calculated according to the formula: Tumor volume $(mm^3)$=(width (mm)×length $(mm))^2/2$. Beginning on Day 5 (CT26) or Day 7 (MC38), all tumors were measured, and mice were randomly assigned to treatment groups. Mice were administered either Mouse IgG1 (Clone MOPC-21) or anti-CSF1R antibody (cmFPA008). Studies were concluded 21-24 days after inoculation, and tumors were excised and snap frozen in liquid nitrogen.

Figure 8:
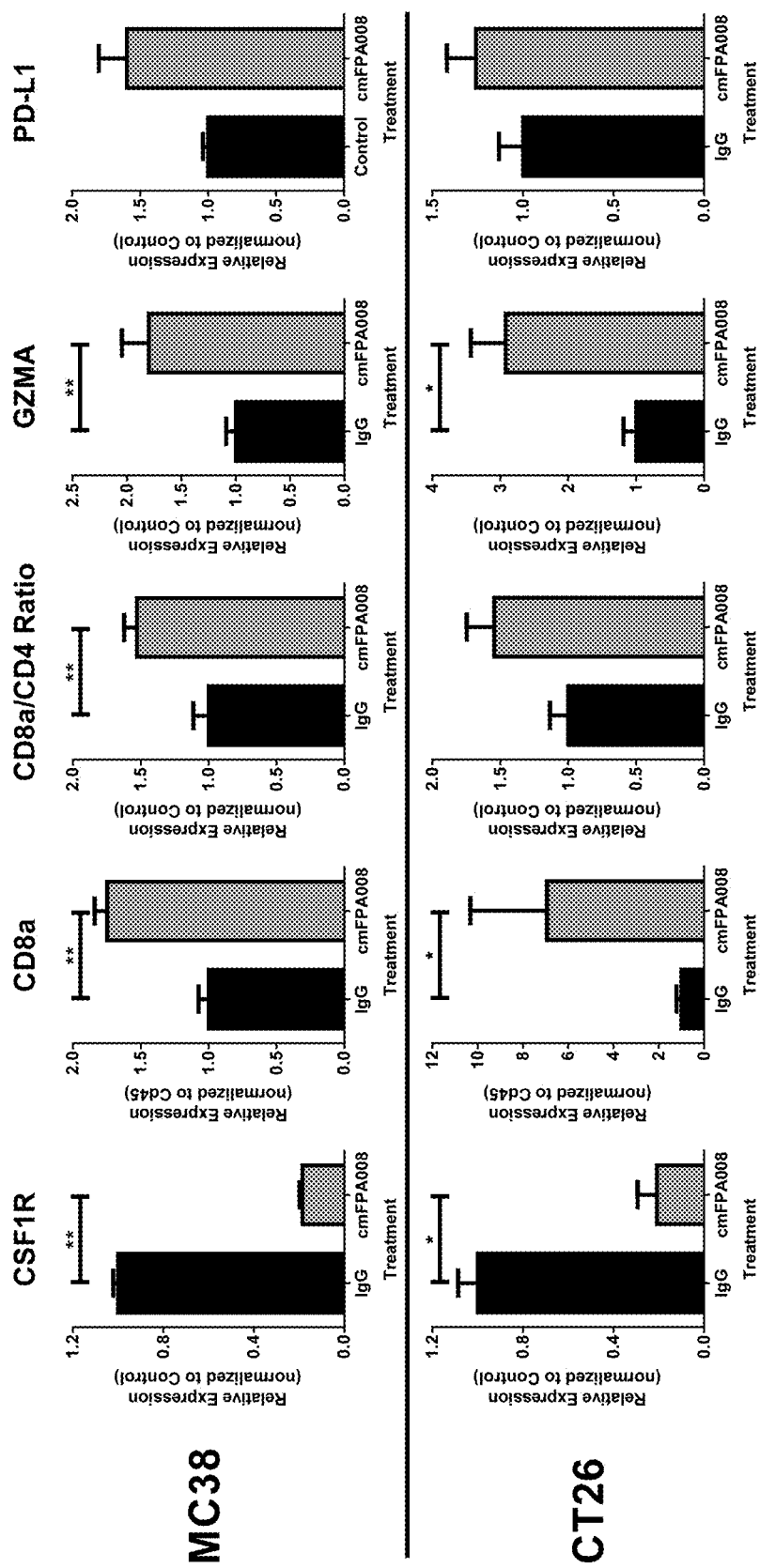
FIG. 8 shows that treatment with an anti-CSF1R antibody (called cmFPA008) increases the frequency of cytotoxic T cells and expression of PD-L1 and other genes in two colorectal mouse tumor models. Immunocompetent mice were inoculated subcutaneously with MC38 (top) or CT26 (bottom) colorectal carcinoma cells and dosed with cmFPA008 or mouse IgG1 as a control. Gene expression was assessed in tumor samples (n≥7 per group) and normalized to multiple housekeeping genes. Expression values shown are relative to the IgG control. Statistical significance was determined via two-tailed, unpaired t-Test (* p<0.05, **p<0.01).

To assess gene expression, QuantiGene Plex assays were utilized. Tumor tissue from 7-10 mice per treatment group were lysed, and relative expression of multiple genes were assessed, including PTPRC (CD45), CD8a, CD4, GZMA, CSF1R, and CD274 (PD-L1). Gene expression values were normalized against PPIB, GUSB, and HPRT, which were utilized as controls. Cd8a expression was further normalized against CD45 to assess relative CD8 abundance or CD4 to examine the ratio of CD8 to CD4 cells. FIG. 8 shows the normalized expression values relative to IgG-treated mice for each of MC38 and CT26 tumors.

Comparisons of relative gene expression were determined to be statistically significant if P<0.05. P-values were calculated using unpaired, two-tailed t-test analyses of the calculated gene expression of anti-CSF1R antibody (cmFPA008)-treated tumors compared to IgG control. Statistical significance is shown in FIG. 8 as follows: *p<0.05, ** p<0.01.

Example 6: Combination Therapy with an Anti-CSF1R Antibody and a PD-1/PD-L1 Inhibitor Anti-CSF1R antibody (an antibody comprising heavy chain and light chain variable regions of SEQ ID NOs: 53 and 60, respectively) are administered in combination with an anti-PD-1 antibody at increasing dosages in subjects with a variety of tumor types, including NSCLC, melanoma, SCCHN, bladder cancer, and pancreatic cancer. The anti-CSF1R antibody is administered at doses ranging from 1 mg/kg to 10 mg/kg. The anti-CSF1R antibody and the anti-PD-1 antibody are dosed concurrently every 2 weeks.

Anti-CSF1R antibody and anti-PD-1 antibody are administered to three subsets of patients with melanoma: naïve (have never received either antibody), acquired resistance (have progressed after an initial anti-PD-1 antibody response), and de novo resistance (did not respond to PD-1/PD-L1 inhibitor therapy).

Pre- and post-treatment core needle biopsies are obtained in a subset of subjects to evaluate potential changes in immune cells, stroma, and tumor cells after treatment. In addition to hematoxylin and eosin staining to assess the overall cellularity of the tumor, specific assays are used to monitor macrophage numbers and subtypes. Patients are additionally monitored for overall response, immune-related response, and overall survival.

For some, most, or all patients, the number of CD8+ T cells increases after treatment with the combination and/or the number of Treg cells decreases after treatment with the combination. In addition, for some, most, or all patients, the number of tumor enhancing M2 macrophages decreases and the number of tumor suppressing M1 macrophages increases after treatment with the combination. Finally, for some, most, or all patients, tumor necrosis increases after treatment with the combination.

Example 7: Summary of a Monotherapy and Combination Therapy Clinical Trial with an Anti-CSF1R Antibody and an Anti-PD-1 Antibody Anti-CSF1R antibody HuAB1 is given as a monotherapy and in combination with the anti-PD-1 antibody nivolumab in patients with selected advanced cancers and who have not previously received a CSF1R pathway inhibitor in an open-label, multicenter, dose escalation and dose expansion study. Nivolumab has previously been approved for use in melanoma, metastatic NSCLC, and in combination with ipilmumab, an anti-CTLA-4 antibody, for the treatment of metastatic melanoma. For the combination arms of the study, HuAB1 and nivolumab will be given on Day 1 of each 14-day treatment cycle; nivolumab will be given as an IV infusion over 30 minutes first, with a 30-minute rest between 2 infusions, followed by a 30-minute HuAB1 IV infusion.

The first phase of the study (Phase 1a) comprises two HuAB1 monotherapy reference cohorts (1aM1 and 1aM2) and three dose-escalation cohorts of HuAB1 in combination with nivolumab (1aC1, 1aC2, and 1aC3). The second phase of the study (Phase 1b) comprises eight cohorts (1b1 through 1b8) across six cancer types. Approximately 270 total patients will take part in the study, 30 in the first phase and 240 in the second phase with 30 in each of the 8 cohorts of the second phase. Individual patients will be enrolled in no more than one of the study arms 1aM, 1aC, or 1b. FIG. 6 shows a schematic of the study design.

In Phase 1a, monotherapy patients in cohorts 1aM1 and 1aM2 are given 2 mg/Kg or 4 mg/Kg HuAB1 once every 14 days (q2w). Combination therapy cohorts 1aC1, 1aC2, and 1aC3 are given 1, 2, or 4 mg/Kg HuAB1 and 3 mg/Kg nivolumab once every 14 days (q2w). Patients in the 1aM1 and 1aC1 cohorts are treated for a total of two 14-day cycles within a 28-day period, followed by the other cohorts. A 3 mg/Kg HuAB1 and 3 mg/Kg nivolumab cohort may also be included. In Phase 1a, patients may be included in either the monotherapy or combination therapy cohorts if they have a histologically or cytologically confirmed solid tumor that is locally recurrent or metastatic and has progressed following standard treatment or is not appropriate for standard treatment. Patients with any prior exposure to any PD-1 pathway targeting drug are excluded.

In Phase 1b, eight patient cohorts are treated, as follows.

Cohort 1b1: NSCLC (Anti-PD-1 Therapy Naïve, Second or Third Lines).

This cohort may include patients with histologically or cytologically documented squamous or non-squamous NSCLC who present with Stage IIIB or IV disease (according to version 7 of the international association for the Study of Lung Cancer Staging manual in Thoracic oncology) and with recurrent or progressive disease following multi-modal therapy (radiation therapy, surgical resection or definitive chemoradiation) for locally advanced or metastatic disease. It may include patients with progression or recurrence during/after a platinum doublet-based chemotherapy regimen for advanced or metastatic disease. Patients with any prior exposure to any PD-1 pathway targeting drug are excluded.

Cohort 1b2: NSCLC (Patients Refractory to Anti-PD-1 Targeting Drugs).

This cohort may include patients with histologically or cytologically documented NSCLC who present with Stage IIIB locally advanced or Stage IV disease, and patients with radiological evidence of disease progression during treatment with a PD-1 pathway targeting drug that did not produce a clinical response (i.e., neither CR nor PR) and with progressive disease as the best response. In the context of this cohort, refractory patients are patients that have had no clinical response after receiving at least 2 doses of any PD-1 targeting drug. Patients that are intolerant to any PD-1 pathway targeting drug are excluded, where intolerance is defined as any treatment-related Grade 4 adverse event, or any treatment-related Grade 2 or 3 adverse event that is unacceptable to the patient and persists despite standard countermeasures.

Cohort 1b3: Melanoma (Anti-PD-1 Therapy Naïve)

This cohort may include patients with histologically or cytologically documented Stage III or IV melanoma as per the American Joint Committee on Cancer (AJCC) staging system who are either refractory to, intolerant to, or have refused, standard therapy for treatment of metastatic melanoma. Included patients may demonstrate objective evidence of disease progression despite treatment with a BRAF inhibitor or may be BRAF wild-type. Patients with any prior exposure to any PD-1 pathway targeting drug, who are BRAF mutant, or whose BRAF mutational status is not known or cannot be determined are excluded.

Cohort 1b4: Melanoma (Refractory or Relapsed on Anti-PD-1 Targeting Drug)

Patients in this cohort may have histologically or cytologically documented unresectable Stage III or IV melanoma as per the AJCC staging system. Included patents may show radiological evidence of disease progression during treatment with a Checkpoint inhibitor or a PD-1 targeting drug that did not produce a clinical benefit, or may show, while receiving treatment with a PD-1 targeting drug, progressive disease as the best response or disease progression after an initial clinical benefit. In the context of this cohort, refractory patients are patients that have had no clinical response after receiving at least 2 doses of any PD-1 targeting drug. Included patients may demonstrate objective evidence of disease progression despite treatment with a BRAF inhibitor or may be BRAF wild-type. Any prior anticancer therapy including dacarbazine, BRAF inhibitor (if BRAF V600 mutation positive) and/or ipilimumab and palliative radiotherapy are completed at least 3 weeks prior to study drug administration and treatment with a PD-1 targeting drug is discontinued at least 6 weeks prior to first dose of the study drug. Patients that are intolerant to any PD-1 pathway targeting drug as defined above are excluded, as are pateints who are BRAF mutant or whose BRAF mutational status is either unknown or cannot be determined.

Cohort 1b5: Squamous Cell Carcinoma of the Head and Neck (SCCHN) (Second Line)

Patients with histologically or cytologically documented recurrent or metastatic SCCHN (oral cavity, pharynx, larynx), stage III or IV and not amenable to local therapy with curative intent (surgery or radiation therapy with or without chemotherapy) may be included in this cohort. Patients may also have progression or recurrence within 6 months of the last dose of platinum therapy in the adjuvant (i.e. with radiation after surgery), primary (i.e., with radiation), recurrent, or metastatic setting. Clinical progression after platinum therapy is an allowable event for entry and is defined as progression of a lesion at least 10 mm in size that is amenable to caliper measurement (e.g., superficial skin lesion as per RECIST v1.1) or a lesion that has been visualized and photographically recorded with measurements and shown to have progressed. Patients with prior exposure to an anti-PD-1 drug are excluded.

Cohort 1b6: Pancreatic Cancer (Second Line)

Included patients may have histologically or cytologically documented localized or metastatic adenocarcinoma of the pancreas, which has failed (or are not indicated for) standard therapy. Patients may also have received prior surgery, radiation therapy for the management of locally advanced or metastatic adenocarcinoma of the pancreas providing that disease progression has been documented. All toxicities should be resolved, and the last fraction of radiation treatment was completed at least 4 weeks prior to first study drug administration. Patients with prior exposure to an anti-PD-1 drug are excluded.

Cohort 1b7: Colorectal Cancer (Third Line)

Included patients may have histologically or cytologically documented adenocarcinoma of colon or rectum, and they may have metastatic colorectal cancer with documented disease progression after the last administration of standard therapies or intolerance to standard therapies (and approved therapies had to include a fluoropyrimidine, oxaliplatin, irinotecan, bevacizumab, and, if KRAS wild-type, cetuximab or panitumumab). Patients with prior exposure to an anti-PD-1 drug are excluded.

Cohort 1b8: Malignant Glioma (First Recurrence)

Patients in this cohort may have histologically or cytologically documented advanced World Health Organization (WHO) Grade IV malignant glioma (glioblastoma or gliosarcoma) and may have had previous treatment with surgery, radiotherapy and temozolomide. Patients may have a documented first recurrence by diagnostic biopsy or contrast-enhanced MRI performed within 21 days of first study drug administration per Response Assessment in Neurooncology (RANO) criteria. Patients are exluded if they have received prior treatment with bevacizumab or another VEGF or VEGF receptor targeting agent, more than 1 recurrence of glioblastoma or gliosarcoma, or prior exposure to any PD-1 targeting drug.

Monotherapy patients are administered HuAB1 as a 30 minute IV infusion. Combination therapy patients receive the nivolumab infusion first at a dose of 3 mg/kg as a 30-minute IV infusion, on Day 1 of each 14-day treatment cycle. They receive HuAB1 following the nivolumab infusion on Day 1 of each 14-day treatment cycle, with a 30-minute rest between the two infusions.

A biopsy at the tumor site is collected prior to Day 1 of the first cycle of the study and again on Day 29. Patients are also assessed for overall survival post-study, progression-free survival, and duration of response for those patients with confirmed responses, based on the criteria of RECIST v1.1. CT/MRI (chest, abdomen, pelvis, and brain) are performed before Day 1, during treatment, and following the study, and measurements of tumor burden are taken. The primary response parameter is the objective response rate, which is the number of patients with complete or partial response divided by the total number of treated patients with measurable disease at baseline. Tumor response is assessed using RECIST v1.1, Appendix F.

Example 8: Complete Clinical Trial Phase 1a and 1b Protocol—Monotherapy and Combination Therapy Clinical Trial with an Anti-CSF1R Antibody (HuAB1 Also Known as FPA008) and an Anti-PD-1 Antibody (Nivolumab)

1 INTRODUCTION AND STUDY RATIONALE

Colony Stimulating Factor 1 Receptor and Tumor-Associated Macrophages

Macrophages are myeloid-derived cells that carry out a variety of functions in the human body. They can colonize tissues (and tumors) through two distinct mechanisms: hematogenous seeding from circulating monocytes or local self-renewal in the form of tissue-resident macrophages (Lavin, 2013). Recent studies have shown that macrophages exert their physiological effect within, and play roles unique to, the tissues in which they are active (Lavin, 2014). Macrophage regulation is complex as these cells actively secrete and respond to multiple cytokine and chemokine gradients within their local environment.

Tumor-associated macrophages (TAMs) are among the most abundant immune cell types in the tumor microenvironment. Substantial evidence suggests that TAMs are polarized towards an anti-inflammatory phenotype (M2) that inhibits anti-tumor immune responses (Noy, 2014) through both cell-cell contact and soluble factors such as immunosuppressive cytokines. Consistent with this, increased levels of TAMs are associated with a poor prognosis in a majority of cancers (Komohara, 2014).

Following treatment with anti-CSF1R agents, the macrophages that have not been depleted may be repolarized from an M2 immunosuppressive state to an M1 anti-tumor state which would support T-cell responses. This conversion, associated with concurrent treatment modalities, such as anti-PD-1 treatment, could have an increased effect on reduction of tumor growth (Ruffell, 2015).

Response rates in ongoing PD-L1 studies have been shown to correlate with the concentration of PD-1/PD-L1 in the tumor stroma (Tumeh, 2014). Of note, there is also a significant amount of macrophages in the tumor stroma as recruitment of monocytes into the tumor stroma leads to their development into suppressive M2 macrophages. The association of monocytes and macrophages with PD-L1 has been shown to suppress tumor-specific T-cell immunity and correlate with poor survival in patients. Predictably, blockade of monocyte-associated PD-L1 positive cells in vivo was demonstrated to improve tumor-specific T-cell immunity. In vitro studies have also shown that activated monocytes expressing PD-L1 demonstrate considerable prevention of tumor-specific T-cell proliferation, cytokine production, and cytotoxic potential (Kuang, 2009).

Colony stimulating factor 1 receptor (CSF1R) signaling plays a fundamental role in the differentiation, maintenance, and function of macrophages and a subset of other myeloid lineage cells that includes monocytes, and osteoclasts (Hamilton, 2013). The two known ligands for CSF1R are CSF1 and IL34. Both of these agonists bind to overlapping regions of CSF1R with similar affinity (Masteller, 2014), even though they have little amino acid homology in common. Mice lacking CSF1R have deficiencies in macrophages, underscoring the essential role of the CSF1R pathway in the biology of this cell type (Dai, 2002). Pharmacologic treatments that block CSF1R in cancer settings are expected to reduce or reprogram TAMs and reduce immune suppression. Overall, this could produce a tumor microenvironment that is more conducive to immune-based anti-cancer therapies.

HuAB1 is a recombinant, humanized immunoglobulin G4 (IgG4) monoclonal antibody that binds to human CSF1R. The interaction of HuAB1 and CSF1R antagonizes the binding of both CSF1 and IL34 to CSF1R, thereby preventing receptor activation. HuAB1 inhibits both CSF1 and IL34-induced CSF1R phosphorylation in a cell line engineered to overexpress CSF1R (CHO-CSF1R), demonstrating experimentally that HuAB1 blocks the activation of ligand-induced CSF1R signaling pathways. HuAB1 also inhibits CSF1 and IL34-induced proliferation and survival of peripheral blood monocytes in vitro, demonstrating that HuAB1 inhibits not only the initiation of CSF1 and IL34 signaling pathways, but also the subsequent physiologic responses of primary human monocytes to these ligands.

Taken together, these and other emerging data suggest that blocking CSF1R with HuAB1 treatment could alleviate the immunosuppressive tumor environment that is generated by TAMs and could improve the efficacy of immune-based anti-cancer therapies.

PD-1

Programmed Cell Death-1 (PD-1; CD279) is a cell surface signaling receptor that delivers inhibitory signals that regulate the balance between T-cell activation and tolerance by interacting with its ligands, PD-L1 (CD274; B7-H1) and PD-L2 (B7-DC/CD273). It is a 55 kD type I transmembrane protein that is a member of the CD28 family of T-cell costimulatory receptors, which also includes inducible co-stimulator (ICOS), cytotoxic T lymphocyte antigen-4 (CTLA-4), and B- and T-lymphocyte attenuator (BTLA) (Freeman, 2000). PD-1 contains an intracellular membrane proximal immunoreceptor tyrosine inhibitory motif (ITIM) and a membrane distal immunoreceptor tyrosine-based switch motif (ITSM). PD-1 is primarily expressed on activated T cells, B cells, and myeloid cells (Nishimura, 2001a). Its ligands, PD-L1 and PD-L2, have been shown to down-regulate T-cell activation upon binding to PD-1 in both murine and human systems (Carter, 2002; Latchman, 2001). PD-1 delivers a negative signal by the recruitment of SHP-2 to the phosphorylated tyrosine residue in the ITSM in its cytoplasmic region (Chemnitz, 2004; Sheppard, 2004).

Evidence for a negative regulatory role of PD-1 comes from studies of PD-1-deficient mice, which develop various autoimmune phenotypes, including dilated cardiomyopathy and a lupus-like syndrome with arthritis and nephritis (Nishimura, 1999; Nishimura, 2001b; Okazaki, 2003). The emergence of these autoimmune phenotypes is dependent on the genetic background of the mouse strain; many of these phenotypes emerge at different times and show variable penetrance. In addition to the phenotypes of null mutations, PD-1 inhibition by antibody-mediated blockade in several murine models has been found to play a role in the development of autoimmune diseases such as encephalomyelitis, graft-versus-host disease, and type I diabetes (Ansari, 2003; Blazar, 2003; Salama, 2003). Taken together, these results suggest that PD-1 blockade has the potential to activate anti-self T-cell responses, but these responses are variable and dependent upon various host genetic factors. Thus, PD-1 deficiency or inhibition is not accompanied by a universal loss of tolerance to self-antigens.

The PD-1 targeting agent, nivolumab has been clinically tested in several tumor types including NSCLC, melanoma, and renal cell carcinoma (RCC) as a single agent or in combination with other treatments. Some of the efficacy data from the nivolumab Investigator's Brochure (IB) are shown in Table 1, below. Nivolumab as a single agent has remarkable durable efficacy in a subpopulation of patients. The enhanced effect of nivolumab combinations suggests the potential for opportunities with further benefits for patients as a combination regimen with other untested agents.

Nivolumab is currently FDA-approved for unresectable or metastatic melanoma and disease progression following ipilimumab and, if BRAF V600 mutation positive, a BRAF inhibitor. It is also approved for metastatic squamous non-small cell lung cancer (NSCLC) with progression on or after platinum-based chemotherapy.

TABLE 1

Summary of nivolumab clinical efficacy data in melanoma, NSCLC, and RCC

| Study Number | Study Drugs | Tumor Type | Response | | |
|---|---|---|---|---|---|
| | | | ORR | DOR | OS |
| MDX1106-03 | Nivolumab | NSCLC | 17% | 17 months | 24% @ 24 mo |
| CA209012 | Nivolumab | NSCLC | 30% | NR | — |
| | Nivolumab + ipilimumab | NSCLC | 13-20% | NR | — |
| | Nivolumab + chemotherapy | NSCLC | 33-47% | 25.4-45 weeks | — |

TABLE 1-continued

Summary of nivolumab clinical efficacy data in melanoma, NSCLC, and RCC

| Study Number | Study Drugs | Tumor Type | ORR | DOR | OS |
|---|---|---|---|---|---|
| | Nivolumab + erlotinib | NSCLC | 19% | NR | — |
| CA209017[a] | Nivolumab | NSCLC | — | — | 9.2 months |
| CA209063[b] | Nivolumab | NSCLC | 14.5% | NR | — |
| MDX1106-03 | Nivolumab | Melanoma | 31% | >6 months | 48% @ 24 mo |
| CA209004 | Nivolumab + ipilimumab | Melanoma | 42-43% | — | 85% @ 12 mo |
| CA209037[c] | Nivolumab | Melanoma | 31.7% | — | — |
| CA209038 | Nivolumab | Melanoma | 18-32% | — | — |
| MDX1106-03 | Nivolumab | RCC | 21% | >6 months | 48% @ 24 mo |
| CA209010 | Nivolumab | RCC | 20-22% | — | 18.2 months |
| CA209016 | Nivolumab + ipilimumab | RCC | 43-48% | — | — |
| | Nivolumab + sunitinib | RCC | 52% | — | — |
| | Nivolumab + pazopanib | RCC | 45% | — | — |

[a]Opdivo Package Insert, 2015
[b]Rizvi, 2015
[c]Weber, 2015

1.1 Rationale for HuAB1 and Nivolumab Combination Therapy

HuAB1 is a humanized monoclonal antibody directed against CSF1R. Targeting the CSF1R pathway with antibodies or small molecule inhibitors has been shown to be effective in syngeneic mouse tumor models. In an MC38 colon adenocarcinoma model in mice, a CSF1R targeting antibody resulted in a significant reduction of TAMs, which was accompanied by a positive shift of the CD8$^+$ to CD4$^+$ ratio towards cytotoxic CD8$^+$ T cells. In a recent clinical study, RG7155 (a CSF1R targeting antibody) was tested in patients with solid tumors and was shown to substantially reduce CSF1R$^+$CD163$^+$ macrophages in tumors (Ries, 2014). This reduction in macrophages was also associated with a decrease in FOXP3$^+$ regulatory T cells. These data suggest that other immune effector cells were indirectly influenced by CSF1R blockade. In a mouse proneural glioblastoma multiforme (GBM) model, small molecule inhibition of CSF1R significantly increased survival and regressed established tumors (Pyonteck, 2013). In this model, TAMs were not depleted, but instead converted to a more pro-inflammatory phenotype in the presence of CSF1R inhibition.

In an orthotopic pancreatic ductal adenocarcinoma (PDAC) model, CSF1R pathway blockade with a small molecule or an anti-CSF1 antibody selectively decreased immunosuppressive TAMs, subsequently reducing immunosuppression. This decrease in immunosuppressive TAMs enabled the remaining pro-inflammatory TAMs to support antigen presentation and bolster the anti-tumor T-cell response (Zhu, 2014). This, in turn, led to an increased interferon response that upregulated T-cell checkpoint inhibitors, including PD-L1, on tumor cells. This counter-regulation served to limit the anti-tumor T-cell response through engagement of the T-cell inhibitor PD-1. Importantly, anti-PD-1 treatment was able to overcome the PD-L1-mediated inhibition. Targeting PD-1 as a single agent showed limited efficacy in restraining PDAC tumor growth, but combining PD-1 blockade with CSF1R inhibition potently elicited tumor regression even in large, established tumors.

Together, these data suggest that reprogramming the TAM compartment in tumors via HuAB i-mediated CSF1R blockade could reduce immunosuppressive TAMs in the tumor microenvironment and improve the efficacy of checkpoint-based immunotherapies such as nivolumab.

1.2 Rationale for HuAB1/Nivolumab Combination Therapy in Selected Tumor Types TAMs can potently suppress anti-tumor immune responses. CSF1R is a cell surface receptor that is expressed on TAMs and regulates their survival and function. CSF1R-blocking antibodies have been shown to reduce TAMs in both murine and human tumors (Ries, 2014). TAMs are present in many human cancers suggesting that CSF1R blocking antibodies, such as HuAB1, could be used to treat multiple tumor types. In addition, TAMs have been shown to correlate with poor prognosis in a number of cancers, including lung, pancreatic, head and neck, and melanoma, among others (Komohara, 2014). Furthermore, analysis of The Cancer Genome Atlas shows high correlation of CSF1R with PD-1/PD-L1 co-expression, and T-cell signatures in head and neck, lung, and melanoma cancers, as well as others. In preclinical models, CSF1R inhibition has also been shown to alter macrophage polarization and block glioma progression (Pyonteck, 2013). CSF1R blockade also reduces TAMs and synergizes with PD-1 and CTLA4 checkpoint blockade in pancreatic cancer models (Zhu, 2014). It was also shown that colorectal tumor cells express relatively lower levels of PD-L1 compared to melanoma or lung cancers and that the levels of PD-L1 observed are present on infiltrating myeloid cells (Llosa, 2015).

Nivolumab is currently being tested in multiple tumor types, including all of the tumor types proposed for the Phase 1b portion of this study. As the nivolumab data mature, they will help inform the Phase 1b expansion of this study into selected tumor types.

In addition to the ongoing studies, nivolumab has been approved for use in melanoma and squamous NSCLC. The melanoma approval was based on the results of the CheckMate 037 study. In this study, the efficacy and safety of nivolumab were compared with investigator's choice of chemotherapy (ICC) as a second-line or later-line treatment in patients with advanced melanoma. In this study, 272 patients were randomized to nivolumab and 133 to ICC. Confirmed objective responses were reported in 32% of the first 120 patients in the nivolumab group versus 11% of patients in the ICC group. Grade 3-4 adverse events attributed to nivolumab included increased lipase, increased ALT, anemia, and fatigue (1% each); for ICC, these included neutropenia (14%), thrombocytopenia (6%), and anemia (5%). There were also Grade 3-4 drug-related SAEs in 5% of nivolumab-treated patients and 9% of patients in the ICC group. No treatment-related deaths occurred (Weber, 2015).

The approval in NSCLC for nivolumab was based on the results of the CheckMate 017 and CheckMate 063 studies. CheckMate 017 enrolled patients with metastatic squamous NSCLC who had experienced disease progression during or after one prior platinum doublet-based chemotherapy regimen. OS with nivolumab treatment was 9.2 months, versus 6.0 months with docetaxel (Opdivo Package Insert, 2015). CheckMate 063 assessed the activity of nivolumab in patients with advanced, refractory, squamous NSCLC. The study enrolled and treated 117 patients. Of these, 14.5% of patients had an objective response as assessed by an independent radiology review committee and 26% had stable disease. Median time to response was 3.3 months and median duration of response was not reached. Of the 17 responses, 77% were ongoing at the time of analysis. Of the 117 patients, 17% reported Grade 3-4 treatment-related AEs, including: fatigue (4%), pneumonitis (3%), and diarrhea (3%). There were two treatment-associated deaths caused by pneumonia and ischemic stroke that occurred in patients with multiple comorbidities in the setting of progressive disease (Rizvi, 2015).

The data reported above support investigation of HuAB1 in combination with nivolumab in melanoma, NSCLC, head and neck, pancreatic, colorectal, and glioma cancers.

1.3 Rationale for Starting Dose for HuAB1 Monotherapy and Combination Dose Escalation The Sponsor has already initiated a first-in-human Phase 1 clinical study designed in 3 parts to evaluate safety, PK and biomarkers of single agent HuAB1 in healthy volunteers and rheumatoid arthritis (RA) patients (Study FPA008-001). In Parts 1 and 2 of this study, HuAB1 was tested in healthy volunteers at doses of 0.2, 1, 3, and 10 mg/kg body weight. In the healthy volunteer group, at 1 mg/kg, 7 subjects received a single dose and 5 subjects received 2 doses; at 3 mg/kg, 10 subjects received a single dose and 2 subjects received 2 doses; at 10 mg/kg, 6 subjects received a single dose of HuAB1. Multiple-dose cohorts were given doses 14 days apart and all subjects were followed up for dose limiting toxicities (DLTs) through a 28-day window.

As of Sep. 23, 2014, 48 subjects have completed Parts 1 and 2 of the study. No DLTs were reported in Parts 1 or 2. All adverse events (AEs) were Grade 1 or 2 and self-limited with the most common HuAB1 treatment-related toxicities being pruritus, eyelid edema along with facial swelling, fatigue, and headache. Temporary elevations in serum enzymes such as creatinine kinase (CK), lactate dehydrogenase (LDH), alanine aminotransferase (ALT) and aspartate aminotransferase (AST) were observed.

In the ongoing Part 3 arm of the Phase 1 study, RA patients who did not respond to disease-modifying anti-rheumatic drugs (DMARDs) are participating in an open-label study at different dose levels of HuAB1 at 1, 3, and 6 mg/kg body weight. These patients are required to be on a stable weekly dose of methotrexate before and during the study and will receive 2 doses of HuAB1, 14 days apart. In addition to other analyses, the patients are being followed for safety, pharmacokinetics (PK), and pharmacodynamics (PD) after the 2-dose regimen.

In summary, 36 healthy volunteers and 6 RA patients have received HuAB1 to date, no DLTs were reported in Parts 1 or 2, and no significant treatment-related toxicities have been reported from RA patients in the 1 mg/kg or 3 mg/kg dose levels. The safety profile of nivolumab is well established and supported by the recent U.S. marketing authorizations for the treatment of melanoma and squamous NSCLC. The number of subjects dosed, the dose levels evaluated, and the current overall AE profile of HuAB1 and nivolumab support concurrent initiation of the 2 mg/kg HuAB1 monotherapy and 1 mg/kg HuAB1 with 3 mg/kg nivolumab combination therapy cohorts in this study.

The Phase 1a portion of this study will consist of a two-step monotherapy dose escalation of HuAB1 at 2 mg/kg followed by 4 mg/kg HuAB1. There will also be a three-step dose escalation of a fixed dose of 3 mg/kg nivolumab in combination with 1 mg/kg HuAB1, followed by 2 mg/kg HuAB1, then 4 mg/kg HuAB1.

Figure 7:
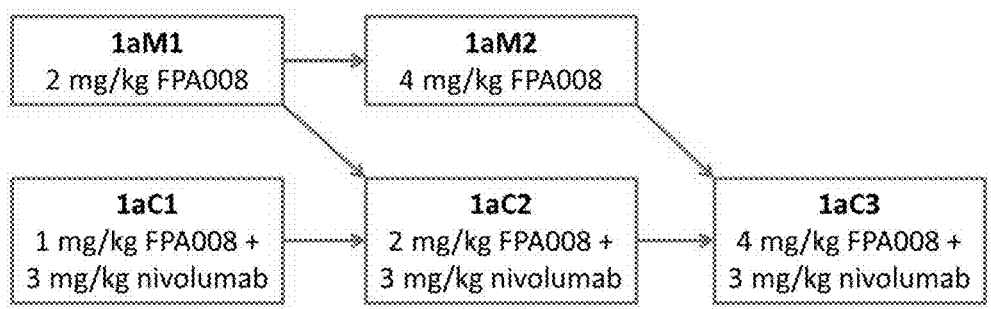
FIG. 7 shows dose escalation crieteria for the clinical experiments of Examples 7 and 8.

The 4 mg/kg HuAB1 monotherapy cohort will be opened after the 28-day DLT period clears in the 2 mg/kg HuAB1 monotherapy cohort. The 2 mg/kg HuAB1/nivolumab combination cohort will only start after the DLT period clears in the 1 mg/kg HuAB1/nivolumab combination cohort and 2 mg/kg HuAB1 monotherapy cohort. The 4 mg/kg HuAB1/nivolumab combination cohort will be opened after the DLT period clears in the 1 mg/kg and 2 mg/kg HuAB1/nivolumab combination cohorts and in the 2 mg/kg and 4 mg/kg HuAB1 monotherapy cohorts. The dose escalation schematic is shown in FIG. 7.

All patients will be on a continuous dosing schedule every 14 days and followed up until disease progression, unacceptable toxicity or withdrawal of consent.

1.4 Rationale for 30-Minute Infusion Administration for Each Study Drug

Long infusion times, especially when multiple agents are administered sequentially to an individual, place a burden on patients and treatment centers.

HuAB1, a CSF1R inhibitor, has been dosed over 30 minutes in studies in healthy volunteers and also for patients with RA.

Nivolumab has been administered safely over 60 minutes at doses ranging up to 10 mg/kg over extended treatment durations. In Study CA209010, (a Phase 2, randomized, double blinded, dose-ranging study of nivolumab in subjects with advanced/metastatic clear-cell RCC), a dose association was observed for infusion site reactions and hypersensitivity reactions (1.7% at 0.3 mg/kg, 3.7% at 2 mg/kg and 18.5% at 10 mg/kg). All events were Grade 1 or 2 and manageable. An infusion duration of 30 minutes for 3 mg/kg nivolumab (30% of the dose provided at 10 mg/kg) is not expected to present more serious safety concerns compared to the prior experience of 10 mg/kg nivolumab infused over 60 minutes.

Overall, infusion reactions, including high-grade hypersensitivity reactions, have been uncommon across nivolumab and HuAB1 clinical studies. Furthermore, a 30 minute break following the nivolumab infusion in the combination cohorts will ensure time for appropriate safety monitoring before the start of the HuAB1 infusion. Overall, a variation in the safety profile is not anticipated with a 30-minute infusion of nivolumab or HuAB1 either alone or in combination.

1.5 Research Purposes

The purpose of the Phase 1a arm of this trial is to evaluate safety and tolerability following administration of HuAB1 monotherapy as well as in combination with nivolumab in patients with advanced cancers and to identify the recommended dose (RD) of HuAB1 for the Phase 1b combination arm of this study.

The purpose of the Phase 1b arm of this trial is to further characterize the safety profile of HuAB1 in combination with nivolumab and to evaluate the clinical benefit at the RD of HuAB1/nivolumab combination therapy in patients with selected, advanced cancers.

1.6 Objectives 1.6.1 Phase 1a Objectives 1.6.1.1 Primary

To assess the safety and tolerability of HuAB1 as monotherapy

To assess the safety and tolerability of HuAB1 in combination with nivolumab

To determine the RD of HuAB1 in combination with a fixed dose of nivolumab 1.6.1.2 Secondary To characterize the PK profile of HuAB1

To characterize the PK peak and trough concentration profile of nivolumab when administered in combination with HuAB1

To characterize the PD profile of HuAB1 and nivolumab

To characterize the immunogenicity of HuAB1 and nivolumab

To assess the association of selected biomarker measures and clinical efficacy measures using pre-treatment and on-treatment tumor biopsies 1.6.1.3 Exploratory To further characterize the PD profile of HuAB1 and nivolumab 1.6.2 Phase 1b Objectives 1.6.2.1 Primary To evaluate the clinical benefit of HuAB1 in combination with nivolumab in patients with selected advanced cancers through the analysis of objective response rate (ORR).

To evaluate the safety and tolerability of HuAB1 in combination with nivolumab in patients with selected advanced cancers treated at the RD 1.6.2.2 Secondary To evaluate the clinical benefit of HuAB1 in combination with nivolumab in patients with selected advanced cancers through the analysis of overall survival (OS), duration of response (DOR), and progression free survival (PFS)

To characterize the PK profile of HuAB1

To characterize the PK peak and trough concentration profile of nivolumab when administered in combination with HuAB1

To characterize the PD profile of HuAB1 and nivolumab

To characterize the immunogenicity of HuAB1 and nivolumab

To assess the association of selected biomarker measures and clinical efficacy measures using pre-treatment and on-treatment tumor biopsies 1.6.2.3 Exploratory To further characterize the PD profile of HuAB1 and nivolumab 1.7 Product Development Background 1.7.1 Mechanism of Action 1.7.1.1 HuAB1

HuAB1 is a recombinant, humanized IgG4 monoclonal antibody that binds to human CSF1R. Binding of HuAB1 to CSF1R antagonizes its natural ligands, CSF1 and IL34, thereby preventing activation of CSF1R. HuAB1 contains a single amino acid substitution in the hinge region to prevent hemi-dimer exchange.

HuAB1 inhibits both CSF1 and IL34-induced CSF1R phosphorylation in a cell line engineered to overexpress CSF1R (CHO-CSF1R), demonstrating that HuAB1 blocks the activation of ligand-induced CSF1R signaling pathways. HuAB1 also inhibits CSF1 and IL34-induced proliferation and survival of peripheral blood monocytes in vitro, demonstrating that HuAB1 inhibits not only the initiation of CSF1 and IL34 signaling pathways, but also the subsequent physiologic responses of primary human monocytes to these ligands.

CSF1R is expressed on cells of the monocyte/macrophage lineage and signaling through CSF1R via its ligands, CSF1 and IL34, supports differentiation, maintenance, and function of monocytes, macrophages, and osteoclasts. TAMs are among the most abundant immune cell types in the tumor microenvironment. Substantial evidence suggests that TAMs are polarized towards an anti-inflammatory phenotype and through both cell surface inhibitors and soluble factors, such as immunosuppressive cytokines, play a major role in inhibiting anti-tumor immune responses (Noy, 2014). CSF1 is a major survival factor for TAMs and targeting CSF1R through HuAB1 should reduce TAM-mediated immune suppression resulting in strengthening the anti-tumor response to immunotherapy. Therefore, a drug that inhibits CSF1R should limit the immune-suppressive influence of TAMs on the tumor microenvironment and could be complementary and augment current cancer therapies.

Since HuAB1 does not cross-react to mouse CSF1R, a surrogate antibody, cmHuAB1, was developed that binds and blocks mouse CSF1R with similar potency observed for HuAB1 against human CSF1R. cmHuAB1 contains rat variable regions and a mouse IgG1 Fc region. Binding of cmHuAB1 to mouse CSF1R was demonstrated in a direct binding enzyme-linked immunosorbent assay (ELISA), and cmHuAB1 inhibitory activity was demonstrated by its ability to inhibit CSF1-induced and IL34-induced proliferation of a CSF1/IL34-dependent cell line (mNFS60). The $EC_{50}$ value for cmHuAB1 binding to mouse CSF1R is 2.4 ng/mL, and the $IC_{50}$ values for inhibition of mouse CSF1-induced and mouse IL34-induced proliferation/survival of mNFS60 cells are 32.9 and 9.1 ng/mL, respectively.

1.7.1.2 Nivolumab

Cancer immunotherapy rests on the premise that tumors can be recognized as foreign rather than as self and can be effectively attacked by an activated immune system. An effective immune response in this setting is thought to rely on immune surveillance of tumor antigens expressed on cancer cells that ultimately results in an adaptive immune response and cancer cell death. Meanwhile, tumor progression may depend upon acquisition of traits that allow cancer cells to evade immunosurveillance and escape effective innate and adaptive immune responses (Dunn, 2002; Jemal, 2011; Pardoll, 2003; Zitvogel, 2006). Current immunotherapy efforts attempt to break the apparent tolerance of the immune system to tumor cells and antigens by either introducing cancer antigens by therapeutic vaccination or by modulating regulatory checkpoints of the immune system.

T-cell stimulation is a complex process involving the integration of numerous positive as well as negative co-stimulatory signals in addition to antigen recognition by the T-cell receptor (TCR) (Greenwald, 2004). Collectively, these signals govern the balance between T-cell activation and tolerance. PD-1 signaling has been shown to inhibit CD28-mediated upregulation of L-2, IL-10, IL-13, interferon-γamma (IFN-γ) and Bcl-xL. PD-1 signaling has also been noted to inhibit T-cell activation, and expansion of previously activated cells. Evidence for a negative regulatory role of PD-1 comes from studies of PD-1 deficient mice, which develop a variety of autoimmune phenotypes (Sharpe, 2007). These results suggest that PD-1 blockade has the potential to promote anti-self T-cell responses, but these responses are variable and dependent upon various host genetic factors. Thus, PD-1 deficiency or inhibition is not accompanied by a universal loss of tolerance to self antigens.

In vitro, nivolumab binds to PD-1 with high affinity ($EC_{50}$ 0.39-2.62 nM), and inhibits the binding of PD-1 to its ligands, PD-L1 and PD-L2 ($IC_{50}$ □1 nM). Nivolumab binds specifically to PD-1 and not to related members of the CD28 family such as CD28, ICOS, CTLA-4 and BTLA. Blockade of the PD-1 pathway by nivolumab results in a reproducible enhancement of both proliferation and IFN-γ release in a mixed lymphocyte reaction (MLR).

Using a cytomegalovirus (CMV) re-stimulation assay with human peripheral blood mononuclear cells (PBMCs), the effect of nivolumab on antigen-specific recall response is indicative of nivolumab-augmented IFN-γ secretion from CMV-specific memory T cells in a dose-dependent manner versus an isotype-matched control. In vivo blockade of PD-1 by a murine analog of nivolumab enhances the anti-tumor immune response and results in tumor rejection in several immunocompetent mouse tumor models (MC38, SA1/N, and PAN02) (Wolchok, 2009).

1.7.2 Preclinical Summary
1.7.2.1 HuAB1

The ability of cmHuAB1 to inhibit cancer growth in vivo was studied in an MC38 colon cancer model in immune-competent mice. These mice were selected to allow for the establishment of an intact tumor-immune interaction. Treatment with cmHuAB1 began when tumors reached approximately 100 mm$^3$. Mice were treated once per week by intraperitoneal injection of cmHuAB1 at 30 mg/kg, and the tumor growth was compared to mice treated with albumin alone. cmHuAB1 significantly reduced the growth of MC38 tumors compared to control-treated mice. Flow cytometry analysis of control mice showed that the CD11b$^+$ myeloid compartment in MC38 tumors was dominated by CD206$^+$ macrophages. CD206 is a marker of immunosuppressive M2 macrophages. These CD206$^+$ M2 immunosuppressive macrophages were significantly reduced upon treatment with cmHuAB1. The reduction of M2 macrophages was accompanied by an increase in CD8$^+$ cytotoxic T cells relative to total CD4$^+$ T cells or regulatory T cells defined as CD4$^+$ CD25$^{high}$ cells. These data suggest reduction of immunosuppressive macrophages by cmHuAB1 results in a shift towards a greater cytotoxic T cell response in the tumor.

The PK profile of HuAB1 is complex and characterized by nonlinear clearance that is likely mediated by binding to CSF1R on cells. As monocyte and macrophage cells are dependent on CSF1R for viability, these target-bearing cells are reduced in number following HuAB1 treatment, resulting in a decrease of target-mediated clearance. As target-mediated clearance becomes saturated at high or repeat doses, HuAB1 clearance is similar to other human IgG antibodies.

Three PD biomarkers correlate with HuAB1 exposure in nonclinical studies: CSF1 serum levels, circulating CD16-positive peripheral blood monocytes (CD16$^+$ monocytes), and serum markers of bone resorption (Trap5b and CTX). CSF1 serum levels rapidly rise and CD16$^+$ monocyte levels rapidly fall in a dose-dependent manner that correlates closely with HuAB1 plasma concentration. Saturation of the PD response is achieved at a low dose of HuAB1 (3 mg/kg weekly) in cynomolgus monkeys. The half-maximal response (IC$_{50}$) for reduction of CD16$^+$ monocytes occurs at a serum concentration of approximately 3 µg/mL and the maximal response occurs at approximately 10 µg/mL. The level of CD16-negative (CD16-) monocytes does not change with exposure to HuAB1.

In the in vivo toxicology studies in cynomolgus monkeys, HuAB1 was generally well tolerated. Test article-related findings included clinical observations, hematology and clinical chemistry changes, and histopathological changes. The majority of these observations were considered non-adverse. The most prominent clinical observation was reversible periorbital edema, seen after prolonged exposure to HuAB1. The onset of the edema did not show a clear relationship to exposure levels, but edema resolved after systemic clearance of the drug. Periorbital edema is a known side effect of drugs affecting the CSF1 pathway (Cassier, 2014; Ries, 2014). The main hematologic change was a reversible decrease in circulating CD16$^+$ monocytes, which was considered a PD effect. HuAB1-related clinical chemistry effects included reversible increased ALT, AST, CK, and LDH serum levels. These laboratory abnormalities were not associated with any histopathological evidence of liver, cardiac, or muscle tissue injury. Additionally, cardiac troponin, skeletal troponin (SkTnI), myoglobin, and aldolase did not show any changes further confirming the lack of any liver or muscle injury. The increased serum levels are attributed to diminished clearance of ALT, AST, CK, and LDH molecules from serum due to a reduced number of liver Kupffer cells (Radi, 2011). Accordingly, ALT, AST, CK, and LDH elevations are considered non-toxic and an indirect PD effect of HuAB1 exposure.

A noteworthy histopathological finding was the reversible expansion of the submucosal collagen fibers by clear space and varying amounts of a blue, granular extracellular matrix (ECM) in a variety of tissues. This change was neither associated with inflammatory cells nor with any sign of degeneration or other alteration of the collagen fibers, fibroblasts, or the smooth muscle cells within the area of expansion. A similar observation was also seen in op/op mice that lack functional CSF1. The reduction of tissue macrophages is the likely cause of the observed accumulation of ECM due to a decreased clearance of glycosaminoglycans, especially hyaluronic acid, that are prominent in connective tissue and are normally catabolized by macrophages (Radi, 2009). This change is also considered to be an indirect PD effect of HuAB1.

Cardiac troponin I was below the limit of quantitation (LOQ) in all samples except for one female monkey in the 150 mg/kg group at Day 28. This animal did have a corresponding microscopic finding in the heart. While elevations of cardiac troponin I are highly specific for myocardial injury, the level detected in this monkey (0.26 ng/mL) was marginally above the assay LOQ (0.20 ng/mL) and much lower than what would be expected for an adverse cardiac event.

The no-observable-adverse-effect level (NOAEL) for HuAB1 was determined to be 100 mg/kg when administered for 13 weekly doses to cynomolgus monkeys, which provides a 32-fold safety factor based on body surface area calculation for the starting dose of 1 mg/kg in humans.

The minimum anticipated biological effect level (MABEL) was evaluated to guide starting dose decisions in healthy volunteers in the first-in-human study. The PD markers identified as representative of a biological effect were changes in CD16$^+$ monocyte levels, elevation of plasma CSF1, and elevation of serum ALT, AST, CK, and LDH. The lowest HuAB1 plasma concentration at which a biological effect occurred for each marker ranged from 5 µg/mL to 105 µg/mL, and the HuAB1 dose that corresponded to 5 µg/mL at the maximum serum concentration ($C_{max}$) was estimated to be 0.2 mg/kg, the recommended starting dose in healthy volunteers.

1.7.2.2 Nivolumab

Nivolumab has been shown to bind specifically to the human PD-1 receptor and not to related members of the CD28 family, such as ICOS, CTLA-4, and BTLA (Nivolumab IB, 2014). Nivolumab inhibits the interaction of PD-1 with its ligands, PD-L1 and PD-L2, resulting in enhanced T-cell proliferation and IFN-γ release in vitro (Velu, 2009; Nivolumab IB, 2014). Fluorescent-activated cell sorter (FACS) analysis confirmed that nivolumab binds to transfected Chinese hamster ovary (CHO) and activated human T cells expressing cell surface PD-1 and to cynomolgus monkey PD-1, but not to rat or rabbit PD-1 molecules. Nivolumab has also been shown to bind to PD-1 on virus-specific CD8$^+$ T cells from chronically infected hepatitis C virus patients (Kaufmann, 2008; Rutebemberwa, 2008). PD-1 inhibition in an MLR resulted in a reproducible concentration-dependent enhancement of IFN-γ release in the MLR up to 50 µg/mL. No effect was observed with a human IgG4 isotype control or CD4+ T cells and dendritic cell (DC) controls (Wang, 2014).

In intravenous (IV) repeat-dose toxicology studies in cynomolgus monkeys, nivolumab was well tolerated at doses up to 50 mg/kg, administered weekly for 5 weeks, and at doses up to 50 mg/kg, administered twice weekly for 27 doses. Nivolumab-related findings were limited to a reversible decrease of 28% in triiodothyronine ($T_3$) among the females administered 27 doses of 50 mg/kg nivolumab. No corresponding changes in the level of thyroxine ($T_4$), thyroid-stimulating hormone (TSH), or histologic changes in the thyroid were observed. While nivolumab alone was well tolerated in cynomolgus monkeys, combination studies have highlighted the potential for enhanced toxicity when combined with other immunostimulatory agents (Nivolumab IB, 2014).

Ipilimumab (BMS-734016), an anti-CTLA-4 monoclonal antibody (mAb) that blocks the down-regulation of T-cell activation, was used in combination with nivolumab to investigate the effects of concurrent inhibition of the PD-1 and CTLA-4 receptors in nonhuman primates (Nivolumab IB, 2014). Although gastrointestinal (GI) toxicity has not been observed in cynomolgus monkeys treated with nivolumab alone, dose-dependent GI toxicity was evident in cynomolgus monkeys treated weekly for 4 weeks with a combination of nivolumab+ipilimumab at combinations of 10 and 3 mg/kg and 50 and 10 mg/kg, respectively. GI effects have also been observed at a low incidence after ipilimumab administration (Nivolumab IB).

In addition, an enhanced pre- and post-natal development (ePPND) study in pregnant cynomolgus monkeys with nivolumab was conducted (Nivolumab IB, 2014). Administration of nivolumab at up to 50 mg/kg every 2 weeks was well tolerated by pregnant monkeys; however, nivolumab was determined to be a selective developmental toxicant when administered from the period of organogenesis to parturition at ≥10 mg/kg (area under the concentration-time curve [AUC] from time zero to 168 hours [AUC(0-168 h)] 117,000 µg·h/mL). Specifically, increased developmental mortality (including late gestational fetal losses and extreme prematurity with associated neonatal mortality) was noted in the absence of overt maternal toxicity. There were no nivolumab-related changes in surviving infants tested throughout the 6-month postnatal period. Although the cause of these pregnancy failures was undetermined, nivolumab-related effects on pregnancy maintenance are consistent with the established role of PD-L1 in maintaining fetomaternal tolerance in mice (Habicht, 2007).

1.7.3 Clinical Summary
1.7.3.1 HuAB1
1.7.3.1.1 Ongoing Study Summary of HuAB1

HuAB1 is currently being evaluated in a double-blind, randomized, placebo-controlled first-in-human trial designed in 3 parts to study safety, PK, and PD in healthy volunteers and RA patients. The first two parts of the study were conducted in healthy volunteers and have been completed. In Part 1, 8 healthy volunteers were randomized (3:1) to receive a single IV infusion of HuAB1 or placebo, per dose cohort of 0.2, 1, 3, or 10 mg/kg. In Part 2, 8 healthy volunteers were randomized (3:1) to receive 2 doses of HuAB1 or placebo administered 14 days apart, at 1 mg/kg or 3 mg/kg. Part 3 of the study will evaluate HuAB1 in RA patients and is currently ongoing. The data for Parts 1 and 2 are summarized below.

1.7.3.1.2 Clinical Pharmacology Summary of HuAB1

The PK of HuAB1 was evaluated by measuring systemic drug levels over time in all 36 subjects who received HuAB1 in Parts 1 and 2. Blood samples for determination of serum HuAB1 concentrations were collected pre-dose and at various time points up to 112 days (for Part 1) or 98 days (for Part 2) post-first dose. In addition, blood samples for determination of anti-HuAB1 antibodies were collected pre-dose and at various time points from Day 15 to Day 85 (for Part 1) or Day 15 to Day 99 (for Part 2).

Following a single administration of HuAB1 at 0.2, 1, 3, and 10 mg/kg, total clearance decreased with increasing dose and ranged from 38.7 to 2.55 mL/day/kg. The total clearance of 2.55 mL/day/kg at 10 mg/kg is within the range for a typical human IgG monoclonal antibody. The $C_{max}$ increased proportionally with dose, but the AUC did not. Following 2 doses given 14 days apart, there was no accumulation at 1 mg/kg. However, when the dose increased to 3 mg/kg, a mean of 1.60-fold drug accumulation was observed between the first and the second dose for the AUC from Day 1 to Day 15, while minimum accumulation was observed for $C_{max}$ at the same dose level. The observed PK data suggested that CSF1R expressed on monocyte/macrophage lineage and other cell types contributed to target-mediated clearance of HuAB1. As monocyte and macrophage cells are dependent on CSF1R for viability, these target-bearing cells are reduced in number following HuAB1 treatment, resulting in a decrease of target-mediated clearance. Once target-mediated clearance is saturated at high or repeat doses, HuAB1 clearance is similar to other human IgG antibodies.

Immunogenicity of HuAB1 was assessed using a validated electrochemiluminescence assay (ECLA) that measured total anti-HuAB1 antibodies in serum. The limit of detection (sensitivity) of the assay was 39.1 ng/mL. Three subjects in cohort 2 (1 mg/kg single dose) had trace positive antibody titers, resulting in 8.3% incidence (3 of 36 subjects that received HuAB1). The trace positive antibody titers were first observed on Day 15 for 2 subjects and on Day 57 for 1 subject. Two subjects still had ADA-positive titers on Day 85 (the last time point tested). The presence of ADAs had negligible impact on HuAB1 exposure, if any, when compared to the subjects without ADAs in the same dose cohort, and there were no associated clinical sequelae based on the available data.

HuAB1 treatment induced a dose-dependent reduction of nonclassical CD16+ monocytes as a PD marker for HuAB1 treatment. The relationship between HuAB1 serum concentration and reduction of nonclassical CD16+ monocytes was analyzed and found to be concentration-dependent based on the data collected 72 hours post-treatment until the end of the study. At ≥5 µg/mL HuAB1 in serum, maximum reduction of nonclassical CD16+ monocytes was noted. Therefore, the dose to achieve trough serum concentration at ≥5 µg/mL in majority of patients is expected to be the target dose for maximum reduction of nonclassical CD16+ monocytes. The optimal exposure required to achieve clinical efficacy remains to be explored in clinical trials using HuAB1 in patients.

In summary, HuAB1 exhibited nonlinear clearance in the dose range tested. The PK characteristics observed in healthy volunteers support dosing of HuAB1 once every 2 weeks or less frequently to maintain desired drug exposure.

1.7.3.1.3 Clinical Safety Summary of HuAB1

The total number of subjects that received HuAB1 was 36 for both Part 1 and Part 2 with 6 subjects in each dose cohort. Dose escalation decisions were based on the incidence of DLTs plus attributed AEs beyond the DLT period.

HuAB1 was well tolerated in healthy volunteers up to 3 mg/kg multiple doses. The most common HuAB1 treatment-related toxicities were pruritus, eyelid edema along with facial swelling, fatigue, and headache. The events were Grade 1 or 2, and self-limited. The AE profile is similar to what has been reported in other compounds targeting the CSF1R pathway (Cassier, 2014). At 10 mg/kg, all 6 active subjects experienced moderate (Grade 2) eyelid edema or facial swelling, some accompanied with swelling in hands and feet, blurry vision, and weight increase. The events lasted up to 3 months and coincided with prolonged HuAB1 exposure at this dose level.

HuAB1 has shown elevation of liver enzymes, peaking at 2-8 weeks following drug administration and returning to normalization 12 weeks after discontinuation of drug. Dose-dependent elevations of CK up to 6.8 times the upper limit of normal (ULN) and LDH up to 3.2 times ULN were noted at 1 mg/kg and above; AST elevations up to 2.4 times ULN occurred at 3 mg/kg and above and occurred in a greater percentage of healthy volunteers with increasing dose; and mild ALT elevation up to 1.2 times ULN occurred at 10 mg/kg in 1 subject. These elevations were considered to be due more to the mechanism of action of HuAB1-mediated inhibition of Kupffer cells, rather than any organic failure or injury and were not considered clinically significant. HuAB1 was initially tested in healthy volunteers at a dose of 1 mg/kg and 3 mg/kg body weight. At 1 mg/kg, 7 subjects received a single dose and 5 subjects received 2 doses at 14 day intervals and were followed up through the 28 day DLT window. In the 3 mg/kg healthy volunteer group, 10 subjects received a single dose and 2 subjects received 2 doses 14 days apart and were followed up for DLTs. Only 1 subject in the 3 mg/kg cohort had a Grade 1 concurrent increase of alkaline phosphatase and AST.

1.7.3.2 Nivolumab 1.7.3.2.1 Clinical Pharmacology Summary of Nivolumab

Single-dose PK of nivolumab was evaluated in patients with multiple tumor types in CA209001, whereas multiple-dose PK is being evaluated in patients in CA209003. In addition, a preliminary population pharmacokinetic (PPK) model has been developed with data from 350 patients from CA209001, CA209002, and CA209003.

The PK of nivolumab was studied in patients over a dose range of 0.1 to 20 mg/kg administered as a single dose or as multiple doses every 2 or 3 weeks. Based on a PPK analysis using data from 909 patients, the clearance (CL) (CV %) is 9.5 mL/h (49.7%), geometric mean volume of distribution at steady state (Vss) is 8.0 L (30.4%), and geometric mean elimination half-life ($t_{1/2}$) is 26.7 days (101%). Steady-state concentrations of nivolumab were reached by 12 weeks when administered at 3 mg/kg every 2 weeks, and systemic accumulation was approximately 3-fold. The exposure to nivolumab increased dose proportionally over the dose range of 0.1 to 10 mg/kg administered every 2 weeks (Opdivo Package Insert, 2015).

Based on a population PK analysis using data from 909 patients, the clearance of nivolumab increased with increasing body weight supporting a weight-based dose. The population PK analysis suggested that the following factors had no clinically important effect on the clearance of nivolumab: age (29 to 87 years), gender, race, baseline LDH, PD-L1 expression, tumor type, tumor size, renal impairment, and mild hepatic impairment (Opdivo Package Insert, 2015).

1.7.3.2.2 Safety Summary of Nivolumab

Overall, the safety profile of nivolumab monotherapy as well as combination therapy is manageable and generally consistent across completed and ongoing clinical trials with no MTD reached at any dose tested up to 10 mg/kg. There was no pattern in the incidence, severity, or causality of AEs to the nivolumab dose level. Most AEs were low-grade (Grade 1 to 2) with relatively few related high-grade (Grade 3 to 4) AEs. Most high-grade events were manageable with the use of corticosteroids or hormone replacement therapy (endocrinopathies) as instructed in the management algorithms provided in the nivolumab IB (Nivolumab IB, 2014).

A total of 39 and 306 patients with selected recurrent or treatment-refractory malignancies have been treated in a completed Phase 1 single-dose study (CA209001) and an ongoing Phase 1 multi-dose study (CA209003), respectively. As the safety profile from CA209003 to date is consistent with that observed for CA209001, only data from the larger and more recent study, CA209003, are presented below.

In CA209003 (n=306, including 129 patients with NSCLC), as of the 5 Mar. 2013 database lock, drug-related AEs of any grade occurred in 75% of patients. The most frequent drug-related AEs occurring in at least 5% of patients included fatigue (28%), rash (15%), diarrhea (13%), pruritus (11%), nausea (9%), decreased appetite (9%), decreased hemoglobin (6%), and pyrexia (6%). The majority of events were low grade, with Grade ¾ drug-related AEs observed in 17% of patients. The most common Grade ¾ drug-related AEs occurring in at least 1% of patients were fatigue (2%), pneumonitis (1%), diarrhea (1%), abdominal pain (1%), hypophosphatemia (1%), and lymphopenia (1%). Drug-related SAEs occurred in 14% of patients; 8% were Grade ¾ including pneumonitis (1%) and diarrhea (1%). The spectrum, frequency, and severity of drug-related AEs were generally similar across the dose levels tested. A review of the safety data by tumor type (RCC, NSCLC, metastatic castration-resistant prostate cancer [mCRPC], colorectal cancer [CRC], and melanoma) also did not show any clinically meaningful differences in the proportion of patients with AEs noted across tumor type.

Select AEs with potential immune-related causality, previously termed "immune-related adverse events" or "adverse events of special interest" were also analyzed taking into account multiple events, with rates adjusted for treatment duration. Most events occurred within the first 6 months of therapy; cumulative or novel toxicities were not observed with prolonged drug exposure. Nineteen of 306 patients (6%) experienced Grade ¾ treatment-related select AEs. Fifty-two of 230 patients (23%) with drug-related AEs required management with systemic glucocorticoids and/or other immunosuppressive agents. Twenty-one of 52 (40%) resumed nivolumab therapy after toxicity resolved, while the others discontinued therapy.

Although tumor progression was the most common cause of mortality, there were 3 drug-related deaths associated with Grade ¾ pneumonitis. Pneumonitis (any grade) occurred in 12 of 306 patients (4%), and Grade ¾ pneumonitis occurred in 4 patients (1%), with clinical presentations ranging from asymptomatic radiographic abnormalities to progressive, diffuse pulmonary infiltrates associated with cough, fever, and/or dyspnea. No clear relationship between the occurrence of pneumonitis and tumor type, dose level, or treatment duration was noted. In 9 of 12 patients, pneumonitis was reversible after treatment discontinuation and/or with immunosuppressive therapy (glucocorticoids, infliximab, mycophenolate).

Additional details on the safety profile of nivolumab, including results from other clinical studies, are also available in the IB and package insert (Nivolumab IB, 2014; Opdivo Package Insert, 2015).

1.8 Overall Risk/Benefit Assessment

A number of drug candidates that target the CSF1R pathway are being studied in the clinic. These include antibodies that block agonist ligand binding to CSF1R or inhibit CSF1R dimerization as well as small molecules that block the kinase activity of CSF1R. The safety, PK, and PD of PD-0360324, an antibody to CSF1, in healthy volunteers has been reported (Sadis, 2009). The most significant treatment-emergent findings (increased liver enzyme levels) and AEs (i.e., periorbital edema) exhibited with PD-0360324 treatment are consistent with the data obtained to date with HuAB1.

A clinical study of RG7155 (an anti-dimerization CSF1R antibody) included patients with diffuse-type giant cell tumors (Dt-GCT). All seven evaluable patients showed partial metabolic response in FDG-PET imaging (according to the European Organization for Research and Treatment of Cancer), with two patients approaching a complete metabolic response. Five of the seven patients went on to achieve partial responses at the first assessment. As with other agents targeting the CSF1R pathway, periorbital edema was the most common AE (Ries, 2014).

CSF1 is a major survival factor for TAMs and targeting CSF1R through HuAB1 should reduce TAM-mediated immunosuppression, resulting in strengthening the anti-tumor response to immunotherapy. Inhibition of CSF1R by HuAB1 could limit the influence of TAMs on the tumor microenvironment and be complementary to, and augment current cancer therapies.

Nivolumab has demonstrated clinical activity across several tumor types, particularly melanoma and NSCLC, where it has already been granted FDA approval. Nivolumab has also demonstrated a manageable safety profile. The most common AEs included fatigue, rash, pruritus, diarrhea, and nausea.

Preliminary reports of specific CSF1R inhibitors suggest that HuAB1 may be a beneficial treatment for patients with solid tumor malignancies. The robust clinical activity demonstrated by nivolumab in patients with advanced melanoma, NSCLC and RCC in combination with a manageable safety profile supports the further development of this treatment in patients with advanced cancers.

Based on available clinical safety data, toxicities for HuAB1 and nivolumab do not overlap (with the notable exception of liver enzyme elevations, discussed below) and therefore, cumulative toxicities are not expected as a result of this combination. HuAB1 has been linked to periorbital edema, and there has been only one case of peripheral edema with nivolumab. Additionally, nivolumab has been linked to immune-related AEs, and there have been no immune-related AEs with HuAB1 to date.

There is a temporary increase in liver enzymes (CK, AST, ALT, and LDH) in patients taking HuAB1 due to a reduction of Kupffer cells, and this has not been associated with any histopathological evidence of liver, cardiac, or skeletal tissue damage. Nivolumab is known to cause hepatic toxicities at a low frequency. Because of the potential for the combination of HuAB1 and nivolumab to yield elevated liver enzymes with different underlying mechanisms, risk mitigation guidelines have been designed to rapidly detect, and appropriately respond to, any evidence of liver perturbation during this study (Appendix E).

There remains an unmet medical need for cancer patients. Given the robust nonclinical and clinical data supporting these two molecules, the non-redundant, immune-based mechanisms of actions, and current body of safety data from multiple clinical studies, the logical combination of these two drugs may be beneficial for patients with cancer who are in need of expanded therapeutic options.

2 INVESTIGATIONAL PLAN

2.1 Study Design and Duration

This study is a Phase 1a and 1b, open-label, multicenter, dose escalation and dose expansion study to evaluate the safety, tolerability, PK, and PD of HuAB1 as monotherapy and in combination with nivolumab in patients with selected advanced cancers. HuAB1 is a humanized monoclonal antibody directed against CSF1R and nivolumab is a fully human monoclonal antibody directed against PD-1. For the combination arms of the study, HuAB1 and nivolumab will be given on Day 1 of each 14-day treatment cycle; nivolumab will be given as an IV infusion over 30 minutes first, with a 30-minute rest between 2 infusions, followed by a 30-minute HuAB1 IV infusion.

The study will include a Phase 1a dose escalation and a Phase 1b dose expansion. Phase 1a consists of two HuAB1 monotherapy reference cohorts (1aM1 and 1aM2) and three dose-escalation cohorts of HuAB1 in combination with nivolumab (1aC1, 1aC2, and 1aC3). Phase 1b consists of eight cohorts (1b through 1b8) across six cancer types. Patients will be enrolled into either Phase 1aM, 1aC, or Phase 1b of the study, but not two or all three. The study schematic is shown in FIG. 6.

The study will consist of 3 periods including screening (up to 28 days), treatment, and follow-up/survival follow-up.

2.1.1 Screening Period

All screening evaluations must be completed and reviewed by the Investigator following the Study Reference Manual for the enrollment process to confirm that patients meet all eligibility criteria before the first infusion of study drug. Written informed consent for participation in the study must be obtained before performing any study specific screening tests or procedures, which are not considered standard of care. Screening assessments will be performed within 28 days prior to the first dose of study drug unless otherwise specified.

Study procedure-related AEs that occur after signing of the ICF and before administration of the first study drug dose will be collected during this period.

2.1.2 Treatment Period

2.1.2.1 Phase 1a Monotherapy Cohorts (1aM1 and 1aM2) and Combination Dose Escalation Cohorts (1aC1, 1aC2, and 1aC3)

Phase 1a consists of two HuAB1 monotherapy reference cohorts and three dose-escalation cohorts of HuAB1 in combination with nivolumab with minimum of 3 patients enrolled in each cohort. The planned dose levels and schedules for the Phase 1a cohorts are as follows:

Cohort 1aM1: 2 mg/kg HuAB1, q2w
Cohort 1aM2: 4 mg/kg HuAB1, q2w
Cohort 1aC1: 1 mg/kg HuAB1+3 mg/kg nivolumab, q2w
Cohort 1aC2: 2 mg/kg HuAB1+3 mg/kg nivolumab, q2w
Cohort 1aC3: 4 mg/kg HuAB1+3 mg/kg nivolumab, q2w The 2 mg/kg HuAB1 monotherapy cohort (1aM1) and the 1 mg/kg HuAB1+nivolumab combination cohort (1aC1) will be initiated first in parallel with sequential enrollment order, following a 3+3 design, starting with the 1aM1 monotherapy cohort. Patients in these cohorts will be treated for a total of two 14-day treatment cycles within the 28-day DLT period.

The 4 mg/kg HuAB1 monotherapy cohort (1aM2) will open after the DLT period is cleared in the 2 mg/kg HuAB1 monotherapy cohort (1aM1); the 2 mg/kg HuAB1/ nivolumab combination cohort will only start after the DLT periods are cleared in both the 1aC1 HuAB1/nivolumab combination and 1aM1 HuAB1 monotherapy cohorts. The 4 mg/kg HuAB1/nivolumab combination cohort (1aC3) will open only after the DLT periods are cleared in the 1aC2 HuAB1/nivolumab combination and 1aM2 HuAB1 monotherapy cohorts. Depending on the outcome of the 4 mg/kg HuAB1 monotherapy cohort, higher or a lower intermedian dose cohorts for both monotherapy and combination therapy (e.g., 3 mg/kg HuAB1 alone or in combination with nivolumab) may be opened up per the decision of Cohort Review Committee. All dose escalation decisions will be based on assessment of DLTs, overall safety, and tolerability. Dose escalation decisions will be agreed upon between the Investigators and the Sponsor. Prior to initiating each new dose level or expanding an existing dose level, a safety teleconference will be held wherein the Investigator(s) and Sponsor will review patient data, including, but not limited to, demographics, drug dosing, concomitant medications, hematology and serum chemistry, and AEs; and confer and document agreement that dose escalation or expanding an existing dose level is considered appropriate. If the Investigator(s) and Sponsor collectively agree, following review of safety, PK, and PD data, that a different dose escalation scheme (e.g., an intermediate HuAB1 dose of 3 mg/kg alone or in combination with nivolumab) should be used than the one outlined, this will be permitted. Review of safety, PK, and PD parameters may inform decisions to add cohorts with alternative dose levels or dose regimens (e.g., less frequent dosing) in order to reach an optimal target exposure.

DLT evaluation and enrollment decisions will follow the guidance in the Table 2 below:

TABLE 2

Algorithm for Phase 1a dose escalation decisions

| Number of Patients with DLT at a Given Dose Level | Dose Escalation Decision Rule |
|---|---|
| 0/3 | Escalation will occur into the next highest dose cohort |
| 1/3 | Enroll three more patients in same cohort |
| ≥2/3 | Stop enrollment. Enter three more patients at the lower dose level, if only three were previously entered |
| 1/6 | Open next cohort |
| ≥2/6 | Stop enrollment. Enter three more patients at the lower dose level, if only three were previously entered |

Dose escalation will continue in the monotherapy and combination treatment arms until either the MTD or maximum planned dose of HuAB1 is reached, with a minimum of 3 patients enrolled in each cohort.

The MTD is defined as the highest dose associated with DLTs in less than 33% of patients (less than 2 out of 6 patients) receiving HuAB1 or HuAB1+nivolumab combination therapy, administered during the 28-day DLT period. This will normally be the dose recommended for further study; however, based on review of safety, PK, and PD data, the RD could be lower than the MTD. If the MTD is not reached, and the highest evaluated HuAB1 dose alone or in combination with nivolumab is well tolerated, the data will be reviewed to assess whether further dose escalations up to 6 mg/kg HuAB1 are warranted.

If the MTD is not reached during the Phase 1a combination dose escalation, or subsequent cycles of treatment in cleared Phase 1a combination cohorts provide additional insight on the safety profile, an RD may be selected based on overall tolerability, safety, PK, and PD.

If a patient in Phase 1aC does not receive 2 doses of each study drug and does not complete the safety assessment (e.g., safety lab and/or AE reporting) in the 28-day DLT period for reasons other than drug-related AEs (e.g., disease progression or withdrawal of consent), then an additional patient will be enrolled into the cohort so that the cohort has at least three patients evaluable for the DLT period. All such discussions and decisions will be documented as part of the dose escalation decision-making process.

Upon completion of the 28-day DLT period, Phase 1a patients may participate in an Extended Treatment Period following the guidelines in Section 4.1.2.2.

2.1.2.1.1 Dose Limiting Toxicity

A DLT is defined as a study drug-related≥Grade 3 AE (using National Cancer Institute [NCI] Common Terminology Criteria for Adverse Events [CTCAE] v4.03) occuring during the first 28-day DLT period, excluding: Grade 3 tumor flare (defined as local pain, irritation, or rash localized at sites of known or suspected tumor), Grade 3 rash, Grade 3 immune-related adverse event (irAE, defined below) that resolved to a Grade 1 or less within 28 days, or a transient (resolving within 6 hours of onset) Grade 3 infusion-related AE. An irAE is defined as a clinically significant AE that is associated with study drug exposure, of unknown etiology, and is consistent with an immune-mediated mechanism.

2.1.2.2 Phase 1a Extended Treatment Period

Upon completion of the DLT period, patients from the Phase 1aM and 1aC cohorts may participate in an Extended Treatment Period, which begins on Day 1 of Cycle 3 (Study Day 29).

Patients from the Phase 1aM cohorts are allowed to continue to receive HuAB1 monotherapy at the same HuAB1 dose level and patients from the Phase 1aC cohorts are allowed to continue to receive HuAB1 in combination with nivolumab at the same dose levels until disease progression, unacceptable toxicity, or other reason for treatment discontinuation.

2.1.2.3 Phase 1b Expansion Cohorts

To further characterize safety and efficacy of HuAB1 in combination with nivolumab, Phase 1b will enroll up to 8 expansion cohorts in 6 advanced cancer types. Enrollment in Phase 1b will begin when an RD has been identified by the Cohort Review Committee based on Overall Safety, Tolerability, PK, and PD Data.

2.1.3 Follow-up Period

Patients who discontinue treatment while showing clinical benefit (complete response [CR], partial response [PR], or stable disease [SD]) for reasons other than disease progression should have follow-up for tumor assessments and any study drug-related AEs as specified below. The follow-up period begins at the Treatment Completion/Early Termination visit.

Follow-up visits include the following (refer to Section 6 for the full schedule):

Tumor assessments will continue every 12 (+2) weeks.

Review of study drug-related AEs, until these AEs resolve, return to baseline or are stabilized per treating Investigator's assessment. All AEs will be documented for a minimum of 100 days after the last dose OR until any one of the above conditions is met.

During the follow-up period, if the patient undergoes local therapy (e.g., resection, radiation) or a new systemic therapy is initiated, the patient should be followed for survival every 3 months (Section 4.1.4).

2.1.4 Survival Follow-Up

A patient who agrees to survival follow-up after withdrawal from study treatment, discontinues from study drug treatment due to progression of disease, or discontinues follow-up visits described in Section 4.1.3 will be followed every 3 months for survival, or more frequently as needed. Follow-up for survival may be conducted by telephone, rather than a required in-person visit.

2.1.5 Study Duration

Patients who receive study drug(s) may continue as long as they experience clinical benefit in the opinion of the investigator or until unacceptable toxicity or symptomatic deterioration attributed to disease progression as determined by the investigator after an integrated assessment of radiographic data, biopsy results (if available), and clinical status, or withdrawal of consent.

2.1.6 Stopping Rules 2.1.6.1 Stopping Rules for Phase 1a

If 2 or more patients in any dose level experience a DLT within the 28-day DLT evaluation period, the Investigators and Sponsor will review the data and follow the guidelines in Table 2 (Section 4.1.2.1). If dose escalation is terminated due to DLTs, then the evaluated dose below that which the stopping rule was invoked will be declared the MTD.

2.1.6.2 Stopping Rules for all Cohorts

Management of drug-related Grade 4 or 5 toxicities will follow the Adverse Event Management Tables (Appendix E and F).

The Sponsor will discuss such cases with the Cohort Review Committee and the study Investigators as appropriate to determine further enrollment. IRBs will be notified by the Investigators of all cases and decisions regarding continued enrollment.

2.1.6.3 Stopping Rules for Clinical Deterioration

Accumulating clinical evidence indicates that the emergence of objective responses to agents that activate anti-tumor immune responses may follow delayed kinetics of weeks or months, and can be preceded by initial apparent progression of disease with the appearance of new lesions or some enlarging of lesions while certain index lesions are regressing ("mixed response"). It is thus reasonable to allow patients experiencing apparent progression to continue to receive treatment until progression is confirmed at the next imaging assessment (Section 5.3.8). These considerations should be balanced by clinical judgment as to whether the patient is clinically deteriorating and unlikely to receive any benefit from continued treatment.

Such deterioration will be assessed to have occurred after a clinical event that, in the Investigator's opinion, is attributable to disease progression and is unlikely to reverse with continued study treatment and therefore indicates that the patient is not benefiting from study treatment and cannot be managed by the addition of supportive care. The decision to stop treatment should be discussed with the Sponsor's Medical Monitor or designee. Examples of events that may, in the Investigator's opinion, indicate a lack of clinical benefit include, but are not limited to, the following:

Eastern Cooperative Oncology Group (ECOG) score increase of at least 2 points from baseline (e.g. from 0 to 2).

Habitual changes such as changes in activities and symptoms including reduction in appetite and/or sleep, altered awareness, and increased pain-related symptoms due to cancer.

Progression of disease confirmed by the treating Investigator.

Any setting where the initiation of new anti-neoplastic therapy has been deemed beneficial to the patient even in the absence of any such documented clinical events.

2.2 Study Population 2.2.1 Planned Number of Patients and Study Centers

The total number of patients planned for this study is estimated to be 270; approximately 30 patients in Part 1a and 240 patients in Part 1b (approximately 30 patients for each of the eight Phase 1b cohorts). There will be 65 to 70 study centers participating in this study. During enrollment of any expansion cohort, if the observed number of responses makes it unlikely to achieve a target response rate for that indication (e.g., 10%), then further recruitment to that cohort may be suspended or terminated.

2.2.2 Inclusion Criteria for all Cohorts

For entry into the study, ALL of the following criteria must be met.

1. Measurable disease by Computed tomography (CT)/magnetic resonance imaging (MRI) as per Response Evaluation Criteria in Solid Tumors (RECIST) v1.1 and preferably performed within 28 days of first dose.
2. Patients must have at least 1 tumor site that can be biopsied and are willing to recommended pre-treatment, on-treatment, and post-progression biopsies (except for patients in the Glioblastoma cohort); post-progression biopsy is optional for patients in Phase 1b cohorts. Biopsies will be performed according to treating institution's own guidelines from minimum of 10 patients in each Phase 1b cohort.
3. Archival formalin-fixed paraffin-embedded (FFPE) tumor material, if available
4. Understand and sign an IRB/IEC-approved ICF prior to any study-specific evaluation
5. Age ≥18 years
6. ECOG performance status of 0 or 1
7. Willing and able to comply with all study procedures
8. Prior focal radiotherapy must be completed at least 2 weeks before first dose of study drug administration. No radiopharmaceuticals (strontium, samarium) within 8 weeks before study drug administration.
9. Prior surgery that requires general anesthesia must be completed at least 2 weeks before study drug administration. Surgery requiring local/epidural anesthesia must be completed at least 72 hours before study drug administration and patients should be recovered.
10. Screening laboratory values must meet the following criteria:
    Hematological
    a. White blood cells (WBCs)≥2000 cells/μL
    b. Neutrophils ≥1500 cells/μL
    c. Platelets ≥100×10³/μL
    d. Hemoglobin ≥9.0 g/dL
       Serum creatinine ≤1.5×ULN or creatinine clearance of ≥40 mL/minute (using Cockcroft/Gault Formula)

$$\text{Female CrCl} = \frac{(140 - \text{age in years}) \times (\text{weight in kg}) \times 0.85}{72 \times (\text{serum creatinine in mg/dL})}$$

$$\text{Male CrCl} = \frac{(140 - \text{age in years}) \times (\text{weight in kg})}{72 \times (\text{serum creatinine in mg/dL})}$$

e. PT/INR≤1.5×ULN and PTT (aPTT)≤1.5×ULN
Hepatic
   a. AST or ALT≤3×ULN without, and ≤5×ULN with hepatic metastasis
   b. Bilirubin ≤1.5×ULN (except patients with Gilbert's syndrome, who must have total bilirubin <3 mg/dL)
11. Women of childbearing potential (WOCBP) must have a negative serum β-human chorionic gonadotropin (β-hCG) at Screening and agree to use a reliable form of contraception (e.g., oral contraceptives, intrauterine device or double barrier method of condom and spermicidal) for at least 28 days prior to the first dose of any study drug during the Treatment Period (and Treatment/Follow-up if receiving study drug), and for at least 23 weeks after the last dose of any study drug. Specific country requirements will be followed (e.g., in the United Kingdom, women of childbearing potential and male patients and their partners of childbearing potential must use two methods of contraception, one of which must be a barrier method, for the duration of the study).
12. Men who are sexually active with WOCBP must agree to follow instructions for method(s) of contraception for the duration of treatment with study drug plus 31 weeks post-treatment completion.

2.2.3 Exclusion Criteria of all Cohorts

Patients who meet ANY of the following criteria will be excluded from study entry.

1. Current or history of clinically significant muscle disorders (e.g., myositis), recent unresolved muscle injury, or any condition known to elevate serum CK levels
2. Immunosuppressive doses of systemic medications, such as steroids or absorbed topical steroids (doses >10 mg/day prednisone or equivalent daily) must be discontinued at least 2 weeks before study drug administration except in the case of tumor-related AE treatment. Patients with a condition requiring chronic systemic treatment with either corticosteroids (inhaled or topical steroids and adrenal replacement steroid doses >10 mg/day prednisone equivalent) or other immunosuppressive medications within 2 weeks of treatment are permitted in the absence of active autoimmune disease.
3. Decreased cardiac function with NYHA>Class 2
4. Uncontrolled or significant heart disorder such as unstable angina
5. Significant abnormalities on ECG at screening. QTcF>450 msec for males or >470 msec for females at screening
6. History of anti-drug antibodies, severe allergic, anaphylactic, or other infusion-related reaction to a previous biologic agent
7. Known history of sensitivity to Tween 20 (polysorbate 20) and polysorbate 80 containing infusions
8. Consumption of non-pasteurized milk on a regular basis, or known significant risk of exposure to opportunistic intracellular infections such as *listeria* or other such pathogens
9. Non-oncology vaccine therapies for prevention of infectious diseases (e.g., HPV vaccine) within 4 weeks of study drug administration. The inactivated seasonal influenza vaccine can be given to subjects before treatment and while on therapy without restriction. Influenza vaccines containing live virus or other clinically indicated vaccinations for infectious diseases (i.e., pneumovax, varicella, etc.) may be permitted; but must be discussed with the Sponsor's Medical Monitor and may require a study drug washout period prior to and after administration of vaccine.
10. Current unresolved infection or history of chronic, active, clinically significant infection (viral, bacterial, fungal, or other) which, in the opinion of the Investigator, would preclude the patient from exposure to a biologic agent, or pose a risk to patient safety
11. Positive test for latent tuberculosis (TB) at Screening (Quantiferon test) or evidence of active TB
12. Lack of peripheral venous access or any condition that would interfere with drug administration or collection of study samples
13. Any uncontrolled medical condition or psychiatric disorder which, in the opinion of the Investigator, would pose a risk to patient safety or interfere with study participation or interpretation of individual patient results
14. Concomitant use of statins while on study. However, a patient using statins for over 3 months prior to study drug administration and in stable status without CK rise may be permitted to enroll
15. Pregnant or breastfeeding
16. Active, known or suspected autoimmune disease. Patients with type I diabetes mellitus, hypothyroidism requiring only hormone replacement, skin disorders (such as vitiligo, psoriasis, or alopecia) not requiring systemic treatment, or conditions not expected to recur in the absence of an external trigger are permitted to enroll.
17. Participation in a another investigational drug trial within 28 days prior to first dose of study drug administration, or while on this study
18. Known history of testing positive for human immunodeficiency virus (HIV) 1&2 or known acquired immunodeficiency syndrome (AIDS)
19. Positive test for hepatitis B virus surface antigen (HBsAg) or detectable hepatitis C virus ribonucleic acid (HCV RNA) indicating acute or chronic infection
20. Symptomatic interstitial lung disease or inflammatory pneumonitis
21. Untreated or active central nervous system (CNS) or leptomeningeal metastases. Patients are eligible if metastases have been treated and patients are neurologically returned to baseline (except for residual signs or symptoms related to the CNS treatment) for at least 2 weeks prior to first dose of study drug administration
22. Evidence of hepatic cirrhosis, confirmed by alkaline phosphatase elevations and concomitantly elevated ALT/AST ratio and hypoalbuminemia (<3.0 g/dL)
23. Evidence of coagulopathy or bleeding diathesis
24. Any uncontrolled inflammatory GI disease including Crohn's Disease and ulcerative colitis.
25. Prior exposure to any CSF1R pathway inhibitors
26. Transfusion completed within 72 hours prior to first dose of study drug administration 2.2.4 Additional Inclusion and Exclusion Criteria for Selected Cohorts 2.2.4.1 Phase 1a 2.2.4.1.1 HuAB1 Monotherapy Cohorts Inclusion:
1. Histologically or cytologically confirmed solid tumor that is locally recurrent or metastatic and has progressed following standard treatment or is not appropriate for standard treatment 2.2.4.1.2 HuAB1+Nivolumab Combination Cohorts
Inclusion:
1. Histologically or cytologically confirmed solid tumor that is locally recurrent or metastatic and has progressed following standard treatment or is not appropriate for standard treatment Exclusion
1. Prior exposure to any PD-1 pathway targeting drug 2.2.4.2 Phase 1b
2.2.4.2.1 Cohort 1b1: NSCLC, (Anti-PD-1 Therapy Naïve, Second or Third Lines)
Inclusion:
1. Patients with histologically or cytologically documented squamous or non-squamous NSCLC who present with Stage IIIB or IV disease (according to version 7 of the international association for the Study of Lung Cancer Staging manual in Thoracic oncology) and with recurrent or progressive disease following multi-modal therapy (radiation therapy, surgical resection or definitive chemoradiation) for locally advanced or metastatic disease
2. Disease progression or recurrence during/after a platinum doublet-based chemotherapy regimen for advanced or metastatic disease.
   Maintenance therapy following platinum doublet-based chemotherapy is not considered a separate therapy regimen.
   Subjects who received platinum-containing adjuvant, neoadjuvant or definitive chemoradiation therapy given for locally advanced disease, and developed recurrent (local or metastatic) disease within 6 months of completing therapy are eligible.
   Subjects with recurrent disease >6 months after platinum-containing adjuvant, neoadjuvant or definitive chemo-radiation therapy given for locally advanced disease, who also subsequently progressed during or after a platinum doublet-based regimen given to treat the recurrence, are eligible.

Exclusion:
1. Prior exposure to any PD-1 pathway targeting drug 2.2.4.2.2 Cohort 1b2: NSCLC (Refractory on Anti-PD-1 Targeting Drugs)
Inclusion
1. Patients with histologically or cytologically documented NSCLC who present with Stage IIIB locally advanced or Stage IV disease.
2. Patient has radiological evidence of disease progression during treatment with a PD-1 pathway targeting drug that did not produce a clinical response (i.e., neither CR nor PR) and with progressive disease as the best response.
3. To be considered refractory, patients should have had no clinical response after receiving at least 2 doses of any PD-1 targeting drug Exclusion
1. Intolerance to any PD-1 pathway targeting drug.
   Intolerance is defined as any treatment-related Grade 4 AE, or any treatment-related Grade 2 or 3 AE that is unacceptable to the patient and persists despite standard countermeasures.

2.2.4.2.3 Cohort 1b3 Melanoma (Anti-PD-1 Therapy Naïve)
Inclusion
1. Patients with histologically or cytologically documented Stage III or IV melanoma as per the American Joint Committee on Cancer (AJCC) staging system who are either refractory to, intolerant to, or have refused, standard therapy for treatment of metastatic melanoma.
2. Objective evidence of disease progression (clinical or radiological) during or after at least 1 BRAF inhibitor (if BRAF V600 mutation positive)
3. Known BRAF wild-type as per regionally acceptable V600 mutational status testing Exclusion
1. Prior therapy with any PD-1 pathway targeting drug.
2. BRAF mutant subjects and those with indeterminate or unknown BRAF status are not permitted to participate in this study 2.2.4.2.4 Cohort 1b4: Melanoma (Refractory or Relapsed on Anti-PD-1 Targeting Drug)
Inclusion:
1. Patients with histologically or cytologically documented unresectable Stage III or IV melanoma as per the AJCC staging system
2. Patient has radiological evidence of disease progression during treatment with a Checkpoint inhibitor or PD-1 targeting drug that did not produce a clinical benefit (no CR, PR, or SD) and progressive disease as the best response or disease progression after the initial clinical benefit of either CR, PR or SD while receiving treatment with a PD-1 targeting drug
3. To be considered refractory, patients should have had no response after receiving at least 2 doses of any PD-1 targeting drug
4. Objective evidence of disease progression (clinical or radiological) during or after at least 1 BRAF inhibitor (if BRAF V600 mutation positive)
5. Prior anticancer therapy including dacarbazine, BRAF inhibitor (if BRAF V600 mutation positive) and/or ipilimumab and palliative radiotherapy must have been completed at least 3 weeks prior to study drug administration
6. No prior treatment with PD-1 targeting drug within 6 weeks prior to first dose of study drug Exclusion:
1. BRAF mutant subjects and those with indeterminate or unknown BRAF status are not permitted to participate in this study
2. Ocular melanoma.
3. Prior intolerance to any PD-1 targeting drug
   Intolerance is defined as any treatment-related Grade 4 AE, or any treatment-related Grade 2 or 3 AE that is unacceptable to the patient and persists despite standard countermeasures. The reason for intolerance should be fully documented.

2.2.4.2.5 Cohort 1b5: Squamous Cell Carcinoma of the Head and Neck (SCCHN) (Second line)
Inclusion:
1. Patients with histologically or cytologically documented recurrent or metastatic SCCHN (oral cavity, pharynx, larynx), stage III or IV and not amenable to local therapy with curative intent (surgery or radiation therapy with or without chemotherapy)
2. Tumor progression or recurrence within 6 months of the last dose of platinum therapy in the adjuvant (i.e. with radiation after surgery), primary (i.e., with radiation), recurrent, or metastatic setting. Clinical progression after platinum therapy is an allowable event for entry and is defined as progression of a lesion at least 10 mm in size that is amenable to caliper measurement (e.g., superficial skin lesion as per RECIST v1.1) or a lesion that has been visualized and photographically recorded with measurements and shown to have progressed.

Exclusion:
1. Histologically confirmed recurrent or metastatic carcinoma of the nasopharynx and any salivary gland or non-squamous histology
2. Prior exposure to any PD-1 pathway targeting drug 2.2.4.2.6 Cohort 1b6: Pancreatic Cancer (Second line)

Inclusion:
1. Histologically or cytologically documented localized or metastatic adenocarcinoma of the pancreas, which has failed (or are not indicated for) standard therapy
2. Patients who may have received prior surgery, radiation therapy for the management of locally advanced or metastatic adenocarcinoma of the pancreas providing that disease progression has been documented. All toxicities should be resolved, and the last fraction of radiation treatment was completed at least 4 weeks prior to first study drug administration Exclusion:
1. Patients with islet cell neoplasms, neuroendocrine or other primary tumors in the pancreas
2. Patients with active pancreatitis
3. Prior exposure to any PD-1 pathway targeting drug
4. Ascites of Grade 2 or higher 2.2.4.2.7 Cohort 1b7: Colorectal Cancer (Third Line)

Inclusion:
1. Histologically or cytologically documented adenocarcinoma of colon or rectum
2. Metastatic CRC with documented disease progression after the last administration of standard therapies or intolerance to standard therapies (and approved therapies had to include a fluoropyrimidine, oxaliplatin, irinotecan, bevacizumab, and, if KRAS wild-type, cetuximab or panitumumab).

Exclusion:
1. Prior exposure to any PD-1 pathway targeting drug 2.2.4.2.8 Cohort 1b8: Malignant Glioma (First Recurrence)

Inclusion:
1. Histologically or cytologically documented advanced World Health Organization (WHO) Grade IV malignant glioma (glioblastoma or gliosarcoma)
2. Previous treatment with surgery, radiotherapy and temozolomide
3. Documented first recurrence of GBM by diagnostic biopsy or contrast-enhanced MRI performed within 21 days of first study drug administration per Response Assessment in Neuro-oncology (RANO) criteria
4. If on steroids, dose must be stable or decreased for a minimum of 5 days prior to baseline MRI Exclusion:
1. Prior treatment with bevacizumab or another VEGF- or VEGFR-targeting agent
2. Recent evidence of more than Grade 1 CNS hemorrhage on baseline MRI scan
3. History or evidence upon physiological/neurological exam of CNS disease (e.g., seizures) unrelated to cancer unless adequately controlled by medication or potentially interfering with the study treatment
4. Patients unable to have a head contrast-enhanced MRI due to a pre-existing medical condition including a pacemaker or implantable cardioverter defibrillator (ICD) device
5. More than 1 recurrence of glioblastoma or gliosarcoma
6. Prior exposure to any PD-1 pathway targeting drug 2.3 Concomitant Medications All medications taken within 28 days before the administration of the first dose of any study drug and all concomitant therapy administered during the study until 100 days after last dose of any study drug will be recorded.

Information on all prior treatments indicated for advanced cancer, including chemotherapy, biochemotherapy, immunotherapy, radiation, surgery, biologic, and experimental therapy will be collected.

No concomitant medication information will be collected following patient discontinuation from the study except for concomitant medication use associated with study drug-related AEs or AEs that lead to discontinuation from the study.

2.3.1 Prohibited and/or Restricted Treatments

The following medications are prohibited during the study (unless utilized to treat a drug-related AE or specified in the eligibility section):

Immunosuppressive Agents

Immunosuppressive doses of systemic corticosteroids. Inhaled or topical steroids, and adrenal replacement steroid doses >10 mg daily prednisone equivalent, are permitted in the absence of active autoimmune disease. Steroids are also permitted to treat tumor-related AEs as clinically indicated.

Vaccines except as noted in Section 4.3.2

Statins for treatment of hypercholesterolemia. Statins will be allowed only if the patient is on a stable dose for over 3 months prior to the study and is in stable status without any CK elevations Other therapies including biologic, immunotherapy, extensive non-palliative radiation therapy, standard treatments, or investigational agents or devices 2.3.2 Permitted Therapy Patients are permitted to use of topical, ocular, intra-articular, intranasal, and inhaled corticosteroids (with minimal systemic absorption). Adrenal replacement steroid doses >10 mg daily prednisone are permitted. A brief (less than 3 weeks) course of corticosteroids for prophylaxis (e.g., contrast dye allergy) or for treatment of non-autoimmune conditions (e.g., delayed-type hypersensitivity reaction caused by a contact allergen) and also for the treatment of tumor-related AE is permitted.

Concomitant palliative and supportive care for disease-related symptoms (including bisphosphonates and RANK-L inhibitors) is allowed if initiated prior to first dose of study drug administration. Transfusions are permitted as needed.

The inactivated seasonal influenza vaccine can be given to subjects while on therapy without restriction. Influenza vaccines containing live virus or other clinically indicated vaccinations for infectious diseases (i.e., pneumovax, varicella, etc.) may be permitted; but must be discussed with the Sponsor's Medical Monitor and may require a study drug washout period prior to and after administration of the vaccine.

Concomitant use of statins will be allowed only if the patient is on a stable dose for over 3 months prior to the study and is in stable status without any CK elevations.

No routine premedication will be administered for initial HuAB1 and nivolumab doses. If a patient develops nausea, vomiting, or other infusion-related AEs, the patient may be pre-medicated with anti-emetics, steroids, or antihistamines prior to subsequent infusions of study drugs at the discretion of the Investigator. The treatment will be administered according to the institution's standard practice, and should be captured on the patient's CRF.

2.4 Discontinuation of Patients Following any Treatment with Study Drug

Patients MUST discontinue study drugs for any of the following reasons:

Withdrawal of informed consent (patient's decision to withdraw for any reason)

Any clinical significant AE, abnormal laboratory test results or intercurrent illness which, in the opinion of the Investigator, indicates that continued participation in the study is not in the best interest of the patient Patients Who are Required to have Prohibited Concomitant Medications Pregnancy Termination of the Study by the Sponsor Loss of ability to freely provide consent through imprisonment or involuntary incarceration for treatment of either a psychiatric or physical (e.g., infectious disease) illness Documented disease progression or clinical deterioration while receiving active study therapy Non-Compliance by the Patient All patients who discontinue study treatment should comply with protocol specified follow-up procedures as outlined in Section 6. The only exception to this requirement is when a patient withdraws consent for all study procedures or loses the ability to consent freely (i.e., is imprisoned or involuntarily incarcerated for the treatment of either a psychiatric or physical illness).

If a patient was withdrawn before completing the study, the reason for withdrawal must be entered on the appropriate CRF. The date and reason for cessation of HuAB1 and/or nivolumab will be documented, and the Investigator must make every effort to perform the Treatment Completion/Early Termination visit procedures. Patients will be followed for 100 days after the last dose of HuAB1 for safety and those with ongoing SAEs will be followed until either resolution or stabilization.

2.5 Post-Treatment Follow Up

Patients who discontinue treatment while still receiving clinical benefit (i.e., CR, PR or SD) should get follow-up tumor scans per-protocol to determine the duration of response, unless consent is withdrawn.

3 STUDY DRUGS

In this study, both the study drugs, HuAB1 and nivolumab, are considered Investigational [Medicinal] Products (IP/IMP). The product descriptions for HuAB1 and nivolumab are described in Table 3 and Table 4:

TABLE 3

Study Drug for Phase 1a Monotherapy Cohorts

| Product Description/Class and Dosage Form | Potency | IP | Open Label | Packaging/Appearance | Storage Conditions (per label) |
|---|---|---|---|---|---|
| HuAB1 Solution for Injection | 100 mg (20 mg/mL) | 5 mL per vial | X vials per carton/open-label | Sterile, aqueous, colorless, pyrogen-free solution in 5 mL Type 1 glass vials fitted with butyl rubber stoppers and flip-up aluminum seals | 2-8° C. (36-46° F.). Protect from freezing |

TABLE 4

Study Drugs for Phase 1a Combination Dose Escalation and Phase 1b Dose Expansion Cohorts

| Product Description/Class and Dosage Form | Potency | IP | Open Label | Packaging/Appearance | Storage Conditions (per label) |
|---|---|---|---|---|---|
| Nivolumab Solution for Injection | 100 mg (10 mg/mL) | 10 mL per vial | 10 vials per carton/Open-label | Clear to opalescent colorless to pale yellow liquid. May contain particles | 2-8° C. Protect from light and freezing |
| HuAB1 Solution for Injection | 100 mg (20 mg/mL) | 5 mL per vial | X vials per carton/open-label | Sterile, aqueous, colorless, pyrogen-free solution in 10 mL Type 1 glass vials fitted with butyl rubber stoppers and flip-up aluminum seals | 2-8° C. (36-46° F.). Protect from freezing |

3.1 Investigational Products

An investigational product, also known as investigational medicinal product in some regions, is defined as a pharmaceutical form of an active substance or placebo being tested or used as a reference in a clinical study, including products already with a marketing authorization but used or assembled (formulated or packaged) differently than the authorized form, or used for an unauthorized indication, or when used to gain further information about the authorized form. In this protocol, the investigational products are HuAB1 and nivolumab.

3.2 Study Drug Dosing and Dose Modification 3.2.1 Dosing

For the combination therapy, nivolumab should always be administered first as a 30-minute IV infusion, with a 30-minute rest between 2 infusions, followed by HuAB1 30-minute infusion. Patients may be dosed no less than 12 days from the previous dose.

For the 4 mg/kg monotherapy cohort (1aM2) and combination dose escalation cohorts 1aC2 and 1aC3, the dose interval between the first and second patients in each cohort should be at least 24 hours for safety monitoring.

Dosing calculations should be based on the body weight assessed at Cycle 1 Day 1 prior to the first dose of study drug administration. It is not necessary to re-calculate subsequent doses if the patient's weight is within 10% of the weight used to calculate the previous dose. All doses should be rounded to the nearest milligram.

Patients should be carefully monitored for infusion reactions during study drug administration. If an acute infusion reaction is noted, patients should be managed according to the guidelines in Section 5.3.10 and Appendix E and F.

Doses of study drugs may be interrupted, delayed, or discontinued depending on how well the patient tolerates the treatment.

All vials are for single use only. Further instructions on study drug preparation and administration will be provided in the Pharmacy Manual.

3.2.1.1 Nivolumab Dosing

Patients in combination therapy cohorts will receive the nivolumab infusion first at a dose of 3 mg/kg as a 30-minute IV infusion, on Day 1 of each 14-day treatment cycle.

There will be no dose escalations or reductions of nivolumab allowed. Patients may be dosed no less than 12 days from the previous dose. There are no pre-medications recommended for nivolumab on the first cycle. Refer to the nivolumab IB for preparation and handling instructions.

3.2.1.2 HuAB1 Dosing

For patients in the combination therapy cohorts, the HuAB1 infusion will be administered 30 minutes after the end of the nivolumab infusion as a 30-minute IV infusion, on Day 1 of each 14-day treatment cycle. For patients in the monotherapy cohorts, the HuAB1 infusion can be initiated at any time as a 30-minute IV infusion on Day 1 of each 14-day treatment cycle.

HuAB1 dosing may be modified based on toxicities noted during the treatment period. If necessary, the dose will be adjusted based on the toxicity-modification table (Appendices E and F).

A research pharmacist (or other responsible personnel) will prepare the solution for administration. After calculating the number of vials, based on the patient's weight, the study drug product will be diluted with 0.9% Sodium Chloride Injection, USP. Prepared HuAB1 should be administered within 6 hours after preparation (ambient temperature). The IV administration setup for HuAB1 infusion must contain a 0.22 µm in-line filter or a 0.22 µm syringe filter.

HuAB1 will be administered under medical supervision as a 30 minute (±5 minutes) IV infusion via a peripheral vein or central venous catheter. No incompatibilities between HuAB1 infusion and polyvinyl chloride (PVC), ethylene/propylene IV components, or glass bottles have been observed.

3.2.2 Dose Delay for HuAB1 and Nivolumab

Administration of HuAB1 in monotherapy or HuAB1/nivolumab in combination therapy should be delayed for the following:

Any Grade 3 fatigue which does not resolve to Grade 1 or baseline before the next treatment visit Any Grade 2 or 3 drug-related laboratory abnormalities would not require a dose delay unless clinically indicated or specified in the protocol or Adverse Event Management table. Please discuss with the Sponsor's Medical Monitor or designee as needed.

For dose delays or modifications for all other AEs please refer to the AE Management tables in Appendix E.

Patients who require a dose delay of HuAB1 or HuAB1+ nivolumab should be re-evaluated weekly or more frequently if clinically indicated and resume study drug dosing when re-treatment criteria are met.

If a patient experiences an infusion reaction to HuAB1, or nivolumab, or both study drugs, the infusion reaction should be treated following the infusion reaction treatment guidelines in Section 5.3.10 and Appendix E and F.

3.2.3 Criteria to Resume Treatment with HuAB1 and Nivolumab

Patients may resume treatment with HuAB1 or HuAB1+ nivolumab when the drug-related AE(s) resolve(s) to Grade ≤1 or baseline as noted in the AE management tables in Appendices E and F.

3.2.4 Dose Reduction with HuAB1

Dose reductions for HuAB1 may be permitted for patients on prolonged treatment beyond the DLT period in Phase 1a or any patient in Phase 1b per the guidelines in the appropriate AE management tables in Appendices E and F. If dose reductions or interruptions that do not fall within these guidelines are being considered by the Investigator, these will require discussion with and approval by the Sponsor, or designee.

3.2.5 Dose Discontinuation Criteria for HuAB1 and Nivolumab

Treatment of HuAB1 in monotherapy or HuAB1 in combination with nivolumab should be permanently discontinued for the following:

Any Grade 2 drug-related uveitis, eye pain or blurred vision that does not respond to topical therapy and does not improve to Grade 1 within the second re-treatment period OR that requires systemic treatment Any Grade 3 or higher infusion related reactions and hypersensitivity requiring discontinuation and re-initiation of therapy will require consultation with the Sponsor's Medical Monitor or designee.

Any Grade 3 non-skin, drug-related AE lasting >7 days, including drug-related uveitis, pneumonitis, hypoxia, bronchospasm, and endocrinopathies with the following exceptions:

Grade 3 drug-related endocrinopathies adequately controlled with only physiologic hormone replacement do not require discontinuation Grade 3 drug-related laboratory abnormalities do not require treatment discontinuation except:

Grade 3 drug-related thrombocytopenia >7 days or associated with Grade ≥2 bleeding requires discontinuation Any drug-related liver function test (LFT) abnormality that meets the following criteria requires discontinuation:

AST or ALT 10×ULN

Total bilirubin >3×ULN (>5×ULN with concurrent liver metastases)

AST or ALT >3×ULN AND total bilirubin >2×ULN, in the absence of a concurrent increase of alkaline phosphatase Any Grade 4 drug-related AE or laboratory abnormality, except for the following events which do not require discontinuation:

Grade 4 neutropenia ☐ 7 days

Grade 4 lymphopenia or leukopenia ☐ 7 days

Isolated Grade 4 amylase or lipase abnormalities that are not associated with symptoms or clinical manifestations of pancreatitis. The Sponsor's Medical Monitor should be consulted for Grade 4 amylase or lipase abnormalities.

Isolated Grade 4 electrolyte imbalances/abnormalities that are not associated with clinical sequelae and are corrected with supplementation/appropriate management within 72 hours of their onset Grade 4 drug-related endocrinopathy AEs, such as adrenal insufficiency, adrenocorticotropic hormone (ACTH) deficiency, hyper- or hypothyroidism, or glucose intolerance, which resolve or are adequately controlled with physiologic hormone replacement (corticosteroids, thyroid hormones) or glucose-controlling agents, respectively, may not require discontinuation after discussion with and approval from the Sponsor's Medical Monitor.

Any event that leads to delay in dosing lasting >6 weeks from the previous dose requires discontinuation, with the following exceptions:

Dosing delays to allow for prolonged steroid tapers to manage drug-related adverse events are allowed. Prior to re-initiating treatment in a patient with a dosing delay lasting >6 weeks from the previous dose, the Sponsor's Medical Monitor must be consulted. Tumor assessments should continue as per-protocol even if dosing is delayed. Periodic study visits to assess safety and laboratory studies should also continue per protocol, or more frequently if clinically indicated during such dosing delays or per the Investigator's discretion Dosing delays lasting >6 weeks from the previous dose that occur for non-drug-related reasons may be allowed if approved by the Sponsor's Medical Monitor. Prior to re-initiating treatment in a patient with a dosing delay lasting >6 weeks, the Sponsor's Medical Monitor must be consulted. Tumor assessments should continue per protocol every 8 weeks even if dosing is delayed. Periodic study visits to assess safety and laboratory studies should also continue per-protocol or more frequently if clinically indicated during such dosing delays or per the Investigator's discretion.

Any AE, laboratory abnormality, or intercurrent illness which, in the judgment of the Investigator, presents a substantial clinical risk to the patient with continued HuAB1 and/or nivolumab dosing Any Grade 3 or higher neurological toxicity Any Grade 3 or higher periorbital edema and persistent Grade 2 periorbital edema requiring 2 missed doses unless approved by Sponsor's Medical Monitor Any Grade 3 or higher drug-related diarrhea or colitis interfering with activities of daily living.

Any Grade 3 or 4 skin toxicity

Any Grade 3 or higher uveitis

If the causality of the adverse event requiring discontinuation is confirmed to be due to one of the study drugs in the combination therapy, the other drug may be continued per protocol schedule under the following scenarios:

Timely resolution of the adverse event based on the treatment modification table Clinical benefit is shown by the subject based on Investigator assessment 3.2.6 Infusion Delays and Missed Doses with HuAB1 and Nivolumab In the case that an infusion cannot be administered at a scheduled visit, it must be administered as soon as possible. If the delay is between 1 and 3 days, the procedures at the original scheduled visit should be performed. If the delay is more than 3 days, the procedures at the next visit should be performed, and subsequent visits will be reset to follow a 2-week dosing interval (the infusion at the original scheduled visit will be considered a missed dose). The time between two treatment cycles should be no less than 12 days.

Patients may miss up to 2 consecutive doses (up to 6 weeks between doses) and may resume the study drug if the event returns to baseline or ≤Grade 1 within 6 weeks of treatment interruption. Omission of additional dosing longer than 6 weeks for AEs will necessitate the patient's discontinuation from the study unless allowed by the Sponsor. Patients may miss doses in the course of participation in the study, including missed doses for scheduled vacations or other personal reasons as needed, but not more than 2 doses sequentially unless approved by the Sponsor's Medical Monitor.

3.2.7 Intra-Patient Dose Escalation with HuAB1 and Nivolumab

Intra-patient dose escalation is not allowed for nivolumab or HuAB1.

3.2.8 Treatment Beyond Disease Progression with HuAB1 and Nivolumab

Accumulating evidence indicates a minority of patients treated with immunotherapy may derive clinical benefit despite initial evidence of progressive disease (Wolchok, 2009)

Patients treated with HuAB1 and nivolumab will be permitted to continue HuAB1 and nivolumab treatment beyond initial RECIST v1.1 defined progressive disease, assessed by the Investigator, as long as the following criteria are met:

Patients who will be treated beyond disease progression must review and sign an ICF before continuing on study drug Investigator-assessed clinical benefit, and do not have rapid disease progression Tolerance of study drugs Stable performance status Treatment beyond progression will not delay an imminent intervention to prevent serious complications of disease progression (e.g., CNS metastases)

A radiographic assessment/scan should be performed approximately 8 weeks after initial Investigator-assessed progression to determine whether there has been a decrease in the tumor size or continued progressive disease. The assessment of clinical benefit should be balanced by clinical judgment as to whether the patient is clinically deteriorating and unlikely to receive any benefit from continued treatment with HuAB1 and nivolumab.

If the Investigator feels that the HuAB1 and nivolumab patient continues to achieve clinical benefit by continuing treatment, the patient should remain on the trial and continue to receive monitoring according to the time and event schedules per protocol.

For the patients who continue nivolumab study therapy beyond progression, further progression is defined as an additional 10% increase in tumor burden from time of initial progression. This includes an increase in the sum of diameters of all target lesions and/or the diameters of new measurable lesions compared to the time of initial progression. HuAB1 and nivolumab treatment should be discontinued permanently upon documentation of further progression.

Assessment for new lesions will follow guidelines in RECIST v1.1 (Appendix G).

3.2.9 Dose Modification Algorithms for Immuno-Oncology Agents

Immuno-oncology agents are associated with AEs that can differ in severity and duration compared to AEs caused by other therapeutic classes. HuAB1 and nivolumab are considered immuno-oncology agents in this protocol. Early recognition and management of AEs associated with immuno-oncology agents may mitigate severe toxicity. Management algorithms have been developed to assist Investigators in assessing and managing the following classes of AEs:

Gastrointestinal
Renal
Pulmonary
Hepatic
Endocrinopathy
Skin
Neurological
Infusion reaction
Periorbital edema
Uveitis 3.2.10 Treatment of HuAB1 and Nivolumab Related Infusion Reactions HuAB1 and nivolumab may induce infusion or hypersensitivity reactions. If such a reaction were to occur, it may manifest with fever, chills, rigors, headache, rash, pruritus, arthralgia, hypo- or hypertension, bronchospasm, or other symptoms.

Infusion reactions should be graded according to CTCAE v4.03 guidelines. Any Grade 3 or 4 infusion reaction should be reported within 24 hours to the study Medical Monitor and reported as an SAE if it meets the criteria.

The nivolumab infusion will be administered first, with a 30-minute rest between the 2 infusions, followed by HuAB1 30-minute infusion. It may be unclear if an infusion reaction is due to HuAB1, nivolumab, or to both study drugs. Therefore, one set of treatment recommendations (based on the most conservative treatments for infusion reactions due to either study drug) is provided below and may be modified based on clinical judgment, local treatment standards and guidelines, and/or specific symptoms, as appropriate:

For Grade 1 Symptoms:

(Mild reaction [e.g., localized cutaneous reactions including mild pruritus, flushing, rash], requires infusion rate to be decreased; intervention may be indicated.)

Decrease the rate of the study drug infusion until recovery from symptoms.

Remain at bedside and monitor the patient's vital signs until resolution of symptoms. Diphenhydramine 50 mg may be administered at the discretion of the treating physician.

When symptoms resolve, restart the infusion at the original infusion rate.

If a patient has an infusion reaction with nivolumab, HuAB1 can be given (without prophylactic medications) if the infusion reaction resolves within 3 hours. For scheduling purposes, HuAB1 infusion may be given the next day. Prophylactic pre-infusion medications should be given prior to all subsequent nivolumab infusions.

If a patient has an infusion reaction with HuAB1, prophylactic pre-infusion medications should be given prior to all subsequent HuAB1 and nivolumab infusions.

The following prophylactic pre-infusion medications are recommended prior to future infusions of HuAB1 and nivolumab: diphenhydramine 50 mg (or equivalent) and/or paracetamol (acetaminophen) 325 to 1000 mg at least 30 minutes before additional study drug administrations.

For Grade 2 Symptoms:

(Moderate reaction [i.e., any symptom not listed above (mild symptoms) or below (severe symptoms) such as generalized pruritus, flushing, rash, dyspnea, hypotension with systolic blood pressure >80 mmHg], requires infusion interruption but responds promptly to symptomatic treatment [e.g., antihistamines, nonsteroidal anti-inflammatory drugs, narcotics, corticosteroids, IV fluids]; prophylactic pre-infusion medications indicated for <24 hours.)

Interrupt the study drug infusion.

Begin an IV infusion of normal saline, and treat the patient with diphenhydramine 50 mg IV (or equivalent) and/or paracetamol (acetaminophen) 325 to 1000 mg.

Remain at bedside and monitor the patient's vital signs until resolution of symptoms. Corticosteroid therapy may be administered at the discretion of the treating physician.

When symptoms resolve, restart the infusion at 50% of the original infusion rate; if no further complications ensue after 30 minutes, the rate may be increased to 100% of the original infusion rate.

Monitor the patient closely. If symptoms recur, immediately discontinue the infusion; no further study drug will be administered at that visit. Administer diphenhydramine 50 mg IV, and remain at bedside and monitor the patient until resolution of symptoms.

If a patient has an infusion reaction with nivolumab infusion, HuAB1 infusion can be given (without prophylactic medications) if the infusion reaction resolves within 3 hours. For scheduling purposes, the HuAB1 infusion may be given the next day. Prophylactic pre-infusion medications should be given prior to all subsequent nivolumab infusions.

If a patient has an infusion reaction with HuAB1, prophylactic pre-infusion medications should be given prior to all subsequent HuAB1 and nivolumab infusions.

The following prophylactic pre-infusion medications are recommended prior to future infusions of HuAB1 and nivolumab: diphenhydramine 50 mg (or equivalent) and/or paracetamol (acetaminophen) 325 to 1000 mg should be administered at least 30 minutes before additional study drug administrations. If necessary, corticosteroids (up to 25 mg of SoluCortef or equivalent) may be used.

The amount of study drug infused must be recorded.

For Grade 3 or Grade 4 Symptoms:

(Severe reaction such as bronchospasm, generalized urticaria, systolic blood pressure <80 mmHg, or angioedema; Grade 3 symptoms including prolonged symptom, which requires 6 or more hours to respond to symptomatic medication and/or discontinuation of infusion; recurrence of symptoms following initial improvement; hospitalization indicated for other clinical sequelae, such as renal impairment, pulmonary infiltrates; Grade 4: life-threatening; pressor or ventilation support indicated.)

Immediately discontinue the study drug infusion. No further study drug will be administered. The amount of study drug infused must be recorded on the CRF.

Begin an IV infusion of normal saline, and treat the patient as follows: Recommend bronchodilators, epinephrine 0.2 to 1.0 mg of a 1:1,000 solution for subcutaneous administration or 0.1 to 0.25 mg of a 1:10,000 solution injected slowly for IV administration, and/or diphenhydramine 50 mg IV with methylprednisolone 100 mg IV (or equivalent), as needed.

Remain at bedside and monitor the patient's vital signs until recovery from symptoms.

The patient should be monitored until the Investigator is comfortable that the symptoms will not recur.

Investigators should follow their institutional guidelines for the treatment of anaphylaxis.

In the case of late-occurring hypersensitivity symptoms (e.g., appearance of a localized or generalized pruritus within 1 week after treatment), symptomatic treatment may be given (e.g., oral antihistamine, or corticosteroids).

3.3 Method of Assigning Patient Identification

Patients must be able to provide written informed consent and meet all eligibility criteria. No waivers of inclusion or exclusion criteria will be granted by Sponsor or its designee for any patient enrolled in the study. Before enrolling a patient, all eligibility criteria must be satisfied.

Patients who qualify for Phase 1a of the study will be enrolled as follows:

Three patients in the Phase 1aM1 monotherapy cohort will be enrolled first to be treated with 2 mg/kg HuAB1 every 14 days during the 28-day DLT period.

Once the above monotherapy cohort is fully enrolled, a cohort (1aC1) of 3 new patients will be enrolled to be treated with 1 mg/kg HuAB1 in combination with 3 mg/kg nivolumab every 14 days during the 28-day DLT period.

Dose escalation into the 4 mg/kg HuAB1 monotherapy cohort (1aM2) will proceed once the DLT period is cleared in the 2 mg/kg HuAB1 monotherapy cohort (1aM1).

Dose escalation into increasing dose levels of HuAB1 in combination with nivolumab will proceed until DLTs are observed either in the HuAB1 monotherapy or the HuAB1 in combination with nivolumab cohorts after discussion and agreement between the participating Investigators and Sponsor's Medical Monitor.

In Phase 1b, approximately 30 patients will be enrolled per cohort. Enrollment will be open for all cohorts in parallel and will continue until the enrollment target is reached. Once a cohort is filled, further enrollment will be restricted to the cohort(s) that have not been filled. A total of approximately 240 patients will be enrolled in the Phase 1b arm of the study.

The Investigator may repeat qualifying lab tests and vitals/ECGs prior to enrollment if a non-qualifying finding is considered an error or an acute finding is likely to meet eligibility criteria upon repeat testing.

3.4 Blinding/Unblinding

This is an open-label study and there will be no blinding or unblinding of patients during this study.

4 STUDY ASSESSMENTS AND PROCEDURES 4.1 Schedule of Assessments

The schedule of assessment tables are attached to the protocol as Appendices A, B, and C.

4.2 Study Procedures by Visit 4.2.1 Phase 1a Monotherapy 4.2.1.1 Screening Period (Day −28 to Day 0)

Patients who have fully consented to participation in the study will undergo Screening assessments within 28 days (4 weeks) prior to administration of the first infusion of HuAB1 (unless otherwise stated). To determine if the patient meets all inclusion criteria and does not violate any exclusion criteria, the following procedures will be performed (Appendix A):

Written, signed informed consent must be collected prior to any study-specific procedures Complete medical and disease history Demographic and baseline characteristics Complete physical examination, including height and weight Vital signs (blood pressure, pulse, respiratory rate, and temperature in supine position after 5 minutes rest)

ECOG performance status evaluation

Screening labs (as described in Appendix A, footnote g)

Clinical safety labs (as described in Appendix A, footnote h)

12-lead ECG (required at Screening, and if clinically indicated during the study)

Radiological imaging: CT/MRI is to be performed within 28 days prior to the first infusion of HuAB1. If the MRI is performed as part of the patient's standard of care within 28 days of the first study infusion it does not need to be repeated if the documentation of results is provided and is adequate for an assessment.

Serum pregnancy test (β-hCG), for women of childbearing potential

Biopsy collection (for analyses described in Appendix D)

SAE reporting, if applicable

Document prior and concurrent medications 4.2.1.2 Cycle 1, Day 1

The following procedures will be performed:

Prior to HuAB1 infusion (within <72 hours unless otherwise stated):

Verification of eligibility

Update medical and disease history to capture any changes from Screening

Physical examination, including weight

Vital signs (blood pressure, pulse, respiratory rate and temperature in supine position after 5 minutes rest)

ECOG performance status evaluation

Clinical safety labs (as described in Appendix A, footnote h); results must be reviewed before dosing)

Serum β-hCG (evaluated by local laboratories) will be performed prior to the first dose of HuAB1 only on women of childbearing potential Blood collection for:

Serum (for analyses described in Appendix D, excluding nivolumab analyses)

Whole blood (for analyses described in Appendix D)

Frozen PBMC (for T cell phenotype analysis)

AE reporting, if applicable

Review of concomitant medications

Study drug administration: HuAB1 by IV infusion over 30 minutes

Post HuAB1 administration:

Post-dose vital signs (heart rate, blood pressure, and temperature in supine position after 5 minutes rest) at the following time points after completion of the IV infusion:

5 MINUTES, 15 MINUTES, 30 MINUTES, AND 1 HOUR 15 minutes (+5 minutes) post-dose:

Blood collection for serum (for HuAB1 PK)

4 hours (±60 minutes) post-dose:

Blood collection for serum (for HuAB1 PK)

4.2.1.3 Cycle 1, Day 2

Study patients will return to the study center on Day 2 for 24-hour (±6 hours) post-dose assessments. No treatment will be administered during this visit, but the following assessments will be completed:
Blood collection for:
Serum (for HuAB1 PK and cytokine multiplex panel)
Whole blood (for gene expression analysis)
AE reporting, if applicable
Review of concomitant medications

4.2.1.4 Cycle 1, Day 4

Study patients will return to the study center on Day 4 for 72-hour (±12 hours) post-dose assessments. No treatment will be administered during this visit, but the following assessments will be completed:
Blood collection
Serum (for HuAB1 PK)
Whole blood (for $CD14^+/CD16^+$ monocyte and gene expression analyses)
AE reporting, if applicable
Review of concomitant medications

4.2.1.5 Cycle 1, Day 8

Study patients will return to the study center on Day 8 for 168-hour (±24 hours) post-dose assessments. No treatment will be administered during this visit, but the following assessments will be completed:
Physical examination
Vital signs (blood pressure, pulse, respiratory rate, and temperature in supine position after 5 minutes rest)
Clinical safety labs (as described in Appendix A, footnote h)
Blood collection for:
Serum (for HuAB1 PK and cytokine multiplex panel)
Whole blood (for $CD14^+/CD16^+$ monocyte and gene expression analyses)
Frozen PBMC (for T cell phenotype analysis)
AE reporting, if applicable
Review of concomitant medications

4.2.1.6 Cycle 2, Day 1

The following procedures will be performed:
Prior to HuAB1 infusion (within ≤72 hours unless otherwise stated):
Physical examination, including weight
Vital signs (blood pressure, pulse, respiratory rate, and temperature in supine position after 5 minutes rest)
ECOG performance status evaluation
Clinical Safety Labs (as Described in Appendix a, Footnote h; Results Must be Reviewed Before Dosing:
Blood collection for:
Serum (for analyses described in Appendix D, excluding nivolumab analyses)
Whole blood (for analyses described in Appendix D, except the MDSC panel)
Frozen PBMC (for T cell phenotype analysis)
AE reporting, if applicable
Review of concomitant medications
Study drug administration: HuAB1 by IV infusion over 30 minutes
Post HuAB1 administration:
Post-dose vital signs (blood pressure, pulse, respiratory rate, and temperature in supine position after 5 minutes rest) at the following time points after completion of the IV infusion:
5 minutes, 15 minutes, 30 minutes, and 1 hour
15 minutes (+5 minutes) post-dose:
Blood Collection for Serum (for HuAB1 PK)

4.2.1.7 End of Cycle 2

For Phase 1a patients in monotherapy cohort, if at the end of Cycle 2, the Investigator determines that the patient may benefit from continued dosing with HuAB1, entry into the Extended Treatment Period may be offered.

If the patient is continuing onto the Extended Treatment Period (Cycle 3 and beyond), proceed to procedures outlined in Section 6.2.1.8.

If the patient does not qualify to receive further doses of HuAB1, the patient will return to the clinic for the Treatment Completion/Early Termination visit outlined in Section 6.2.1.9.

4.2.1.8 Extended Treatment—Cycle 3 and Subsequent Cycles, Day 1

Phase 1a extended treatment for patients in monotherapy cohort may begin on Cycle 3, Day 1 (Study Day 29). Dosing will be discontinued if the patient experiences either disease progression or unacceptable toxicity.

At each infusion visit, patients are to remain at the study site after each administration of HuAB1 until completion of all post-dose assessments for safety monitoring. The following assessments will be performed at each visit unless otherwise noted (Appendix A):
Prior to each infusion of study drug (within 72 hours unless otherwise stated):
Physical examination, including weight
Vital signs (blood pressure, pulse, respiratory rate, and temperature in supine position after 5 minutes rest)
ECOG performance status evaluation
Clinical safety labs (as described in Appendix A, footnote h; results must be reviewed before dosing)
Radiological imaging: CT/MRI scan performed every 8 weeks for the first 12 months for patients who remain on treatment (and every 12 weeks thereafter) and 28 days (+7 days) after the last dose of study treatment.
Biopsy Collection (Prior to Cycle 3 Only; for Analyses Described in Appendix D)
Blood collection for:
Serum (for analyses described in Appendix D) with the following exceptions:
HuAB1 PK for Cycles 3, 5, 9, 13, and 21
HuAB1 ADA for Cycles 3, 5, 13, and 21
ANA for Cycles 3, 5, 9, 13, 21, then every 6 cycles while on treatment
CSF1 and IL34 for Cycle 3 and 9
Cytokine multiplex panel for Cycles 3, 9, and 21
Whole blood (for analyses described in Appendix D) with the following exceptions:
$CD14^+/CD16^+$ monocytes for Cycle 3, and 9
MDSC panel for Cycle 3 only
Gene expression analysis for Cycle 3, 5, 9, 13, and 21
AE reporting, if applicable
Review of concomitant medications
Study drug administration: HuAB1 by IV infusion over 30 minutes
Post HuAB1 administration:
Post-dose vital signs (blood pressure, pulse, respiratory rate, and temperature in supine position after 5 minutes rest) at the following time points after completion of the IV infusion:
5 MINUTES, 15 MINUTES, 30 MINUTES, AND 1 HOUR
15 minutes (+5 minutes) post-dose:
Blood collection for serum (for analyses described in Appendix D) with the following exceptions:
HuAB1 PK for Cycle 8 only

4.2.1.9 Treatment Completion or Early Termination Visit

Patients will return to the study center approximately 28 (±7) days after their last infusion of HuAB1.

The following assessments will be performed:
Physical examination, including weight
Vital signs (blood pressure, pulse, respiratory rate, and temperature in supine position after 5 minutes rest)
ECOG performance status evaluation
Clinical safety labs (as described in Appendix A, footnote h)
12-lead ECG
Radiological imaging: CT/MRI scan does not need to be repeated if performed within 8 weeks prior to the Treatment Completion/Early Termination Visit or if tumor progression was previously determined.
Serum pregnancy test (β-hCG), if applicable
Biopsy for patients who progressed (for analyses described in Appendix D)
Blood collection
Serum (for analyses described in Appendix D, excluding nivolumab analyses)
Whole blood (for $CD14^+/CD16^+$ monocyte analysis and gene expression analysis only)
AE reporting, if applicable
Review of concomitant medications

4.2.2 Phase 1a Combination Dose Escalation

4.2.2.1 Screening Period (Day −28 to Day 0)

Patients who have consented to participation in the study will undergo screening assessments within 28 days (4 weeks) prior to administration of the first infusion of HuAB1 and nivolumab (unless otherwise stated). To determine if the patient meets all inclusion criteria and does not violate any exclusion criteria, the following procedures will be performed (Appendix B):

Written, signed informed consent must be collected prior to any study-specific procedures
Complete medical and disease history
Demographic and baseline characteristics
Complete physical examination, including height and weight
Vital signs (blood pressure, pulse, respiratory rate, and temperature in supine position after 5 minutes rest; pulse oximetry at rest and after exertion)
ECOG performance status evaluation
Screening labs (as described in Appendix B, footnote g)
Clinical safety labs (as described in Appendix B, footnote h)
12-lead ECG (required at Screening, and if clinically indicated during the study)
Radiological imaging: CT/MRI to be performed within 28 days prior to Cycle 1 Day 1. If the CT/MRI is performed as part of the patient's standard of care within 28 days of Cycle 1 Day 1, it does not need to be repeated if the documentation of results is provided and is adequate for RECIST 1.1
Serum pregnancy test (β-hCG), ≤δ days prior to Cycle 1, Day 1, for women of childbearing potential
Biopsy collection (for analyses described in Appendix D)
SAE reporting, if applicable
Document prior and concurrent medications

4.2.2.2 Cycle 1, Day 1

The following procedures will be performed:
Prior to HuAB1 and nivolumab infusion (within ≤72 hours unless otherwise stated):
Verification of eligibility
Update medical and disease history to capture any changes from Screening
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Serum β-hCG (evaluated by local laboratories) will be performed prior to the first dose of study drug only on women of childbearing potential
Blood collection for:
Serum (for analyses described in Appendix D)
Whole blood (for analyses described in Appendix D)
Frozen PBMC (for T cell phenotype analysis)
AE reporting, if applicable
Review of concomitant medications
Study drug administration: HuAB1 and nivolumab will each be administered by IV infusion over 30 minutes. Nivolumab will be given first, with a 30-minute rest between the 2 infusions, followed by HuAB1 30.
Post HuAB1 and nivolumab administration:
Post-dose vital signs (blood pressure, pulse, respiratory rate, and temperature in supine position after 5 minutes rest) at the following time points after completion of each IV infusion:
5 minutes and 15 minutes after nivolumab dose
5 minutes, 15 minutes, 30 minutes, and 1 hour after HuAB1 dose
15 minutes (±5 minutes) post-HuAB1 dose:
Blood collection for serum (for HuAB1 and nivolumab PK analysis)
4 hours (±60 minutes) post-HuAB1 dose:
Blood collection for serum (for HuAB1 PK only)

4.2.2.3 Cycle 1, Day 2

Study patients will return to the study center on Day 2 for 24-hour (±6 hours) post-dose assessments. No treatment will be administered during this visit, but the following assessments will be completed:
Blood collection for:
Serum (for HuAB1 PK and cytokine multiplex panel)
Whole blood (for gene expression analysis)
AE reporting, if applicable
Review of concomitant medications

4.2.2.4 Cycle 1, Day 4

Study patients will return to the study center on Day 4 for 72 hour (±12 hours) post-dose assessments. No treatment will be administered during this visit, but the following assessments will be completed:
Blood collection for:
Serum (for PK only)
Whole blood (for $CD14^+/CD16^+$ monocyte and gene expression analyses)
AE reporting, if applicable
Review of concomitant medications

4.2.2.5 Cycle 1, Day 8

Study patients will return to the study center on Day 8 for 168-hour (+24 hours) post-dose assessments. No treatment will be administered during this visit, but the following assessments will be completed:
Physical Examination
Vital signs (blood pressure, pulse, respiratory rate, and temperature in supine position after 5 minutes rest; pulse oximetry at rest and after exertion)

Clinical safety labs (as described in Appendix B, footnote h)

Blood collection for:

Serum (for HuAB1 PK and cytokine multiplex panel)

Whole blood (for CD14$^+$/CD16$^+$ monocyte and gene expression analyses)

Frozen PBMC (for T cell phenotype analysis)

AE reporting, if applicable

Review of concomitant medications 4.2.2.6 Cycle 2, Day 1

The following procedures will be performed:

Prior to HuAB1 and nivolumab infusion (within ≤72 hours unless otherwise stated):

Physical examination, including weight

Vital signs (blood pressure, pulse, respiratory rate, and temperature in supine position after 5 minutes rest; pulse oximetry at rest and after exertion)

ECOG performance status evaluation

Clinical safety labs (as described in Appendix B, footnote h; results must be reviewed before dosing)

Blood collection for:

Serum (for analyses described in Appendix D)

Whole blood (for analyses described in Appendix D, except the MDSC panel)

Frozen PBMC (for T cell phenotype analysis)

AE reporting, if applicable

Review of concomitant medications

Study drug administration: HuAB1 and nivolumab will each be administered by IV infusion over 30 minutes. Nivolumab will be given first, with a 30-minute rest between the 2 infusions, followed by HuAB1.

Post HuAB1 and Nivolumab Administration:

Post-dose vital signs (blood pressure, pulse, respiratory rate, and temperature in supine position after 5 minutes rest) at the following time points after completion of the IV infusion:

5 minutes and 15 minutes after nivolumab dose 5 minutes, 15 minutes, 30 minutes, and 1 hour after HuAB1 dose 15 minutes (+5 minutes) post-HuAB1 dose:

Blood Collection for Serum (for HuAB1 PK Only)

4.2.2.7 End of Cycle 2

For Phase 1a patients in the combination cohort, if at the end of Cycle 2 the Investigator determines that the patient may benefit from continued dosing with HuAB1 and nivolumab, entry into the Extended Treatment Period may be offered.

If the patient is continuing onto the Extended Treatment Period (Cycle 3 and beyond), proceed to procedures outlined in Section 6.2.2.8.

If the patient does not qualify to receive further study drug, the patient will return to the clinic for the Treatment Completion/Early Termination visit outlined in Section 6.2.2.9.

4.2.2.8 Extended Treatment—Cycle 3 and Subsequent Cycles, Day 1

Phase 1a extended treatment for patients in combination dose escalation cohorts may begin on Cycle 3, Day 1 (Study Day 29).

At each infusion visit, patients are to remain at the study site after each administration of HuAB1 and nivolumab until completion of all post-dose assessments for safety monitoring. The following assessments will be performed at each visit unless otherwise noted (Appendix B):

Prior to each infusion of study drugs (within ≤72 hours unless otherwise stated):

Physical examination, including weight

Vital signs (blood pressure, pulse, respiratory rate, and temperature in supine position after 5 minutes rest; pulse oximetry at rest and after exertion)

ECOG performance status evaluation

Clinical safety labs (as described in Appendix B, footnote h; results must be reviewed before dosing)

Radiological imaging: CT/MRI scan performed every 8 weeks for the first 12 months for patients who remain on treatment (and every 12 weeks thereafter) and 28 days (±7 days) after the last dose of study treatment.

Biopsy collection (for analyses described in Appendix D)

Blood collection for:

Serum (for analyses described in Appendix D) with the following exceptions:

HuAB1 PK for Cycles 3, 5, 9, 13, and 21 only

Nivolumab PK for Cycles 3, 5, 9, 13, and 21 only

HuAB1 and nivolumab ADA for Cycles 3, 5, 13, and 21 only

ANA for Cycles 3, 5, 9, 13, 21, then every 6 cycles while on treatment

CSF1, IL34 for Cycle 3 and 9 only

Cytokine multiplex panel for Cycles 3, 9, and 21 only

Whole blood (for analyses described in Appendix D) with the following exceptions:

CD14$^+$/CD16$^+$ for Cycle 3 and 11 only

Myeloid-derived suppressor cell panel for Cycle 3 only

Gene expression analysis for Cycle 3, 5, 9, 13, and 21 only

AE reporting, if applicable

Review of concomitant medications

Study drug administration: HuAB1 and nivolumab will each be administered by IV infusion over 30 minutes. Nivolumab will be given first, with a 30-minute rest between the 2 infusions, followed by HuAB1.

Post HuAB1 and Nivolumab Administration:

Post-dose vital signs (blood pressure, pulse, respiratory rate, and temperature in supine position after 5 minutes rest) at the following time points after completion of the IV infusion:

5 minutes and 15 minutes after nivolumab dose 5 minutes, 15 minutes, 30 minutes, and 1 hour after HuAB1 dose 15 minutes (±5 minutes) post-HuAB1 dose:

Blood collection for serum (for analyses described in Appendix D) with the following exceptions:

HuAB1 and nivolumab PK for Cycle 8 only 4.2.2.9 Treatment Completion or Early Termination Visit Patients will return to the study center approximately 28 (±7) days after their last infusion of HuAB1 and nivolumab, or in the event a patient discontinues prematurely from the study.

The following assessments will be performed:

Physical examination, including weight

Vital signs (blood pressure, pulse, respiratory rate, and temperature in supine position after 5 minutes rest; pulse oximetry at rest and after exertion)

ECOG performance status evaluation

Clinical safety labs (as described in Appendix B, footnote h)

12-lead ECG

Radiological imaging: CT/MRI scan does not need to be repeated if performed within 8 weeks prior to the Treatment Completion/Early Termination Visit or if tumor progression was previously determined.

Serum pregnancy test (β-hCG), if applicable

Biopsy for patients who progressed (for analyses described in Appendix D)

Blood collection for:
Serum (for Analyses Described in Appendix D)
Whole blood (for $CD14^+/CD16^+$ monocyte analysis and gene expression by RNA sequencing only)
AE reporting, if applicable
Review of concomitant medications 4.2.3 Phase 1b Combination Dose Expansion 4.2.3.1 Screening Period (Day −28 to Day 0)

Patients who have fully consented to participation in the study will undergo Screening assessments within 28 days (4 weeks) prior to administration of the first infusion of HuAB1 and nivolumab (unless otherwise stated). To determine if the patient meets all inclusion criteria and does not violate any exclusion criteria, the following procedures will be performed (Appendix B):

Written, signed informed consent must be collected prior to any study-specific procedures
Complete medical and disease history
Demographic and baseline characteristics
Complete physical examination, including height and weight
Vital signs (blood pressure, pulse, respiratory rate, and temperature in supine position after 5 minutes rest; pulse oximetry at rest and after exertion)
ECOG performance status evaluation
Screening labs (as described in Appendix B, footnote g)
Clinical safety labs (as described in Appendix B, footnote h)
12-lead ECG (required at Screening, and if clinically indicated during the study)
Radiological imaging: CT/MRI to be performed within 28 days prior to the first infusion of study drug. If the MRI is performed as part of the patient's standard of care within 28 days of the first study infusion it does not need to be repeated if the documentation of results is provided and is adequate for RECIST 1.1.
Serum pregnancy test (β-HCG), <5 days prior to Cycle 1, Day 1, for women of childbearing potential
Biopsy Collection (for Analyses Described in Appendix D)
SAE reporting, if applicable
Document prior and concurrent medications 4.2.3.2 Cycle 1, Day 1

The following procedures will be performed:
Prior to HuAB1 and nivolumab infusion (within ≤72 hours unless otherwise stated):
Verification of Eligibility
Update medical and disease history to capture any changes from Screening
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Serum β-hCG (evaluated by local laboratories) will be performed prior to the first dose of study drug only on women of childbearing potential
Blood collection for:
Serum (for analyses described in Appendix D)
Whole blood (for analyses described in Appendix D)
Frozen PBMC (for T cell phenotype analysis)
AE reporting, if applicable
Review of concomitant medications
Study drug administration: HuAB1 and nivolumab will each be administered by IV infusion over 30 minutes. Nivolumab will be given first, with a 30-minute rest between the 2 infusions, followed by HuAB1.

Post-HuAB1 and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after HuAB1 dose
15 minutes (±5 minutes) post-HuAB1 dose:
Blood collection for serum (for HuAB1 and nivolumab PK analysis)
4 hours (±60 minutes) post-HuAB1 dose:
Blood collection for serum (for HuAB1 PK only)

4.2.3.3 Cycle 1, Day 2

Study patients will return to the study center on Day 2 for 24-hour (±6 hours) post-dose assessments. No treatment will be administered during this visit, but the following assessments will be completed:
Blood collection for:
Serum (for HuAB1 PK and cytokine multiplex panel)
Whole blood (for gene expression analysis)
AE reporting, if applicable
Review of concomitant medications 4.2.3.4 Cycle 1, Day 4

Study patients will return to the study center on Day 4 for 72-hour (±12 hours) post-dose assessments. No treatment will be administered during this visit, but the following assessments will be completed:
Blood collection for:
Serum (for HuAB1 PK only)
Whole blood (for $CD14^+/CD16^+$ monocyte and gene expression analyses)
AE reporting, if applicable
Review of concomitant medications 4.2.3.5 Cycle 1, Day 8

Study patients will return to the study center on Day 8 for 168-hour (+24 hours) post-dose assessments. No treatment will be administered during this visit, but the following assessments will be completed:
Physical examination
Vital signs (blood pressure, pulse, respiratory rate, and temperature in supine position after 5 minutes rest; pulse oximetry at rest and after exertion)
Clinical safety labs (as described in Appendix B, footnote h)
Blood collection for:
Serum (for HuAB1 PK and cytokine multiplex panel)
Whole blood (for $CD14^+/CD16^+$ monocyte and gene expression analyses)
Frozen PBMC (for T cell phenotype analysis)
AE reporting, if applicable
Review of concomitant medications 4.2.3.6 Cycle 2, Day 1

The following procedures will be performed:
Prior to HuAB1 and nivolumab infusion (within ≤72 hours unless otherwise stated):
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)

Blood collection for:
Serum (for analyses described in Appendix D)
Whole blood (for analyses described in Appendix D, except the MDSC panel)
Frozen PBMC (for T cell phenotype analysis)
AE reporting, if applicable
Review of concomitant medications
Study drug administration: HuAB1 and nivolumab will each be administered by IV infusion over 30 minutes. Nivolumab will be given first, with a 30-minute rest between the 2 infusions, followed by HuAB1.
Post-HuAB1 and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after HuAB1 dose
15 minutes (±5 minutes) post-HuAB1 dose:
Blood collection for serum (for HuAB1 PK only)

4.2.3.7 Cycle 3 and Subsequent Cycles, Day 1

At each infusion visit, patients are to remain at the study site after each administration of HuAB1 and nivolumab until completion of all post-dose assessments for safety monitoring. The following assessments will be performed at each visit unless otherwise noted (Appendix B):
Prior to each infusion of study drugs (within ≤72 hours unless otherwise stated):
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h; results must be reviewed before dosing)
Radiological imaging: CT/MRI scan performed every 8 weeks for the first 12 months for patients who remain on treatment (and every 12 weeks thereafter) and 28 days (±7 days) after the last dose of study treatment.
Biopsy collection (for analyses described in Appendix D)
Blood collection
Serum (for analyses described in Appendix D) with the following exceptions:
HuAB1 PK for Cycles 3, 5, 9, 13, and 21 only
Nivolumab PK for Cycles 3, 5, 9, 13, and 21 only
HuAB1 and nivolumab ADA for Cycles 3, 5, 13, and 21 only
ANA for Cycles 3, 5, 9, 13, 21, then every 6 cycles while on treatment
CSF1, IL34 for Cycle 3 and 9 only
Cytokine multiplex panel for Cycles 3, 9, and 21 only
Whole blood (for analyses described in Appendix D) with the following exceptions:
CD14$^+$/CD16$^+$ for Cycle 3 and 9 only
MDSC panel for Cycle 3 only
Gene expression analysis for Cycle 3, 5, 9, 13, and 21 only
AE reporting, if applicable
Review of concomitant medications
Study drug administration: HuAB1 and nivolumab will each be administered by IV infusion over 30 minutes. Nivolumab will be given first, with a 30-minute rest between the 2 infusions, followed by HuAB1.
Post-HuAB1 and nivolumab administration:
Post-dose vital signs (blood pressure, pulse, respiratory rate, and temperature in supine position after 5 minutes rest) at the following time points after completion of the IV infusion:
5 minutes and 15 minutes after nivolumab dose
5 minutes, 15 minutes, 30 minutes, and 1 hour after HuAB1 dose
15 minutes (+5 minutes) post-HuAB1 dose:
Blood collection for serum (for analyses described in Appendix D) with the following exceptions:
HuAB1 and nivolumab PK for Cycle 8 only 4.2.3.8 Treatment Completion or Early Termination Visit Patients will return to the study center approximately 28 (±7) days after their last infusion of HuAB1 and nivolumab, or in the event a patient discontinues prematurely from the study.
The following assessments will be performed:
Physical examination, including weight
Vital signs (blood pressure, pulse, respiratory rate, and temperature in supine position after 5 minutes rest; pulse oximetry at rest and after exertion)
ECOG performance status evaluation
Clinical safety labs (as described in Appendix B, footnote h)
12-lead ECG
Radiological imaging: CT/MRI scan does not need to be repeated if performed within 8 weeks prior to the Treatment Completion/Early Termination Visit or if tumor progression was previously determined.
Serum pregnancy test (β-HCG)
Optional Biopsy for Patients Who Progressed (for Analyses Described in Appendix D)
Blood collection
Serum (for analyses described in Appendix D)
Whole blood (for CD14$^+$/CD16$^+$ monocyte analysis only)
AE reporting, if applicable
Review of concomitant medications 4.2.4 Follow-Up and Survival Follow-Up for all Patients After the Study Treatment Discontinuation Visit, each ongoing AE should be followed until the event has resolved to baseline grade, the event is assessed by the Investigator as stable, the patient is lost to follow-up, the patient withdraws consent, or when it has been determined that the study treatment is not the cause of the AE.
The occurrence of SAEs will be collected until 100 days after the last dose of study treatment or until resolved. Thereafter, only SAEs determined by the Investigator to be related to the study treatment will be collected.
In addition, serum will also be collected 100 days after last dose to analyze for HuAB1 PK, HuAB1 ADA, and nivolumab ADA.
Patients who have discontinued study treatment for reasons other than disease progression will continue to undergo tumor assessments approximately every 8 weeks (+2 weeks) from Study Treatment Discontinuation Visit until disease progression.
After the Study Treatment Discontinuation Visit, all patients (regardless of reason for discontinuation) will have anti-cancer therapies recorded and will be followed for survival every 3 months until death, loss to follow-up, withdrawal of consent, or study termination by the Sponsor.
For patients who withdraw their consent from the study but agree to participate in the survival follow-up, only survival information will be collected every 3 months.

4.3 Study Assessments
4.3.1 Safety Assessments

At baseline, a medical history will be obtained to capture relevant underlying conditions. The baseline examinations should include weight, height, ECOG Performance Status (Appendix G), ECG, blood pressure (BP), heart rate (HR), temperature, and oxygen saturation by pulse oximetry at rest (also monitor amount of supplemental oxygen, if applicable) within 28 days prior to first dose.

Safety assessments including serum hematology, chemistry, ECOG, weight and other assessments including ECG (if clinically indicated) will be done as part of standard care during each visit prior to dosing as noted in Appendices A, B, and C. The patient will also be monitored for any infusion-related AEs during dosing and followed up accordingly based on protocol guidelines. Pre-medications including steroids, antihistamines or other treatments will be given prior to future dosing if the patient develops infusion reactions per protocol guidelines.

Any patient who has received study drug will be evaluated for safety. Toxicity assessments will be continuous during the treatment phase and follow-up visits in-person. Once patients reach the survival follow-up phase, documented telephone calls/email correspondence to assess the patient's status are acceptable.

AEs and laboratory values will be graded according to the NCI CTCAE v4.03

Oxygen saturation by pulse oximetry at rest (also monitor amount of supplemental oxygen, if applicable) should be assessed at each on-study visit prior to dosing. If a patient shows changes on pulse oximetry or other pulmonary-related signs (hypoxia, fever) or symptoms (e.g. dyspnea, cough, fever) consistent with possible pulmonary AEs, the patient should be immediately evaluated to rule out pulmonary toxicity, according to the suspected pulmonary toxicity management table in Appendix E.

Physical examinations are to be performed as clinically indicated. If there are any new or worsening clinically significant changes since the last exam, report changes on the appropriate non-serious AE or SAE page.

Additional measures, including non-study required laboratory tests, should be performed as clinically indicated or to comply with local regulations. Laboratory toxicities (e.g., suspected drug induced liver enzyme evaluations) will be monitored during the follow-up phase via on site/local labs until all study drug-related toxicities resolve, return to baseline, or are deemed stable.

Some of the assessments referred to in this section may not be captured as data in the CRF. They are intended to be used as safety monitoring by the treating physician. Additional testing or assessments may be performed as clinically necessary or where required by institutional or local regulations.

4.3.2 Efficacy Assessments
4.3.2.1 Primary Efficacy Parameters

The primary efficacy parameter is the objective response rate (ORR; number of patients with confirmed response of CR or PR, divided by the total number of treated patients with measurable disease at baseline). Tumor response status will be assessed using RECIST v1.1 (Appendix F). Independent review of tumor assessments may be requested at the discretion of the Sponsor.

4.3.2.2 Additional Efficacy Parameters

Additional efficacy parameters may include the following: Overall Survival (OS, 1-year OS, and median OS), progression-free survival (PFS), and duration of response (DOR) for those patients with confirmed responses, based on RECIST v1.1.

CT/MRI (chest, abdomen, pelvis, and brain) will be performed at Screening, during the treatment and at the end of study/early termination per protocol. Measurements of change in tumor burden must be reviewed and documented after each measurement.

4.3.2.3 Tumor Biopsy

Biopsy at the primary tumor site will be collected at screening and also at 29 days on-treatment (prior to Cycle 3, Day 1) for all Phase 1a patients and 10 patients per cohort in Phase 1b. Patients in the Phase 1a portion of the study will also have post-treatment biopsy upon documented tumor progression. This post-progression biopsy will be optional for patients in Phase 1b. Biopsies will be assessed for tumor associated leukocytes, tumor proliferation, and cell death markers.

4.3.3 Pharmacokinetic Assessments

Blood samples for the PK evaluation of both HuAB1 and nivolumab will be collected from all patients (Phase 1a and 1b).

Blood samples will be collected for measurement of serum HuAB1 concentration during Cycle 1 on Days 1, 2, 4, and 8. Blood samples will be collected both before and at the end of the infusion for Cycle 2. In addition, blood samples will be collected at the end of the infusion for Cycle 8 and before the infusion on Cycles 3, 5, 9, 13, and 21. A blood sample will also be collected for PK analysis 100 days post-last dose and at the Treatment Completion/Early Termination visit.

Patients enrolled in dose escalation of phase 1a and phase 1b will have blood sampling for measurement of serum nivolumab concentration both before and at the end of infusion for Cycle 1. In addition, blood samples will be collected prior to infusion of Cycles 2, 3, 5, 9, 13, and 21. A blood sample will also be collected for PK analysis 100 days post-last dose and at the Treatment Completion/Early Termination visit.

Standard PK parameters will be determined based on serum HuAB1 concentration-time data, as appropriate. Potential pharmacokinetic drug-drug interaction between HuAB1 and nivolumab will be evaluated.

4.3.3.1 Pharmacokinetic Collection and Processing

Blood samples will be collected and processed for serum according to the instructions provided in a separate Laboratory Manual.

4.3.3.2 Pharmacokinetic Sample Analysis

HuAB1 concentration in serum will be determined in serum using a validated ELISA method. Nivolumab concentration in serum will be determined in serum using a validated ECLA method.

4.3.4 Immunogenicity Assessments

Blood samples will be collected before the infusion on Cycles 1, 2, 3, 5, 13, and 21, at 100 days post-last dose and at the Treatment Completion/Early Termination visit to measure ADA for HuAB1 and nivolumab. ADA for HuAB1 in serum will be measured by a validated bridging ECLA that utilizes Meso Scale Discovery (MSD) technology. ADA for nivolumab in serum will be measured by a validated ECLA method.

4.3.5 Biomarker Assessments

A variety of factors that could potentially predict clinical response to the combination of HuAB1 and nivolumab will be investigated in all peripheral blood and in tumor specimens taken from patients prior to and during treatment. Data from these investigations will be evaluated for associations with response and/or safety (AE) data. In addition, analyses of markers between the treatment arms will provide the necessary data to identify and validate biomarkers with predictive vs prognostic value. Complete instructions on the collection, processing, handling and shipment of all samples described herein will be provided in a Biomarker Manual.

4.3.5.1 Tumor Tissue Specimens

Tumor tissue specimens in the form of a paraffin embedded block or unstained slides will be submitted for central IHC assessment. These biopsy samples should be excisional, incisional or core needle as fine needle aspirates or other cytology specimens are insufficient for downstream biomarker analyses. Tissue samples are being collected to evaluate the PD effect of study drugs on the tumor microenvironment. These samples may also undergo gene sequencing to determine the effect of study drugs on gene pathways as well as identified gene signatures associated with resistance to response. These analyses may help predict future response to treatment. A summary of analyses to be performed are described in Appendix D.

Tumor biopsy specimens will be obtained before treatment, as well as on-treatment, to examine immune infiltrates and expression of selected tumor markers. The tumor tissue that is obtained from these samples will be divided as appropriate between a fresh frozen sample to be used for gene expression analysis, and a formalin fixed sample to be used for IHC.

Stained tissue sections will be submitted to the central lab, where they will be assessed by a pathologist and scored for PD-L1 positivity.

Samples may be assessed for the expression of immune or disease related genes, RNAs and/or proteins, as well as for the presence of immune cell populations using a variety of methodologies inclusive of, but not limited to IHC, qRT-PCR, genetic mutation detection and fluorescent in situ hybridization (FISH). Other methods of tumor biomarker expression are being evaluated.

4.3.5.2 Serum

Blood samples for exploratory serum biomarker analyses will be drawn at the time points indicated in the Schedule of Assessments (Appendices A, B, and C). Blood samples will be processed to collect serum and then put in frozen storage prior to analysis. In addition to the PK and ADA analyses mentioned above, serum samples will be analyzed to determine the PD effect of study drugs on cytokine and CSF1R ligand concentrations. Samples may be assessed by ELISA, seromics and/or other relevant multiplex-based protein assay methods. Serum marker analyses may also help establish a biomarker signature that may predict benefit or correlate with efficacy that can be used to inform this and future studies. Timings of sample collection are listed in Appendix C and analyses to be performed are described in Appendix D.

4.3.5.3 Whole Blood for Single Nucleotide Polymorphism (SNP) Assessment

Whole blood samples for exploratory pharmacogenetic assessment will be collected from all patients and put in frozen storage prior to analysis. Genomic DNA will be extracted and subsequently assessed for single nucleotide polymorphisms and other genetic variations in candidate genes that may predispose patients to benefit or AEs. Additional use of these data may include correlative analyses aimed at identifying genotypic associations with clinically-relevant biomarkers identified by other methodologies described in this section.

4.3.5.4 Flow Cytometry

Pre-treatment and on-treatment samples will be analyzed by flow cytometry to study the effects of HuAB1 and nivolumab on various peripheral blood immune cell subsets. Whole blood samples will be assessed to confirm the predicted PD effect of HuAB1 on the reduction of $CD16^+$-monocytes. PBMC samples will be analyzed to determine whether blockade of PD-1 combined with CSF1R targeting will impact peripheral T cell activation and function. PBMC samples may be assessed for the levels of myeloid-derived suppressor cells and for monocyte phenotype. Timings of sample collection are listed in Appendix C and analyses to be performed are described in Appendix D.

4.3.5.5 Gene Expression Profiling

Alterations in the pattern of gene expression in tumor samples will be assessed, using RNA sequencing and qPCR, with particular emphasis on pathways of immune function. All samples collected will be stored, and may be used for subsequent research relevant to tumor immune response.

5 STATISTICAL CONSIDERATIONS

All analyses will be descriptive and will be presented by dose group and overall as appropriate. Data collected in this study will be presented using summary tables and patient data listings. Continuous variables will be summarized using descriptive statistics, specifically the mean, median, standard deviation, minimum, and maximum. Categorical variables will be summarized by frequencies and percentages.

5.1 Sample Size Determination

Approximately 30 patients will be enrolled in Phase 1a (dose escalation); between 3 and 6 patients are expected to be treated at each dose escalation cohort according to the algorithm outlined in FIG. 6. Table 5 summarizes the probability of escalating to the next dose cohort for various true DLT rates.

TABLE 5

Probability of Dose Escalation and Dose Limiting Toxicities

| | True DLT rate | | | | |
|---|---|---|---|---|---|
| | 1% | 5% | 10% | 30% | 50% |
| Probability of dose escalation | 0.999 | 0.973 | 0.906 | 0.494 | 0.172 |

Objective Response Rate is the primary efficacy variable for the Phase 1b portion of the study. With approximately 30 patients in each disease type, the 95% confidence interval half-width for the corresponding response rate would be within 18%.

5.2 Populations for Analyses

All Enrolled Population: All patients who sign the ICF and were registered in IXRS.

Safety Population: All patients who receive at least one dose of HuAB1 and/or nivolumab.

PK Population: All patients who receive at least one dose of HuAB1 and have available serum concentration data evaluable for the determination of PK profile. All patients who received at least one dose of nivolumab, the peak and trough PK profile will be determined.

Biomarker Patients: All patients who receive at least one dose of HuAB1 and/or nivolumab and have available biomarker data.

Immunogenicity Patients: All patients who receive at least one dose of HuAB1 and/or nivolumab and have available ADA data.

5.3 Endpoints
5.3.1 Phase 1a Endpoints
5.3.1.1 Primary
Safety

The incidence of Grade 3 and Grade 4 AEs and clinical laboratory abnormalities defined as DLTs.

The incidence of AEs, clinical laboratory abnormalities, and ECG abnormalities 5.3.1.2 Secondary
Pharmacokinetic The following PK parameters will be derived from concentration-time data for HuAB1 when appropriate and applicable. Other parameters, such as dose dependency and accumulation ratio, may also be calculated. The potential pharmacokinetic drug-drug interaction between HuAB1 and nivolumab will be assessed as appropriate.

Area under serum concentration-time curve (AUC)
Maximum serum concentration ($C_{max}$)
Minimum serum concentration ($C_{min}$)
Volume of distribution at steady state ($V_{ss}$)

The peak and trough concentration PK profile will be derived from nivolumab serum concentration data when appropriate and applicable.

Immunogenicity

Immunogenicity, defined as an immune response to either HuAB1 or nivolumab, will be assessed by measurement of total anti-HuAB1 antibodies and total anti-nivolumab antibodies from all patients. Immunogenicity testing will consist of screening, confirmation, and titration for both HuAB1 and nivolumab.

Pharmacodynamic Biomarkers

Changes in whole blood monocyte subsets by flow cytometry

Changes in cytokine levels multiplex analysis

Biomarker expression levels in tumor biopsy samples as measured by IHC 5.3.1.3 Exploratory
Pharmacodynamic Biomarkers Changes in serum levels of selected markers Changes in peripheral T cell and other leukocyte phenotypes by flow cytometry Levels of peripheral MDSC by flow cytometry Changes in gene expression in whole blood or PBMC 5.3.2 Phase 1b Endpoints
5.3.2.1 Primary
Efficacy The objective response rate (ORR) will be defined as the total number of patients with confirmed responses of either CR or PR divided by the total number of response-evaluable patients Safety The incidence of AEs, SAEs, clinical laboratory abnormalities, and ECG abnormalities The incidence of treatment discontinuations, modifications, interruptions due to adverse events Grade 3 and Grade 4 AEs and clinical laboratory abnormalities 5.3.2.2 Secondary
Pharmacokinetic The following PK parameters will be derived from concentration-time data for HuAB1 when appropriate and applicable. Other parameters, such as dose dependency and accumulation ratio, may also be calculated. The potential pharmacokinetic drug-drug interaction between HuAB1 and nivolumab will be assessed as appropriate.

Area under serum concentration-time curve (AUC)
Maximum serum concentration ($C_{max}$)
Minimum serum concentration ($C_{min}$)
Volume of distribution at steady state ($V_{ss}$)

The peak and trough concentration PK profile will be derived from nivolumab serum concentration data when appropriate and applicable.

Immunogenicity

Immunogenicity, defined as an immune response to either HuAB1 or nivolumab, will be assessed by measurement of total anti-HuAB1 antibodies and total anti-nivolumab antibodies from all patients. Immunogenicity testing will consist of screening, confirmation, and titration for both HuAB1 and nivolumab.

Pharmacodynamic Biomarkers

Changes in whole blood monocyte subsets by flow cytometry

Changes in cytokine levels multiplex analysis

Biomarker expression levels in tumor biopsy samples as measured by IHC

Efficacy

Overall Survival (OS) will be defined as the time between the first dose of study drug and death.

One-year OS
Median OS

Duration of response (DOR) will be defined as the time from response (CR or PR) until the onset of PD that is subsequently confirmed.

Progression-free survival (PFS) will be defined for each patient as the time from the first dose to the first observation of disease progression or death due to any cause.

5.3.2.3 Exploratory
Pharmacodynamic Biomarkers

Changes in serum levels of selected markers

Changes in peripheral T cell and other leukocyte phenotypes by flow cytometry

Levels of peripheral MDSC by flow cytometry

Changes in gene expression in whole blood or PBMC 5.4 Analyses
5.4.1 Demographics and Baseline Characteristics Demographic data, medical history, other baseline characteristics, concomitant disease, and concomitant medication will be summarized by cohort and overall. To determine whether the criteria for study conduct are met, corresponding tables and listings will be provided. These will include an assessment of protocol deviations, study drug accountability, and other data that may impact the general conduct of the study.

5.4.2 Efficacy Analyses

For each disease type, response to treatment will be summarized by ORR, defined as the ratio of the number of patients that achieve an objective response to the number of patients enrolled. Exact confidence interval will be constructed for the response rate. Overall Survival, survival at 1 year, and median survival will be estimated by the Kaplan-Meier method. The corresponding confidence interval will also be presented.

5.4.3 Safety Analyses

Safety analyses will be performed for patients included in the safety population. AEs, clinical laboratory information, vital signs, ECOG performance status, weight, and ECGs will be tabulated and summarized.

AEs will be summarized overall and with separate summaries for SAEs, AEs leading to discontinuation, AEs leading to death, and NCI-CTCAE version 4.03 Grade 3 or higher AEs.

Weight and vital signs will be summarized descriptively (n, mean, standard deviation, median, minimum, and maximum). ECOG performance status will be summarized categorically and descriptively.

Shift tables displaying patient counts and percentages classified by baseline grade and maximum grade on treatment will be provided for laboratory data by cohort and overall. A marked laboratory change is defined as a shift from a baseline Grade 0 to Grade 3 (non-hematologic) or Grade 4 (hematologic) on treatment, or a shift from a baseline Grade 1 to Grade 4 on treatment. The number and percentage of patients with marked laboratory changes will be tabulated by cohort and overall.

5.4.4 Pharmacokinetic Analyses

Individual and mean serum concentration of HuAB1 and nivolumab versus time data will be plotted by dose level. Summary statistics will be tabulated for the serum concentration-time data and estimated PK parameters of HuAB1, as appropriate. Potential PK drug-drug interaction between HuAB1 and nivolumab will be evaluated.

For HuAB1, PK parameters including $C_{max}$, AUC, $C_{trough}$, $C_L$, and $V_{ss}$ will be estimated. Other PK parameters as well as inter-patient variability, HuAB1 accumulation and dose proportionality will be evaluated when data are available. PK data (HuAB1 and/or nivolumab) collected from this study may be used in combination with other studies for exposure-response or population PK modeling, which will be part of a separate report.

5.4.5 Immunogenicity

A listing will be provided of all available immunogenicity data for both HuAB1 and nivolumab. Additionally, a listing of immunogenicity data from those patients with at least one positive ADA at any time point will be provided by dose level. The frequency of patients with at least one positive ADA assessment, and frequency of patients who develop ADA after a negative baseline assessment will be provided by dose. To examine the potential relationship between immunogenicity and safety, the frequency and type of AEs of special interest may be examined by overall immunogenicity status. Associations between pre-dose concentrations of HuAB1 or nivolumab and corresponding ADA assessments may be explored.

5.4.6 Biomarker Analyses

To assess the PD effects of HuAB1 and nivolumab on various exploratory biomarkers (such as soluble factors, peripheral blood immune cell subsets, and other markers as assessed by IHC) summary statistics for these markers and their changes (or percent changes) from baseline will be tabulated by visit and dose. In addition, the time course of exploratory biomarker outcomes will be investigated graphically, by summary plots or individual patient plots over time. Patterns of change in these biomarker values over time and how the patterns differed among dose levels may be additionally investigated using appropriate modeling, for example, by linear mixed effects models.

Possible associations of biomarker measures with clinical efficacy measures including OS will be investigated based on data availability. Methods such as, but not limited to, logistic regression may be used to further investigate such associations.

If, at the time of database lock for the primary and secondary endpoints, biomarker data related to the exploratory objectives are not available, these biomarker analyses results may not be included in the CSR but reported separately.

Selected Serum Marker Expression:

Analyses of expression are descriptive in nature and intended to examine the distribution of expression and assess potential associations between expression and efficacy measures. If there is an indication of a meaningful association, future work will evaluate expression as a predictive biomarker, including selection of an optimal expression cut-off to classify patients as positive or negative. Cut-off selection and validation will be conducted across studies and reported outside of individual CSRs. Additionally, analyses detailed below may be reported outside of the CSR in order to ensure the integrity of any potential validation analyses using data from this study.

The following analyses will be performed:

Listing of selected biomarker data

Summary of tumor specimen acquisition and characteristics

Summary statistics of expression by select subgroups, and overall

Box plot of expression by treatment group and overall

OS curves for each treatment group will be estimated using the Kaplan-Meier (KM) product limit method for each Expression Quartile subgroup and for the subgroup of patients with an unknown or indeterminate IHC result. Expression quartiles will be defined based on overall population. Two-sided, 95% confidence intervals for median OS will be computed by Brookmeyer and Crowley method.

Investigator-determined PFS curves for each treatment group will be estimated using the KM product-limit method for each Expression Quartile subgroup and for the subgroup of patients with an unknown or indeterminate IHC result. Expression quartiles will be defined based on overall population. Two-sided, 95% confidence intervals for median PFS will be computed by Brookmeyer and Crowley method.

Investigator-determined ORRs will be computed by treatment group along with exact 95% CIs using the Clopper-Pearson method for each Expression Quartile subgroup and for the subgroup of patients with an unknown or indeterminate expression result. Expression quartiles will be defined based on overall population. Associated odds ratios and 95% CIs will be calculated.

Box plots of expression versus Response Status by treatment group

Cumulative distribution plot of expression versus population percentile by treatment group and overall Waterfall plots of individual expression by treatment group Forest plot of OS and PFS Hazard Ratios with 95% CIs for each Expression Quartile subgroup and for the subgroup of patients with an unknown or indeterminate IHC result. Expression Quartiles will be defined based on overall population.

5.5 Interim Analysis

No formal interim analysis is planned.

The Sponsor (and/or designee) and Investigator(s) will review safety data from each dose cohort prior to dose escalation or de-escalation. In addition, an interim data summary may be performed at several times prior to completion of the study in order to facilitate program decisions and to support presentations or publications.

| Term | Definition |
|------|------------|
| ACTH | Adrenocorticotropic hormone |
| ADA | Anti-drug antibody |
| AE | Adverse event |
| ALT | Alanine aminotransferase |

| Term | Definition |
| --- | --- |
| ANA | Antinuclear antibody |
| ANC | Absolute neutrophil count |
| AST | Aspartate aminotransferase |
| AT | Aminotransferases |
| AUC | Area under the concentration-time curve |
| AUC(INF) | Area under the concentration-time curve from time zero extrapolated |
| β-HCG | Beta-human chorionic gonadotropin |
| BID | Bis in die; twice daily |
| BMI | Body mass index |
| BMS | Bristol-Myers Squibb |
| BP | Blood pressure |
| BTLA | B- and T-lymphocyte attenuator |
| BUN | Blood urea nitrogen |
| ° C. | Degrees Celsius |
| CBC | Complete blood count |
| CD | Cluster of differentiation |
| CFR | Code of Federal Regulations |
| CHO | Chinese hamster ovary |
| CI | Confidence interval |
| CK | Creatinine kinase |
| CL | Clearance |
| $C_{max}$, CMAX | Maximum observed concentration |
| $C_{min}$, CMIN | Trough observed concentration |
| CMV | Cytomegalovirus |
| CNS | Central nervous system |
| CR | Complete response |
| CRC | Colorectal cancer |
| CRF | Case report form, may be paper or electronic |
| CRO | Contract research organization |
| CRP | C-reactive protein |
| CSF1 | Colony stimulating factor 1 |
| CSF1R | Colony stimulating factor 1 receptor |
| CSR | Clinical study report |
| CT | Computed tomography |
| CTA | Clinical trials agreement |
| CTCAE v4.03 | Common Terminology Criteria for Adverse Events, version 4.03 |
| CTLA-4 | Cytotoxic T lymphocyte antigen 4 |
| $C_{trough}$ | Trough observed plasma concentration |
| CTX | C-terminal collagen crosslink peptides |
| CV | Coefficient of variation |
| DC | Dendritic cell |
| DEHP | Di-(2-ethylhexyl)phthalate |
| DILI | Drug-induced liver injury |
| dL | Deciliter |
| DLT | Dose-limiting toxicity |
| DMARD | Disease-modifying anti-rheumatic drug |
| DNA | Deoxyribonucleic acid |
| DOR | Duration of response |
| $EC_{50}$ | Half-maximal effective concentration |
| ECG | electrocardiogram |
| ECLA | Electrochemiluminescence assay |
| ECM | Extracellular matrix |
| ECOG | Eastern Cooperative Oncology Group |
| eCRF | Electronic case report form |
| EDC | Electronic data capture |
| e.g. | exempli gratia (for example) |
| ELISA | Enzyme-linked immunosorbent assay |
| ePPND | Enhanced pre- and post-natal development |
| ESR | Erythrocyte sedimentation rate |
| ° F. | Degrees Fahrenheit |
| FACS | Fluorescent-activated cell sorter |
| Fc | Fragment crystallizable |
| FDA | Food and Drug Administration |
| FFPE | Formalin-fixed, paraffin-embedded |
| FISH | Fluorescent in situ hybridization |
| FivePrime | Five Prime Therapeutics, Inc. |
| FSH | Follicle stimulating hormone |
| g | Gram |
| GBM | Glioblastoma multiforme |
| GCP | Good Clinical Practice |
| GI | Gastrointestinal |
| h | Hour |
| HBcAg | Hepatitis B core antigen |
| HBsAg | Hepatitis B surface antigen |
| HBV | Hepatitis B virus |
| HCV | Hepatitis C virus |
| HIV | Human Immunodeficiency Virus |
| HR | Heart rate |
| HRP | Horseradish peroxidase |
| HRT | Hormone replacement therapy |
| IB | Investigator's Brochure |
| $IC_{50}$ | Half-maximal inhibitory concentration |
| ICD | Implantable Cardioverter Defibrillator |
| ICF | Informed consent form |
| ICH | International Conference on Harmonisation |
| ICOS | Inducible co-stimulator |
| ID | Infectious disease |
| i.e. | id est (that is) |
| IEC | Independent ethics committee |
| IFN | Interferon |
| IgG | Immunoglobulin G |
| IHC | Immunohistochemistry |
| IL | Interleukin |
| IM | Intramuscular |
| IMP | Investigational medicinal product |
| IND | Investigational new drug |
| INR | International normalized ratio |
| I-O | Immuno-oncology |
| irAE | Immune-related adverse event |
| IRB | Institutional review board |
| ITIM | Immunoreceptor tyrosine inhibitory motif |
| ITSM | Immunoreceptor tyrosine-based switch motif |
| IU | International unit |
| IV | Intravenous |
| IXRS | Integrated voice and web response system |
| kg | Kilogram |
| KM | Kaplan-Meier |
| LAG-3 | Lymphocyte-activate gene 3 |
| LDH | Lactate dehydrogenase |
| LFT | Liver function test |
| LLOQ | Lower limit of quantification |
| MABEL | Minimum anticipated biological effect level |
| mCRPC | Metastatic castration-resistant prostate cancer |
| MDSC | Myeloid-derived suppressor cell |
| mg | Milligram |
| min | Minute |
| μL | Microliter |
| mL | Milliliter |
| MLR | Mixed lymphocyte reaction |
| μM | Micrometer |
| mM | Millimolar |
| $mm^3$ | Cubic millimeters |
| mmHg | millimeters of mercury |
| MRI | Magnetic resonance imaging |
| MSD | Meso Scale Discovery |
| MTD | Maximum tolerated dose |
| N | Number of patients or observations |
| NCA | Non-compartmental analysis |
| NCI | National Cancer Institute |
| ng | Nanogram |
| NOAEL | No-observable-adverse-effect level |
| NSCLC | Non-small cell lung cancer |
| NYHA | New York Heart Association |
| NSAID | Non-steroidal, anti-inflammatory drug |
| ORR | Objective response rate |
| OS | Overall survival |
| PBMC | Peripheral blood mononuclear cell |
| PD | Pharmacodynamics |
| PD-1 | Programmed death 1 |
| PDAC | Pancreatic ductal adenocarcinoma |
| PD-L1 | Programmed death ligand 1 |
| PD-L2 | Programmed death ligand 2 |
| PFS | Progression-free survival |
| PK | Pharmacokinetics |
| PO | Per os; by mouth |
| PPK | Population pharmacokinetics |
| PR | Partial response |
| PTT (aPTT) | Partial thromboplastin time |
| PVC | Polyvinyl chloride |
| q2w | Every two weeks |
| qPCR | Quantitative real-time polymerase chain reaction |
| qRT-PCR | Quantitative reverse-transcription polymerase chain |

-continued

| Term | Definition |
|---|---|
| | reaction |
| QTcF | Fridericia's correction formula for QT interval |
| RBC | Red blood cell |
| RCC | Renal cell carcinoma |
| RD | Recommended Dose |
| RECIST v1.1 | Response Evaluation Criteria in Solid Tumors, version 1.1 |
| RNA | Ribonucleic acid |
| SAE | Serious adverse event |
| SAP | Statistical analysis plan |
| SCCHN | Squamous-cell carcinoma of the head and neck |
| SD | Stable disease |
| SkTnI | Skeletal troponin |
| SOP | Standard operating procedure |
| $T_3$ | Triiodothyronine |
| $T_4$ | Thyroxine |
| TAM | Tumor-associated macrophage |
| TB | Tuberculosis |
| TCR | T-cell receptor |
| TIL | Tumor-infiltrating lymphocyte |
| $T_{max}$, TMAX | Time of maximum observed concentration |
| TNF | Tumor necrosis factor |
| Trap5b | Tartrate resistant acid phosphatases 5b |
| ULN | Upper limit of normal |
| USP | United States Pharmacopeia |
| Vss | Volume of distribution at steady state |
| Vz | Volume of distribution of terminal phase (if IV and if multi- |
| WBC | White blood cell |
| WHO | World Health Organization |
| WOCBP | Women of childbearing potential |

6 REFERENCES

Ansari M J, Salama A D, Chitnis T, Smith R N, Yagita H, Akiba H, et al. The programmed death-1 (PD-1) pathway regulates autoimmune diabetes in nonobese diabetic (NOD) mice. J Exp Med. 2003; 198(1):63-9.

Blazar B R, Carreno B M, Panoskaltsis-Mortari A, Carter L, Iwai Y, Yagita H, et al. Blockade of programmed death-1 engagement accelerates graft-versus-host disease lethality by an IFN-α-dependent mechanism. J Immunol. 2003; 171:1272-7.

Carter L L, Fouser L A, Jussif J, Fitz L, Deng B, Wood C R, et al. PD-1:PD-L inhibitory pathway affects both CD4$^+$ and CD8$^+$ T cells and is overcome by IL-2. Eur J Immunol. 2002; 32(3):634-43.

Cassier P, Gomez-Roca C, Italiano A, Cannarile M, Ries C, Brillouet A, et al. Phase 1 study of RG7155, a novel anti-CSF1R antibody, in patients with locally advanced pigmented villonodular synovitis (PVNS). J Clin Oncol suppl. 2014; 32:5 abstract 10504.

Chemnitz J M, Parry R V, Nichols K E, June C H, Riley J L. SHP-1 and SHP-2 associate with immunoreceptor tyrosine-based switch motif of programmed death 1 upon primary human T cell stimulation, but only receptor ligation prevents T cell activation. J Immunol. 2004; 173:945-54.

Dai X, Ryan G, Hapel A, Dominguez M, Russell R, Kapp S, et al. Targeted disruption of the mouse colony-stimulating factor 1 receptor gene results in osteopetrosis, mononuclear phagocyte deficiency, increased primitive progenitor cell frequencies, and reproductive defects, Blood. 2002; 99:111-20.

Dunn G P, Bruce A T, Ikeda H, Old L J, Schreiber R D. Cancer immunoediting: from immunosurveillance to tumor escape. Nat Immunol. 2002; 3:991-8.

Freeman G J, Long A J, Iwai Y, Bourque K, Chernova T, Nishimura H, et al. Engagement of the PD 1 immunoinhibitory receptor by a novel B7 family member leads to negative regulation of lymphocyte activation. J Exp Med. 2000; 192(7): 1027-34.

Gabbay M B, Thomas J, Gibbs A, Hold P. A randomized crossover trial of the impact of additional spermicide on condom failure rates. Sex Transm Dis. 2008; 35:862-8.

Greenwald R J, Freeman G H, Sharpe A H. The B7 family revisited. Annu Rev Immunol. 2004; 23:515-48.

Habicht A, Dada S, Jurewicz M, Fife B T, Yagita H, Azuma M, et al. A link between PDL1 and T regulatory cells in fetomatemal tolerance. J Immunol. 2007; 179:5211-9.

Hamilton J, Achuthan A. Colony stimulating factors and myeloid cell biology in health and disease. Trends in Immunology, 2013; 34:81-89.

Kaufmann D E, Walker B D. Programmed death-1 as a factor in immune exhaustion and activation in HIV infection. Curr Opin HIV Aids. 2008; 3(3):362-7.

Kestelman P, Trussel, J. Efficacy of the simultaneous use of condoms and spermicides. Family Planning Perspectives. 1991; 23(5):226-7.

Komohara Y, Jinushi M, Takeya M. Clinical significance of macrophage heterogeneity in human malignant tumors. Cancer Sci. 2014; 105:1-8.

Kuang D M, Zhao Q, Peng C, Xu J, Zhang J P, Wu C, et al. Activated monocytes in peritumoral stroma of hepatocellular carcinoma foster immune privilege and disease progression through P D-L1. J Exp Med. 2009; 206(6): 1327-37.

Latchman Y, Wood C R, Chernova T, Chaudhary D, Borde M, Chernova I, et al., P D-L2 is a second ligand for PD-1 and inhibits T cell activation. Nat Immunol. 2001; 2(3): 261-268.

Lavin Y, Merad M. Macrophages: gatekeepers of tissue integrity. Cancer Immunol Res. 2013; 1(4):201-9.

Lavin Y, Winter D, Blecher-Gonen R, David E, Keren-Shaul H, Merad M, et al. Tissue-dependent macrophage enhancer landscapes are shaped by the local microenvironment. Cell. 2014; 159:1312-26.

Llosa N J, Cruise M, Tam A, Wicks E C, Hechenbleikner E M, Taube J M, et al. The vigorous immune microenvironment of microsatellite instable colon cancer is balanced by multiple counter-inhibitory checkpoints. Cancer Discov. 2015; 5(1):43-51.

Masteller E, Wong, B. Targeting IL-34 in chronic inflammation. Drug Discov Today, 2014; 19:1212-16.

Nishimura H, Nose M, Hiai H, Minato N, Honjo T. Development of lupus-like autoimmune diseases by disruption of the PD-1 gene encoding an ITIM motif-carrying immunoreceptor. Immunity. 1999; 11:141-51.

Nishimura H, Honjo T. PD-1: an inhibitory immunoreceptor involved in peripheral tolerance. Trends Immunol. 2001a; 22: 265-8.

Nishimura H, Okazaki T, Tanaka Y, Nakatani K, Hara M, Matsumori A, et al. Autoimmune dilated cardiomyopathy in PD-1 receptor-deficient mice. Science. 2001b; 291: 319-22.

Nivolumab Investigator's Brochure. Version 13. Bristol-Myers Squibb. 21 Jul. 2014 Noy R, Pollard J. Tumor-associated macrophages: from mechanisms to therapy. Immunity. 2014; 41:49-61.

Okazaki T, Tanaka Y, Nishio R, Mitsuiye T, Mizoguchi A, Wang J, et al. Autoantibodies against cardiac troponin I are responsible for dilated cardiomyopathy in PD-1-deficient mice. Nat Med. 2003; 9:1477-83.

Opdivo [package insert]. Princeton, N.J.: Bristol-Myers Squibb Company; March, 2015.

Pardoll D. Does the immune system see tumors as foreign or self? Annu Rev Immunol. 2003; 21:807-39.

Pyonteck S, Akkari L, Schuhmacher A, Bowman R, Sevenich L, Quail D, et al. CSF-1R inhibition alters macrophage polarization and blocks glioma progression. Nat Med. 2013; 19:1264-72.

Radi Z, Guzman R, Bell R. Increased connective tissue extracellular matrix in the op/op model of osteopetrosis. Pathobiology. 2009; 76:199-203

Radi Z, Koza-Taylor P, Bell R, Obert L, Runnels H, Beebe J, et al. Increased serum enzyme levels associated with Kupffer cell reduction with no signs of hepatic or skeletal muscle injury. Am J Pathol. 2011; 179: 240-247.

Ries C, Cannarile M, Hoves S, Benz J, Wartha K, Runza V, et al. Targeting tumor-associated macrophages with anti-CSF-1R antibody reveals a strategy for cancer therapy. Cancer Cell. 2014; 25:846-59.

Rizvi N A, Mazeires J, Planchard D, Stinchcombe T E, Dy G K, Antonia S J, et al. Activity and safety of nivolumab, an anti-PD-1 immune checkpoint inhibitor, for patients with advanced, refractory squamous non-small-cell lung cancer (CheckMate 063): a phase 2, single-arm trial. Lancet Oncol. 2015; 16(3):257-65.

Ruffell B, Coussens L M. Macrophages and therapeutic resistance in cancer. Cancer Cell. 2015; 27:462-72.

Rutebemberwa A, Ray S C, Astemborski J L, Levine J, Liu L, Dowd K A, et al. High-programmed death-1 levels on hepatitis C virus-specific T cells during acute infection are associated with viral persistence and require preservation of cognate antigen during chronic infection. J Immunol. 2008; 181:8215-25.

Sadis S, Mukherjee A, Olson S, Dokmanovich M, Maher R, Cai C, et al. Safety, pharmacokinetics, and pharmacodynamics of PD-0360324, a human monoclonal antibody to monocyte/macrophage colony stimulating factor, in healthy volunteers. ACR/ARHP Scientific Meeting 2009, Oct. 17-21, Philadelphia, Pa., Poster 408.

Salama A D, Chitnis T, Imitola J, Ansari M J, Akiba H, Tushima F, et al. Critical role of the programmed death-1 (PD-1) pathway in regulation of experimental autoimmune encephalomyelitis. J Exp Med. 2003; 198:71-8.

Sharpe A H, Wherry E J, Ahmed R, Freeman G J. The function of programmed cell death 1 and its ligands in regulating autoimmunity and infection. Nature Immunol. 2007; 8:239-45.

Sheppard K A, Fitz L J, Lee J M, Benander C, George J A, Wooters J, et al. PD-1 inhibits T-cell receptor induced phosphorylation of the ZAP70/CD3zeta signalosome and downstream signaling to PKC-theta. FEBS Letters. 2004; 574:37-41.

Tumeh P C, Harview $C_L$, Yearley J H, Shintaku I P, Taylor EJM, Robert L, et al. PD-1 blockade induces responses by inhibiting adaptive immune resistance. Nature. 2014; 515: 568-71.

Velu V, Titanji K, Zhu B, Husain S, Pladevega A, Lai L, et al. Enhancing SIV-specific immunity in vivo by PD-1 blockade. Nature. 2009; 458:206-10.

Wang C, Thudium K B, Han M, Wang X T, Huang H, Feingersh D, et al. In vitro characterization of the anti-PD-1 antibody nivolumab, BMS-936558, and in vivo toxicology in non-human primates. Cancer Immunol Res. 2014; 2:846-56.

Weber J S, D'Angelo S P, Minor D, Hodi F S, Gutzmer R, Neyns B, et al. Nivolumab versus chemotherapy in patients with advanced melanoma who progressed after anti-CTLA-4 treatment (CheckMate 037): a randomised, controlled, open-label, phase 3 trial. Lancet Oncol. 2015; 16(4):375-84.

Wolchok J D, Hoos A, O'Day S, Weber J S, Hamid O, Lebbe C. Guidelines for the evaluation of immune therapy activity in solid tumors: immune-related response criteria. Clin Cancer Res. 2009; 15:7412-20.

Zitvogel L, Tesniere A, Kroemer G. Cancer despite immunosurveillance: immunoselection and immunosubversion. Nat Rev Immunol. 2006; 6:715-27.

Zhu Y, Knolhoff B, Meyer M, Nywening T, West B, Luo J, et al. CSF1/CSF1R blockade reprograms tumor-infiltrating macrophages and improves response to T-cell checkpoint immunotherapy in pancreatic cancer models. Cancer Res. 2014; 74:5057-69.

APPENDIX A

Schedule of Assessments
Phase 1a HuAB1 Monotherapy and Combination - Schedule of Patient Assessments

| Procedure[a,b] | Screening Day -28 to Day 0 Week 0 | Cycle 1 Day 1 | Cycle 1 Day 2 Week 1 | Cycle 1 Day 4 | Cycle 1 Day 8 Week 2 | Cycle 2 Day 1 Week 3 | Cycle x[r] Day 1 Week ≥5 | Treatment Completion/ Early Termination Visit |
|---|---|---|---|---|---|---|---|---|
| Informed Consent | x | | | | | | | |
| Review/Confirm Eligibility | x | x | | | | | | |
| Medical History/ | x | x | | | | | | |
| Physical Examination[c] | x | x | | | x | x | x | x |
| Height and Weight[d] | x | x | | | | x | x | x |
| Vital Signs[e] | x | x | | | x | x | x | x |
| ECOG Performance Status[f] | x | x | | | | x | x | x |
| Screening Labs[g] | x | | | | | | | |
| Clinical Safety Labs[h] | x | x | | | x | x | x | x |
| 12-Lead ECG[i] | x | | | | | | | x |
| CT/MRI Tumor Assessment[j,k] | x | | | | | | x | x |
| Serum Pregnancy Test[l] | x | x | | | | | | x |
| Biopsy[m] | x | | | | | | x | x |
| PK Sampling[n,o] | | x | x | x | x | x | x | x |
| PD Sampling[n] | | x | x | x | x | x | x | x |
| ADA Sampling[n] | | x | | | | x | x | x |

APPENDIX A-continued

Schedule of Assessments
Phase 1a HuAB1 Monotherapy and Combination - Schedule of Patient Assessments

| Procedure[a, b] | Screening Day −28 to Day 0 Week 0 | Cycle 1 Day 1 | Cycle 1 Day 2 Week 1 | Cycle 1 Day 4 | Cycle 1 Day 8 Week 2 | Cycle 2 Day 1 Week 3 | Cycle x[r] Day 1 Week ≥5 | Treatment Completion/ Early Termination Visit |
|---|---|---|---|---|---|---|---|---|
| ANA Testing[p] | | x | | | | x | x | x |
| Study Drug(s)[q] | | x | | | | x | x | |
| Adverse Events | x----------------------------------------------------------------------------------------------------x | | | | | | | x |
| Prior/Concomitant | x----------------------------------------------------------------------------------------------------x | | | | | | | x |

Notes for Phase 1a Schedule of Assessments

[a]Unless specified, procedure is to be completed within ±72 hours of scheduled time point and to be synchronized with administration day of HuAB1 infusion.
[b]Any clinical assessment, laboratory study, or additional non-specified tests may be obtained at any time, if clinically indicated.
[c]Standard physical examination will be performed as determined by the Investigator, particularly to follow physical findings to resolution. Targeted physical exams should be conducted at any time to follow up on AE reports.
[d]Height is only required to be recorded at Screening (for BMI calculation). Weight is required to be recorded at Day 1 of each cycle. Dose will be adjusted only if weight change is >10% from first dose on Cycle 1 Day 1.
[e]Vital signs include pulse, respiratory rate, blood pressure, and temperature in the supine position. Measure prior to dose and after completion of each IV infusion at the following time points: 5 minutes, 15 minutes, 30 minutes, and 1 hour post-dose (30 minutes and 1 hour after HuAB1 only). Pulse oximetry is performed at rest and after exertion prior to dosing only.
[f]Patient ECOG Status assessments are to be performed within 72 hours prior to dosing (Day 1 of each cycle).
[g]Screening labs include serology for Hepatitis B (HBsAg and HBcAb), Hepatitis C (HCV antibody), HIV antibody, and Quantiferon test (for latent TB).
[h]Clinical Safety Labs:
Hematology including CBC with differential, platelets, hemoglobin, hematocrit, RBC, and RBC indices
Chemistry includes CK (creatinine kinase), AST (aspartate transaminase), ALT (alanine transaminase), bicarbonate, bilirubin, (direct and total), BUN (blood urea nitrogen), calcium, chloride, creatinine, glucose, LDH (lactate dehydrogenase), phosphorus, potassium, sodium, and, if applicable, serum pregnancy. If CK is elevated at any time, obtain troponins (cardiac and skeletal), CK isoenzymes, aldolase, and ECG; repeat CK and these additional tests daily or other interval as clinically indicated, until resolved or stable. If either AST or ALT is elevated, obtain total serum bilirubin, alkaline phosphatase; repeat daily or other interval, as clinically indicated, until resolved or stable. Additional tests may be obtained at any time, if clinically indicated.
Urinalysis will only be done at Screening, and when clinically indicated.
[i]Obtain ECG records at Screening and Treatment Completion/Early Termination Visit (after PK blood draw, record exact time). Additional ECGs should be obtained at any time, if serum CK or cardiac troponin is elevated; if abnormal (excluding sinus tachycardia), ECGs should be obtained (if clinically indicated), until the abnormality is resolved or clinically stable. Additional ECGs may be obtained at any time, if clinically indicated. ECGs for each patient should be obtained from the same machine whenever possible. To minimize variability, it is important that patients be in a resting position for at least 5 minutes prior to each ECG evaluation. Body position should be consistently maintained for each ECG evaluation to prevent changes in heart rate. Environmental distractions (e.g., television, radio, conversation) should be avoided during the pre-ECG resting period and during ECG recording.
[j]CT/MRI of the Tumor sites measured as per Response Evaluation Criteria in Solid Tumors (RECIST) v1.1. If patient terminates prior to scheduled CT/MRI scans, subject should have scans done at Treatment Completion/Early Termination Visit. The same measuring modality should be used by the site to maintain consistency across the various time points.
[k]Performed every 8 weeks for the first 12 months for patients who remain on treatment (and every 12 weeks thereafter) and 28 days (±7 days) after the last dose of study treatment. CT/MRI scans do not need to be repeated if performed within 8 weeks prior to the Treatment Completion/Early Termination Visit or if tumor progression was previously determined.
[l]All women of childbearing potential (including those who have had a tubal ligation) will have a serum pregnancy test at Screening, on Cycle 1 Day 1, and at Treatment Completion/Early Termination Visit and when clinically indicated.
[m]Biopsy at primary tumor or metastatic tumor site will be collected at Screening and prior to Cycle 3, Day 1 dose. It is recommended that patients who have documented progression receive another biopsy at the end of treatment. Biopsies will be assessed for tumor associated leukocytes, tumor proliferation and cell death markers.
[n]Samples will be collected for PK, PD, and ADA analyses. Not all visits will require collection of all three - see Appendix C for collection schedule.
[o]Blood will be collected to evaluate Cmax & Cmin on day 1 of study drugs on Cycles 1, 2, 3, 5, 8, 9, 13, 21, and at the end of treatment.
[p]Antinuclear antibody (ANA) testing by indirect fluorescent antibody (IFA). If the titer is positive, check erythrocyte sedimentation rate (ESR) and C-reactive protein (CRP) to confirm result. Will be checked prior to dose at Cycles 1, 2, 3, 5, 9, 13, 21, then every 6 cycles while on treatment and at Treatment Completion/Early Termination Visit.
[q]HuAB1 +/− nivolumab study drug will be administered every 2 weeks in 14-day cycles for 4 weeks. The dosing may continue until PD or unacceptable toxicity.
[r]These assessments are to be performed prior to each subsequent dose (with the exceptions noted in Appendix B) for those patients who continue treatment without signs of progressive disease or toxicity

APPENDIX B

Schedule of Assessments
Phase 1b HuAB1 + Nivolumab - Schedule of Patient Assessments

| Procedure[a, b] | Screening Day −28 to Day 0 Week 0 | Cycle 1 Day 1 | Cycle 1 Day 2 Week 1 | Cycle 1 Day 4 | Cycle 1 Day 8 Week 2 | Cycle 2 Day 1 Week 3 | Cycle x[s] Day 1 Week ≥5 | Treatment Completion/ Early Termination Visit |
|---|---|---|---|---|---|---|---|---|
| Informed Consent | x | | | | | | | |
| Review/Confirm Eligibility | x | x | | | | | | |
| Medical History/Demographics | x | x | | | | | | |
| Physical Examination[c] | x | x | | | x | x | x | x |
| Height and Weight[d] | x | x | | | | x | x | x |
| Vital Signs[e] | x | x | | | x | x | x | x |
| ECOG Performance Status[f] | x | x | | | | x | x | x |
| Screening Labs[g] | x | | | | | | | |
| Clinical Safety Labs[h] | x | x | | | x | x | x | x |
| 12-Lead ECG[i] | x | | | | | | | x |
| CT/MRI Tumor Assessment[j,k] | x | | | | | | x | x |
| Serum Pregnancy Test[l] | x | x | | | | | | x |

APPENDIX B-continued

Schedule of Assessments
Phase 1b HuAB1 + Nivolumab - Schedule of Patient Assessments

| Procedure[a, b] | Screening Day −28 to Day 0 Week 0 | Cycle 1 Day 1 | Cycle 1 Day 2 Week 1 | Cycle 1 Day 4 | Cycle 1 Day 8 Week 2 | Cycle 2 Day 1 Week 3 | Cycle x[s] Day 1 Week ≥5 | Treatment Completion/ Early Termination Visit |
|---|---|---|---|---|---|---|---|---|
| Biopsy[m] | x | | | | | | x | x |
| PK Sampling[n,o] | | x | x | x | x | x | x | x |
| PD Sampling[n] | | x | x | x | x | x | x | x |
| ADA Sampling[n] | | x | | | | x | x | x |
| ANA Testing[p] | | x | | | | x | x | x |
| Study Drug(s)[q,r] | | x | | | | x | x | |
| Adverse Events | x----------------------------------------------------------------------------------------------------------x | | | | | | | x |
| Prior/Concomitant | x----------------------------------------------------------------------------------------------------------x | | | | | | | x |

Notes for Phase 1b Schedule of Assessments

[a]Unless specified, procedure is to be completed within ±72 hours of scheduled time point and to be synchronized with administration day of HuAB1 infusion.

[b]Any clinical assessment, laboratory study, or additional non-specified tests may be obtained at any time, if clinically indicated.

[c]Standard physical examination will be performed as determined by the Investigator, particularly to follow physical findings to resolution. Targeted physical exams should be conducted at any time to follow up on AE reports. A photo of the subject's eyes will be taken at baseline, and subsequently at follow up visits, as clinically indicated.

[d]Height is only required to be recorded at Screening (for BMI calculation). Weight is required to be recorded at Day 1 of each cycle. Dose will be adjusted only if weight change is >10% from first dose.

[e]Vital signs include pulse, respiratory rate, blood pressure, and temperature in the supine position. Measure prior to dose and after completion of the IV infusion at the following time points: 5 minutes, 15 minutes, 30 minutes, and 1 hour post-dose (30 minutes and 1 hour for HuAB1 only). Pulse oximetry is performed at rest and after exertion prior to dosing only.

[f]Patient ECOG Status assessments are to be performed within 96 hours prior to dosing (Day 1 of each cycle).

[g]Screening labs include serology for Hepatitis B (HBsAg and HBcAb), Hepatitis C (HCV antibody), HIV antibody, and Quantiferon test (for latent TB).

[h]Clinical Safety Labs:
Hematology including CBC with differential, platelets, hemoglobin, hematocrit, RBC, and RBC indices
Chemistry includes CK (creatinine kinase), AST (aspartate transaminase), ALT (alanine transaminase), bicarbonate, bilirubin, (direct and total), BUN (blood urea nitrogen), calcium, chloride, creatinine, glucose, LDH (lactate dehydrogenase), phosphorus, potassium, sodium, and, if applicable, serum pregnancy. If CK is elevated at any time, obtain troponins (cardiac and skeletal), CK isoenzymes, aldolase, and ECG; repeat CK and these additional tests daily or other interval as clinically indicated, until resolved or stable. If either AST or ALT is elevated, obtain total serum bilirubin, alkaline phosphatase; repeat daily or other interval, as clinically indicated, until resolved or stable. Additional tests may be obtained at any time, if clinically indicated. Urinalysis will only be done at Screening, and when clinically indicated.

[i]Obtain ECG records at Screening and Treatment Completion/Early Termination Visit (after PK/PD blood draw, record exact time). Additional ECGs should be obtained at any time, if serum CK or cardiac troponin is elevated; if abnormal (excluding sinus tachycardia), ECGs should be obtained (if clinically indicated), until the abnormality is resolved or clinically stable. Additional ECGs may be obtained at any time, if clinically indicated. ECGs for each patient should be obtained from the same machine whenever possible. To minimize variability, it is important that patients be in a resting position for at least 5 minutes prior to each ECG evaluation. Body position should be consistently maintained for each ECG evaluation to prevent changes in heart rate. Environmental distractions (e.g., television, radio, conversation) should be avoided during the pre-ECG resting period and during ECG recording. Additional tests may be obtained at any time, if clinically indicated.

[j]CT/MRI of the tumor sites measured as per Response Evaluation Criteria in Solid Tumors (RECIST) v1.1. If subject terminates prior to scheduled CT/MRI scan, subject should have scans done at Treatment Completion/Early Termination Visit. Response per CT/MRI will be assessed using RECIST v1.1. In the case of PD-1 resistant melanoma and squamous lung cancer, CT scans need to be done at the end of Cycles 4 and 6. The same measuring modality should be preferably used by the site to maintain consistency across the various time points. The tumor assessments for all other cancer types will be done every 2 months (4 cycles) apart unless clinically indicated.

[k]Performed every 8 weeks for the first 12 months for subjects who remain on treatment (and every 12 weeks thereafter) and 28 days (±7 days) after the last dose of study treatment. CT/MRI scans do not need to be repeated if performed within 8 weeks prior to the Treatment Completion/Early Termination Visit or if tumor progression was previously determined.

[l]All women of childbearing potential (including those who have had a tubal ligation) will have a serum pregnancy test at Screening and at Treatment Completion/Early Termination Visit and when clinically indicated.

[m]Biopsy at primary tumor or metastatic tumor site will be collected at Screening and prior to Cycle 3, Day 1 dose. It is recommended that subjects who have documented progression receive another biopsy at the end of treatment. Biopsies will be assessed for tumor associated leukocytes, tumor proliferation and cell death markers.

[n]Samples will be collected for PK, PD, and ADA analyses. Not all visits will require collection of all three - see Appendix C for collection schedule.

[o]Blood will be collected to evaluate Cmax & Cmin on day 1 of study drugs on Cycles 1, 2, 3, 5, 8, 9, 13, 21, and at the end of treatment.

[p]Antinuclear antibody (ANA) testing by indirect fluorescent antibody (IFA). If the titer is positive, check erythrocyte sedimentation rate (ESR) and C- reactive protein (CRP) to confirm result. Will be checked prior to dose at Cycles 1, 2, 3, 5, 9, 13, 21, then every 6 cycles while on treatment and at Treatment Completion/Early Termination Visit.

[q]HuAB1 and nivolumab will both be administered by IV infusion over 30 minutes. Nivolumab will be given first, with a 30-minute rest between the 2 infusions, followed by HuAB1 30- minute infusion.

[r]HuAB1 + nivolumab study drug will be administered every 2 weeks in 14-day cycles and will continue until PD or unacceptable toxicity.

[s]These assessments are to be performed prior to each subsequent dose (with exceptions noted in Appendix B) for patients who continue treatment without signs of progressive disease or toxicity.

APPENDIX C

Schedule of Sample Collection
Phase 1a/b: Study Flowchart for Pharmacokinetic and Pharmacodynamic Blood Sample Collections

| Study Cycle | Study Day | Time point | Type of Sample |
|---|---|---|---|
| Screening | Screening (Day-28) | Screening | Biopsy Tissue |
| Cycle 1 | Day 1 | Prior to infusion | HuAB1 & Nivo PK (serum) |
| | | | HuAB1 & Nivo ADA (serum) |
| | | | Selected serum markers (serum) |
| | | | ANA (serum) |
| | | | CD14$^+$/CD16$^+$ monocytes, MDSC panel (whole blood) |
| | | | Gene expression by RNAseq (whole Blood) |
| | | | T cell phenotype (frozen PBMC) |
| | | | Cytokine multiplex panel (serum) |

APPENDIX C-continued

Schedule of Sample Collection
Phase 1a/b: Study Flowchart for Pharmacokinetic and Pharmacodynamic Blood Sample Collections

| Study Cycle | Study Day | Time point | Type of Sample |
|---|---|---|---|
| | | 15 min after infusion | HuAB1 & Nivo PK (serum) |
| | | 4 hr after infusion | HuAB1 PK (serum) |
| | Day 2 | 24 hr after infusion | HuAB1 PK (serum) |
| | | | Gene expression by RNASeq (whole blood) |
| | | | Cytokine multiplex panel (serum) |
| | Day 4 | 72 hr after infusion | HuAB1 PK (serum) |
| | | | $CD14^+/CD16^+$ monocytes, (whole blood) |
| | | | Gene expression by RNASeq (whole blood) |
| | Day 8 | 168 hr after infusion | HuAB1 PK (serum) |
| | | | $CD14^+/CD16^+$, (whole blood) |
| | | | Gene expression (whole blood) |
| | | | T cell phenotype (frozen PBMC) |
| | | | Cytokine multiplex panel (serum) |
| Cycles 2-3 | Day 1 | Prior to infusion | Biopsy Tissue (to be taken prior to Cycle 3, Day 1 dose) |
| | | | HuAB1 & Nivo PK(serum) |
| | | | HuAB1 & Nivo ADA (serum) |
| | | | Selected serum markers (serum) |
| | | | ANA (serum) |
| | | | $CD14^+/CD16^+$ monocytes, (whole blood) |
| | | | Gene expression by RNAseq (whole blood) |
| | | | MDSC panel (whole blood) (Cycle 3 only) |
| | | | T cell phenotype (frozen PBMC), (prior to Cycle 3 only; should correspond to tissue biopsy) |
| | | | Cytokine multiplex panel (serum) |
| | | 15 min after infusion | HuAB1 PK (serum) (Cycle 2 only) |
| Cycle 8 | Day 1 | 15 min after infusion | HuAB1 PK and Nivo PK (serum) |
| Cycles 5, 9, 13, 21 | Day 1 | Prior to infusion | HuAB1 and Nivo PK (serum) |
| | | | Selected serum markers (serum) (prior to Cycle 9) |
| | | | ANA (serum) (and every 6 cycles starting after Cycle 21) |
| | | | $CD14^+/CD16^+$ monocytes (whole blood) (prior to Cycle 9) |
| | | | Gene expression by RNASeq (whole blood) |
| | | | HuAB1 & Nivo ADA (serum) (prior to dose for cycles 5, 13, and 21) |
| | | | Cytokine multiplex panel (serum) (prior to dose for Cycles 9 and 21) |
| Treatment Completion/ Early Termination | Study discontinuation/ PD | Post treatment | Biopsy tissue for patients who have documented disease progression |
| | | | HuAB1 & Nivo PK (serum) |
| | | | HuAB1 & Nivo ADA (serum) |
| | | | Selected serum markers (serum) |
| | | | ANA (serum) |
| | | | $CD14^+/CD16^+$ monocytes, (whole blood) |
| | | | Cytokine multiplex panel (serum) |
| | | | Gene expression by RNASeq (whole blood) |
| | 100 days post-last dose | | HuAB1 & Nivo ADA (serum) |
| | | | HuAB1 PK (serum) |

APPENDIX D—SAMPLE COLLECTION FOR PD ANALYSES

Blood samples
Whole blood analyses
CD14+/CD16+ monocytes
Gene expression
DNA for SNP analysis
Serum analyses
PKofHuAB1
PK of nivolumab
ADA ofHuAB1
ADA of nivolumab
ANA (if result is positive, check ESR and CRP to confirm)
Serum cytokine multiplex
Selected serum markers
Frozen PBMC analysis for characterization of T cells, monocytes and myeloid-derived suppressor cells by flow cytometry
Tumor biopsy samples
IHC analysis of selected biomarkers
Gene expression analysis
T-cell receptor clonality
Neo-antigen analysis Table of Sequences Table 10 provides certain sequences discussed herein. All polypeptide and antibody sequences are shown without leader sequences, unless otherwise indicated.

TABLE 10

Sequences and Descriptions

| SEQ ID NO | Description | Sequence |
|---|---|---|
| 1 | hCSF1R (full-length, no leader sequence) | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SPLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHTHP PDEFLFTPVV VACMSIMALL LLLLLLLLYK YKQKPKYQVR WKIIESYEGN SYTFIDPTQL PYNEKWEFPR NNLQFGKTLG AGAFGKVVEA TAFGLGKEDA VLKVAVKMLK STAHADEKEA LMSELKIMSH LGQHENIVNL LGACTHGGPV LVITEYCCYG DLLNFLRRKA EAMLGPSLSP GQDPEGGVDY KNIHLEKKYV RRDSGFSSQG VDTYVEMRPV STSSNDSFSE QDLDKEDGRP LELRDLLHFS SQVAQGMAFL ASKNCIHRDV AARNVLLTNG HVAKIGDFGL ARDIMNDSNY IVKGNARLPV KWMAPESIFD CVYTVQSDVW SYGILLWEIF SLGLNPYPGI LVNSKFYKLV KDGYQMAQPA FAPKNIYSIM QACWALEPTH RPTFQQICSF LQEQAQEDRR ERDYTNLPSS SRSGGSGSSS SELEEESSSE HLTCCEQGDI AQPLLQPNNY QFC |
| 2 | hCSF1R (full-length, + leader sequence) | MGPGVLLLLL VATAWHGQGI PVIEPSVPEL VVKPGATVTL RCVGNGSVEW DGPPSPHWTL YSDGSSSILS TNNATFQNTG TYRCTEPGDP LGGSAAIHLY VKDPARPWNV LAQEVVVFED QDALLPCLLT DPVLEAGVSL VRVRGRPLMR HTNYSFSPWH GFTIHRAKFI QSQDYQCSAL MGGRKVMSIS IRLKVQKVIP GPPALTLVPA ELVRIRGEAA QIVCSASSVD VNFDVFLQHN NTKLAIPQQS DFHNNRYQKV LTLNLDQVDF QHAGNYSCVA SNVQGKHSTS MFFRVVESAY LNLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTF INGSGTLLCA ASGYPQPNVT WLQCSGHTDR CDEAQVLQVW DDPYPEVLSQ EPFHKVTVQS LLTVETLEHN QTYECRAHNS VGSGSWAFIP ISAGAHTHPP DEFLFTPVVV ACMSIMALLL LLLLLLYKY KQKPKYQVRW KIIESYEGNS YTFIDPTQLP YNEKWEFPRN NLQFGKTLGA GAFGKVVEAT AFGLGKEDAV LKVAVKMLKS TAHADEKEAL MSELKIMSHL GQHENIVNLL GACTHGGPVL VITEYCCYGD LLNFLRRKAE AMLGPSLSPG QDPEGGVDYK NIHLEKKYVR RDSGFSSQGV DTYVEMRPVS TSSNDSFSEQ DLDKEDGRPL ELRDLLHFSS QVAQGMAFLA SKNCIHRDVA ARNVLLTNGH VAKIGDFGLA RDIMNDSNYI VKGNARLPVK WMAPESIFDC VYTVQSDVWS YGILLWEIFS LGLNPYPGIL VNSKFYKLVK DGYQMAQPAF APKNIYSIMQ ACWALEPTHR PTFQQICSFL QEQAQEDRRE RDYTNLPSSS RSGGSGSSSS ELEEESSSEH LTCCEQGDIA QPLLQPNNYQ FC |
| 5 | hCSF1R ECD 506 | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SPLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAH |

TABLE 10-continued

Sequences and Descriptions

| SEQ ID NO | Description | Sequence |
|---|---|---|
| 6 | hCSF1R ECD.506-Fc | IPVIEPSVPE LVVKPGATVT LRCVGNGSVE WDGPPSPHWT LYSDGSSSIL STNNATFQNT GTYRCTEPGD PLGGSAAIHL YVKDPARPWN VLAQEVVVFE DQDALLPCLL TDPVLEAGVS LVRVRGRPLM RHTNYSFSPW HGFTIHRAKF IQSQDYQCSA LMGGRKVMSI SIRLKVQKVI PGPPALTLVP AELVRIRGEA AQIVCSASSV DVNFDVFLQH NNTKLAIPQQ SDFHNNRYQK VLTLNLDQVD FQHAGNYSCV ASNVQGKHST SMFFRVVESA YLNLSSEQNL IQEVTVGEGL NLKVMVEAYP GLQGFNWTYL GPFSDHQPEP KLANATTKDT YRHTFTLSLP RLKPSEAGRY SFLARNPGGW RALTFELTLR YPPEVSVIWT FINGSGTLLC AASGYPQPNV TWLQCSGHTD RCDEAQVLQV WDDPYPEVLS QEPFHKVTVQ SLLTVETLEH NQTYECRAHN SVGSGSWAFI PISAGAHEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 7 | cyroCSF1R ECD (with leader sequence) | MGPGVLLLLL VVTAWHGQGI PVIEPSGPEL VVKPGETVTL RCVGNGSVEW DGPISPHWTL YSDGPSSVLT TTNATFQNTR TYRCTEPGDP LGGSAAIHLY VKDPARPWNV LAKEVVVFED QDALLPCLLT DPVLEAGVSL VRLRGRPLLR HTNYSFSPWH GFTIHRAKFI QGQDYQCSAL MGSRKVMSIS IRLKVQKVIP GPPALTLVPA ELVRIRGEAA QIVCSASNID VDFDVFLQHN TTKLAIPQRS DFHDNRYQKV LTLSLGQVDF QHAGNYSCVA SNVQGKHSTS MFFRVVESAY LDLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTS INGSGTLLCA ASGYPQPNVT WLQCAGHTDR CDEAQVLQVW VDPHPEVLSQ EPFQKVTVQS LLTAETLEHN QTYECRAHNS VGSGSWAFIP ISAGAR |
| 8 | cyroCSF1R ECD-Fc (with leader sequence) | MGPGVLLLLL VVTAWHGQGI PVIEPSGPEL VVKPGETVTL RCVGNGSVEW DGPISPHWTL YSDGPSSVLT TTNATFQNTR TYRCTEPGDP LGGSAAIHLY VKDPARPWNV LAKEVVVFED QDALLPCLLT DPVLEAGVSL VRLRGRPLLR HTNYSFSPWH GFTIHRAKFI QGQDYQCSAL MGSRKVMSIS IRLKVQKVIP GPPALTLVPA ELVRIRGEAA QIVCSASNID VDFDVFLQHN TTKLAIPQRS DFHDNRYQKV LTLSLGQVDF QHAGNYSCVA SNVQGKHSTS MFFRVVESAY LDLSSEQNLI QEVTVGEGLN LKVMVEAYPG LQGFNWTYLG PFSDHQPEPK LANATTKDTY RHTFTLSLPR LKPSEAGRYS FLARNPGGWR ALTFELTLRY PPEVSVIWTS INGSGTLLCA ASGYPQPNVT WLQCAGHTDR CDEAQVLQVW VDPHPEVLSQ EPFQKVTVQS LLTAETLEHN QTYECRAHNS VGSGSWAFIP ISAGARGSEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 3 | Light chain leader sequence | METDTLLLWV LLLWVPGSTG |
| 4 | Heavy chain leader sequence | MAVLGLLLCL VTFPSCVLS |
| 9 | Fab 0301 heavy chain variable region | EVQLQQSGPE LVRPGASVKM SCKASGYTFT DNYMIWVKQS HGKSLEWIGD INPYNGGTTF NQKFKGKATL TVEKSSSTAY MQLNSLTSED SAVYYCARES PYFSNLYVMD YWGQGTSVTV SS |
| 10 | Fab 0301 light chain variable region | NIVLTQSPAS LAVSLGQRAT ISCKASQSVD YDGDNYMNWY QQKPGQPPKL LIYAASNLES GIPARFSGSG SGTDFTLNIH PVEEEDAATY YCHLSNEDLS TFGGGTKLEI K |
| 11 | Fab 0302 heavy chain variable region | EIQLQQSGPE LVKPGASVKM SCKASGYTFS DFNIHWVKQK PGQGLEWIGY INPYTDVTVY NEKFKGKATL TSDRSSSTAY MDLSSLTSED SAVYYCASYF DGTFDYALDY WGQGTSITVS S |
| 12 | Fab 0302 light chain variable region | DVVVTQTPAS LAVSLGQRAT ISCRASESVD NYGLSFMNWF QQKPGQPPKL LIYTASNLES GIPARFSGGG SRTDFTLTID PVEADDAATY FCQQSKELPW TFGGGTRLEI K |

TABLE 10-continued

Sequences and Descriptions

| SEQ ID NO | Description | Sequence |
|---|---|---|
| 13 | Fab 0311 heavy chain variable region | EIQLQQSGPD LMKPGASVKM SCKASGYIFT DYNMHWVKQN QGKSLEWMGE INPNNGVVVY NQKFKGTTTL TVDKSSSTAY MDLHSLTSED SAVYYCTRAL YHSNFGWYFD SWGKGTTLTV SS |
| 14 | Fab 0311 light chain variable region | DIVLTQSPAS LAVSLGQRAT ISCKASQSVD YDGDSHMNWY QQKPGQPPKL LIYTASNLES GIPARFSGSG SGADFTLTIH PVEEEDAATY YCQQGNEDPW TFGGGTRLEI K |
| 15 | 0301 heavy chain CDR1 | GYTFTDNYMI |
| 16 | 0301 heavy chain CDR2 | DINPYNGGTT FNQKFKG |
| 17 | 0301 heavy chain CDR3 | ESPYFSNLYV MDY |
| 18 | 0301 light chain CDR1 | KASQSVDYDG DNYMN |
| 19 | 0301 light chain CDR2 | AASNLES |
| 20 | 0301 light chain CDR3 | HLSNEDLST |
| 21 | 0302 heavy chain CDR1 | GYTFSDFNIH |
| 22 | 0302 heavy chain CDR2 | YINPYTDVTV YNEKFKG |
| 23 | 0302 heavy chain CDR3 | YFDGTFDYAL DY |
| 24 | 0302 light chain CDR1 | RASESVDNYG LSFMN |
| 25 | 0302 light chain CDR2 | TASNLES |
| 26 | 0302 light chain CDR3 | QQSKELPWT |
| 27 | 0311 heavy chain CDR1 | GYIFTDYNMH |
| 28 | 0311 heavy chain CDR2 | EINPNNGVVV YNQKFKG |
| 29 | 0311 heavy chain CDR3 | ALYHSNFGWY FDS |
| 30 | 0311 light chain CDR1 | KASQSVDYDG DSHMN |
| 31 | 0311 light chain CDR2 | TASNLES |
| 32 | 0311 light chain CDR3 | QQGNEDPWT |
| 33 | cAb 0301 heavy chain | EVQLQQSGPE LVRPGASVKM SCKASGYTFT DNYMIWVKQS HGKSLEWIGD INPYNGGTTF NQKFKGKATL TVEKSSSTAY MQLNSLTSED SAVYYCARES PYFSNLYVMD YWGQGTSVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |

TABLE 10-continued

Sequences and Descriptions

| SEQ ID NO | Description | Sequence |
|---|---|---|
| 34 | cAb 0301 light chain | NIVLTQSPAS LAVSLGQRAT ISCKASQSVD YDGDNYMNWY QQKPGQPPKL LIYAASNLES GIPARFSGSG SGTDFTLNIH PVEEEDAATY YCHLSNEDLS TFGGGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 35 | cAb 0302 heavy chain | EIQLQQSGPE LVKPGASVKM SCKASGYTFS DFNIHWVKQK PGQGLEWIGY INPYTDVTVY NEKFKGKATL TSDRSSSTAY MDLSSLTSED SAVYYCASYF DGTFDYALDY WGQGTSITVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 36 | cAb 0302 light chain | DVVVTQTPAS LAVSLGQRAT ISCRASESVD NYGLSFMNWF QQKPGQPPKL LIYTASNRLES GIPARFSGGG SRTDFTLTID PVEADDAATY FCQQSKELPW TFGGGTRLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 37 | cAb 0311 heavy chain | EIQLQQSGPD LMKPGASVKM SCKASGYIFT DYNMHWVKQN QGKSLEWMGE INPNNGVVVY NQKFKGTTTL TVDKSSSTAY MDLHSLTSED SAVYYCTRAL YHSNFGWYFD SWGKGTTLTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 38 | cAb 0311 light chain | DIVLTQSPAS LAVSLGQRAT ISCKASQSVD YDGDSHMNWY QQKPGQPPKL LIYTASNLES GIPARFSGSG SGADFTLTIH PVEEEDAATY YCQQGNEDPW TFGGGTRLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 39 | h0301-H0 heavy chain variable region | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SS |
| 40 | h0301-H1 heavy chain variable region | QVQLVQSGAE VKKPGSSVKV SCKASGYTFT DNYMIWVRQA PGQGLEWMGD INPYNGGTTF NQKFKGRVTI TVDKSTSTAY MELSSLRSED TAVYYCARES PYFSNLYVMD YWGQGTLVTV SS |
| 41 | h0301-H2 heavy chain variable region | QVQLVQSGAE VKKPGSSVKV SCKASGYTFT DNYMIWVRQA PGQGLEWIGD INPYNGGTTF NQKFKGRATL TVDKSTSTAY MELSSLRSED TAVYYCARES PYFSNLYVMD YWGQGTLVTV SS |
| 42 | H0302-H1 heavy chain variable region | QVQLVQSGAE VKKPGSSVKV SCKASGYTFS DFNIHWVRQA PGQGLEWMGY INPYTDVTVY NEKFKGRVTI TSDKSTSTAY MELSSLRSED TAVYYCASYF DGTFDYALDY WGQGTLVTVS S |
| 43 | H0302-H2 heavy chain variable region | QVQLVQSGAE VKKPGSSVKV SCKASGYTFS DFNIHWVRQA PGQGLEWIGY INPYTDVTVY NEKFKGRATL TSDKSTSTAY MELSSLRSED TAVYYCASYF DGTFDYALDY WGQGTLVTVS S |
| 44 | H0311-H1 heavy chain variable region | QVQLVQSGAE VKKPGSSVKV SCKASGYIFT DYNMHWVRQA PGQGLEWMGE INPNNGVVVY NQKFKGRVTI TVDKSTSTAY MELSSLRSED TAVYYCTRAL YHSNFGWYFD SWGQGTLVTV SS |
| 45 | H0311-H2 heavy chain variable region | QVQLVQSGAE VKKPGSSVKV SCKASGYIFT DYNMHWVRQA PGQGLEWMGE INPNNGVVVY NQKFKGTTTL TVDKSTSTAY MELSSLRSED TAVYYCTRAL YHSNFGWYFD SWGQGTLVTV SS |

TABLE 10-continued

Sequences and Descriptions

| SEQ ID NO | Description | Sequence |
|---|---|---|
| 46 | h0301-L0 light chain variable region | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 47 | h0301-L1 light chain variable region | NIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI K |
| 48 | H0302-L0 light chain variable region | EIVLTQSPAT LSLSPGERAT LSCRASESVD NYGLSFMNWY QQKPGQAPRL LIYTASNLES GIPARFSGSG SGTDFTLTIS SLEPEDFAVY YCQQSKELPW TFGQGTKVEI K |
| 49 | H0302-L1 light chain variable region | EIVLTQSPAT LSLSPGERAT LSCRASESVD NYGLSFMNWY QQKPGQAPRL LIYTASNLES GIPARFSGSG SRTDFTLTIS SLEPEDFAVY YCQQSKELPW TFGQGTKVEI K |
| 50 | H0302-L2 light chain variable region | EIVVTQSPAT LSLSPGERAT LSCRASESVD NYGLSFMNWF QQKPGQAPRL LIYTASNLES GIPARFSGSG SRTDFTLTIS SLEPEDFAVY YCQQSKELPW TFGQGTKVEI K |
| 51 | H0311-L0 light chain variable region | EIVLTQSPAT LSLSPGERAT LSCKASQSVD YDGDSHMNWY QQKPGQAPRL LIYTASNLES GIPARFSGSG SGTDFTLTIS SLEPEDFAVY YCQQGNEDPW TFGQGTKVEI K |
| 52 | H0311-L1 light chain variable region | DIVLTQSPAT LSLSPGERAT LSCKASQSVD YDGDSHMNWY QQKPGQAPRL LIYTASNLES GIPARFSGSG SGADFTLTIS SLEPEDFAVY YCQQGNEDPW TFGQGTKVEI K |
| 53 | h0301-H0 heavy chain | QVQLVQSGAE VKKPGSSVKV SCKASGYTFT DNYMIWVRQA PGQGLEWMGD INPYNGGTTF NQKFKGRVTI TADKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 54 | h0301-H1 heavy chain | QVQLVQSGAE VKKPGSSVKV SCKASGYTFT DNYMIWVRQA PGQGLEWMGD INPYNGGTTF NQKFKGRVTI TVDKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 55 | h0301-H2 heavy chain | QVQLVQSGAE VKKPGSSVKV SCKASGYTFT DNYMIWVRQA PGQGLEWIGD INPYNGGTTF NQKFKGRATL TVDKSTSTAY MELSSLRSED TAVYYCARES PYFSNLYVMD YWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 56 | H0302-H1 heavy chain | QVQLVQSGAE VKKPGSSVKV SCKASGYTFS DFNIHWVRQA PGQGLEWMGY INPYTDVTVY NEKFKGRVTI TSDKSTSTAY MELSSLRSED TAVYYCASYF DGTFDYALDY WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |

TABLE 10-continued

Sequences and Descriptions

| SEQ ID NO | Description | Sequence |
|---|---|---|
| 57 | H0302-H2 heavy chain | QVQLVQSGAE VKKPGSSVKV SCKASGYTFS DFNIHWVRQA PGQGLEWIGY INPYTDVTVY NEKFKGRATL TSDKSTSTAY MELSSLRSED TAVYYCASYF DGTFDYALDY WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKRVE SKYGPPCPPC PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK |
| 58 | H0311-H1 heavy chain | QVQLVQSGAE VKKPGSSVKV SCKASGYIFT DYNMHWVRQA PGQGLEWMGE INPNNGVVVY NQKFKGRVTI TVDKSTSTAY MELSSLRSED TAVYYCTRAL YHSNFGWYFD SWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 59 | H0311-H2 heavy chain | QVQLVQSGAE VKKPGSSVKV SCKASGYIFT DYNMHWVRQA PGQGLEWMGE INPNNGVVVY NQKFKGTTTL TVDKSTSTAY MELSSLRSED TAVYYCTRAL YHSNFGWYFD SWGQGTLVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 60 | h0301-L0 light chain | EIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 61 | h0301-L1 light chain | NIVLTQSPAT LSLSPGERAT LSCKASQSVD YDGDNYMNWY QQKPGQAPRL LIYAASNLES GIPARFSGSG SGTDFTLTIS SLEPEDFAVY YCHLSNEDLS TFGGGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 62 | H0302-L0 light chain | EIVLTQSPAT LSLSPGERAT LSCRASESVD NYGLSFMNWY QQKPGQAPRL LIYTASNLES GIPARFSGSG SGTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 63 | H0302-L1 light chain | EIVLTQSPAT LSLSPGERAT LSCRASESVD NYGLSFMNWY QQKPGQAPRL LIYTASNLES GIPARFSGSG SRTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 64 | H0302-L2 light chain | EIVVTQSPAT LSLSPGERAT LSCRASESVD NYGLSFMNWF QQKPGQAPRL LIYTASNLES GIPARFSGSG SRTDFTLTIS SLEPEDFAVY YCQQSKELPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 65 | H0311-L0 light chain | EIVLTQSPAT LSLSPGERAT LSCKASQSVD YDGDSHMNWY QQKPGQAPRL LIYTASNLES GIPARFSGSG SGTDFTLTIS SLEPEDFAVY YCQQGNEDPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 66 | H0311-L1 light chain | DIVLTQSPAT LSLSPGERAT LSCKASQSVD YDGDSHMNWY QQKPGQAPRL LIYTASNLES GIPARFSGSG SGADFTLTIS SLEPEDFAVY YCQQGNEDPW TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |

TABLE 10-continued

Sequences and Descriptions

| SEQ ID NO | Description | Sequence |
|---|---|---|
| 67 | Human CSF1 | EEVSEYCSHM IGSGHLQSLQ RLIDSQMETS CQITFEFVDQ EQLKDPVCYL KKAFLLVQDI MEDTMRFRDN TPNAIAIVQL QELSLRLKSC FTKDYEEHDK ACVRTFYETP LQLLEKVKNV FNETKNLLDK DWNIFSKNCN NSFAECSSQG HERQSEGS |
| 68 | Human IL-34 | NEPLEMWPLT QNEECTVTGF LRDKLQYRSR LQYMKHYFPI NYKISVPYEG VFRIANVTRL QRAQVSEREL RYLWVLVSLSATESVQDVLL EGHPSWKYLQ EVQTLLLNVQ QGLTDVEVSP KVESVLSLLN APGPNLKLVR PKALLDNCFR VMELLYCSCC KQSSVLNWQD CEVPSPQSCS PEPSLQYAAT QLYPPPPWSP SSPPHSTGSV RPVRAQGEGL LP |
| 69 | Human acceptor A FR1 | QVQLVQSGAE VKKPGSSVKV SCKAS |
| 70 | Human acceptor A FR2 | WVRQAPGQGL EWMG |
| 71 | Human acceptor A FR3 | RVTITADKST STAYMELSSL RSEDTAVYYC AR |
| 72 | Human acceptor A FR4 | WGQGTLVTVS S |
| 73 | Human acceptor B FR1 | QVQLVQSGAE VKKPGSSVKV SCKAS |
| 74 | Human acceptor B FR2 | WVRQAPGQGL EWMG |
| 75 | Human acceptor B FR3 | RVTITADKST STAYMELSSL RSEDTAVYYC AR |
| 76 | Human acceptor B FR4 | WGQGTLVTVSS |
| 77 | Human acceptor C FR1 | QVQLVQSGAE VKKPGSSVKV SCKAS |
| 78 | Human acceptor C FR2 | WVRQAPGQGL EWMG |
| 79 | Human acceptor C FR3 | RVTITADKST STAYMELSSL RSEDTAVYYC AR |
| 80 | Human acceptor C FR4 | WGQGTLVTVS S |
| 81 | Human acceptor D FR1 | EIVLTQSPAT LSLSPGERAT LSC |
| 82 | Human acceptor D FR2 | WYQQKPGQAP RLLIY |
| 83 | Human acceptor D FR3 | GIPARFSGSG SGTDFTLTIS SLEPEDFAVY YC |

TABLE 10-continued

Sequences and Descriptions

| SEQ ID NO | Description | Sequence |
|---|---|---|
| 84 | Human acceptor D FR4 | FGGGTKVEIK |
| 85 | Human acceptor E FR1 | EIVLTQSPAT LSLSPGERAT LSC |
| 86 | Human acceptor E FR2 | WYQQKPGQAP RLLIY |
| 87 | Human acceptor E FR3 | GIPARFSGSG SGTDFTLTIS SLEPEDFAVY YC |
| 88 | Human acceptor E FR4 | FGQGTKVEIK |
| 89 | Human acceptor F FR1 | EIVLTQSPAT LSLSPGERAT LSC |
| 90 | Human acceptor F FR2 | WYQQKPGQAP RLLIY |
| 91 | Human acceptor F FR3 | GIPARFSGSG SGTDFTLTIS SLEPEDFAVY YC |
| 92 | Human acceptor F FR4 | FGQGTKVEIK |
| 93 | mCSF1R ECD-Fc | APVIEPSGPE LVVEPGETVT LRCVSNGSVE WDGPISPYWT LDPESPGSTL TTRNATFKNT GTYRCTELED PMAGSTTIHL YVKDPAHSWN LLAQEVTVVE GQEAVLPCLI TDPALKDSVS LMREGGRQVL RKTVYFFSPW RGFIIRKAKV LDSNTYVCKT MVNGRESTST GIWLKVNRVH PEPPQIKLEP SKLVRIRGEA AQIVCSATNA EVGFNVILKR GDTKLEIPLN SDFQDNYYKK VRALSLNAVD FQDAGIYSCV ASNDVGTRTA TMNFQVVESA YLNLTSEQSL LQEVSVGDSL ILTVHADAYP SIQHYNWTYL GPFFEDQRKL EFITQRAIYR YTFKLFLNRV KASEAGQYFL MAQNKAGWNN LTFELTLRYP PEVSVTWMPV NGSDVLFCDV SGYPQPSVTW MECRGHTDRC DEAQALQVWN DTHPEVLSQK PFDKVIIQSQ LPIGTLKHNM TYFCKTHNSV GNSSQYFRAV SLGQSKQEPK SSDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK |
| 94 | Human IgG4 S241P | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPPCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK |
| 95 | Human IgIc | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 96 | human PD-1 precursor (with signal sequence) UniProtKB/ Swiss-Prot: Q15116.3, 01-OCT-2014 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |

TABLE 10-continued

Sequences and Descriptions

| SEQ ID NO | Description | Sequence |
|---|---|---|
| 97 | human PD-1 (mature, without signal sequence) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 98 | human PD-L1 precursor (with signal sequence) UniProtKB/Swiss-Prot: Q9NZQ7.1, 01-OCT-2014 | MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 99 | human PD-L1 (mature, without signal sequence) | FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 100 | Nivolumab heavy chain variable region | QVQLVESGGGVVQPGRSLRLDCKASGITFSNSGMHWVRQAPGKGLEWVAVIWYD GSKRYYADSVKGRFTISRDNSKNTLFLQMNSLRAEDTAVYYCATNDDYWGQGTL VTVSS |
| 101 | Nivolumab heavy chain constant region | ASTKGPSVFPLAPCSRSTSESTAALGCLVKDYFPEPVTVSWNSGALTSGVHTFP AVLQSSGLYSLSSVVTVPSSSLGTKTYTCNVDHKPSNTKVDKRVESKYGPPCPP CPAPEFLGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSLSLS LGK |
| 102 | Nivolumab light chain variable region | EIVLTQSPATLSLSPGERATLSCRASQSVSSYLAWYQQKPGQAPRLLIYDASNR ATGIPARFSGSGSGTDFTLTISSLEPEDFAVYYCQQSSNWPRTFGQGTKVEIK |
| 103 | Nivolumab light chain constant region | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 104 | Nivolumab heavy chain variable region FR1 | QVQLVESGGGVVQPGRSLRLDCKASGITFS |
| 105 | Nivolumab heavy chain variable region CDR1 | NSGMH |
| 106 | Nivolumab heavy chain variable region FR2 | WVRQAPGKGLEWVA |
| 107 | Nivolumab heavy chain variable region CDR2 | VIWYDGSKRYYADSVKG |
| 108 | Nivolumab heavy chain variable region FR3 | RFTISRDNSKNTLFLQMNSLRAEDTAVYYCAT |

TABLE 10-continued

Sequences and Descriptions

| SEQ ID NO | Description | Sequence |
|---|---|---|
| 109 | Nivolumab heavy chain variable region CDR3 | NDDY |
| 110 | Nivolumab heavy chain variable region FR4 | WGQGTLVTVSS |
| 111 | Nivolumab light chain variable region FR1 | EIVLTQSPATLSLSPGERATLSC |
| 112 | Nivolumab light chain variable region CDR1 | RASQSVSSYLA |
| 113 | Nivolumab light chain variable region FR2 | WYQQKPGQAPRLLIY |
| 114 | Nivolumab light chain variable region CDR2 | DASNRAT |
| 115 | Nivolumab light chain variable region FR3 | GIPARFSGSGSGTDFTLTISSLEPEDFAVYYC |
| 116 | Nivolumab light chain variable region CDR3 | QQSSNWPRT |
| 117 | Nivolumab light chain variable region FR4 | FGQGTKVEIK |

The invention claimed is:

1. A method of treating cancer in a subject comprising administering to the subject a therapeutically effective amount of an anti-CSF1R antibody and an anti-PD-1 antibody,
   (a) wherein the cancer is selected from non-small cell lung cancer, melanoma, squamous cell carcinoma of the head and neck, ovarian cancer, pancreatic cancer, renal cell carcinoma, hepatocellular carcinoma, bladder cancer, malignant glioma, colorectal cancer, and endometrial cancer; and
   (b) wherein the anti-PD-1 antibody is selected from:
      i) an antibody comprising a heavy chain comprising the sequence of SEQ ID NO: 100 and a light chain comprising the sequence of SEQ ID NO: 102;
      ii) an antibody comprising a heavy chain comprising a heavy chain (HC) CDR1 having the sequence of SEQ ID NO: 105, an HC CDR2 having the sequence of SEQ ID NO: 107, and an HC CDR3 having the sequence of SEQ ID NO: 109, and a light chain comprising a light chain (LC) CDR1 having the sequence of SEQ ID NO: 112, a LC CDR2 having the sequence of SEQ ID NO: 114, and a LC CDR3 having the sequence of SEQ ID NO: 116; and
      iii) an antibody comprising a heavy chain comprising the sequences of SEQ ID NOs: 100 and 101 and a light chain comprising the sequences of SEQ ID NOs: 102 and 103.

2. The method of claim 1, wherein the anti-PD-1 antibody is nivolumab.

3. The method of claim 1, wherein the anti-CSF1R antibody and the anti-PD-1 antibody are administered concurrently or sequentially.

4. The method of claim 3, wherein the anti-CSF1R antibody and the anti-PD-1 antibody are administered concurrently.

5. The method of claim 3, wherein one or more doses of the anti-PD-1 antibody are administered prior to administering the anti-CSF1R antibody.

6. The method of claim 5, wherein the subject received a complete course of anti-PD-1 antibody therapy prior to administration of the anti-CSF1R antibody.

7. The method of claim 6, wherein the anti-CSF1R antibody is administered during a second course of anti-PD-1 antibody therapy.

8. The method of claim 5, wherein the subject received at least one, at least two, at least three, or at least four doses of the anti-PD-1 antibody prior to administration of the anti-CSF1R antibody.

9. The method of claim 1, wherein at least one dose of the anti-PD-1 antibody is administered concurrently with the anti-CSF1R inhibitor.

10. The method of claim 3, wherein one or more doses of the anti-CSF1R antibody are administered prior to administering the anti-PD-1 antibody.

11. The method of claim 10, wherein the subject received at least two, at least three, at least three, or at least four doses of the anti-CSF1R antibody prior to administration of the anti-PD-1 antibody.

12. The method of claim 10, wherein at least one dose of the anti-CSF1R antibody is administered concurrently with the anti-PD-1 antibody.

13. The method of claim 1, wherein the anti-PD-1 antibody is administered at a dose of about 0.5-10 mg/kg, such as at a dose of about 0.5, about 1, about 2, about 3, about 4, about 5, or about 10 mg/Kg.

14. The method of claim 13, wherein the anti-PD-1 antibody is administered at a dose of 3 mg/kg.

15. The method of claim 1, wherein the anti-CSF1R antibody and the anti-PD-1 antibody are administered once per 1, 2, 3, 4, or 5 weeks, such as once per week, or such as once every 2 weeks, or once every 3 weeks.

16. The method of claim 15, wherein the anti-PD-1 antibody is administered every 4 weeks.

17. The method of claim 1, wherein the anti-PD-1 antibody is nivolumab and is administered at a dose of 240 mg every 2 weeks.

18. The method of claim 1, wherein the cancer is recurrent or progressive after a therapy selected from surgery, chemotherapy, radiation therapy, or a combination thereof.

19. The method of claim 1, wherein administration of the anti-CSF1R antibody and the anti-PD-1 antibody results in synergistic inhibition of tumor growth in a mouse model of the cancer.

20. The method of claim 1, wherein the cancer is a colon, rectum, or colorectal cancer and the mouse model comprises colorectal carcinoma cells, such as MC38 colorectal carcinoma cells.

21. The method of claim 1, wherein the cancer is a pancreatic cancer and the mouse model comprises murine pancreatic ductal adenocarcinoma (PDAC) cells, such as KRasG12D/Ink4a−/− pancreatic ductal adenocarcinoma cells.

22. A method of treating cancer in a subject comprising administering to the subject a therapeutically effective amount of an anti-CSF1R antibody and an anti-PD-1 antibody;
   (a) wherein the cancer is non-small cell lung cancer, melanoma, squamous cell carcinoma of the head and neck, ovarian cancer, pancreatic cancer, renal cell carcinoma, hepatocellular carcinoma, bladder cancer, malignant glioma, colorectal cancer, and endometrial cancer;
   (b) wherein the anti-PD-1 antibody is administered at a dose of 240 mg every two weeks; and
   (c) wherein the anti-PD-1 antibody is selected from:
      i) an antibody comprising a heavy chain comprising the sequence of SEQ ID NO: 100 and a light chain comprising the sequence of SEQ ID NO: 102;
      ii) an antibody comprising a heavy chain comprising a heavy chain (HC) CDR1 having the sequence of SEQ ID NO: 105, an HC CDR2 having the sequence of SEQ ID NO: 107, and an HC CDR3 having the sequence of SEQ ID NO: 109, and a light chain comprising a light chain (LC) CDR1 having the sequence of SEQ ID NO: 112, a LC CDR2 having the sequence of SEQ ID NO: 114, and a LC CDR3 having the sequence of SEQ ID NO: 116; and
      iii) an antibody comprising a heavy chain comprising the sequences of SEQ ID NOs: 100 and 101 and a light chain comprising the sequences of SEQ ID NOs: 102 and 103.

23. The method of claim 22, wherein the anti-PD-1 antibody is nivolumab.

24. A method of treating cancer in a subject comprising administering to the subject a therapeutically effective amount of an anti-CSF1R antibody and an anti-PD-1 antibody;
   (a) wherein the cancer is non-small cell lung cancer, melanoma, squamous cell carcinoma of the head and neck, ovarian cancer, pancreatic cancer, renal cell carcinoma, hepatocellular carcinoma, bladder cancer, malignant glioma, colorectal cancer, and endometrial cancer;
   (b) wherein the anti-PD-1 antibody is administered at a flat dose every four weeks; and
   (c) wherein the anti-PD-1 antibody is selected from:
      i) an antibody comprising a heavy chain comprising the sequence of SEQ ID NO: 100 and a light chain comprising the sequence of SEQ ID NO: 102;
      ii) an antibody comprising a heavy chain comprising a heavy chain (HC) CDR1 having the sequence of SEQ ID NO: 105, an HC CDR2 having the sequence of SEQ ID NO: 107, and an HC CDR3 having the sequence of SEQ ID NO: 109, and a light chain comprising a light chain (LC) CDR1 having the sequence of SEQ ID NO: 112, a LC CDR2 having the sequence of SEQ ID NO: 114, and a LC CDR3 having the sequence of SEQ ID NO: 116; and
      iii) an antibody comprising a heavy chain comprising the sequences of SEQ ID NOs: 100 and 101 and a light chain comprising the sequences of SEQ ID NOs: 102 and 103.

25. The method of claim 24, wherein the anti-PD-1 antibody is nivolumab.

* * * * *

UNITED STATES PATENT AND TRADEMARK OFFICE
CERTIFICATE OF CORRECTION

PATENT NO. : 11,566,076 B2
APPLICATION NO. : 16/808910
DATED : January 31, 2023
INVENTOR(S) : Brian Wong et al.

Page 1 of 1

It is certified that error appears in the above-identified patent and that said Letters Patent is hereby corrected as shown below:

In the Claims

Claim 11, Column 263, Line 8, delete the duplicative "at least three,"

Signed and Sealed this
Twenty-eighth Day of March, 2023

Katherine Kelly Vidal
*Director of the United States Patent and Trademark Office*

SEQUENCE LISTING

<160> NUMBER OF SEQ ID NOS: 117

<210> SEQ ID NO 1
<211> LENGTH: 953
<212> TYPE: PRT
<213> ORGANISM: Artificial sequence
<220> FEATURE:
<223> OTHER INFORMATION: hCSF1R (full-length, no leader sequence)

<400> SEQUENCE: 1

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
    370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr

```
             450                 455                 460
Glu Cys Arg Ala His Asn Ser Val Gly Ser Gly Ser Trp Ala Phe Ile
465                 470                 475                 480

Pro Ile Ser Ala Gly Ala His Thr His Pro Asp Glu Phe Leu Phe
                485                 490                 495

Thr Pro Val Val Val Ala Cys Met Ser Ile Met Ala Leu Leu Leu Leu
                500                 505                 510

Leu Leu Leu Leu Leu Leu Tyr Lys Tyr Lys Gln Lys Pro Lys Tyr Gln
            515                 520                 525

Val Arg Trp Lys Ile Ile Glu Ser Tyr Glu Gly Asn Ser Tyr Thr Phe
        530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
                565                 570                 575

Val Val Glu Ala Thr Ala Phe Gly Leu Gly Lys Glu Asp Ala Val Leu
                580                 585                 590

Lys Val Ala Val Lys Met Leu Lys Ser Thr Ala His Ala Asp Glu Lys
            595                 600                 605

Glu Ala Leu Met Ser Glu Leu Lys Ile Met Ser His Leu Gly Gln His
        610                 615                 620

Glu Asn Ile Val Asn Leu Leu Gly Ala Cys Thr His Gly Gly Pro Val
625                 630                 635                 640

Leu Val Ile Thr Glu Tyr Cys Cys Tyr Gly Asp Leu Leu Asn Phe Leu
                645                 650                 655

Arg Arg Lys Ala Glu Ala Met Leu Gly Pro Ser Leu Ser Pro Gly Gln
                660                 665                 670

Asp Pro Glu Gly Gly Val Asp Tyr Lys Asn Ile His Leu Glu Lys Lys
            675                 680                 685

Tyr Val Arg Arg Asp Ser Gly Phe Ser Ser Gln Gly Val Asp Thr Tyr
        690                 695                 700

Val Glu Met Arg Pro Val Ser Thr Ser Ser Asn Asp Ser Phe Ser Glu
705                 710                 715                 720

Gln Asp Leu Asp Lys Glu Asp Gly Arg Pro Leu Glu Leu Arg Asp Leu
                725                 730                 735

Leu His Phe Ser Ser Gln Val Ala Gln Gly Met Ala Phe Leu Ala Ser
                740                 745                 750

Lys Asn Cys Ile His Arg Asp Val Ala Ala Arg Asn Val Leu Leu Thr
            755                 760                 765

Asn Gly His Val Ala Lys Ile Gly Asp Phe Gly Leu Ala Arg Asp Ile
        770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
                805                 810                 815

Ser Asp Val Trp Ser Tyr Gly Ile Leu Leu Trp Glu Ile Phe Ser Leu
                820                 825                 830

Gly Leu Asn Pro Tyr Pro Gly Ile Leu Val Asn Ser Lys Phe Tyr Lys
            835                 840                 845

Leu Val Lys Asp Gly Tyr Gln Met Ala Gln Pro Ala Phe Ala Pro Lys
        850                 855                 860

Asn Ile Tyr Ser Ile Met Gln Ala Cys Trp Ala Leu Glu Pro Thr His
865                 870                 875                 880
```

```
Arg Pro Thr Phe Gln Gln Ile Cys Ser Phe Leu Gln Glu Gln Ala Gln
                885                 890                 895

Glu Asp Arg Arg Glu Arg Asp Tyr Thr Asn Leu Pro Ser Ser Ser Arg
            900                 905                 910

Ser Gly Gly Ser Gly Ser Ser Ser Glu Leu Glu Glu Glu Ser Ser
            915                 920                 925

Ser Glu His Leu Thr Cys Cys Glu Gln Gly Asp Ile Ala Gln Pro Leu
930                 935                 940

Leu Gln Pro Asn Asn Tyr Gln Phe Cys
945                 950

<210> SEQ ID NO 2
<211> LENGTH: 972
<212> TYPE: PRT
<213> ORGANISM: Homo sapiens
<220> FEATURE:
<221> NAME/KEY: MISC_FEATURE
<222> LOCATION: (1)..(972)
<223> OTHER INFORMATION: hCSF1R (full-length, + leader sequence)

<400> SEQUENCE: 2

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
            85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270
```

-continued

```
Ala Gly Asn Tyr Ser Cys Val Ala Ser Asn Val Gln Gly Lys His Ser
            275                 280                 285
Thr Ser Met Phe Phe Arg Val Val Glu Ser Ala Tyr Leu Asn Leu Ser
    290                 295                 300
Ser Glu Gln Asn Leu Ile Gln Glu Val Thr Val Gly Glu Gly Leu Asn
305                 310                 315                 320
Leu Lys Val Met Val Glu Ala Tyr Pro Gly Leu Gln Gly Phe Asn Trp
                325                 330                 335
Thr Tyr Leu Gly Pro Phe Ser Asp His Gln Pro Glu Pro Lys Leu Ala
            340                 345                 350
Asn Ala Thr Thr Lys Asp Thr Tyr Arg His Thr Phe Thr Leu Ser Leu
        355                 360                 365
Pro Arg Leu Lys Pro Ser Glu Ala Gly Arg Tyr Ser Phe Leu Ala Arg
    370                 375                 380
Asn Pro Gly Gly Trp Arg Ala Leu Thr Phe Glu Leu Thr Leu Arg Tyr
385                 390                 395                 400
Pro Pro Glu Val Ser Val Ile Trp Thr Phe Ile Asn Gly Ser Gly Thr
                405                 410                 415
Leu Leu Cys Ala Ala Ser Gly Tyr Pro Gln Pro Asn Val Thr Trp Leu
            420                 425                 430
Gln Cys Ser Gly His Thr Asp Arg Cys Asp Glu Ala Gln Val Leu Gln
        435                 440                 445
Val Trp Asp Asp Pro Tyr Pro Glu Val Leu Ser Gln Glu Pro Phe His
    450                 455                 460
Lys Val Thr Val Gln Ser Leu Leu Thr Val Glu Thr Leu Glu His Asn
465                 470                 475                 480
Gln Thr Tyr Glu Cys Arg Ala His Asn Ser Val Gly Ser Gly Ser Trp
                485                 490                 495
Ala Phe Ile Pro Ile Ser Ala Gly Ala His Thr His Pro Pro Asp Glu
            500                 505                 510
Phe Leu Phe Thr Pro Val Val Ala Cys Met Ser Ile Met Ala Leu
        515                 520                 525
Leu Leu Leu Leu Leu Leu Leu Leu Leu Tyr Lys Tyr Lys Gln Lys Pro
    530                 535                 540
Lys Tyr Gln Val Arg Trp Lys Ile Ile Glu Ser Tyr Glu Gly Asn Ser
545                 550                 555                 560
Tyr Thr Phe Ile Asp Pro Thr Gln Leu Pro Tyr Asn Glu Lys Trp Glu
                565                 570                 575
Phe Pro Arg Asn Asn Leu Gln Phe Gly Lys Thr Leu Gly Ala Gly Ala
            580                 585                 590
Phe Gly Lys Val Val Glu Ala Thr Ala Phe Gly Leu Gly Lys Glu Asp
        595                 600                 605
Ala Val Leu Lys Val Ala Val Lys Met Leu Lys Ser Thr Ala His Ala
    610                 615                 620
Asp Glu Lys Glu Ala Leu Met Ser Glu Leu Lys Ile Met Ser His Leu
625                 630                 635                 640
Gly Gln His Glu Asn Ile Val Asn Leu Leu Gly Ala Cys Thr His Gly
                645                 650                 655
Gly Pro Val Leu Val Ile Thr Glu Tyr Cys Cys Tyr Gly Asp Leu Leu
            660                 665                 670
Asn Phe Leu Arg Arg Lys Ala Glu Ala Met Leu Gly Pro Ser Leu Ser
        675                 680                 685
Pro Gly Gln Asp Pro Glu Gly Gly Val Asp Tyr Lys Asn Ile His Leu
```

```
                    690                 695                 700
Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
        850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
        930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970

<210> SEQ ID NO 3
<211> LENGTH: 20
<212> TYPE: PRT
<213> ORGANISM: Artificial sequence
<220> FEATURE:
<223> OTHER INFORMATION: Light chain leader sequence

<400> SEQUENCE: 3

Met Glu Thr Asp Thr Leu Leu Leu Trp Val Leu Leu Leu Trp Val Pro
1               5                   10                  15

Gly Ser Thr Gly
            20

<210> SEQ ID NO 4
<211> LENGTH: 19
<212> TYPE: PRT
<213> ORGANISM: Artificial sequence
<220> FEATURE:
<223> OTHER INFORMATION: Heavy chain leader sequence

<400> SEQUENCE: 4
```

Met Ala Val Leu Gly Leu Leu Leu Cys Leu Val Thr Phe Pro Ser Cys
1               5                   10                  15

Val Leu Ser

<210> SEQ ID NO 5
<211> LENGTH: 487
<212> TYPE: PRT
<213> ORGANISM: Artificial sequence
<220> FEATURE:
<223> OTHER INFORMATION: hCSF1R ECD.506

<400> SEQUENCE: 5

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
        130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
                180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
        210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
        290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu 340             345             350
Lys Pro Ser Glu Ala Gly Arg Tyr Ser Phe Leu Ala Arg Asn Pro Gly
            355             360             365

Gly Trp Arg Ala Leu Thr Phe Glu Leu Thr Leu Arg Tyr Pro Pro Glu
        370             375             380

Val Ser Val Ile Trp Thr Phe Ile Asn Gly Ser Gly Thr Leu Leu Cys
385             390             395             400

Ala Ala Ser Gly Tyr Pro Gln Pro Asn Val Thr Trp Leu Gln Cys Ser
            405             410             415

Gly His Thr Asp Arg Cys Asp Glu Ala Gln Val Leu Gln Val Trp Asp
            420             425             430

Asp Pro Tyr Pro Glu Val Leu Ser Gln Glu Pro Phe His Lys Val Thr
            435             440             445

Val Gln Ser Leu Leu Thr Val Glu Thr Leu Glu His Asn Gln Thr Tyr
            450             455             460

Glu Cys Arg Ala His Asn Ser Val Gly Ser Gly Ser Trp Ala Phe Ile
465             470             475             480

Pro Ile Ser Ala Gly Ala His
            485

<210> SEQ ID NO 6
<211> LENGTH: 719
<212> TYPE: PRT
<213> ORGANISM: Artificial sequence
<220> FEATURE:
<223> OTHER INFORMATION: hCSF1R ECD.506-Fc

<400> SEQUENCE: 6

Ile Pro Val Ile Glu Pro Ser Val Pro Glu Leu Val Val Lys Pro Gly
1               5               10              15

Ala Thr Val Thr Leu Arg Cys Val Gly Asn Gly Ser Val Glu Trp Asp
            20              25              30

Gly Pro Pro Ser Pro His Trp Thr Leu Tyr Ser Asp Gly Ser Ser Ser
        35              40              45

Ile Leu Ser Thr Asn Asn Ala Thr Phe Gln Asn Thr Gly Thr Tyr Arg
    50              55              60

Cys Thr Glu Pro Gly Asp Pro Leu Gly Gly Ser Ala Ala Ile His Leu
65              70              75              80

Tyr Val Lys Asp Pro Ala Arg Pro Trp Asn Val Leu Ala Gln Glu Val
            85              90              95

Val Val Phe Glu Asp Gln Asp Ala Leu Leu Pro Cys Leu Leu Thr Asp
            100             105             110

Pro Val Leu Glu Ala Gly Val Ser Leu Val Arg Val Arg Gly Arg Pro
        115             120             125

Leu Met Arg His Thr Asn Tyr Ser Phe Ser Pro Trp His Gly Phe Thr
    130             135             140

Ile His Arg Ala Lys Phe Ile Gln Ser Gln Asp Tyr Gln Cys Ser Ala
145             150             155             160

Leu Met Gly Gly Arg Lys Val Met Ser Ile Ser Ile Arg Leu Lys Val
            165             170             175

Gln Lys Val Ile Pro Gly Pro Pro Ala Leu Thr Leu Val Pro Ala Glu
            180             185             190

Leu Val Arg Ile Arg Gly Glu Ala Ala Gln Ile Val Cys Ser Ala Ser
        195             200             205

Ser Val Asp Val Asn Phe Asp Val Phe Leu Gln His Asn Asn Thr Lys

```
            210                 215                 220
Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
                260                 265                 270

Phe Phe Arg Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
            290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
                340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
            370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
                420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
            530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
            610                 615                 620

Pro Ser Arg Asp Glu Leu Thr Lys Asn Gln Val Ser Leu Thr Cys Leu
625                 630                 635                 640
```

Val Lys Gly Phe Tyr Pro Ser Asp Ile Ala Val Glu Trp Glu Ser Asn
              645                 650                 655

Gly Gln Pro Glu Asn Asn Tyr Lys Thr Thr Pro Val Leu Asp Ser
        660                 665                 670

Asp Gly Ser Phe Phe Leu Tyr Ser Lys Leu Thr Val Asp Lys Ser Arg
        675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
705                 710                 715

<210> SEQ ID NO 7
<211> LENGTH: 506
<212> TYPE: PRT
<213> ORGANISM: Artificial sequence
<220> FEATURE:
<223> OTHER INFORMATION: cynoCSF1R ECD (with leader sequence)

<400> SEQUENCE: 7

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
                20                  25                  30

Lys Pro Gly Glu Thr Val Thr Leu Arg Cys Val Gly Asn Gly Ser Val
            35                  40                  45

Glu Trp Asp Gly Pro Ile Ser Pro His Trp Thr Leu Tyr Ser Asp Gly
    50                  55                  60

Pro Ser Ser Val Leu Thr Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Lys Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Leu Arg
    130                 135                 140

Gly Arg Pro Leu Leu Arg His Thr Asn Tyr Ser Phe Ser Pro Trp His
145                 150                 155                 160

Gly Phe Thr Ile His Arg Ala Lys Phe Ile Gln Gly Gln Asp Tyr Gln
                165                 170                 175

Cys Ser Ala Leu Met Gly Ser Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Asn Ile Asp Val Asp Phe Asp Val Phe Leu Gln His Asn
225                 230                 235                 240

Thr Thr Lys Leu Ala Ile Pro Gln Arg Ser Asp Phe His Asp Asn Arg
                245                 250                 255

Tyr Gln Lys Val Leu Thr Leu Ser Leu Gly Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Glu Ser Ala Tyr Leu Asp Leu Ser
290                 295                 300

Ser Glu Gln Asn Leu Ile Gln Glu Val Thr Val Gly Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ala Gly His Thr Asp Arg Cys Asp Glu Ala Gln Val Leu Gln
                435                 440                 445

Val Trp Val Asp Pro His Pro Glu Val Leu Ser Gln Glu Pro Phe Gln
450                 455                 460

Lys Val Thr Val Gln Ser Leu Leu Thr Ala Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala Arg
                500                 505

<210> SEQ ID NO 8
<211> LENGTH: 740
<212> TYPE: PRT
<213> ORGANISM: Artificial sequence
<220> FEATURE:
<223> OTHER INFORMATION: cynoCSF1R ECD-Fc (with leader sequence)

<400> SEQUENCE: 8

Met Gly Pro Gly Val Leu Leu Leu Leu Val Val Thr Ala Trp His
1               5                   10                  15

Gly Gln Gly Ile Pro Val Ile Glu Pro Ser Gly Pro Glu Leu Val Val
                20                  25                  30

Lys Pro Gly Glu Thr Val Thr Leu Arg Cys Val Gly Asn Gly Ser Val
                35                  40                  45

Glu Trp Asp Gly Pro Ile Ser Pro His Trp Thr Leu Tyr Ser Asp Gly
                50                  55                  60

Pro Ser Ser Val Leu Thr Thr Asn Ala Thr Phe Gln Asn Thr Arg
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Lys Glu Val Val Phe Glu Asp Gln Asp Ala Leu Leu Pro Cys Leu
                115                 120                 125

Leu Thr Asp Pro Val Leu Glu Ala Gly Val Ser Leu Val Arg Leu Arg
130                 135                 140

```
Gly Arg Pro Leu Leu Arg His Thr Asn Tyr Ser Phe Ser Pro Trp His
145                 150                 155                 160

Gly Phe Thr Ile His Arg Ala Lys Phe Ile Gln Gly Gln Asp Tyr Gln
                165                 170                 175

Cys Ser Ala Leu Met Gly Ser Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Asn Ile Asp Val Asp Phe Asp Val Phe Leu Gln His Asn
225                 230                 235                 240

Thr Thr Lys Leu Ala Ile Pro Gln Arg Ser Asp Phe His Asp Asn Arg
                245                 250                 255

Tyr Gln Lys Val Leu Thr Leu Ser Leu Gly Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asp Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Ser Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ala Gly His Thr Asp Arg Cys Asp Glu Ala Gln Val Leu Gln
        435                 440                 445

Val Trp Val Asp Pro His Pro Glu Val Leu Ser Gln Glu Pro Phe Gln
    450                 455                 460

Lys Val Thr Val Gln Ser Leu Leu Thr Ala Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala Arg Gly Ser Glu Pro Lys Ser
            500                 505                 510

Ser Asp Lys Thr His Thr Cys Pro Pro Cys Pro Ala Pro Glu Leu Leu
        515                 520                 525

Gly Gly Pro Ser Val Phe Leu Phe Pro Pro Lys Pro Lys Asp Thr Leu
    530                 535                 540

Met Ile Ser Arg Thr Pro Glu Val Thr Cys Val Val Val Asp Val Ser
545                 550                 555                 560
```

```
His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Asn Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ala Pro
    610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Asp Glu Leu Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
    690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740

<210> SEQ ID NO 9
<211> LENGTH: 122
<212> TYPE: PRT
<213> ORGANISM: Artificial sequence
<220> FEATURE:
<223> OTHER INFORMATION: Fab 0301 heavy chain variable region

<400> SEQUENCE: 9

Glu Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Asp Asn
            20                  25                  30

Tyr Met Ile Trp Val Lys Gln Ser His Gly Lys Ser Leu Glu Trp Ile
        35                  40                  45

Gly Asp Ile Asn Pro Tyr Asn Gly Gly Thr Thr Phe Asn Gln Lys Phe
    50                  55                  60

Lys Gly Lys Ala Thr Leu Thr Val Glu Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Ser Val Thr Val Ser Ser
        115                 120

<210> SEQ ID NO 10
<211> LENGTH: 111
<212> TYPE: PRT
<213> ORGANISM: Artificial sequence
<220> FEATURE:
<223> OTHER INFORMATION: Fab 0301 light chain variable region

<400> SEQUENCE: 10
```

```
Asn Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Asn Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His Leu Ser Asn
                85                  90                  95

Glu Asp Leu Ser Thr Phe Gly Gly Gly Thr Lys Leu Glu Ile Lys
            100                 105                 110

<210> SEQ ID NO 11
<211> LENGTH: 121
<212> TYPE: PRT
<213> ORGANISM: Artificial sequence
<220> FEATURE:
<223> OTHER INFORMATION: Fab 0302 heavy chain variable region

<400> SEQUENCE: 11

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
                20                  25                  30

Asn Ile His Trp Val Lys Gln Lys Pro Gly Gln Gly Leu Glu Trp Ile
            35                  40                  45

Gly Tyr Ile Asn Pro Tyr Thr Asp Val Thr Val Tyr Asn Glu Lys Phe
    50                  55                  60

Lys Gly Lys Ala Thr Leu Thr Ser Asp Arg Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Ser Ile Thr Val Ser Ser
            115                 120

<210> SEQ ID NO 12
<211> LENGTH: 111
<212> TYPE: PRT
<213> ORGANISM: Artificial sequence
<220> FEATURE:
<223> OTHER INFORMATION: Fab 0302 light chain variable region

<400> SEQUENCE: 12

Asp Val Val Val Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Leu Ser Phe Met Asn Trp Phe Gln Gln Lys Pro Gly Gln Pro Pro
            35                  40                  45

Lys Leu Leu Ile Tyr Thr Ala Ser Asn Leu Glu Ser Gly Ile Pro Ala
    50                  55                  60

Arg Phe Ser Gly Gly Gly Ser Arg Thr Asp Phe Thr Leu Thr Ile Asp
```

```
                65                  70                  75                  80
Pro Val Glu Ala Asp Asp Ala Ala Thr Tyr Phe Cys Gln Gln Ser Lys
                    85                  90                  95
Glu Leu Pro Trp Thr Phe Gly Gly Gly Thr Arg Leu Glu Ile Lys
                100                 105                 110

<210> SEQ ID NO 13
<211> LENGTH: 122
<212> TYPE: PRT
<213> ORGANISM: Artificial sequence
<220> FEATURE:
<223> OTHER INFORMATION: Fab 0311 heavy chain variable region

<400> SEQUENCE: 13

Glu Ile Gln Leu Gln Gln Ser Gly Pro Asp Leu Met Lys Pro Gly Ala
1               5                   10                  15
Ser Val Lys Met Ser Cys Lys Ala Ser Gly Tyr Ile Phe Thr Asp Tyr
                20                  25                  30
Asn Met His Trp Val Lys Gln Asn Gly Lys Ser Leu Glu Trp Met
            35                  40                  45
Gly Glu Ile Asn Pro Asn Asn Gly Val Val Tyr Asn Gln Lys Phe
50                  55                  60
Lys Gly Thr Thr Thr Leu Thr Val Asp Lys Ser Ser Ser Thr Ala Tyr
65                  70                  75                  80
Met Asp Leu His Ser Leu Thr Ser Glu Asp Ser Ala Val Tyr Tyr Cys
                85                  90                  95
Thr Arg Ala Leu Tyr His Ser Asn Phe Gly Trp Tyr Phe Asp Ser Trp
                100                 105                 110
Gly Lys Gly Thr Thr Leu Thr Val Ser Ser
            115                 120

<210> SEQ ID NO 14
<211> LENGTH: 111
<212> TYPE: PRT
<213> ORGANISM: Artificial sequence
<220> FEATURE:
<223> OTHER INFORMATION: Fab 0311 light chain variable region

<400> SEQUENCE: 14

Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
                20                  25                  30
Gly Asp Ser His Met Asn Trp Tyr Gln Gln Lys Pro Gly Gln Pro Pro
            35                  40                  45
Lys Leu Leu Ile Tyr Thr Ala Ser Asn Leu Glu Ser Gly Ile Pro Ala
50                  55                  60
Arg Phe Ser Gly Ser Gly Ser Gly Ala Asp Phe Thr Leu Thr Ile His
65                  70                  75                  80
Pro Val Glu Glu Glu Asp Ala Ala Thr Tyr Tyr Cys Gln Gln Gly Asn
                85                  90                  95
Glu Asp Pro Trp Thr Phe Gly Gly Gly Thr Arg Leu Glu Ile Lys
                100                 105                 110

<210> SEQ ID NO 15
<211> LENGTH: 10
<212> TYPE: PRT
<213> ORGANISM: Artificial sequence
<220> FEATURE:
```

```
<223> OTHER INFORMATION: 0301 heavy chain CDR1

<400> SEQUENCE: 15

Gly Tyr Thr Phe Thr Asp Asn Tyr Met Ile
1               5                   10

<210> SEQ ID NO 16
<211> LENGTH: 17
<212> TYPE: PRT
<213> ORGANISM: Artificial sequence
<220> FEATURE:
<223> OTHER INFORMATION: 0301 heavy chain CDR2

<400> SEQUENCE: 16

Asp Ile Asn Pro Tyr Asn Gly Gly Thr Thr Phe Asn Gln Lys Phe Lys
1               5                   10                  15

Gly

<210> SEQ ID NO 17
<211> LENGTH: 13
<212> TYPE: PRT
<213> ORGANISM: Artificial sequence
<220> FEATURE:
<223> OTHER INFORMATION: 0301 heavy chain CDR3

<400> SEQUENCE: 17

Glu Ser Pro Tyr Phe Ser Asn Leu Tyr Val Met Asp Tyr
1               5                   10

<210> SEQ ID NO 18
<211> LENGTH: 15
<212> TYPE: PRT
<213> ORGANISM: Artificial sequence
<220> FEATURE:
<223> OTHER INFORMATION: 0301 light chain CDR1

<400> SEQUENCE: 18

Lys Ala Ser Gln Ser Val Asp Tyr Asp Gly Asp Asn Tyr Met Asn
1               5                   10                  15

<210> SEQ ID NO 19
<211> LENGTH: 7
<212> TYPE: PRT
<213> ORGANISM: Artificial sequence
<220> FEATURE:
<223> OTHER INFORMATION: 0301 light chain CDR2

<400> SEQUENCE: 19

Ala Ala Ser Asn Leu Glu Ser
1               5

<210> SEQ ID NO 20
<211> LENGTH: 9
<212> TYPE: PRT
<213> ORGANISM: Artificial sequence
<220> FEATURE:
<223> OTHER INFORMATION: 0301 light chain CDR3

<400> SEQUENCE: 20

His Leu Ser Asn Glu Asp Leu Ser Thr
1               5

<210> SEQ ID NO 21
<211> LENGTH: 10
<212> TYPE: PRT
<213> ORGANISM: Artificial sequence
```

```
<220> FEATURE:
<223> OTHER INFORMATION: 0302 heavy chain CDR1

<400> SEQUENCE: 21

Gly Tyr Thr Phe Ser Asp Phe Asn Ile His
1               5                   10

<210> SEQ ID NO 22
<211> LENGTH: 17
<212> TYPE: PRT
<213> ORGANISM: Artificial sequence
<220> FEATURE:
<223> OTHER INFORMATION: 0302 heavy chain CDR2

<400> SEQUENCE: 22

Tyr Ile Asn Pro Tyr Thr Asp Val Thr Val Tyr Asn Glu Lys Phe Lys
1               5                   10                  15

Gly

<210> SEQ ID NO 23
<211> LENGTH: 12
<212> TYPE: PRT
<213> ORGANISM: Artificial sequence
<220> FEATURE:
<223> OTHER INFORMATION: 0302 heavy chain CDR3

<400> SEQUENCE: 23

Tyr Phe Asp Gly Thr Phe Asp Tyr Ala Leu Asp Tyr
1               5                   10

<210> SEQ ID NO 24
<211> LENGTH: 15
<212> TYPE: PRT
<213> ORGANISM: Artificial sequence
<220> FEATURE:
<223> OTHER INFORMATION: 0302 light chain CDR1

<400> SEQUENCE: 24

Arg Ala Ser Glu Ser Val Asp Asn Tyr Gly Leu Ser Phe Met Asn
1               5                   10                  15

<210> SEQ ID NO 25
<211> LENGTH: 7
<212> TYPE: PRT
<213> ORGANISM: Artificial sequence
<220> FEATURE:
<223> OTHER INFORMATION: 0302 light chain CDR2

<400> SEQUENCE: 25

Thr Ala Ser Asn Leu Glu Ser
1               5

<210> SEQ ID NO 26
<211> LENGTH: 9
<212> TYPE: PRT
<213> ORGANISM: Artificial sequence
<220> FEATURE:
<223> OTHER INFORMATION: 0302 light chain CDR3

<400> SEQUENCE: 26

Gln Gln Ser Lys Glu Leu Pro Trp Thr
1               5

<210> SEQ ID NO 27
<211> LENGTH: 10
<212> TYPE: PRT
```

```
<213> ORGANISM: Artificial sequence
<220> FEATURE:
<223> OTHER INFORMATION: 0311 heavy chain CDR1

<400> SEQUENCE: 27

Gly Tyr Ile Phe Thr Asp Tyr Asn Met His
1               5                   10

<210> SEQ ID NO 28
<211> LENGTH: 17
<212> TYPE: PRT
<213> ORGANISM: Artificial sequence
<220> FEATURE:
<223> OTHER INFORMATION: 0311 heavy chain CDR2

<400> SEQUENCE: 28

Glu Ile Asn Pro Asn Asn Gly Val Val Val Tyr Asn Gln Lys Phe Lys
1               5                   10                  15

Gly

<210> SEQ ID NO 29
<211> LENGTH: 13
<212> TYPE: PRT
<213> ORGANISM: Artificial sequence
<220> FEATURE:
<223> OTHER INFORMATION: 0311 heavy chain CDR3

<400> SEQUENCE: 29

Ala Leu Tyr His Ser Asn Phe Gly Trp Tyr Phe Asp Ser
1               5                   10

<210> SEQ ID NO 30
<211> LENGTH: 15
<212> TYPE: PRT
<213> ORGANISM: Artificial sequence
<220> FEATURE:
<223> OTHER INFORMATION: 0311 light chain CDR1

<400> SEQUENCE: 30

Lys Ala Ser Gln Ser Val Asp Tyr Asp Gly Asp Ser His Met Asn
1               5                   10                  15

<210> SEQ ID NO 31
<211> LENGTH: 7
<212> TYPE: PRT
<213> ORGANISM: Artificial sequence
<220> FEATURE:
<223> OTHER INFORMATION: 0311 light chain CDR2

<400> SEQUENCE: 31

Thr Ala Ser Asn Leu Glu Ser
1               5

<210> SEQ ID NO 32
<211> LENGTH: 9
<212> TYPE: PRT
<213> ORGANISM: Artificial sequence
<220> FEATURE:
<223> OTHER INFORMATION: 0311 light chain CDR3

<400> SEQUENCE: 32

Gln Gln Gly Asn Glu Asp Pro Trp Thr
1               5

<210> SEQ ID NO 33
<211> LENGTH: 449
```

<212> TYPE: PRT
<213> ORGANISM: Artificial sequence
<220> FEATURE:
<223> OTHER INFORMATION: cAb 0301 heavy chain

<400> SEQUENCE: 33

Glu Val Gln Leu Gln Gln Ser Gly Pro Glu Leu Val Arg Pro Gly Ala
1               5                   10                  15

Ser Val Lys Met Ser Cys Lys Ala Ser Gly Tyr Thr Phe Thr Asp Asn
            20                  25                  30

Tyr Met Ile Trp Val Lys Gln Ser His Gly Lys Ser Leu Glu Trp Ile
        35                  40                  45

Gly Asp Ile Asn Pro Tyr Asn Gly Gly Thr Thr Phe Asn Gln Lys Phe
    50                  55                  60

Lys Gly Lys Ala Thr Leu Thr Val Glu Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
            435                 440                 445

Lys

<210> SEQ ID NO 34
<211> LENGTH: 448
<212> TYPE: PRT
<213> ORGANISM: Artificial sequence
<220> FEATURE:
<223> OTHER INFORMATION: cAb 0301 light chain

<400> SEQUENCE: 34

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
            20                  25                  30

Asn Ile His Trp Val Lys Gln Lys Pro Gly Gln Gly Leu Glu Trp Ile
        35                  40                  45

Gly Tyr Ile Asn Pro Tyr Thr Asp Val Thr Val Tyr Asn Glu Lys Phe
    50                  55                  60

Lys Gly Lys Ala Thr Leu Thr Ser Asp Arg Ser Ser Thr Ala Tyr
65                  70                  75                  80

Met Asp Leu Ser Ser Leu Thr Ser Glu Asp Ser Ala Val Tyr Tyr Cys
            85                  90                  95

Ala Ser Tyr Phe Asp Gly Thr Phe Asp Tyr Ala Leu Asp Tyr Trp Gly
            100                 105                 110

Gln Gly Thr Ser Ile Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
        260                 265                 270

Glu Val Gln Phe Asn Trp Tyr Val Asp Gly Val Glu Val His Asn Ala
    275                 280                 285

Lys Thr Lys Pro Arg Glu Glu Gln Phe Asn Ser Thr Tyr Arg Val Val

```
            290                 295                 300
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 35
<211> LENGTH: 448
<212> TYPE: PRT
<213> ORGANISM: Artificial sequence
<220> FEATURE:
<223> OTHER INFORMATION: cAb 0302 heavy chain

<400> SEQUENCE: 35

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Asp Phe
                20                  25                  30

Asn Ile His Trp Val Lys Gln Lys Pro Gly Gln Gly Leu Glu Trp Ile
                35                  40                  45

Gly Tyr Ile Asn Pro Tyr Thr Asp Val Thr Val Tyr Asn Glu Lys Phe
50                  55                  60

Lys Gly Lys Ala Thr Leu Thr Ser Asp Arg Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Ser Tyr Phe Asp Gly Thr Asp Tyr Ala Leu Asp Tyr Trp Gly
                100                 105                 110

Gln Gly Thr Ser Ile Thr Val Ser Ser Ala Ser Thr Lys Gly Pro Ser
                115                 120                 125

Val Phe Pro Leu Ala Pro Cys Ser Arg Ser Thr Ser Glu Ser Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
```

```
                210                 215                 220
Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 36
<211> LENGTH: 218
<212> TYPE: PRT
<213> ORGANISM: Artificial sequence
<220> FEATURE:
<223> OTHER INFORMATION: cAb 0302 light chain

<400> SEQUENCE: 36

Asp Val Val Val Thr Gln Thr Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Leu Ser Phe Met Asn Trp Phe Gln Gln Lys Pro Gly Gln Pro Pro
                35                  40                  45

Lys Leu Leu Ile Tyr Thr Ala Ser Asn Leu Glu Ser Gly Ile Pro Ala
                50                  55                  60

Arg Phe Ser Gly Gly Gly Ser Arg Thr Asp Phe Thr Leu Thr Ile Asp
65                  70                  75                  80

Pro Val Glu Ala Asp Asp Ala Ala Thr Tyr Phe Cys Gln Gln Ser Lys
                85                  90                  95

Glu Leu Pro Trp Thr Phe Gly Gly Gly Thr Arg Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
```

-continued

```
                130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
210                 215

<210> SEQ ID NO 37
<211> LENGTH: 449
<212> TYPE: PRT
<213> ORGANISM: Artificial sequence
<220> FEATURE:
<223> OTHER INFORMATION: cAb 0311 heavy chain

<400> SEQUENCE: 37

Glu Ile Gln Leu Gln Gln Ser Gly Pro Asp Leu Met Lys Pro Gly Ala
1               5                   10                  15

Ser Val Lys Met Ser Cys Lys Ala Ser Gly Tyr Ile Phe Thr Asp Tyr
                20                  25                  30

Asn Met His Trp Val Lys Gln Asn Gly Lys Ser Leu Glu Trp Met
                35                  40                  45

Gly Glu Ile Asn Pro Asn Asn Gly Val Val Tyr Asn Gln Lys Phe
50                  55                  60

Lys Gly Thr Thr Thr Leu Thr Val Asp Lys Ser Ser Ser Thr Ala Tyr
65                  70                  75                  80

Met Asp Leu His Ser Leu Thr Ser Glu Asp Ser Ala Val Tyr Tyr Cys
                85                  90                  95

Thr Arg Ala Leu Tyr His Ser Asn Phe Gly Trp Tyr Phe Asp Ser Trp
                100                 105                 110

Gly Lys Gly Thr Thr Leu Thr Val Ser Ser Ala Ser Thr Lys Gly Pro
                115                 120                 125

Ser Val Phe Pro Leu Ala Pro Cys Ser Arg Ser Thr Ser Glu Ser Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
```

```
            275                 280                 285
Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 38
<211> LENGTH: 218
<212> TYPE: PRT
<213> ORGANISM: Artificial sequence
<220> FEATURE:
<223> OTHER INFORMATION: cAb 0311 light chain

<400> SEQUENCE: 38

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser His Met Asn Trp Tyr Gln Gln Lys Pro Gly Gln Pro Pro
            35                  40                  45

Lys Leu Leu Ile Tyr Thr Ala Ser Asn Leu Glu Ser Gly Ile Pro Ala
50                  55                  60

Arg Phe Ser Gly Ser Gly Ser Gly Ala Asp Phe Thr Leu Thr Ile His
65                  70                  75                  80

Pro Val Glu Glu Glu Asp Ala Ala Thr Tyr Tyr Cys Gln Gln Gly Asn
                85                  90                  95

Glu Asp Pro Trp Thr Phe Gly Gly Gly Thr Arg Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 39
<211> LENGTH: 122
<212> TYPE: PRT
<213> ORGANISM: Artificial sequence
<220> FEATURE:
<223> OTHER INFORMATION: h0301-H0 heavy chain variable region

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 40
<211> LENGTH: 122
<212> TYPE: PRT
<213> ORGANISM: Artificial sequence
<220> FEATURE:
<223> OTHER INFORMATION: h0301-H1 heavy chain variable region

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
                20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 41
<211> LENGTH: 122
<212> TYPE: PRT
```

<213> ORGANISM: Artificial sequence
<220> FEATURE:
<223> OTHER INFORMATION: h0301-H2 heavy chain variable region

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Ile
        35                  40                  45

Gly Asp Ile Asn Pro Tyr Asn Gly Gly Thr Thr Phe Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser
        115                 120

<210> SEQ ID NO 42
<211> LENGTH: 121
<212> TYPE: PRT
<213> ORGANISM: Artificial sequence
<220> FEATURE:
<223> OTHER INFORMATION: H0302-H1 heavy chain variable region

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Met
        35                  40                  45

Gly Tyr Ile Asn Pro Tyr Thr Asp Val Thr Val Tyr Asn Glu Lys Phe
    50                  55                  60

Lys Gly Arg Val Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser
        115                 120

<210> SEQ ID NO 43
<211> LENGTH: 121
<212> TYPE: PRT
<213> ORGANISM: Artificial sequence
<220> FEATURE:
<223> OTHER INFORMATION: H0302-H2 heavy chain variable region

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

```
Asn Ile His Trp Val Arg Gln Ala Pro Gly Gln Gly Leu Glu Trp Ile
         35                  40                  45

Gly Tyr Ile Asn Pro Tyr Thr Asp Val Thr Val Tyr Asn Glu Lys Phe
 50                  55                  60

Lys Gly Arg Ala Thr Leu Thr Ser Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Tyr Phe Asp Gly Thr Phe Asp Tyr Ala Leu Asp Tyr Trp Gly
                100                 105                 110

Gln Gly Thr Leu Val Thr Val Ser Ser
            115                 120

<210> SEQ ID NO 44
<211> LENGTH: 122
<212> TYPE: PRT
<213> ORGANISM: Artificial sequence
<220> FEATURE:
<223> OTHER INFORMATION: H0311-H1 heavy chain variable region

<400> SEQUENCE: 44

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ile Phe Thr Asp Tyr
                 20                  25                  30

Asn Met His Trp Val Arg Gln Ala Pro Gly Gln Gly Leu Glu Trp Met
         35                  40                  45

Gly Glu Ile Asn Pro Asn Asn Gly Val Val Tyr Asn Gln Lys Phe
 50                  55                  60

Lys Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Ala Leu Tyr His Ser Asn Phe Gly Trp Tyr Phe Asp Ser Trp
                100                 105                 110

Gly Gln Gly Thr Leu Val Thr Val Ser Ser
            115                 120

<210> SEQ ID NO 45
<211> LENGTH: 122
<212> TYPE: PRT
<213> ORGANISM: Artificial sequence
<220> FEATURE:
<223> OTHER INFORMATION: H0311-H2 heavy chain variable region

<400> SEQUENCE: 45

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ile Phe Thr Asp Tyr
                 20                  25                  30

Asn Met His Trp Val Arg Gln Ala Pro Gly Gln Gly Leu Glu Trp Met
         35                  40                  45

Gly Glu Ile Asn Pro Asn Asn Gly Val Val Tyr Asn Gln Lys Phe
 50                  55                  60

Lys Gly Thr Thr Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
```

```
                85                  90                  95
Thr Arg Ala Leu Tyr His Ser Asn Phe Gly Trp Tyr Phe Asp Ser Trp
            100                 105                 110

Gly Gln Gly Thr Leu Val Thr Val Ser Ser
        115                 120

<210> SEQ ID NO 46
<211> LENGTH: 111
<212> TYPE: PRT
<213> ORGANISM: Artificial sequence
<220> FEATURE:
<223> OTHER INFORMATION: h0301-L0 light chain variable region

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 47
<211> LENGTH: 111
<212> TYPE: PRT
<213> ORGANISM: Artificial sequence
<220> FEATURE:
<223> OTHER INFORMATION: h0301-L1 light chain variable region

<400> SEQUENCE: 47

Asn Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys
            100                 105                 110

<210> SEQ ID NO 48
<211> LENGTH: 111
<212> TYPE: PRT
<213> ORGANISM: Artificial sequence
<220> FEATURE:
<223> OTHER INFORMATION: H0302-L0 light chain variable region

<400> SEQUENCE: 48
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
                100                 105                 110

<210> SEQ ID NO 49
<211> LENGTH: 111
<212> TYPE: PRT
<213> ORGANISM: Artificial sequence
<220> FEATURE:
<223> OTHER INFORMATION: H0302-L1 light chain variable region

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys
                100                 105                 110

<210> SEQ ID NO 50
<211> LENGTH: 111
<212> TYPE: PRT
<213> ORGANISM: Artificial sequence
<220> FEATURE:
<223> OTHER INFORMATION: H0302-L2 light chain variable region

<400> SEQUENCE: 50

Glu Ile Val Val Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Met Asn Trp Phe Gln Gln Lys Pro Gly Gln Ala Pro
            35                  40                  45

Arg Leu Leu Ile Tyr Thr Ala Ser Asn Leu Glu Ser Gly Ile Pro Ala
        50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys

```
                85                  90                  95
Glu Leu Pro Trp Thr Phe Gly Gln Gly Thr Lys Val Glu Ile Lys
            100                 105                 110

<210> SEQ ID NO 51
<211> LENGTH: 111
<212> TYPE: PRT
<213> ORGANISM: Artificial sequence
<220> FEATURE:
<223> OTHER INFORMATION: H0311-L0 light chain variable region

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser His Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys
            100                 105                 110

<210> SEQ ID NO 52
<211> LENGTH: 111
<212> TYPE: PRT
<213> ORGANISM: Artificial sequence
<220> FEATURE:
<223> OTHER INFORMATION: H0311-L1 light chain variable region

<400> SEQUENCE: 52

Asp Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser His Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Ala Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys
            100                 105                 110

<210> SEQ ID NO 53
<211> LENGTH: 449
<212> TYPE: PRT
<213> ORGANISM: Artificial sequence
<220> FEATURE:
<223> OTHER INFORMATION: h0301-H0 heavy chain

<400> SEQUENCE: 53

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Thr Phe Thr Asp Asn
            20                  25                  30
Tyr Met Ile Trp Val Arg Gln Ala Pro Gly Gln Gly Leu Glu Trp Met
        35                  40                  45
Gly Asp Ile Asn Pro Tyr Asn Gly Gly Thr Thr Phe Asn Gln Lys Phe
 50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Ser Pro Tyr Phe Ser Asn Leu Tyr Val Met Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
```

Ala Leu His Asn His Tyr Thr Gln Lys Ser Leu Ser Leu Ser Leu Gly
            435                 440                 445

Lys

<210> SEQ ID NO 54
<211> LENGTH: 449
<212> TYPE: PRT
<213> ORGANISM: Artificial sequence
<220> FEATURE:
<223> OTHER INFORMATION: h0301-H1 heavy chain

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Met
        35                  40                  45

Gly Asp Ile Asn Pro Tyr Asn Gly Gly Thr Thr Phe Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr

```
                 340             345             350
Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 55
<211> LENGTH: 449
<212> TYPE: PRT
<213> ORGANISM: Artificial sequence
<220> FEATURE:
<223> OTHER INFORMATION: h0301-H2 heavy chain

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Asn
            20                  25                  30

Tyr Met Ile Trp Val Arg Gln Ala Pro Gly Gln Gly Leu Glu Trp Ile
        35                  40                  45

Gly Asp Ile Asn Pro Tyr Asn Gly Gly Thr Thr Phe Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Pro Tyr Phe Ser Asn Leu Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 56
<211> LENGTH: 448
<212> TYPE: PRT
<213> ORGANISM: Artificial sequence
<220> FEATURE:
<223> OTHER INFORMATION: H0302-H1 heavy chain

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Met
            35                  40                  45

Gly Tyr Ile Asn Pro Tyr Thr Asp Val Thr Val Tyr Asn Glu Lys Phe
        50                  55                  60

Lys Gly Arg Val Thr Ile Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 57
<211> LENGTH: 448
<212> TYPE: PRT
<213> ORGANISM: Artificial sequence
<220> FEATURE:
<223> OTHER INFORMATION: H0302-H2 heavy chain

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Phe
            20                  25                  30

Asn Ile His Trp Val Arg Gln Ala Pro Gly Gln Gly Leu Glu Trp Ile
            35                  40                  45

Gly Tyr Ile Asn Pro Tyr Thr Asp Val Thr Val Tyr Asn Glu Lys Phe
            50                  55                  60

Lys Gly Arg Ala Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Phe Asp Gly Thr Phe Asp Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 58
<211> LENGTH: 449
<212> TYPE: PRT
<213> ORGANISM: Artificial sequence
<220> FEATURE:
<223> OTHER INFORMATION: H0311-H1 heavy chain

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Tyr Asn Gln Lys Phe
    50                  55                  60

Lys Gly Arg Val Thr Ile Thr Val Asp Lys Ser Thr Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
    195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu

```
                    420                 425                 430
Ala Leu His Asn His Tyr Thr Gln Lys Ser Leu Ser Leu Ser Leu Gly
            435                 440                 445
Lys

<210> SEQ ID NO 59
<211> LENGTH: 449
<212> TYPE: PRT
<213> ORGANISM: Artificial sequence
<220> FEATURE:
<223> OTHER INFORMATION: H0311-H2 heavy chain

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Thr Asp Tyr
            20                  25                  30

Asn Met His Trp Val Arg Gln Ala Pro Gly Gln Gly Leu Glu Trp Met
        35                  40                  45

Gly Glu Ile Asn Pro Asn Asn Gly Val Val Tyr Asn Gln Lys Phe
    50                  55                  60

Lys Gly Thr Thr Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ala Leu Tyr His Ser Asn Phe Gly Trp Tyr Phe Asp Ser Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 60
<211> LENGTH: 218
<212> TYPE: PRT
<213> ORGANISM: Artificial sequence
<220> FEATURE:
<223> OTHER INFORMATION: h0301-L0 light chain

<400> SEQUENCE: 60

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 61
<211> LENGTH: 218
```

```
<212> TYPE: PRT
<213> ORGANISM: Artificial sequence
<220> FEATURE:
<223> OTHER INFORMATION: h0301-L1 light chain

<400> SEQUENCE: 61
```

Asn Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Asn Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys His Leu Ser Asn
                85                  90                  95

Glu Asp Leu Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

```
<210> SEQ ID NO 62
<211> LENGTH: 218
<212> TYPE: PRT
<213> ORGANISM: Artificial sequence
<220> FEATURE:
<223> OTHER INFORMATION: H0302-L0 light chain

<400> SEQUENCE: 62
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 63
<211> LENGTH: 218
<212> TYPE: PRT
<213> ORGANISM: Artificial sequence
<220> FEATURE:
<223> OTHER INFORMATION: H0302-L1 light chain

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 218
<212> TYPE: PRT
<213> ORGANISM: Artificial sequence
<220> FEATURE:
<223> OTHER INFORMATION: H0302-L2 light chain

<400> SEQUENCE: 64

Glu Ile Val Val Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Met Asn Trp Phe Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Lys
                85                  90                  95

Glu Leu Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 65
<211> LENGTH: 218
<212> TYPE: PRT
<213> ORGANISM: Artificial sequence
<220> FEATURE:
<223> OTHER INFORMATION: H0311-L0 light chain

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser His Met Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln

```
                    115                 120                 125
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 66
<211> LENGTH: 218
<212> TYPE: PRT
<213> ORGANISM: Artificial sequence
<220> FEATURE:
<223> OTHER INFORMATION: H0311-L1 light chain

<400> SEQUENCE: 66

Asp Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Ser His Met Asn Trp Tyr Gln Gln Lys Pro Gly Gln Ala Pro
            35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Ala Asp Phe Thr Leu Thr Ile Ser
65                  70                  75                  80

Ser Leu Glu Pro Glu Asp Phe Ala Val Tyr Tyr Cys Gln Gln Gly Asn
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 67
<211> LENGTH: 158
<212> TYPE: PRT
<213> ORGANISM: Homo sapiens
<220> FEATURE:
<221> NAME/KEY: MISC_FEATURE
```

<222> LOCATION: (1)..(158)
<223> OTHER INFORMATION: Human CSF1

<400> SEQUENCE: 67

```
Glu Glu Val Ser Glu Tyr Cys Ser His Met Ile Gly Ser Gly His Leu
1               5                   10                  15

Gln Ser Leu Gln Arg Leu Ile Asp Ser Gln Met Glu Thr Ser Cys Gln
            20                  25                  30

Ile Thr Phe Glu Phe Val Asp Gln Glu Gln Leu Lys Asp Pro Val Cys
        35                  40                  45

Tyr Leu Lys Lys Ala Phe Leu Leu Val Gln Asp Ile Met Glu Asp Thr
    50                  55                  60

Met Arg Phe Arg Asp Asn Thr Pro Asn Ala Ile Ala Ile Val Gln Leu
65                  70                  75                  80

Gln Glu Leu Ser Leu Arg Leu Lys Ser Cys Phe Thr Lys Asp Tyr Glu
                85                  90                  95

Glu His Asp Lys Ala Cys Val Arg Thr Phe Tyr Glu Thr Pro Leu Gln
            100                 105                 110

Leu Leu Glu Lys Val Lys Asn Val Phe Asn Glu Thr Lys Asn Leu Leu
        115                 120                 125

Asp Lys Asp Trp Asn Ile Phe Ser Lys Asn Cys Asn Asn Ser Phe Ala
    130                 135                 140

Glu Cys Ser Ser Gln Gly His Glu Arg Gln Ser Glu Gly Ser
145                 150                 155
```

<210> SEQ ID NO 68
<211> LENGTH: 222
<212> TYPE: PRT
<213> ORGANISM: Homo sapiens
<220> FEATURE:
<221> NAME/KEY: MISC_FEATURE
<222> LOCATION: (1)..(222)
<223> OTHER INFORMATION: Human IL-34

<400> SEQUENCE: 68

```
Asn Glu Pro Leu Glu Met Trp Pro Leu Thr Gln Asn Glu Glu Cys Thr
1               5                   10                  15

Val Thr Gly Phe Leu Arg Asp Lys Leu Gln Tyr Arg Ser Arg Leu Gln
            20                  25                  30

Tyr Met Lys His Tyr Phe Pro Ile Asn Tyr Lys Ile Ser Val Pro Tyr
        35                  40                  45

Glu Gly Val Phe Arg Ile Ala Asn Val Thr Arg Leu Gln Arg Ala Gln
    50                  55                  60

Val Ser Glu Arg Glu Leu Arg Tyr Leu Trp Val Leu Val Ser Leu Ser
65                  70                  75                  80

Ala Thr Glu Ser Val Gln Asp Val Leu Leu Glu Gly His Pro Ser Trp
                85                  90                  95

Lys Tyr Leu Gln Glu Val Gln Thr Leu Leu Leu Asn Val Gln Gln Gly
            100                 105                 110

Leu Thr Asp Val Glu Val Ser Pro Lys Val Glu Ser Val Leu Ser Leu
        115                 120                 125

Leu Asn Ala Pro Gly Pro Asn Leu Lys Leu Val Arg Pro Lys Ala Leu
    130                 135                 140

Leu Asp Asn Cys Phe Arg Val Met Glu Leu Leu Tyr Cys Ser Cys Cys
145                 150                 155                 160

Lys Gln Ser Ser Val Leu Asn Trp Gln Asp Cys Glu Val Pro Ser Pro
                165                 170                 175
```

Gln Ser Cys Ser Pro Glu Pro Ser Leu Gln Tyr Ala Ala Thr Gln Leu
            180                 185                 190

Tyr Pro Pro Pro Trp Ser Pro Ser Ser Pro His Ser Thr Gly
        195                 200                 205

Ser Val Arg Pro Val Arg Ala Gln Gly Glu Gly Leu Leu Pro
        210                 215                 220

<210> SEQ ID NO 69
<211> LENGTH: 25
<212> TYPE: PRT
<213> ORGANISM: Artificial sequence
<220> FEATURE:
<223> OTHER INFORMATION: Human acceptor A FR1

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 70
<211> LENGTH: 14
<212> TYPE: PRT
<213> ORGANISM: Artificial sequence
<220> FEATURE:
<223> OTHER INFORMATION: Human acceptor A FR2

<400> SEQUENCE: 70

Trp Val Arg Gln Ala Pro Gly Gln Gly Leu Glu Trp Met Gly
1               5                   10

<210> SEQ ID NO 71
<211> LENGTH: 32
<212> TYPE: PRT
<213> ORGANISM: Artificial sequence
<220> FEATURE:
<223> OTHER INFORMATION: Human acceptor A FR3

<400> SEQUENCE: 71

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 72
<211> LENGTH: 11
<212> TYPE: PRT
<213> ORGANISM: Artificial sequence
<220> FEATURE:
<223> OTHER INFORMATION: Human acceptor A FR4

<400> SEQUENCE: 72

Trp Gly Gln Gly Thr Leu Val Thr Val Ser Ser
1               5                   10

<210> SEQ ID NO 73
<211> LENGTH: 25
<212> TYPE: PRT
<213> ORGANISM: Artificial sequence
<220> FEATURE:
<223> OTHER INFORMATION: Human acceptor B FR1

<400> SEQUENCE: 73

Gln Val Gln Leu Val Gln Ser Gly Ala Glu Val Lys Lys Pro Gly Ser

```
                1               5                  10                  15

Ser Val Lys Val Ser Cys Lys Ala Ser
            20                  25

<210> SEQ ID NO 74
<211> LENGTH: 14
<212> TYPE: PRT
<213> ORGANISM: Artificial sequence
<220> FEATURE:
<223> OTHER INFORMATION: Human acceptor B FR2

<400> SEQUENCE: 74

Trp Val Arg Gln Ala Pro Gly Gln Gly Leu Glu Trp Met Gly
1               5                  10

<210> SEQ ID NO 75
<211> LENGTH: 32
<212> TYPE: PRT
<213> ORGANISM: Artificial sequence
<220> FEATURE:
<223> OTHER INFORMATION: Human acceptor B FR3

<400> SEQUENCE: 75

Arg Val Thr Ile Thr Ala Asp Lys Ser Thr Ser Thr Ala Tyr Met Glu
1               5                  10                  15

Leu Ser Ser Leu Arg Ser Glu Asp Thr Ala Val Tyr Tyr Cys Ala Arg
            20                  25                  30

<210> SEQ ID NO 76
<211> LENGTH: 11
<212> TYPE: PRT
<213> ORGANISM: Artificial sequence
<220> FEATURE:
<223> OTHER INFORMATION: Human acceptor B FR4

<400> SEQUENCE: 76

Trp Gly Gln Gly Thr Leu Val Thr Val Ser Ser
1               5                  10

<210> SEQ ID NO 77
<211> LENGTH: 25
<212> TYPE: PRT
<213> ORGANISM: Artificial sequence
<220> FEATURE:
<223> OTHER INFORMATION: Human acceptor C FR1

<400> SEQUENCE: 77

Gln Val Gln Leu Val Gln Ser Gly Ala Glu Val Lys Lys Pro Gly Ser
1               5                  10                  15

Ser Val Lys Val Ser Cys Lys Ala Ser
            20                  25

<210> SEQ ID NO 78
<211> LENGTH: 14
<212> TYPE: PRT
<213> ORGANISM: Artificial sequence
<220> FEATURE:
<223> OTHER INFORMATION: Human acceptor C FR2

<400> SEQUENCE: 78

Trp Val Arg Gln Ala Pro Gly Gln Gly Leu Glu Trp Met Gly
1               5                  10

<210> SEQ ID NO 79
<211> LENGTH: 32
```

```
<212> TYPE: PRT
<213> ORGANISM: Artificial sequence
<220> FEATURE:
<223> OTHER INFORMATION: Human acceptor C FR3

<400> SEQUENCE: 79

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 80
<211> LENGTH: 11
<212> TYPE: PRT
<213> ORGANISM: Artificial sequence
<220> FEATURE:
<223> OTHER INFORMATION: Human acceptor C FR4

<400> SEQUENCE: 80

Trp Gly Gln Gly Thr Leu Val Thr Val Ser Ser
1               5                   10

<210> SEQ ID NO 81
<211> LENGTH: 23
<212> TYPE: PRT
<213> ORGANISM: Artificial sequence
<220> FEATURE:
<223> OTHER INFORMATION: Human acceptor D FR1

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 82
<211> LENGTH: 15
<212> TYPE: PRT
<213> ORGANISM: Artificial sequence
<220> FEATURE:
<223> OTHER INFORMATION: Human acceptor D FR2

<400> SEQUENCE: 82

Trp Tyr Gln Gln Lys Pro Gly Gln Ala Pro Arg Leu Leu Ile Tyr
1               5                   10                  15

<210> SEQ ID NO 83
<211> LENGTH: 32
<212> TYPE: PRT
<213> ORGANISM: Artificial sequence
<220> FEATURE:
<223> OTHER INFORMATION: Human acceptor D FR3

<400> SEQUENCE: 83

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 84
<211> LENGTH: 10
<212> TYPE: PRT
<213> ORGANISM: Artificial sequence
<220> FEATURE:
<223> OTHER INFORMATION: Human acceptor D FR4
```

```
<400> SEQUENCE: 84

Phe Gly Gly Gly Thr Lys Val Glu Ile Lys
1               5                   10

<210> SEQ ID NO 85
<211> LENGTH: 23
<212> TYPE: PRT
<213> ORGANISM: Artificial sequence
<220> FEATURE:
<223> OTHER INFORMATION: Human acceptor E FR1

<400> SEQUENCE: 85

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 86
<211> LENGTH: 15
<212> TYPE: PRT
<213> ORGANISM: Artificial sequence
<220> FEATURE:
<223> OTHER INFORMATION: Human acceptor E FR2

<400> SEQUENCE: 86

Trp Tyr Gln Gln Lys Pro Gly Gln Ala Pro Arg Leu Leu Ile Tyr
1               5                   10                  15

<210> SEQ ID NO 87
<211> LENGTH: 32
<212> TYPE: PRT
<213> ORGANISM: Artificial sequence
<220> FEATURE:
<223> OTHER INFORMATION: Human acceptor E FR3

<400> SEQUENCE: 87

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 88
<211> LENGTH: 10
<212> TYPE: PRT
<213> ORGANISM: Artificial sequence
<220> FEATURE:
<223> OTHER INFORMATION: Human acceptor E FR4

<400> SEQUENCE: 88

Phe Gly Gln Gly Thr Lys Val Glu Ile Lys
1               5                   10

<210> SEQ ID NO 89
<211> LENGTH: 23
<212> TYPE: PRT
<213> ORGANISM: Artificial sequence
<220> FEATURE:
<223> OTHER INFORMATION: Human acceptor F FR1

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys
            20
```

<210> SEQ ID NO 90
<211> LENGTH: 15
<212> TYPE: PRT
<213> ORGANISM: Artificial sequence
<220> FEATURE:
<223> OTHER INFORMATION: Human acceptor F FR2

<400> SEQUENCE: 90

Trp Tyr Gln Gln Lys Pro Gly Gln Ala Pro Arg Leu Leu Ile Tyr
1               5                   10                  15

<210> SEQ ID NO 91
<211> LENGTH: 32
<212> TYPE: PRT
<213> ORGANISM: Artificial sequence
<220> FEATURE:
<223> OTHER INFORMATION: Human acceptor F FR3

<400> SEQUENCE: 91

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 92
<211> LENGTH: 10
<212> TYPE: PRT
<213> ORGANISM: Artificial sequence
<220> FEATURE:
<223> OTHER INFORMATION: Human acceptor F FR4

<400> SEQUENCE: 92

Phe Gly Gln Gly Thr Lys Val Glu Ile Lys
1               5                   10

<210> SEQ ID NO 93
<211> LENGTH: 719
<212> TYPE: PRT
<213> ORGANISM: Artificial sequence
<220> FEATURE:
<223> OTHER INFORMATION: mCSF1R ECD-Fc

<400> SEQUENCE: 93

Ala Pro Val Ile Glu Pro Ser Gly Pro Glu Leu Val Val Glu Pro Gly
1               5                   10                  15

Glu Thr Val Thr Leu Arg Cys Val Ser Asn Gly Ser Val Glu Trp Asp
            20                  25                  30

Gly Pro Ile Ser Pro Tyr Trp Thr Leu Asp Pro Glu Ser Pro Gly Ser
        35                  40                  45

Thr Leu Thr Thr Arg Asn Ala Thr Phe Lys Asn Thr Gly Thr Tyr Arg
    50                  55                  60

Cys Thr Glu Leu Glu Asp Pro Met Ala Gly Ser Thr Thr Ile His Leu
65                  70                  75                  80

Tyr Val Lys Asp Pro Ala His Ser Trp Asn Leu Leu Ala Gln Glu Val
                85                  90                  95

Thr Val Val Glu Gly Gln Glu Ala Val Leu Pro Cys Leu Ile Thr Asp
            100                 105                 110

Pro Ala Leu Lys Asp Ser Val Ser Leu Met Arg Glu Gly Gly Arg Gln
        115                 120                 125

Val Leu Arg Lys Thr Val Tyr Phe Phe Ser Pro Trp Arg Gly Phe Ile
    130                 135                 140

```
Ile Arg Lys Ala Lys Val Leu Asp Ser Asn Thr Tyr Val Cys Lys Thr
145                 150                 155                 160

Met Val Asn Gly Arg Glu Ser Thr Ser Thr Gly Ile Trp Leu Lys Val
                165                 170                 175

Asn Arg Val His Pro Glu Pro Pro Gln Ile Lys Leu Glu Pro Ser Lys
            180                 185                 190

Leu Val Arg Ile Arg Gly Glu Ala Ala Gln Ile Val Cys Ser Ala Thr
        195                 200                 205

Asn Ala Glu Val Gly Phe Asn Val Ile Leu Lys Arg Gly Asp Thr Lys
210                 215                 220

Leu Glu Ile Pro Leu Asn Ser Asp Phe Gln Asp Asn Tyr Tyr Lys Lys
225                 230                 235                 240

Val Arg Ala Leu Ser Leu Asn Ala Val Asp Phe Gln Asp Ala Gly Ile
                245                 250                 255

Tyr Ser Cys Val Ala Ser Asn Asp Val Gly Thr Arg Thr Ala Thr Met
                260                 265                 270

Asn Phe Gln Val Val Glu Ser Ala Tyr Leu Asn Leu Thr Ser Glu Gln
            275                 280                 285

Ser Leu Leu Gln Glu Val Ser Val Gly Asp Ser Leu Ile Leu Thr Val
        290                 295                 300

His Ala Asp Ala Tyr Pro Ser Ile Gln His Tyr Asn Trp Thr Tyr Leu
305                 310                 315                 320

Gly Pro Phe Phe Glu Asp Gln Arg Lys Leu Glu Phe Ile Thr Gln Arg
                325                 330                 335

Ala Ile Tyr Arg Tyr Thr Phe Lys Leu Phe Leu Asn Arg Val Lys Ala
                340                 345                 350

Ser Glu Ala Gly Gln Tyr Phe Leu Met Ala Gln Asn Lys Ala Gly Trp
            355                 360                 365

Asn Asn Leu Thr Phe Glu Leu Thr Leu Arg Tyr Pro Pro Glu Val Ser
        370                 375                 380

Val Thr Trp Met Pro Val Asn Gly Ser Asp Val Leu Phe Cys Asp Val
385                 390                 395                 400

Ser Gly Tyr Pro Gln Pro Ser Val Thr Trp Met Glu Cys Arg Gly His
                405                 410                 415

Thr Asp Arg Cys Asp Glu Ala Gln Ala Leu Gln Val Trp Asn Asp Thr
                420                 425                 430

His Pro Glu Val Leu Ser Gln Lys Pro Phe Asp Lys Val Ile Ile Gln
            435                 440                 445

Ser Gln Leu Pro Ile Gly Thr Leu Lys His Asn Met Thr Tyr Phe Cys
        450                 455                 460

Lys Thr His Asn Ser Val Gly Asn Ser Ser Gln Tyr Phe Arg Ala Val
465                 470                 475                 480

Ser Leu Gly Gln Ser Lys Gln Glu Pro Lys Ser Ser Asp Lys Thr His
                485                 490                 495

Thr Cys Pro Pro Cys Pro Ala Pro Glu Leu Leu Gly Gly Pro Ser Val
                500                 505                 510

Phe Leu Phe Pro Pro Lys Pro Lys Asp Thr Leu Met Ile Ser Arg Thr
            515                 520                 525

Pro Glu Val Thr Cys Val Val Val Asp Val Ser His Glu Asp Pro Glu
        530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
```

```
                      565                 570                 575
Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
            595                 600                 605

Ser Lys Ala Lys Gly Gln Pro Arg Glu Pro Gln Val Tyr Thr Leu Pro
    610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys
705                 710                 715

<210> SEQ ID NO 94
<211> LENGTH: 327
<212> TYPE: PRT
<213> ORGANISM: Artificial sequence
<220> FEATURE:
<223> OTHER INFORMATION: Human IgG4 S241P

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
                  210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 95
<211> LENGTH: 107
<212> TYPE: PRT
<213> ORGANISM: Homo sapiens
<220> FEATURE:
<221> NAME/KEY: MISC_FEATURE
<222> LOCATION: (1)..(107)
<223> OTHER INFORMATION: Human Ig-kappa

<400> SEQUENCE: 95

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 96
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: human PD-1 precursor (with signal sequence)
      UniProtKB/Swiss-Prot: Q15116.3, 01-OCT-2014

<400> SEQUENCE: 96

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
```

```
            50                  55                  60
Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
             100                 105                 110

Ala Arg Arg Asn Asp Ser Gly Thr Tyr Leu Cys Gly Ala Ile Ser Leu
             115                 120                 125

Ala Pro Lys Ala Gln Ile Lys Glu Ser Leu Arg Ala Glu Leu Arg Val
         130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                 165                 170                 175

Leu Leu Gly Ser Leu Val Leu Leu Val Trp Val Leu Ala Val Ile Cys
             180                 185                 190

Ser Arg Ala Ala Arg Gly Thr Ile Gly Ala Arg Arg Thr Gly Gln Pro
             195                 200                 205

Leu Lys Glu Asp Pro Ser Ala Val Pro Val Phe Ser Val Asp Tyr Gly
 210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                 245                 250                 255

Met Gly Thr Ser Ser Pro Ala Arg Arg Gly Ser Ala Asp Gly Pro Arg
             260                 265                 270

Ser Ala Gln Pro Leu Arg Pro Glu Asp Gly His Cys Ser Trp Pro Leu
             275                 280                 285
```

<210> SEQ ID NO 97
<211> LENGTH: 268
<212> TYPE: PRT
<213> ORGANISM: Artificial sequence
<220> FEATURE:
<223> OTHER INFORMATION: human PD-1 (mature, without signal sequence)

<400> SEQUENCE: 97

```
Pro Gly Trp Phe Leu Asp Ser Pro Asp Arg Pro Trp Asn Pro Pro Thr
 1               5                  10                  15

Phe Ser Pro Ala Leu Leu Val Val Thr Glu Gly Asp Asn Ala Thr Phe
                 20                  25                  30

Thr Cys Ser Phe Ser Asn Thr Ser Glu Ser Phe Val Leu Asn Trp Tyr
             35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                 85                  90                  95

Asp Ser Gly Thr Tyr Leu Cys Gly Ala Ile Ser Leu Ala Pro Lys Ala
             100                 105                 110

Gln Ile Lys Glu Ser Leu Arg Ala Glu Leu Arg Val Thr Glu Arg Arg
             115                 120                 125

Ala Glu Val Pro Thr Ala His Pro Ser Pro Ser Pro Arg Pro Ala Gly
```

```
                130             135             140
Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                    165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
                195                 200                 205

Gln Trp Arg Glu Lys Thr Pro Glu Pro Pro Val Pro Cys Val Pro Glu
            210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                    245                 250                 255

Leu Arg Pro Glu Asp Gly His Cys Ser Trp Pro Leu
                260                 265
```

<210> SEQ ID NO 98
<211> LENGTH: 290
<212> TYPE: PRT
<213> ORGANISM: Homo sapiens
<220> FEATURE:
<221> NAME/KEY: MISC_FEATURE
<222> LOCATION: (1)..(290)
<223> OTHER INFORMATION: human PD-L1 precursor (with signal sequence)
      UniProtKB/Swiss-Prot: Q9NZQ7.1, 01-OCT-2014

<400> SEQUENCE: 98

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
```

```
                210                 215                 220
Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 99
<211> LENGTH: 272
<212> TYPE: PRT
<213> ORGANISM: Artificial sequence
<220> FEATURE:
<223> OTHER INFORMATION: human PD-L1 (mature, without signal sequence)

<400> SEQUENCE: 99

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
            260                 265                 270
```

```
<210> SEQ ID NO 100
<211> LENGTH: 113
<212> TYPE: PRT
<213> ORGANISM: Artificial sequence
<220> FEATURE:
<223> OTHER INFORMATION: Nivolumab heavy chain variable region

<400> SEQUENCE: 100

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 101
<211> LENGTH: 327
<212> TYPE: PRT
<213> ORGANISM: Artificial sequence
<220> FEATURE:
<223> OTHER INFORMATION: Nivolumab heavy chain constant region

<400> SEQUENCE: 101

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
            195                 200                 205
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 102
<211> LENGTH: 107
<212> TYPE: PRT
<213> ORGANISM: Artificial sequence
<220> FEATURE:
<223> OTHER INFORMATION: Nivolumab light chain variable region

<400> SEQUENCE: 102

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105
```

<210> SEQ ID NO 103
<211> LENGTH: 107
<212> TYPE: PRT
<213> ORGANISM: Artificial sequence
<220> FEATURE:
<223> OTHER INFORMATION: Nivolumab light chain constant region

<400> SEQUENCE: 103

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 104
<211> LENGTH: 30
<212> TYPE: PRT
<213> ORGANISM: Artificial sequence
<220> FEATURE:
<223> OTHER INFORMATION: Nivolumab heavy chain variable region FR1

<400> SEQUENCE: 104

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser
                20                  25                  30
```

<210> SEQ ID NO 105
<211> LENGTH: 5
<212> TYPE: PRT
<213> ORGANISM: Artificial sequence
<220> FEATURE:
<223> OTHER INFORMATION: Nivolumab heavy chain variable region CDR1

<400> SEQUENCE: 105

```
Asn Ser Gly Met His
1               5
```

<210> SEQ ID NO 106
<211> LENGTH: 14
<212> TYPE: PRT
<213> ORGANISM: Artificial sequence
<220> FEATURE:
<223> OTHER INFORMATION: Nivolumab heavy chain variable region FR2

<400> SEQUENCE: 106

```
Trp Val Arg Gln Ala Pro Gly Lys Gly Leu Glu Trp Val Ala
1               5                   10
```

<210> SEQ ID NO 107
<211> LENGTH: 17
<212> TYPE: PRT
<213> ORGANISM: Artificial sequence
<220> FEATURE:
<223> OTHER INFORMATION: Nivolumab heavy chain variable region CDR2

<400> SEQUENCE: 107

```
Val Ile Trp Tyr Asp Gly Ser Lys Arg Tyr Tyr Ala Asp Ser Val Lys
1               5                   10                  15

Gly
```

<210> SEQ ID NO 108
<211> LENGTH: 32
<212> TYPE: PRT
<213> ORGANISM: Artificial sequence
<220> FEATURE:
<223> OTHER INFORMATION: Nivolumab heavy chain variable region FR3

<400> SEQUENCE: 108

```
Arg Phe Thr Ile Ser Arg Asp Asn Ser Lys Asn Thr Leu Phe Leu Gln
1               5                   10                  15
```

```
Met Asn Ser Leu Arg Ala Glu Asp Thr Ala Val Tyr Tyr Cys Ala Thr
                20                  25                  30

<210> SEQ ID NO 109
<211> LENGTH: 4
<212> TYPE: PRT
<213> ORGANISM: Artificial sequence
<220> FEATURE:
<223> OTHER INFORMATION: Nivolumab heavy chain variable region CDR3

<400> SEQUENCE: 109

Asn Asp Asp Tyr
1

<210> SEQ ID NO 110
<211> LENGTH: 11
<212> TYPE: PRT
<213> ORGANISM: Artificial sequence
<220> FEATURE:
<223> OTHER INFORMATION: Nivolumab heavy chain variable region FR4

<400> SEQUENCE: 110

Trp Gly Gln Gly Thr Leu Val Thr Val Ser Ser
1               5                   10

<210> SEQ ID NO 111
<211> LENGTH: 23
<212> TYPE: PRT
<213> ORGANISM: Artificial sequence
<220> FEATURE:
<223> OTHER INFORMATION: Nivolumab light chain variable region FR1

<400> SEQUENCE: 111

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 112
<211> LENGTH: 11
<212> TYPE: PRT
<213> ORGANISM: Artificial sequence
<220> FEATURE:
<223> OTHER INFORMATION: Nivolumab light chain variable region CDR1

<400> SEQUENCE: 112

Arg Ala Ser Gln Ser Val Ser Ser Tyr Leu Ala
1               5                   10

<210> SEQ ID NO 113
<211> LENGTH: 15
<212> TYPE: PRT
<213> ORGANISM: Artificial sequence
<220> FEATURE:
<223> OTHER INFORMATION: Nivolumab light chain variable region FR2

<400> SEQUENCE: 113

Trp Tyr Gln Gln Lys Pro Gly Gln Ala Pro Arg Leu Leu Ile Tyr
1               5                   10                  15

<210> SEQ ID NO 114
<211> LENGTH: 7
<212> TYPE: PRT
<213> ORGANISM: Artificial sequence
<220> FEATURE:
<223> OTHER INFORMATION: Nivolumab light chain variable region CDR2
```

```
<400> SEQUENCE: 114

Asp Ala Ser Asn Arg Ala Thr
1               5

<210> SEQ ID NO 115
<211> LENGTH: 32
<212> TYPE: PRT
<213> ORGANISM: Artificial sequence
<220> FEATURE:
<223> OTHER INFORMATION: Nivolumab light chain variable region FR3

<400> SEQUENCE: 115

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 116
<211> LENGTH: 9
<212> TYPE: PRT
<213> ORGANISM: Artificial sequence
<220> FEATURE:
<223> OTHER INFORMATION: Nivolumab light chain variable region CDR3

<400> SEQUENCE: 116

Gln Gln Ser Ser Asn Trp Pro Arg Thr
1               5

<210> SEQ ID NO 117
<211> LENGTH: 10
<212> TYPE: PRT
<213> ORGANISM: Artificial sequence
<220> FEATURE:
<223> OTHER INFORMATION: Nivolumab light chain variable region FR4

<400> SEQUENCE: 117

Phe Gly Gln Gly Thr Lys Val Glu Ile Lys
1               5                   10
```